(12) United States Patent
Kim et al.

(10) Patent No.: US 11,711,978 B2
(45) Date of Patent: Jul. 25, 2023

(54) HETEROCYCLIC COMPOUND AND ORGANIC LIGHT-EMITTING DEVICE INCLUDING THE SAME

(71) Applicant: Samsung Display Co., Ltd., Yongin-si (KR)

(72) Inventors: Minji Kim, Yongin-si (KR); Dongjun Kim, Yongin-si (KR); Eunjae Jeong, Yongin-si (KR); Sohee Jo, Yongin-si (KR); Sanghyun Han, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 451 days.

(21) Appl. No.: 16/850,208

(22) Filed: Apr. 16, 2020

(65) Prior Publication Data
US 2021/0083201 A1    Mar. 18, 2021

(30) Foreign Application Priority Data

Sep. 16, 2019   (KR) .................. 10-2019-0113526

(51) Int. Cl.
*H10K 85/60* (2023.01)
*H10K 50/15* (2023.01)
(Continued)

(52) U.S. Cl.
CPC ....... *H10K 85/6574* (2023.02); *H10K 85/631* (2023.02); *H10K 85/6572* (2023.02);
(Continued)

(58) Field of Classification Search
CPC ............. H01L 51/0073; H01L 51/0059; H01L 51/0072; H01L 51/0074; H01L 51/4273;
(Continued)

(56) References Cited

U.S. PATENT DOCUMENTS

| 4,720,432 A | 1/1988 | VanSlyke et al. |
| 5,061,569 A | 10/1991 | VanSlyke et al. |

(Continued)

FOREIGN PATENT DOCUMENTS

| CN | 108752221 A | * 11/2018 | ............. H01L 51/54 |
| CN | 108864013 A | * 11/2018 | ............. H01L 51/54 |

(Continued)

OTHER PUBLICATIONS

EPO European Search Report dated Jan. 12, 2021 for EP Application No. 20195352.8, 7 pages.

*Primary Examiner* — Thinh T Nguyen
(74) *Attorney, Agent, or Firm* — Lewis Roca Rothgerber Christie LLP

(57) ABSTRACT

An organic light-emitting device includes a heterocyclic compound represented by Formula 1

Formula 1

Formula 2-1

(Continued)

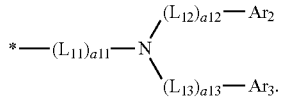

Formula 2-2

In Formula 1, X is O or S, one selected from $R_1$ to $R_8$ is a group represented by Formula 2-1, and one selected from the remaining groups is a group represented by Formula 2-2, wherein, when X is O, one selected from $R_1$, $R_2$, $R_4$, $R_5$, $R_7$, and $R_8$ is a group represented by Formula 2-1.

20 Claims, 4 Drawing Sheets

(51) Int. Cl.
  *H10K 50/17* (2023.01)
  *H10K 30/30* (2023.01)
  *H10K 50/16* (2023.01)
(52) U.S. Cl.
  CPC ....... *H10K 85/6576* (2023.02); *H10K 30/353* (2023.02); *H10K 50/15* (2023.02); *H10K 50/16* (2023.02); *H10K 50/171* (2023.02)
(58) Field of Classification Search
  CPC ............ H01L 51/5056; H10K 85/6574; H10K 85/631; H10K 85/6576; H10K 8565/72; H10K 30/353; H10K 50/171
  USPC .................................. 257/49, 40; 438/82, 99
  See application file for complete search history.

(56) References Cited

U.S. PATENT DOCUMENTS

| | | | |
|---|---|---|---|
| 6,242,115 | B1 | 6/2001 | Thomson et al. |
| 9,478,753 | B2 | 10/2016 | Jung et al. |
| 9,947,874 | B2 | 4/2018 | Pflumm et al. |
| 10,014,477 | B2 | 7/2018 | Kato et al. |
| 2015/0001494 | A1* | 1/2015 | Kim et al. ............. H01L 51/50 257/40 |
| 2018/0186764 | A1 | 7/2018 | Jung et al. |
| 2019/0157568 | A1 | 5/2019 | Hwang et al. |

FOREIGN PATENT DOCUMENTS

| | | |
|---|---|---|
| CN | 109053698 A | 12/2018 |
| JP | 11-144873 A | 5/1999 |
| JP | 2000-302756 A | 10/2000 |
| JP | 2003-133075 A | 5/2003 |
| JP | 2004-79265 A | 3/2004 |
| JP | 2006-151979 A | 6/2006 |
| KR | 10-2012-0017382 A | 2/2012 |
| KR | 10-2013-0099098 A | 9/2013 |
| KR | 10-1453768 B1 | 10/2014 |
| KR | 10-2015-0048137 A | 5/2015 |
| KR | 10-2015-0074603 A | 7/2015 |
| KR | 10-2017-0030289 A | 3/2017 |

* cited by examiner

| 190 |
|-----|
| 150 |
| 110 |

| 190 |
|-----|
| 150 |
| 110 |
| 210 |

| 220 |
|---|
| 190 |
| 150 |
| 110 |

| 220 |
|-----|
| 190 |
| 150 |
| 110 |
| 210 |

HETEROCYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0113526, filed on Sep. 16, 2019, in the Korean Intellectual Property Office, the entire content of which is incorporated herein by reference.

BACKGROUND

1. Field

One or more aspects of embodiments of the present disclosure relate to a heterocyclic compound and an organic light-emitting device including the same.

2. Description of Related Art

Organic light-emitting devices are self-emission devices that produce full-color images, and may also have wide viewing angles, high contrast ratios, short response times, as well as excellent characteristics in terms of brightness, driving voltage, and/or response speed.

An example of organic light-emitting device may include a first electrode disposed on a substrate, and a hole transport region, an emission layer, an electron transport region, and a second electrode sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons may transition from an excited state to the ground state, thereby generating light.

SUMMARY

One or more aspects of embodiments of the present disclosure are directed toward a novel heterocyclic compound and an organic light-emitting device including the same.

Additional aspects will be set forth in part in the description which follows and, in part, will be apparent from the description, or may be learned by practice of the presented embodiments of the disclosure.

One or more example embodiments of the present disclosure provide a heterocyclic compound represented by Formula 1:

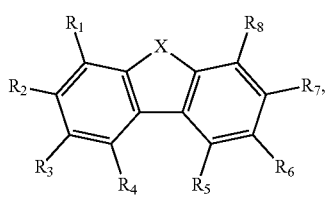

Formula 1

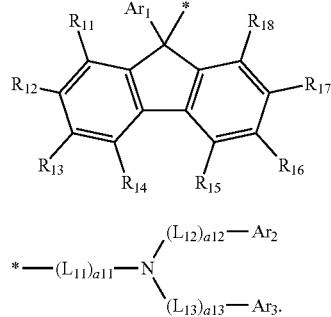

Formula 2-1

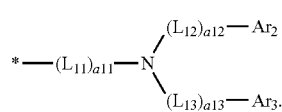

Formula 2-2

In Formulae 1, 2-1, and 2-2,

X is O or S, $R_1$ to $R_8$ are each independently selected from a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_1)(Q_2)$, —B$(Q_1)(Q_2)$, —C(=O)$(Q_1)$, —S(=O)$_2(Q_1)$, and —P(=O)$(Q_1)(Q_2)$, one selected from $R_1$ to $R_8$ is a group represented by Formula 2-1, and (another) one selected from the remaining groups is a group represented by Formula 2-2, wherein, when X is O, one selected from $R_1$, $R_2$, $R_4$, $R_5$, $R_7$, and $R_8$ is a group represented by Formula 2-1, $R_{11}$ to $R_{18}$ are each independently selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_1)(Q_2)$, —B$(Q_1)(Q_2)$, —C(=O)$(Q_1)$, —S(=O)$_2(Q_1)$, and —P(=O)$(Q_1)(Q_2)$, two adjacent groups among $R_1$ to $R_8$ and two adjacent groups among $R_{11}$ to $R_{18}$ are optionally linked to each other to form a ring, $Ar_1$ to $Ar_3$ are each independently a substituted or unsubstituted $C_5$-$C_{60}$ carbocyclic group or a substituted or unsubstituted $C_1$-$C_{60}$ heterocyclic group, $Ar_2$ and $Ar_3$ are optionally linked to each other via a single bond, —C($Q_4$)($Q_5$)-, —Si($Q_4$)($Q_5$)-, —O—, —S—, —N($Q_4$)-, —B($Q_4$)-, C(=O)—, —S(=O)—, —S(=O)($Q_4$)-, or —P(=O)($Q_4$)- to form a condensed heteroring, $L_{11}$ to $L_{13}$ are each independently a substituted or unsubstituted $C_5$-$C_{60}$ carbocyclic group or a substituted or unsubstituted $C_1$-$C_{60}$ heterocyclic group, a11 to a13 are each independently an integer from 0 to 3, when a11 is 0, *-$(L_{11})_{a11}$-*' indicates a single bond, when a12 is 0, *-$(L_{12})_{a12}$-*' indicates a single bond, and when a13 is 0, *-$(L_{13})_{a13}$-*' indicates a single bond.

at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_5$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a group represented by Formula 1, and *' indicates a binding site to a neighboring atom.

One or more example embodiments of the present disclosure provide an organic light-emitting device including: a first electrode; a second electrode facing the first electrode; and an organic layer between the first electrode and the second electrode and including an emission layer, wherein the organic layer includes at least one heterocyclic compound represented by Formula 1.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 1 to 4 are each a schematic view of a structure of an organic light-emitting device according to an embodiment.

DETAILED DESCRIPTION

The present disclosure will now be described more fully with reference to the accompanying drawings, in which example embodiments of the disclosure are shown. Like reference numerals in the drawings denote like elements throughout, and redundant descriptions thereof may be omitted. The terminology used herein is for the purpose of describing particular example embodiments only and is not intended to limit the example embodiments described herein.

As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, expressions such as "at least one of", "one of", and "selected from", when preceding a list of elements, modify the entire list of elements and do not modify the individual elements of the list. As used herein, the term "and/or" includes any and all combinations of one or more of the associated listed items. Further, the use of "may" when describing embodiments of the present disclosure refers to "one or more embodiments of the present disclosure".

One or more example embodiments of the present disclosure provide a heterocyclic compound represented by Formula 1:

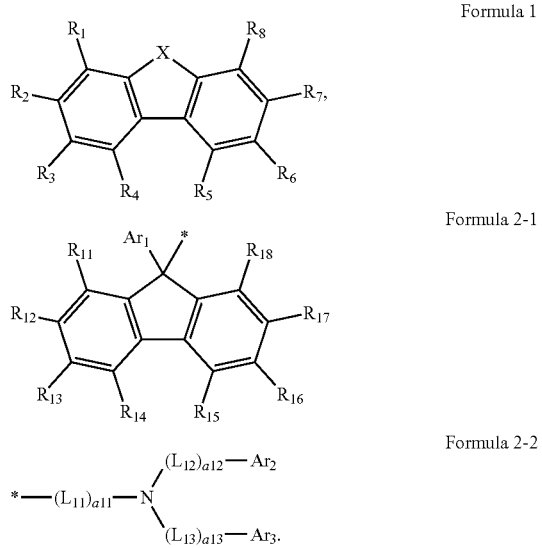

Formula 1

Formula 2-1

Formula 2-2

In Formulae 1, 2-1, and 2-2, X, $R_1$ to $R_8$, $R_{11}$ to $R_{18}$, $L_{11}$ to $L_{13}$, a11 to a13, and $Ar_1$ to $Ar_3$ will be described in more detail.

X in Formula 1 may be O or S.

$R_1$ to $R_8$ in Formula 1 may each independently be selected from a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), and one selected from $R_1$ to $R_8$ may be a group represented by Formula 2-1, and (another) one selected from the remaining groups may be a group represented by Formula 2-2, wherein, when X is O, one selected from $R_1$, $R_2$, $R_4$, $R_5$, $R_7$, and R may be a group represented by Formula 2-1.

In one embodiment, in Formula 1, X may be O, one selected from $R_1$, $R_2$, and $R_4$ may be a group represented by Formula 2-1, and one selected from $R_5$ to R may be a group represented by Formula 2-2.

For example, in Formula 1, when X is O, $R_1$ may be a group represented by Formula 2-1, and $R_5$ may be a group represented by Formula 2-2; $R_1$ may be a group represented by Formula 2-1, and $R_6$ may be a group represented by Formula 2-2; $R_1$ may be a group represented by Formula 2-1, and $R_7$ may be a group represented by Formula 2-2; $R_1$ may be a group represented by Formula 2-1, and $R_8$ may be a group represented by Formula 2-2; $R_2$ may be a group represented by Formula 2-1, and $R_5$ may be a group represented by Formula 2-2; $R_2$ may be a group represented by Formula 2-1, and $R_6$ may be a group represented by Formula 2-2; $R_2$ may be a group represented by Formula 2-1, and $R_7$ may be a group represented by Formula 2-2; $R_2$ may be a group represented by Formula 2-1, and $R_8$ may be a group represented by Formula 2-2; $R_4$ may be a group represented by Formula 2-1, and $R_5$ may be a group represented by Formula 2-2; $R_4$ may be a group represented by Formula 2-1, and $R_6$ may be a group represented by Formula 2-2; $R_4$ may be a group represented by Formula 2-1, and $R_7$ may be a group represented by Formula 2-2; or $R_4$ may be a group represented by Formula 2-1, and $R_8$ may be a group represented by Formula 2-2.

In one or more embodiments, in Formula 1, X may be S, one selected from $R_1$ to $R_4$ may be a group represented by Formula 2-1, and one selected from $R_5$ to R may be a group represented by Formula 2-2.

For example, in Formula 1, when X is S, $R_1$ may be a group represented by Formula 2-1, and $R_5$ may be a group represented by Formula 2-2; $R_1$ may be a group represented by Formula 2-1, and $R_6$ may be a group represented by Formula 2-2; $R_1$ may be a group represented by Formula 2-1, and $R_7$ may be a group represented by Formula 2-2; $R_1$ may be a group represented by Formula 2-1, and $R_8$ may be a group represented by Formula 2-2; $R_2$ may be a group represented by Formula 2-1, and $R_5$ may be a group represented by Formula 2-2; $R_2$ may be a group represented by Formula 2-1, and $R_6$ may be a group represented by Formula 2-2; $R_2$ may be a group represented by Formula 2-1, and $R_7$ may be a group represented by Formula 2-2; $R_2$ may be a group represented by Formula 2-1, and $R_8$ may be a group represented by Formula 2-2; $R_3$ may be a group represented by Formula 2-1, and $R_5$ may be a group represented by Formula 2-2; $R_3$ may be a group represented by Formula 2-1, and $R_6$ may be a group represented by Formula 2-2; $R_3$ may be a group represented by Formula 2-1, and $R_7$ may be a group represented by Formula 2-2; $R_3$ may be a group represented by Formula 2-1, and $R_8$ may be a group represented by Formula 2-2; $R_4$ may be a group represented by Formula 2-1, and $R_5$ may be a group represented by Formula 2-2; $R_4$ may be a group represented by Formula 2-1, and $R_6$ may be a group represented by Formula 2-2; $R_4$ may be a group represented by Formula 2-1, and $R_7$ may be a group represented by Formula 2-2; or $R_4$ may be a group represented by Formula 2-1, and $R_8$ may be a group represented by Formula 2-2.

In one or more embodiments, in Formula 1, X may be O, one selected from $R_1$, $R_2$, and $R_4$ may be a group represented by Formula 2-1, and one selected from $R_1$ to $R_4$ that is not a group represented by Formula 2-1 may be a group represented by Formula 2-2.

For example, in Formula 1, when X is O, $R_1$ may be a group represented by Formula 2-1, and $R_2$ may be a group represented by Formula 2-2; $R_1$ may be a group represented by Formula 2-1, and $R_3$ may be a group represented by Formula 2-2; $R_1$ may be a group represented by Formula 2-1, and $R_4$ may be a group represented by Formula 2-2; $R_2$ may be a group represented by Formula 2-1, and $R_1$ may be a group represented by Formula 2-2; $R_2$ may be a group represented by Formula 2-1, and $R_3$ may be a group represented by Formula 2-2; $R_2$ may be a group represented by Formula 2-1, and $R_4$ may be a group represented by Formula 2-2; $R_4$ may be a group represented by Formula 2-1, and $R_1$ may be a group represented by Formula 2-2; $R_4$ may be a group represented by Formula 2-1, and $R_2$ may be a group represented by Formula 2-2; or $R_4$ may be a group represented by Formula 2-1, and $R_3$ may be a group represented by Formula 2-2.

In one or more embodiments, in Formula 1, X may be S, one selected from $R_1$ to $R_4$ may be a group represented by Formula 2-1, and one selected from the remaining groups may be a group represented by Formula 2-2.

For example, in Formula 1, when X is S, $R_1$ may be a group represented by Formula 2-1, and $R_2$ may be a group represented by Formula 2-2; $R_1$ may be a group represented by Formula 2-1, and $R_3$ may be a group represented by Formula 2-2; $R_1$ may be a group represented by Formula 2-1, and $R_4$ may be a group represented by Formula 2-2; $R_2$ may be a group represented by Formula 2-1, and $R_1$ may be a group represented by Formula 2-2; $R_2$ may be a group represented by Formula 2-1, and $R_3$ may be a group represented by Formula 2-2; $R_2$ may be a group represented by Formula 2-1, and $R_4$ may be a group represented by Formula 2-2; $R_3$ may be a group represented by Formula 2-1, and $R_1$ may be a group represented by Formula 2-2; $R_3$ may be a group represented by Formula 2-1, and $R_2$ may be a group represented by Formula 2-2; $R_3$ may be a group represented by Formula 2-1, and $R_4$ may be a group represented by Formula 2-2; $R_4$ may be a group represented by Formula 2-1, and $R_1$ may be a group represented by Formula 2-2; $R_4$ may be a group represented by Formula 2-1, and $R_2$ may be a group represented by Formula 2-2; or $R_4$ may be a group represented by Formula 2-1, and $R_3$ may be a group represented by Formula 2-2.

In one embodiment, $R_1$ to $R_8$ in Formula 1 may each independently be selected from:

a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group; and a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from deuterium, —F, —Cl, —Br, and —I, but embodiments of the present disclosure are not limited thereto.

In some embodiments, among $R_1$ to $R_8$, the groups not represented by Formula 2-1 or Formula 2-2 may each be hydrogen.

$R_{11}$ to $R_{18}$ in Formula 2-1 may each independently be selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$).

In one embodiment, $R_{11}$ to $R_{18}$ may each independently be selected from:

hydrogen, deuterium, —F, —Cl, —Br, —I, a hydroxyl group, a cyano group, a nitro group, an amino group, an amidino group, a hydrazino group, a hydrazono group, a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group; and a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from deuterium, —F, —Cl, —Br, and —I, but embodiments of the present disclosure are not limited thereto.

For example, $R_{11}$ to $R_{18}$ may each independently be selected from:

hydrogen, deuterium, —F, —Cl, —Br, —I, a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonylgroup, a tert-nonyl-group, an n-decylgroup, an isodecylgroup, a sec-decyl group, and a tert-decyl group; and a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from deuterium, —F, —Cl, —Br, and —I.

In some embodiments, for example, $R_{11}$ to $R_{18}$ may each independently be selected from:

hydrogen, deuterium, —F, —Cl, —Br, —I, a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, and tert-hexyl group; and a methyl group, an ethyl group, an n-propyl group, an isopropyl group, an n-butyl group, an isobutyl group, a sec-butyl group, a tert-butyl group, an n-pentyl group, a tert-pentyl group, an neo-pentyl group, an isopentyl group, a sec-pentyl group, a 3-pentyl group, a sec-isopentyl group, an n-hexyl group, an isohexyl group, a sec-hexyl group, and a tert-hexyl group, each substituted with at least one selected from deuterium, —F, —Cl, —Br, and —I.

In Formulae 1 and 2-1, two adjacent groups among $R_1$ to R and two adjacent groups among $R_{11}$ to $R_{18}$ may optionally be linked to each other to form a ring.

In one embodiment, two adjacent groups among $R_1$ to R and two adjacent groups among $R_{11}$ to $R_{18}$ may optionally be linked to each other to form a substituted or unsubstituted $C_5$-$C_{60}$ carbocyclic group or a substituted or unsubstituted $C_1$-$C_{60}$ heterocyclic group.

$L_{11}$ to $L_{13}$ in Formula 2-2 may each independently be a substituted or unsubstituted $C_5$-$C_{60}$ carbocyclic group or a substituted or unsubstituted $C_1$-$C_{60}$ heterocyclic group.

In one embodiment, $L_{11}$ to $L_{13}$ may each independently be selected from:

a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group;

a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), but embodiments of the present disclosure are not limited thereto, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

For example, $L_{11}$ to $L_{13}$ may each independently be a group represented by one selected from Formulae 3-1 to 3-39:

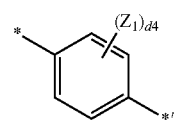

3-1

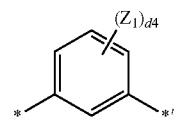

3-2

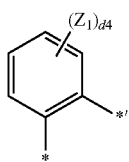
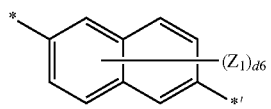
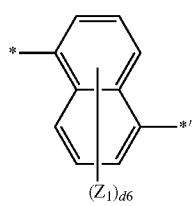
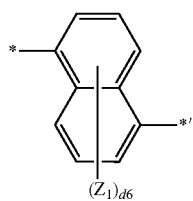
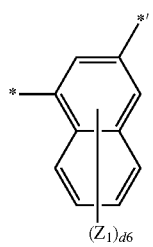
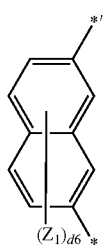
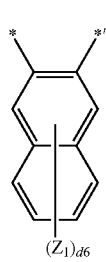
3-3
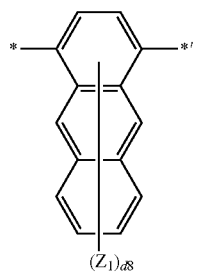
3-4
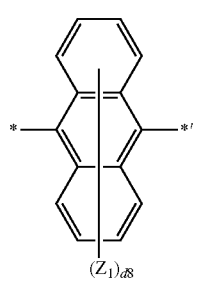
3-5
3-6
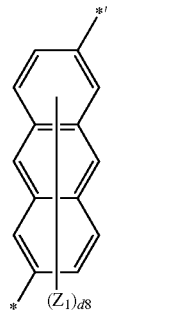
3-7
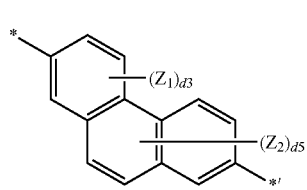
3-8
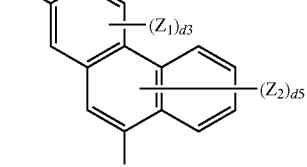
3-9
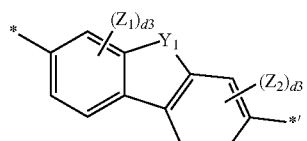
3-10
3-11
3-12
3-13
3-14
3-15
3-16
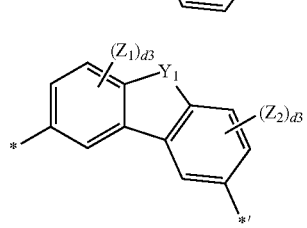

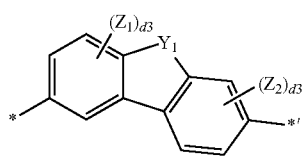
3-17
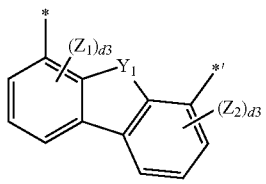
3-18
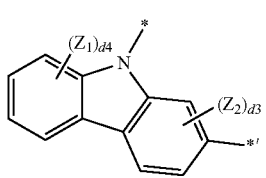
3-19
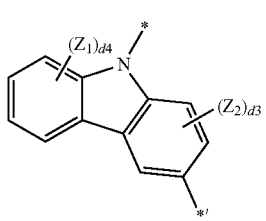
3-20
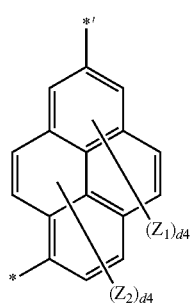
3-21
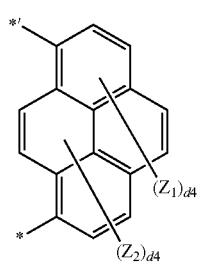
3-22
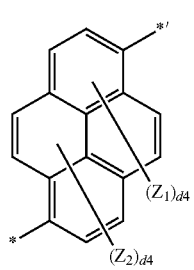
3-23
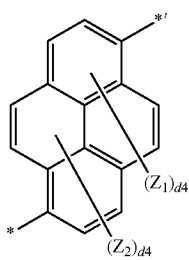
3-24
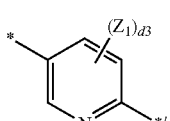
3-25
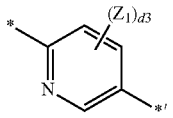
3-26
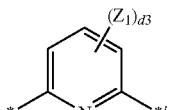
3-27
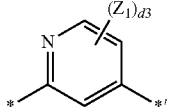
3-28
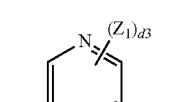
3-29
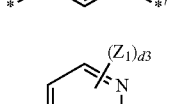
3-30
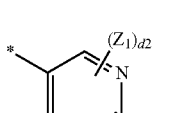
3-31
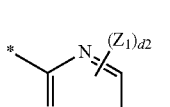
3-32
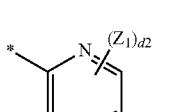
3-33
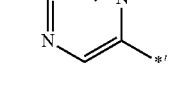
3-34

-continued

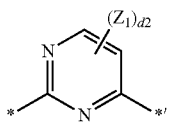
3-35

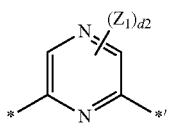
3-36

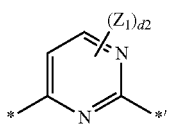
3-37

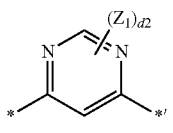
3-38

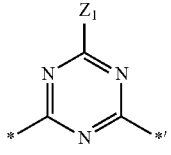
3-39

In Formulae 3-1 to 3-39, $Y_1$ may be O, S, $C(Z_3)(Z_4)$, $N(Z_3)$, or $Si(Z_3)(Z_4)$, $Z_1$ to $Z_4$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, and —$Si(Q_{31})(Q_{32})(Q_{33})$, $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group, $Z_3$ and $Z_4$ may optionally be linked to form a substituted or unsubstituted $C_5$-$C_{10}$ carbocyclic group or a substituted or unsubstituted $C_1$-$C_{10}$ heterocyclic group, d2 may be an integer from 0 to 2,
d3 may be an integer from 0 to 3,
d4 may be an integer from 0 to 4,
d5 may be an integer from 0 to 5,
d6 may be an integer from 0 to 6,
d8 may be an integer from 0 to 8, and

* and *' each indicate a binding site to a neighboring atom.

In Formula 2-2, a11 to a13 may each independently be an integer from 0 to 3. When a11 is 0 *-$(L_{11})_{a11}$-* indicates a single bond, when a12 is 0, *-$(L_{12})_{a12}$-* indicates a single bond, and when a13 is 0, *-$(L_{13})_{a13}$-* indicates a single bond.

In some embodiments, for example, a11 may be 0.

$Ar_1$ to $Ar_3$ in Formulae 2-1 and 2-2 may each independently be a substituted or unsubstituted $C_5$-$C_{60}$ carbocyclic group or a substituted or unsubstituted $C_1$-$C_{60}$ heterocyclic group.

In one embodiment, $Ar_1$ to $Ar_3$ may each independently be selected from:

a benzene group, a pentalene group, an indene group, a naphthalene group, an azulene group, a heptalene group, an indacene group, an acenaphthalene group, a fluorene group, a spiro-cyclopentane-fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group;

a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-cyclopentane-fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, but embodiments of the present disclosure are not limited thereto, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group.

For example, $Ar_1$ to $Ar_3$ may each independently be a group represented by one selected from Formulae 4-1 to 4-24:

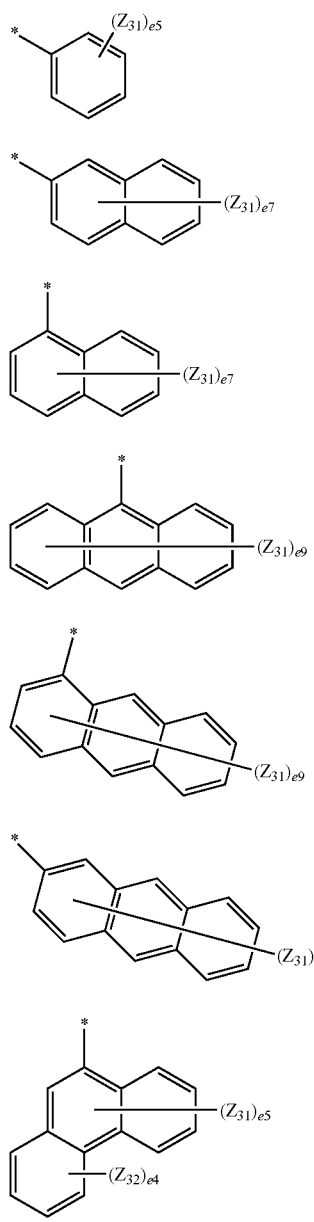
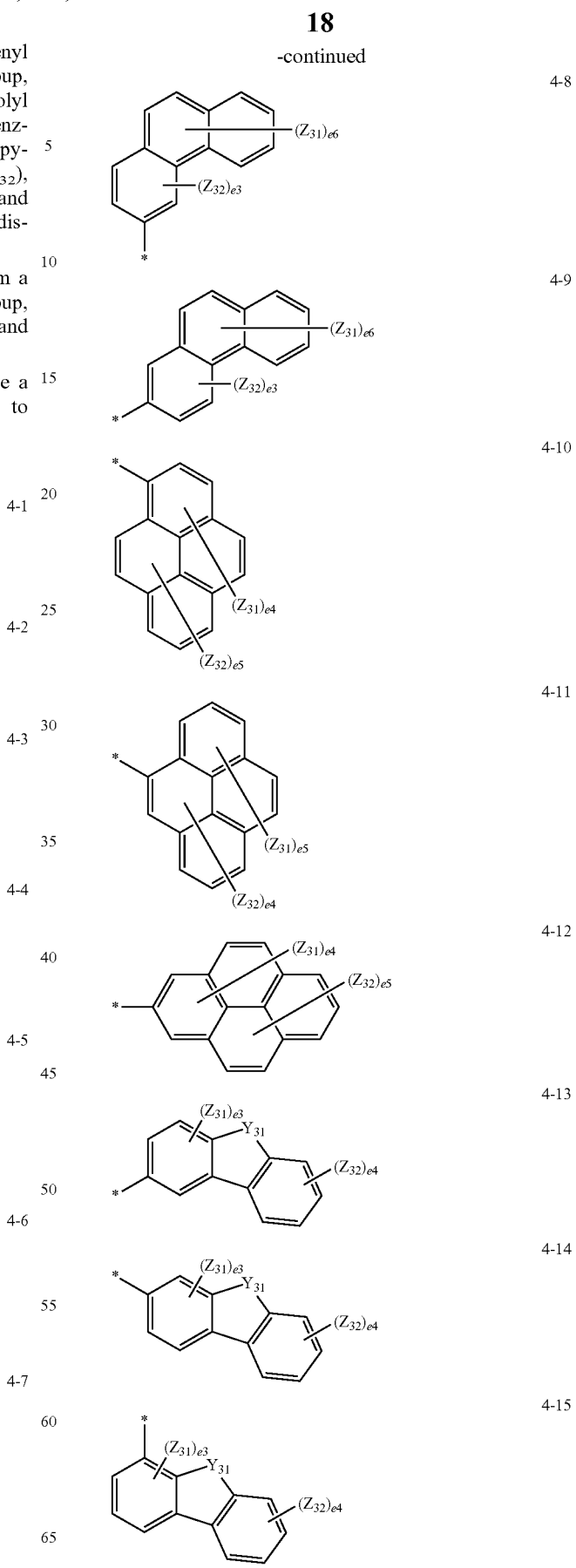

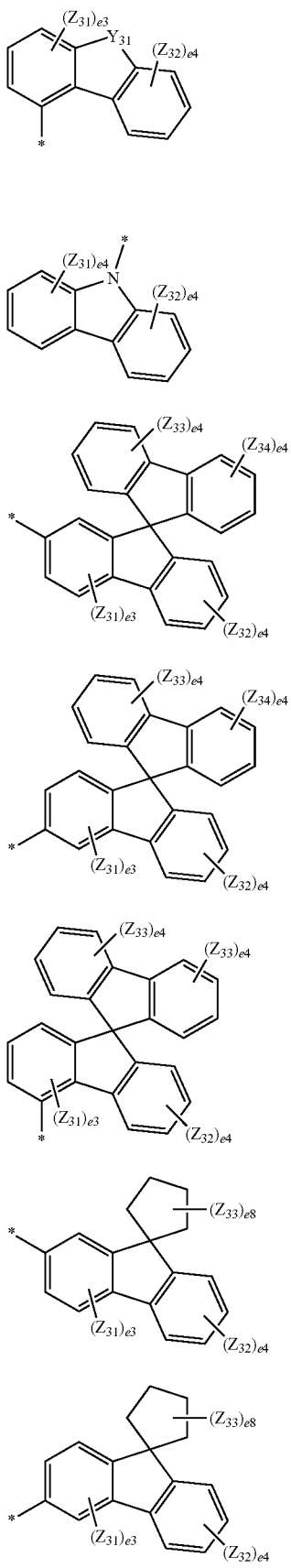

In Formulae 4-1 to 4-24, $Y_{31}$ may be O, S, $C(Z_{35})(Z_{36})$, $N(Z_{35})$, or $Si(Z_{35})(Z_{36})$, $Z_{31}$ to $Z_{36}$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-cyclopentane-fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, and —$Si(Q_{31})(Q_{32})(Q_{33})$, $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, and a pyridinyl group, e3 may be an integer from 0 to 3,
e4 may be an integer from 0 to 4,
e5 may be an integer from 0 to 5,
e6 may be an integer from 0 to 6,
e7 may be an integer from 0 to 7,
e8 may be an integer from 0 to 8,
e9 may be an integer from 0 to 9, and
* indicates a binding site to a neighboring atom.

In one embodiment, $Ar_1$ to $Ar_3$ may each independently be selected from:

a benzene group, a naphthalene group, a fluorene group, a spiro-cyclopentane-fluorene group, a spiro-bifluorene group, a benzofluorene group, a dibenzofluorene group, a dibenzofuran group, a dibenzothiophene group, a carbazole group, and a dibenzosilole group; and a benzene group, a naphthalene group, a fluorene group, a spiro-bifluorene group, a benzofluorene group, a dibenzofluorene group, a dibenzofuran group, a dibenzothiophene group, a carbazole group, and a dibenzosilole group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a phenyl group, a biphenyl group, a terphenyl group, a naphthyl group, a spiro-cyclopentane-fluorenyl group, a spiro-bifluorenyl group, a benzofluorenyl group, a dibenzofluorenyl group, a dibenzofuranyl group, a dibenzothiophenyl group, a carbazolyl group, a dibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$).

In one embodiment, $Ar_1$ in Formula 2-1 may be a benzene group, and $Ar_2$ and $Ar_3$ in Formula 2-2 may each independently be selected from:

a benzene group, a naphthalene group, a fluorene group, a spiro-cyclopentane-fluorene group, a spiro-bifluorene group, a benzofluorene group, a dibenzofluorene group, a dibenzofuran group, a dibenzothiophene group, a carbazole group, and a dibenzosilole group; and a benzene group, a naphthalene group, a fluorene group, a spiro-bifluorene group, a benzofluorene group, a dibenzofluorene group, a dibenzofuran group, a dibenzothiophene group, a carbazole group, and a dibenzosilole group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a phenyl group, a biphenyl group, a terphenyl group, a naphthyl group, a spiro-cyclopentane-fluorenyl group, a spiro-bifluorenyl group, a benzofluorenyl group, a dibenzofluorenyl group, a dibenzofuranyl group, a dibenzothiophenyl group, a carbazolyl group, a dibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), but embodiments of the present disclosure are not limited thereto.

$Ar_2$ and $Ar_3$ in Formula 2-2 may optionally be linked to each other via a single bond, —C($Q_4$)($Q_5$)-, —Si($Q_4$)($Q_5$)-, —O—, —S—, —N($Q_4$)-, —B($Q_4$)-, C(=O)—, —S(=O)$_2$—, —S(=O)($Q_4$)-, or —P(=O)($Q_4$)- to form a condensed heteroring.

For example, $Ar_2$ and $Ar_3$ may optionally be linked to each other via a single bond to form a condensed heteroring. For example, when each of $Ar_2$ and $Ar_3$ is a benzene group, $Ar_2$ and $Ar_3$ may optionally be linked to each other via a single bond to form a carbazole group.

In one embodiment, the heterocyclic compound may be selected from Compounds 1 to 348:

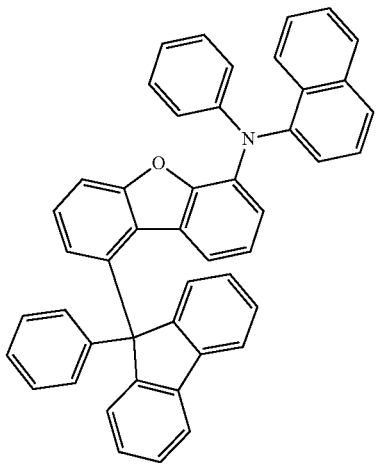

1

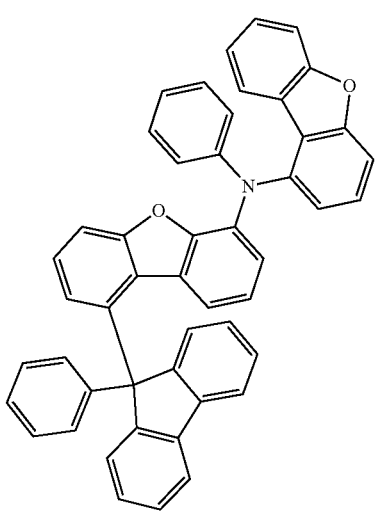

2

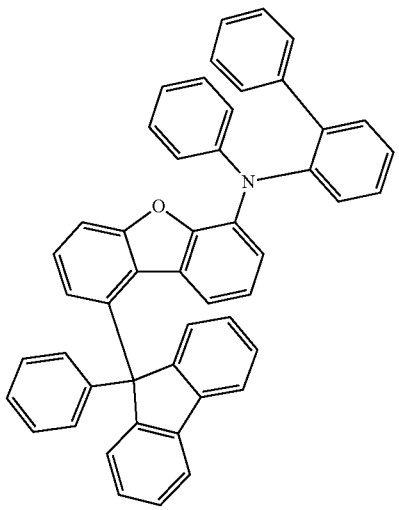

3

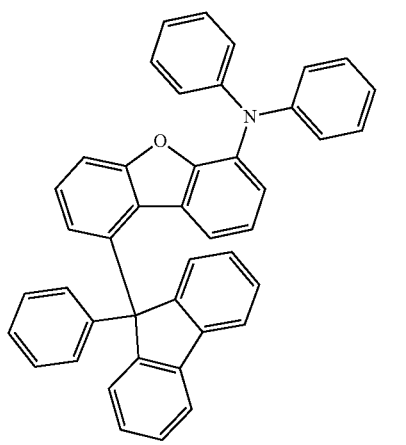

4

5
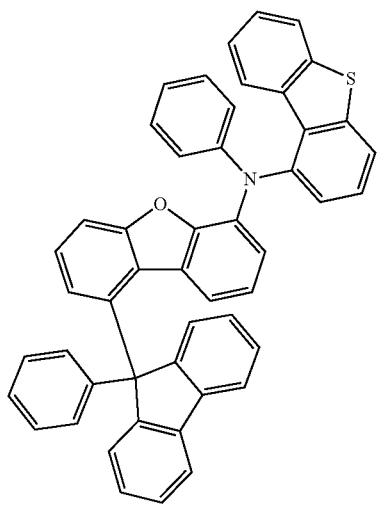
6
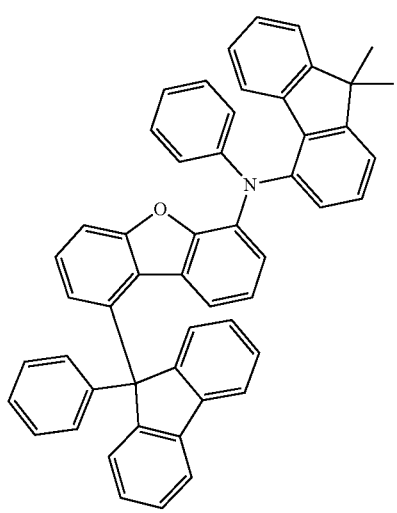
7
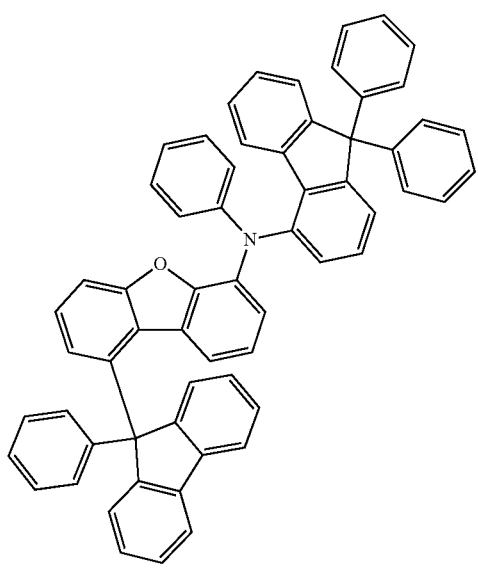
8
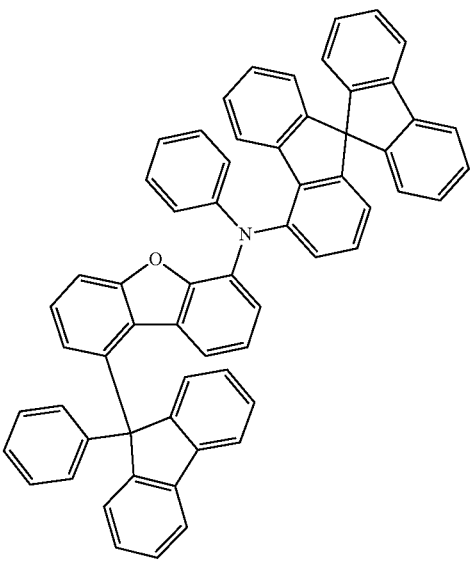
9
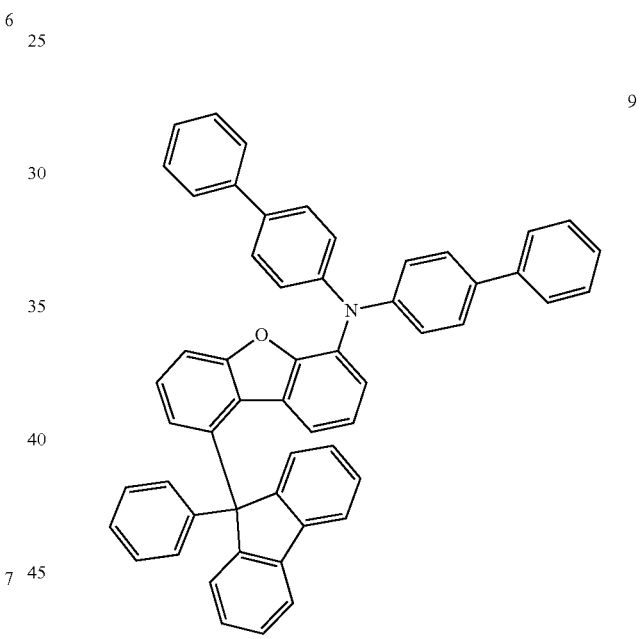
10
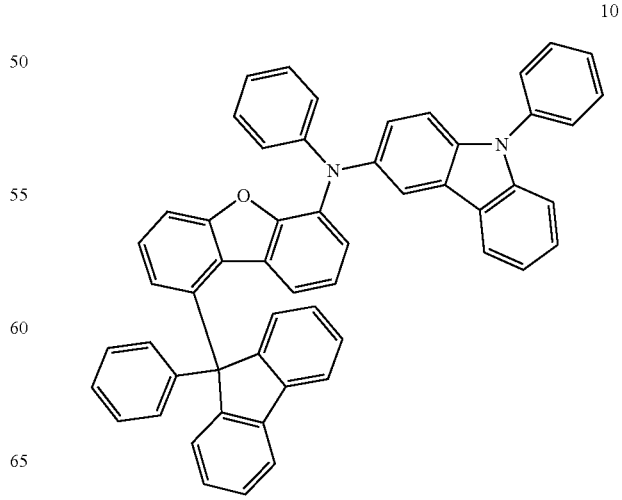

11
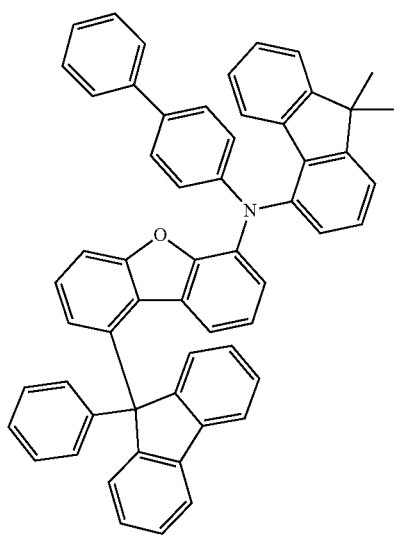
12
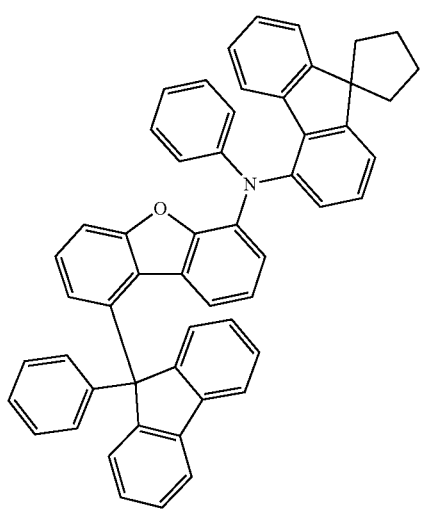
13
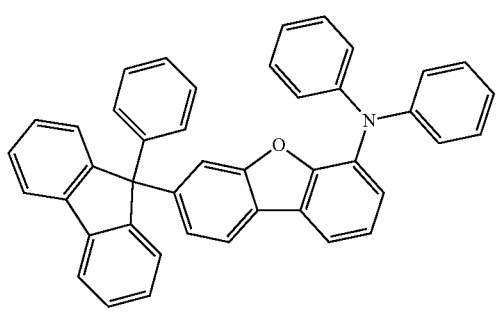
14
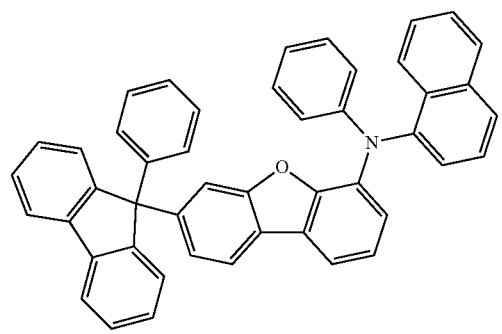
15
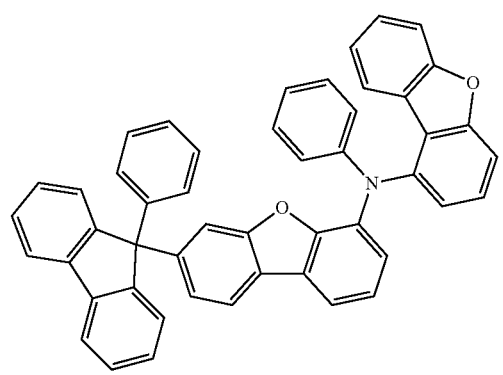
16
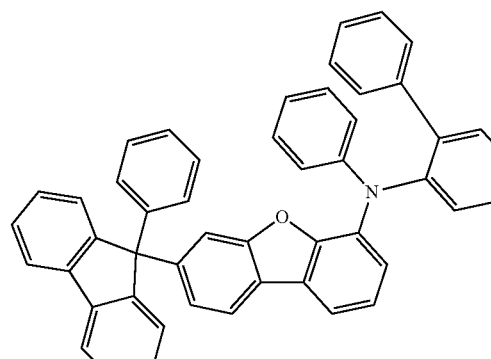
17
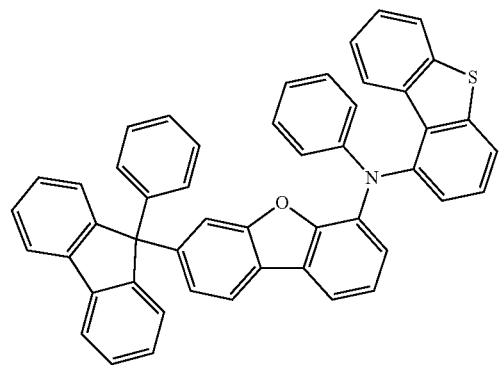

18
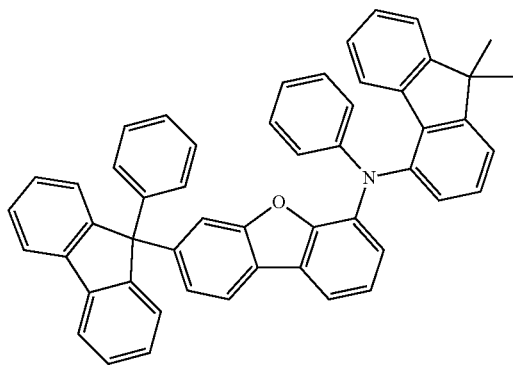
19
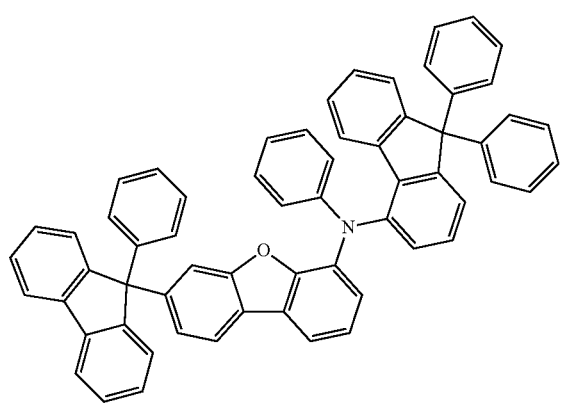
20
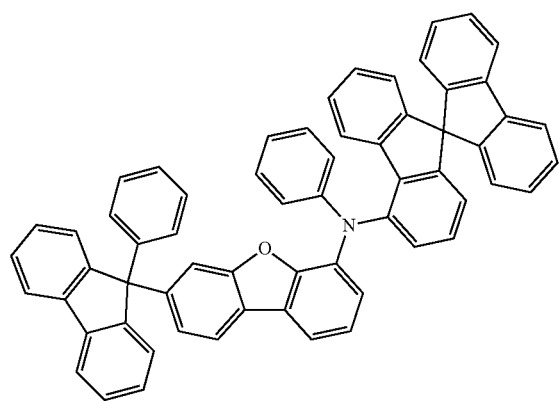
21
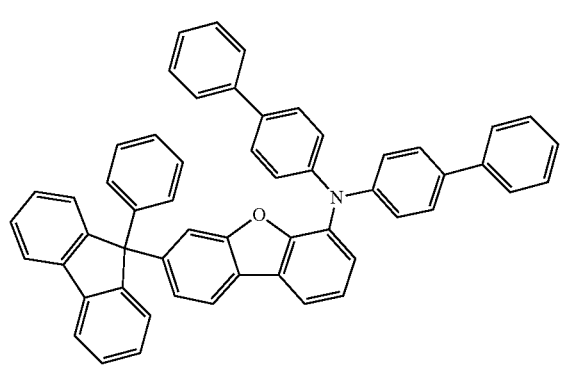
22
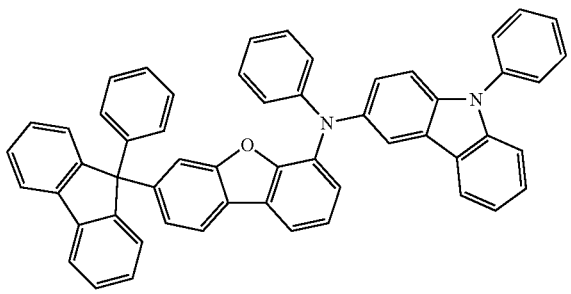
23
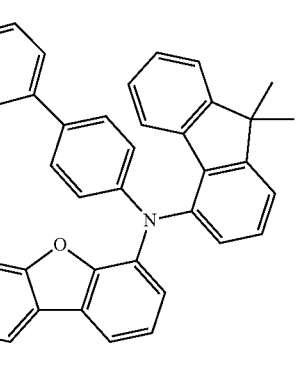
24
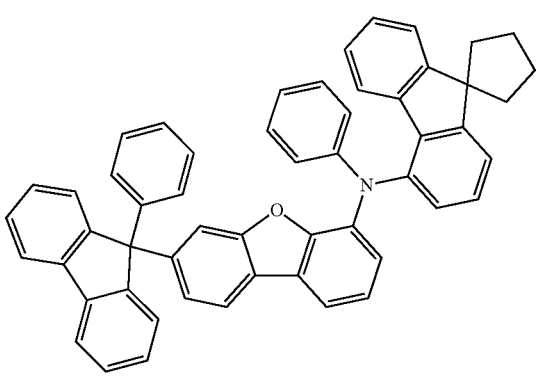
25
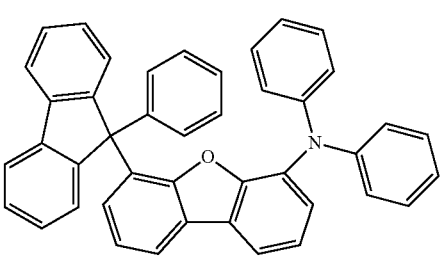
26
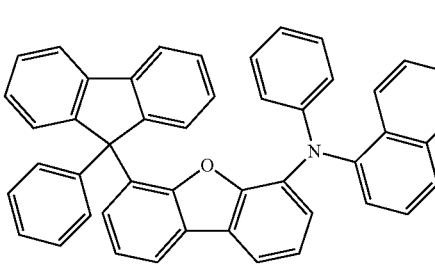

27
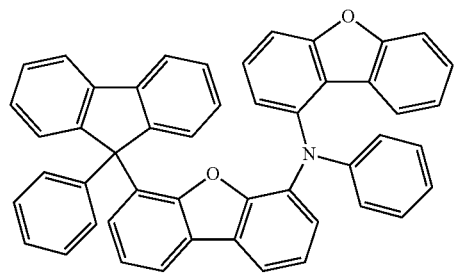
28
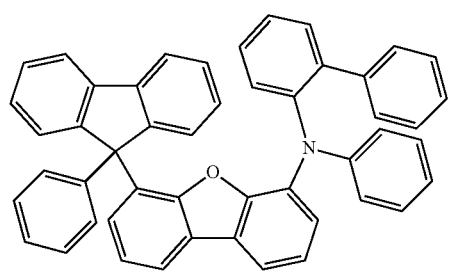
29
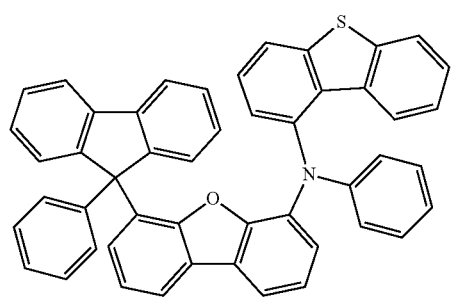
30
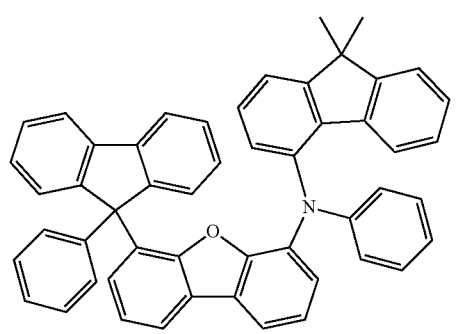
31
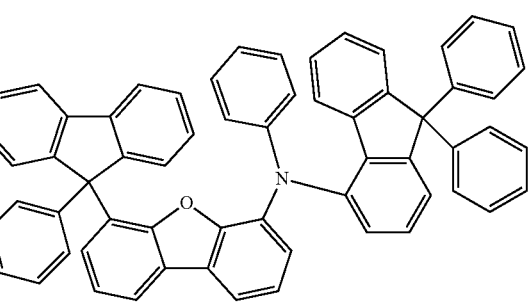
32
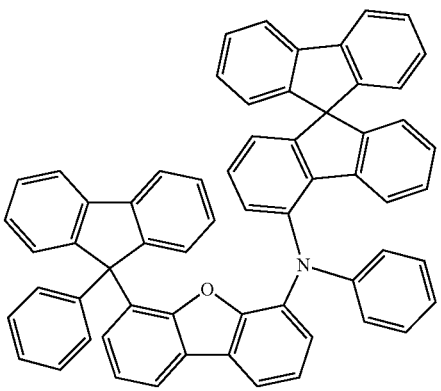
33
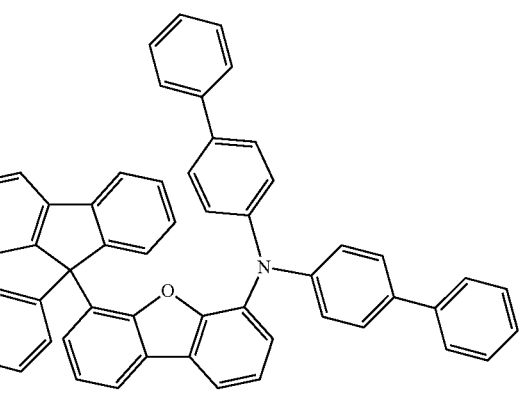
34
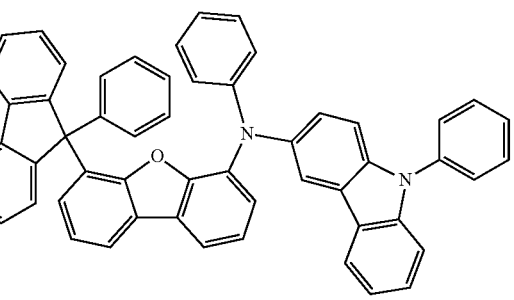
35
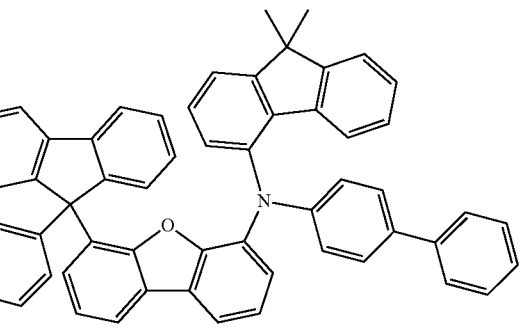

36
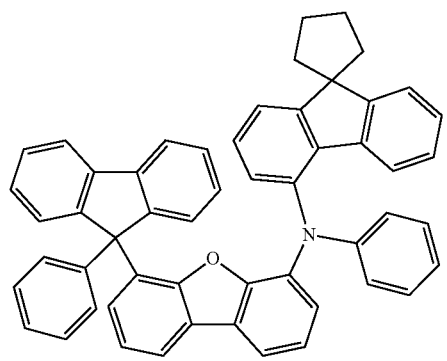
37
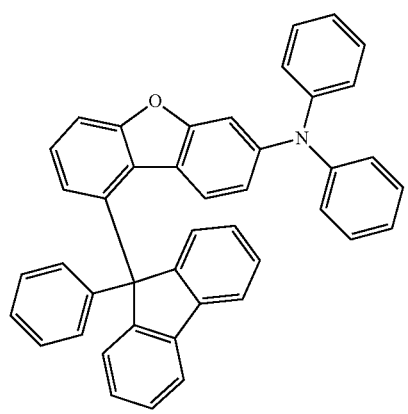
38
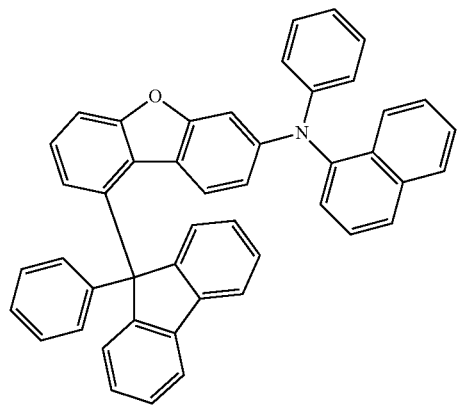
39
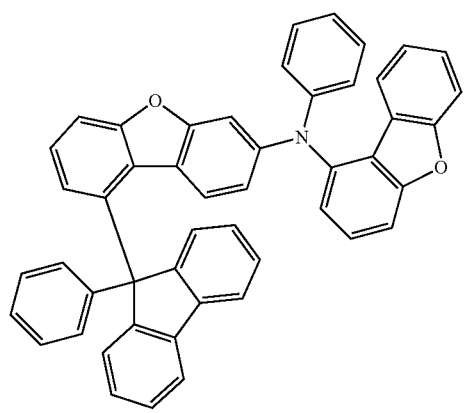
40
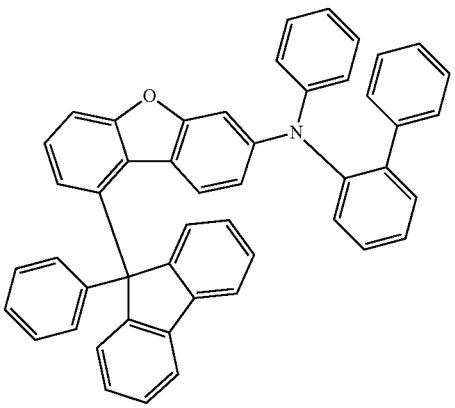
41
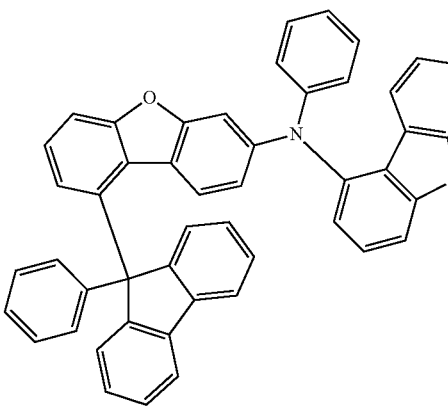
42
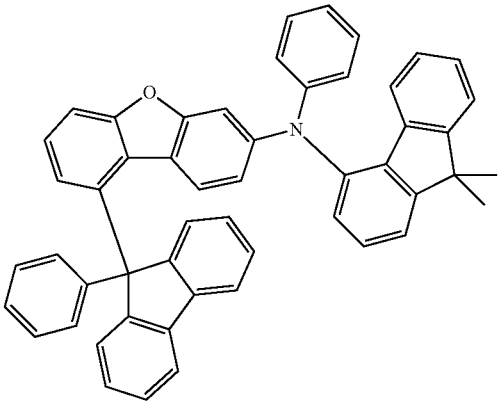
43
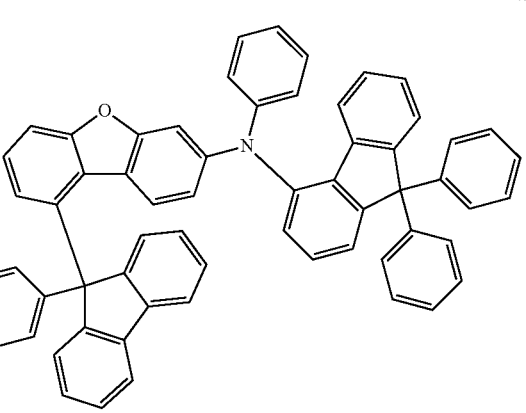

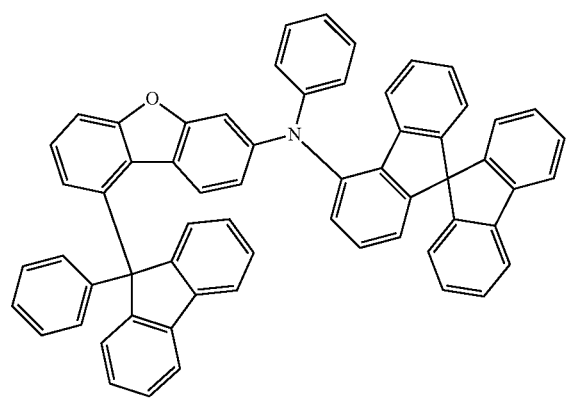
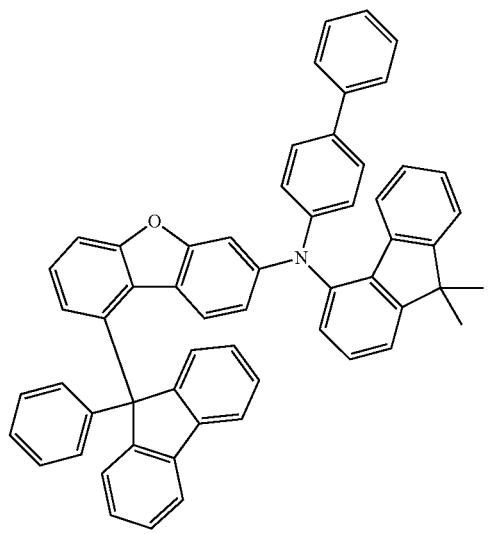
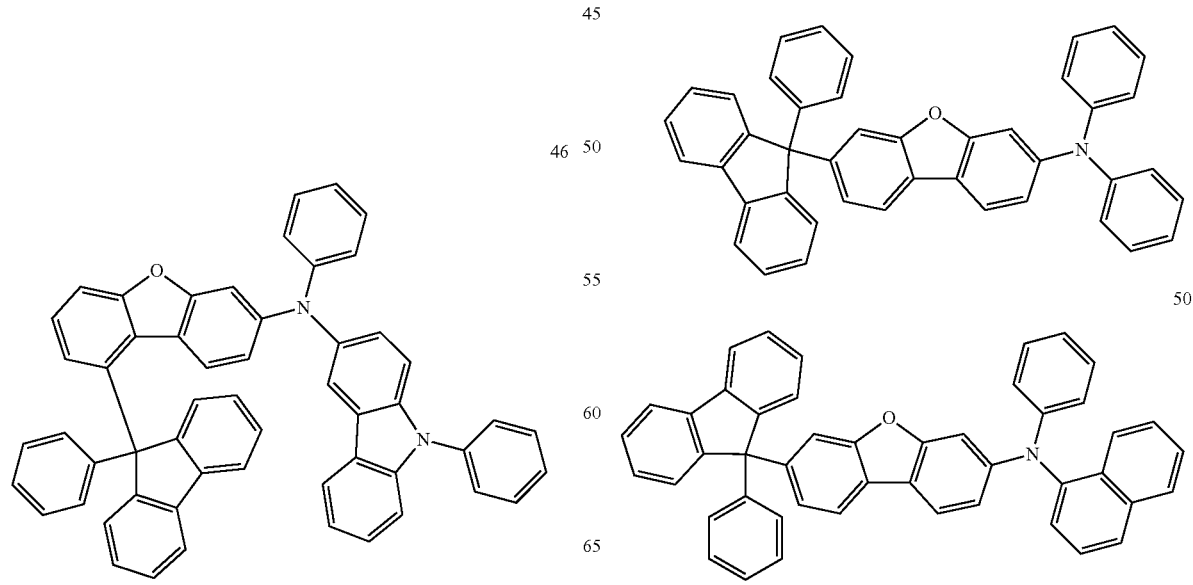

51
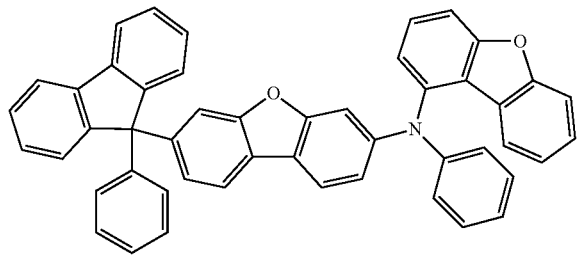
52
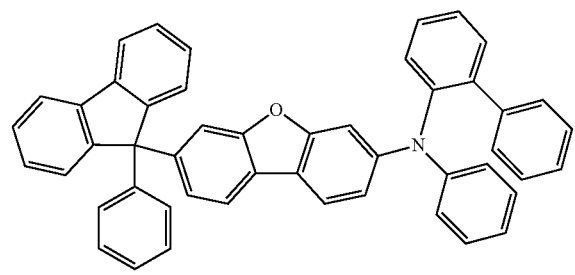
53
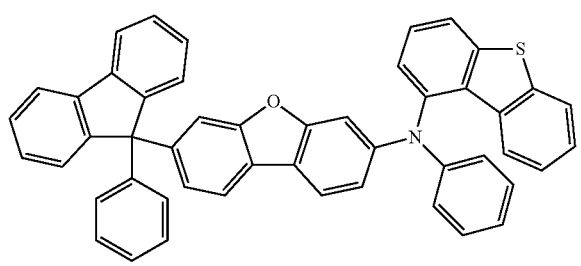
54
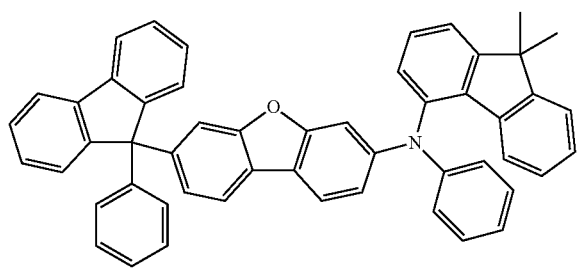
55
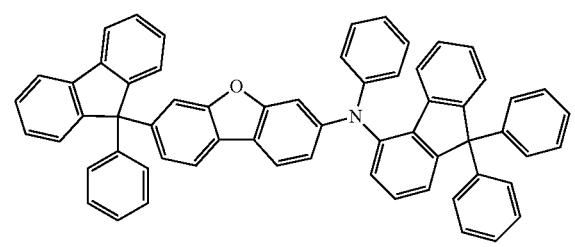
56
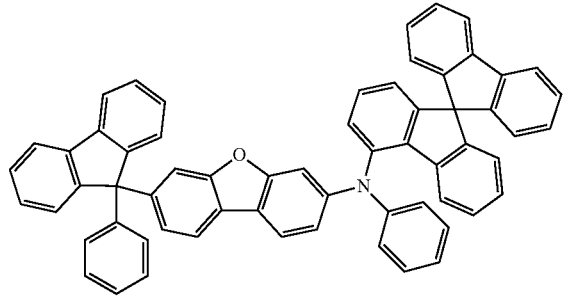
57
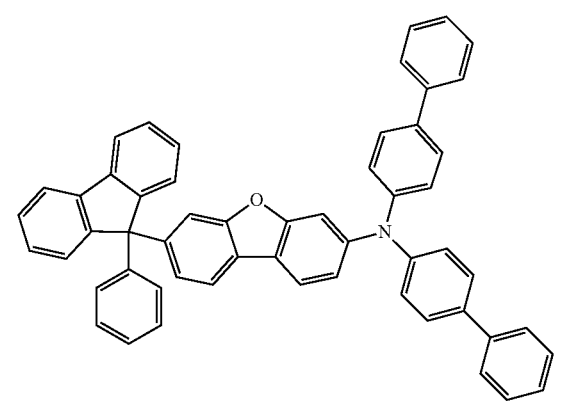
58
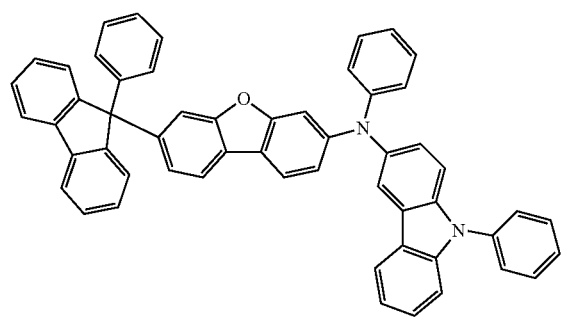
59
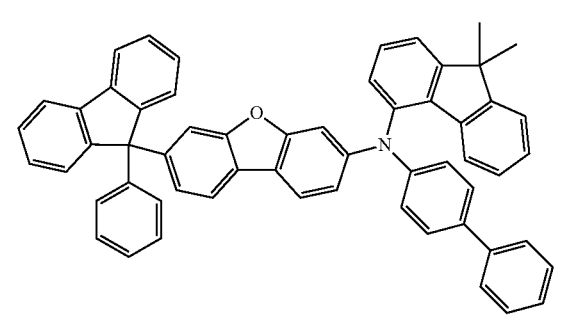

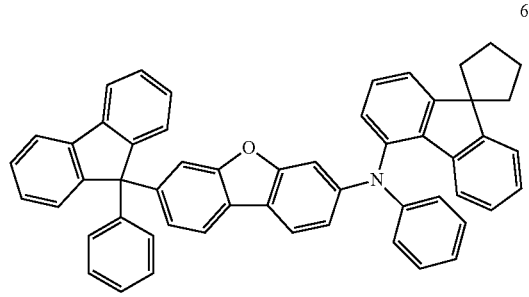
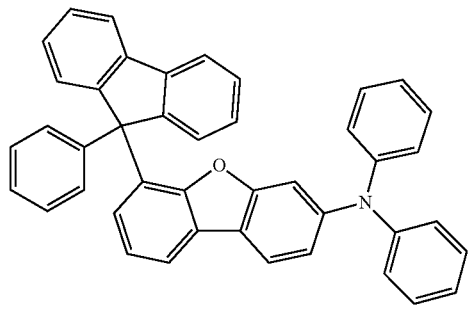
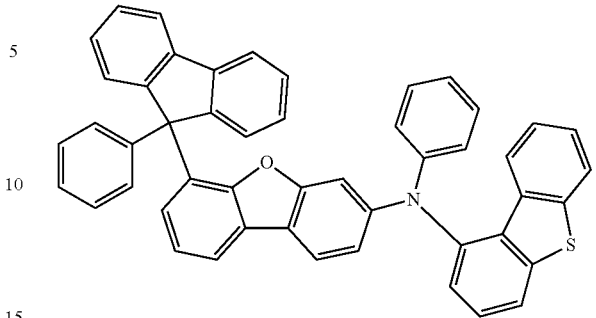
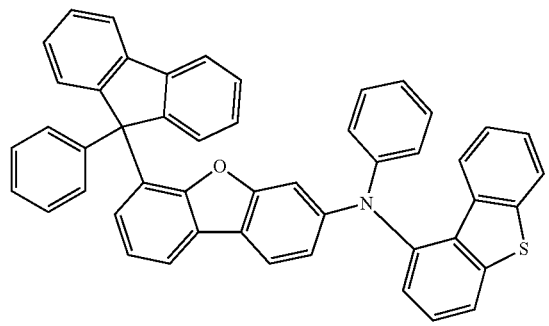

69
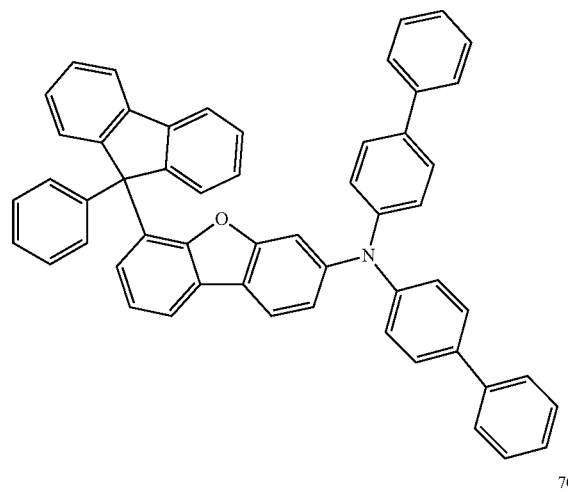
70
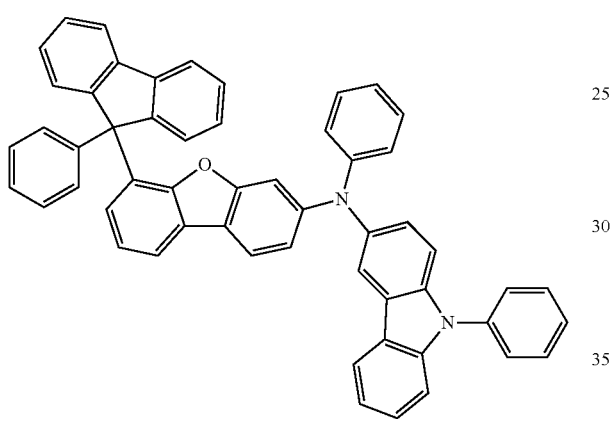
71
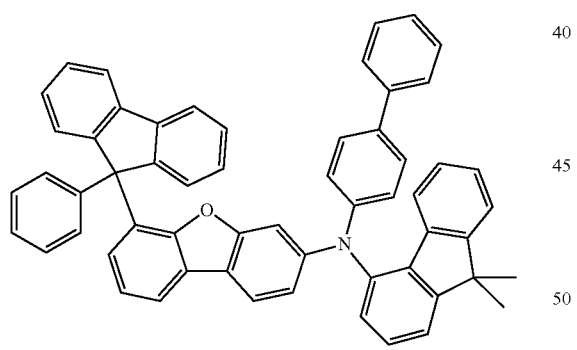
72
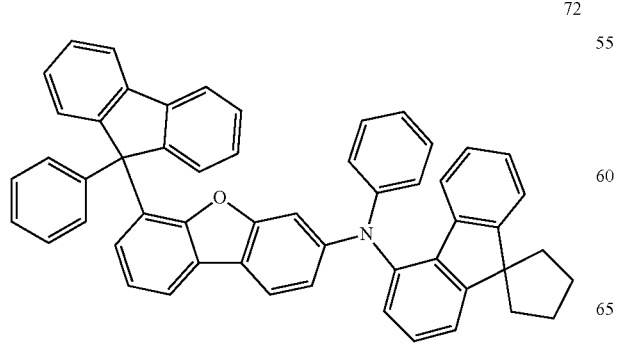
73
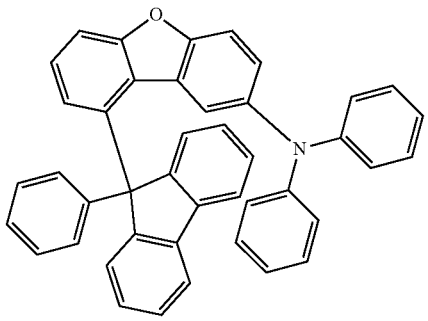
74
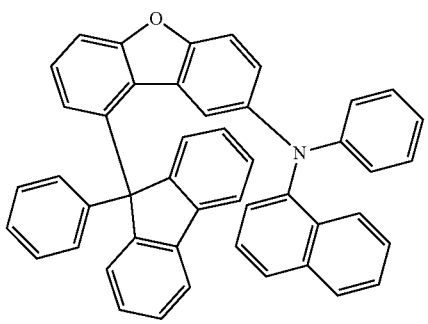
75
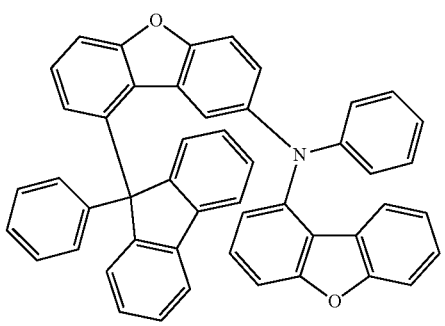
76
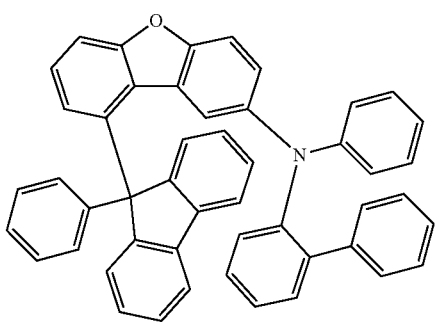
77
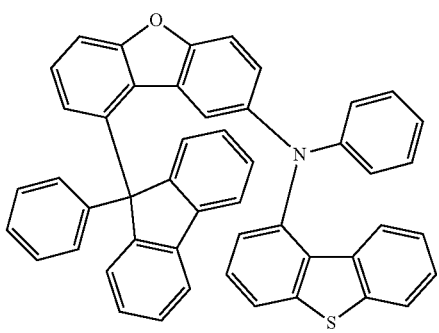

78
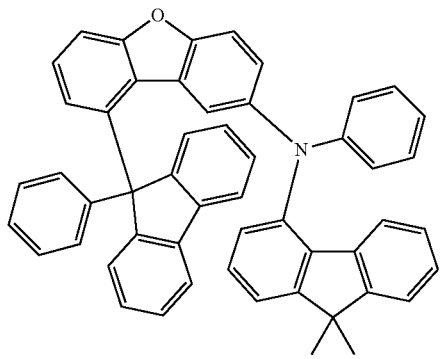
79
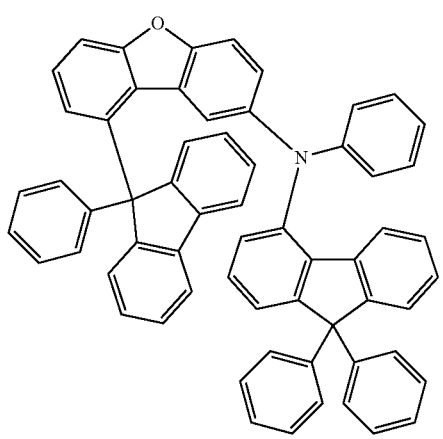
80
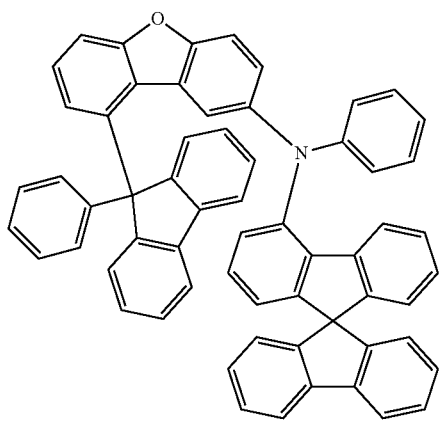
81
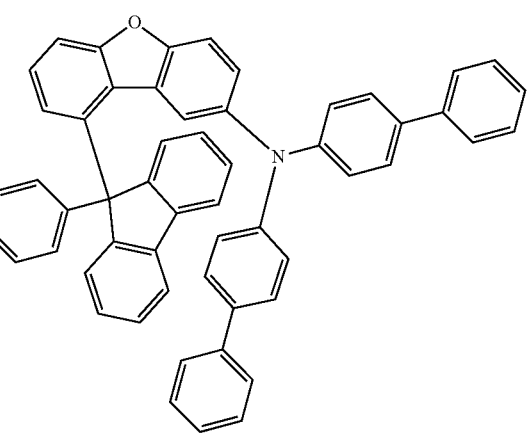
82
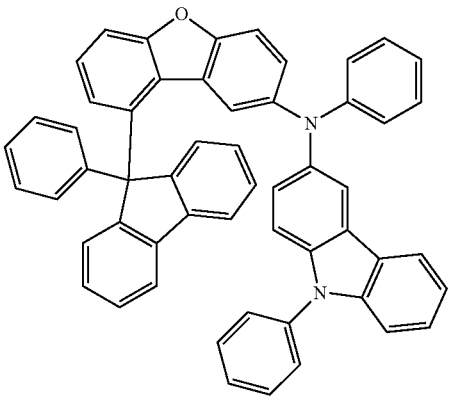
83
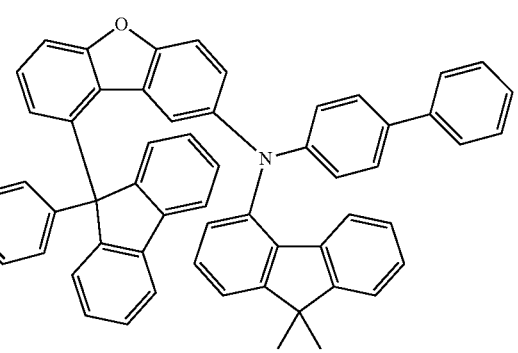
84
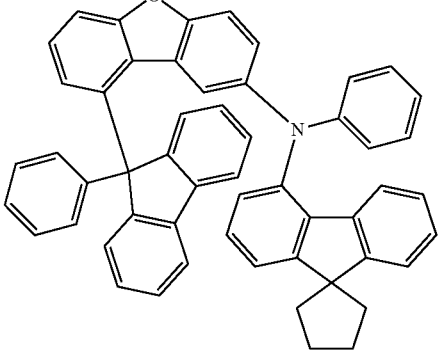
85
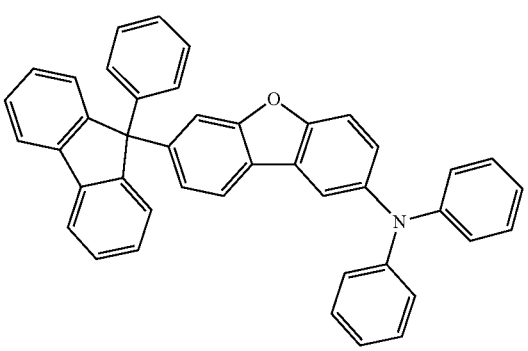

86
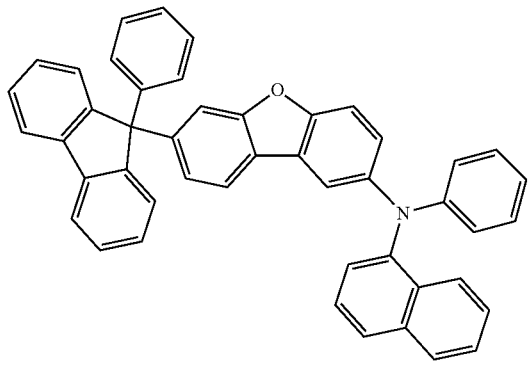
87
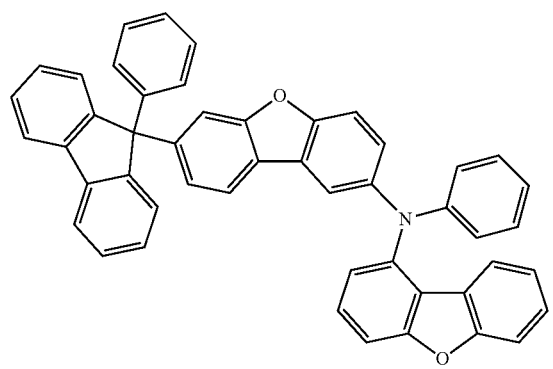
88
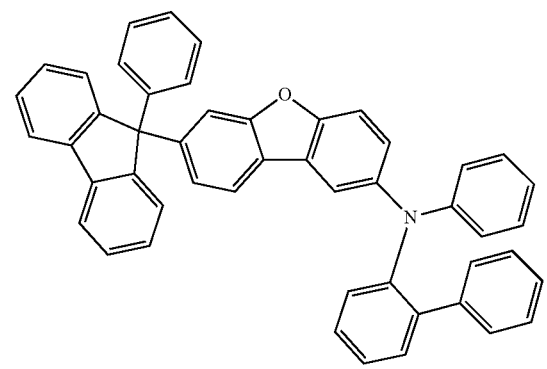
89
90
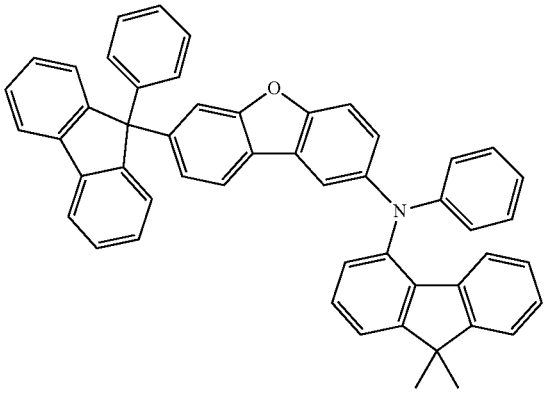
91
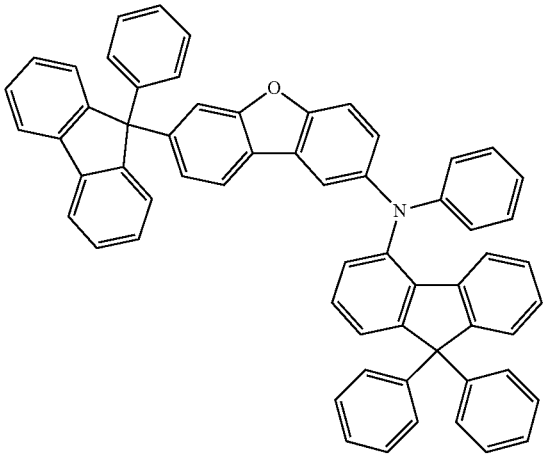
92
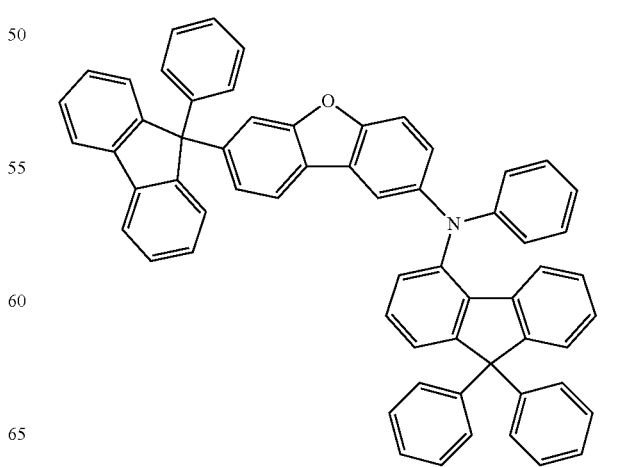

93
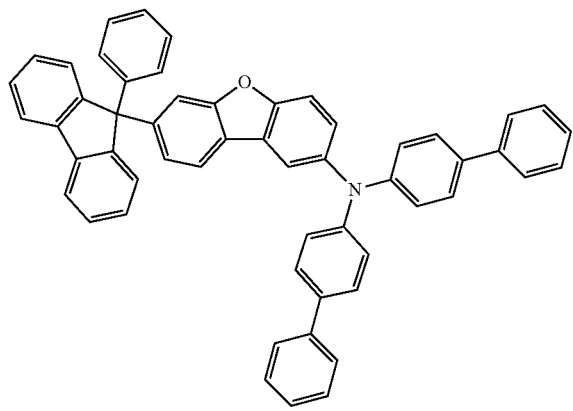
94
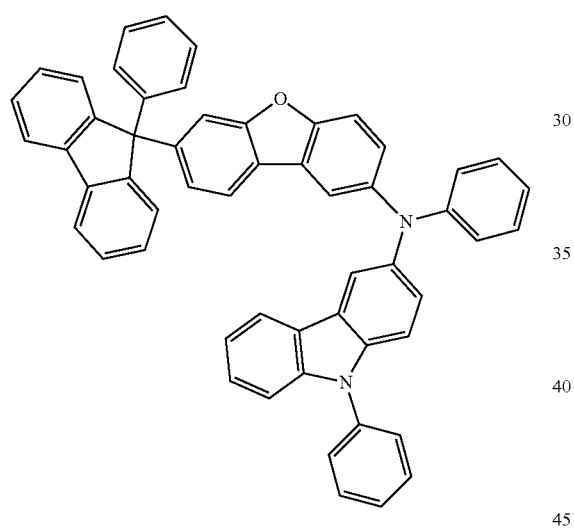
95
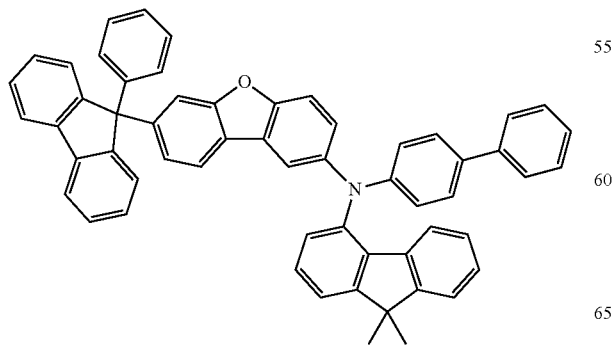
96
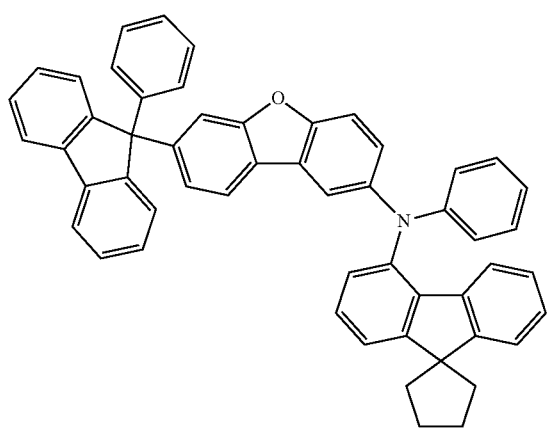
97
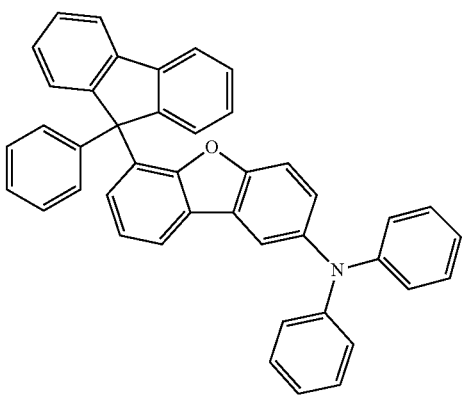
98
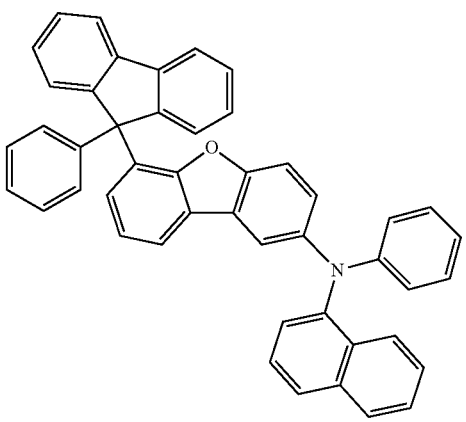

99
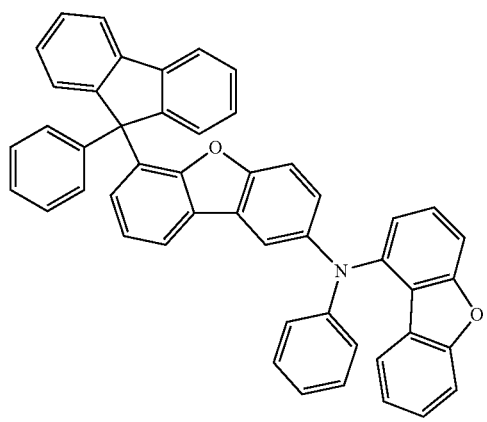
100
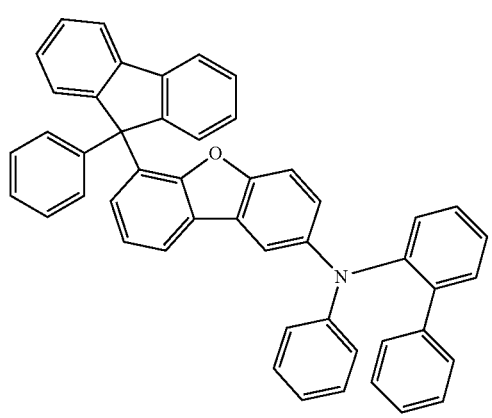
101
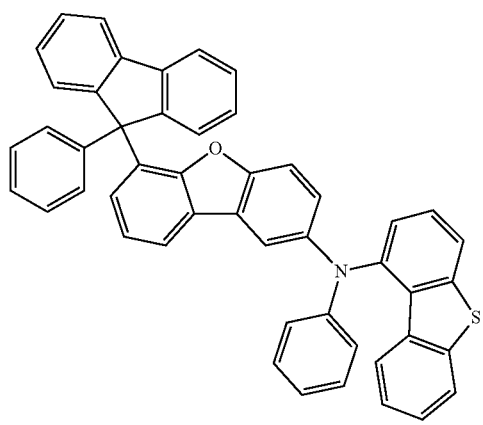
102
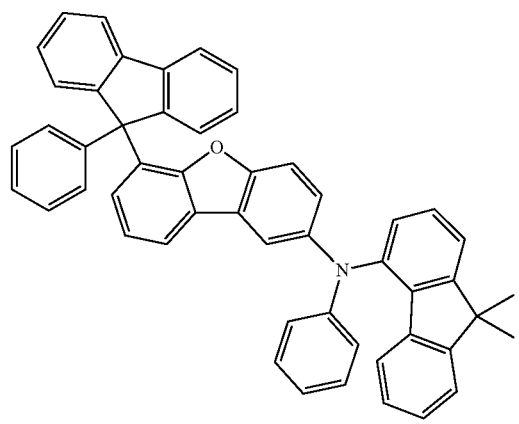
103
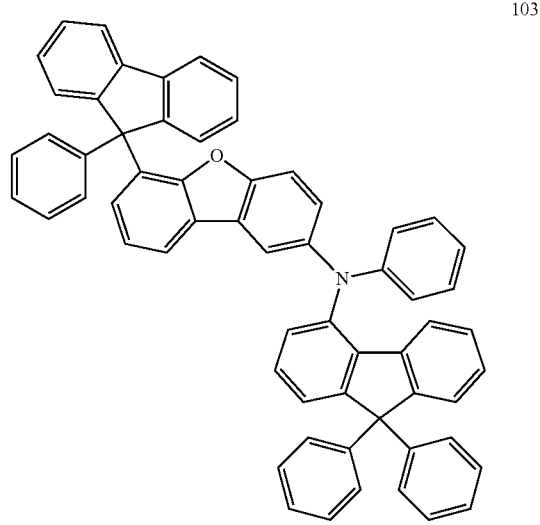
104
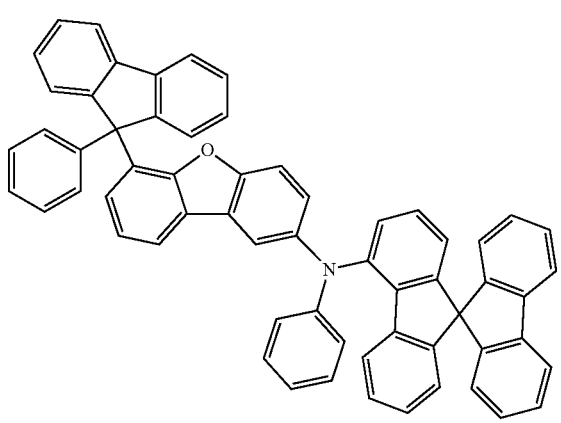

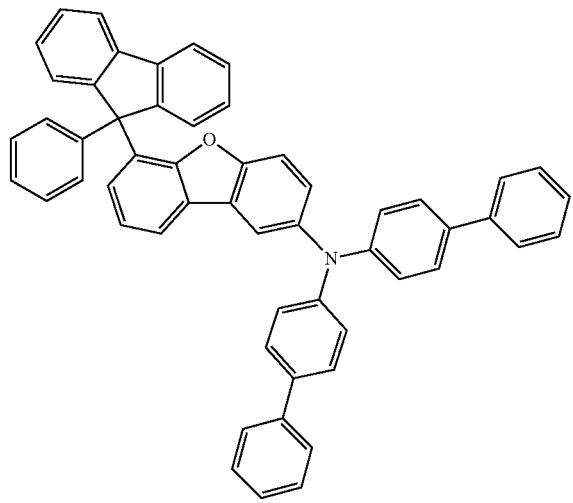
105
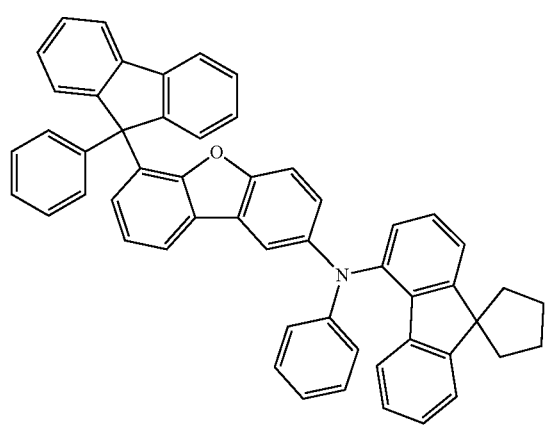
108
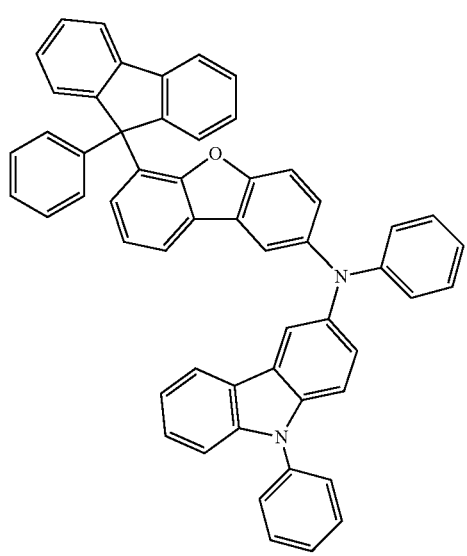
106
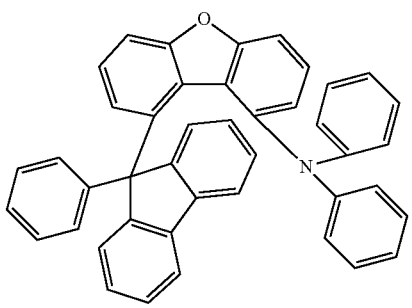
109
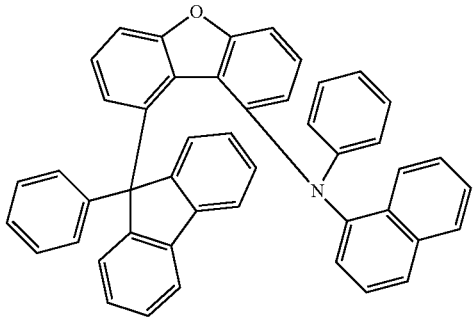
110
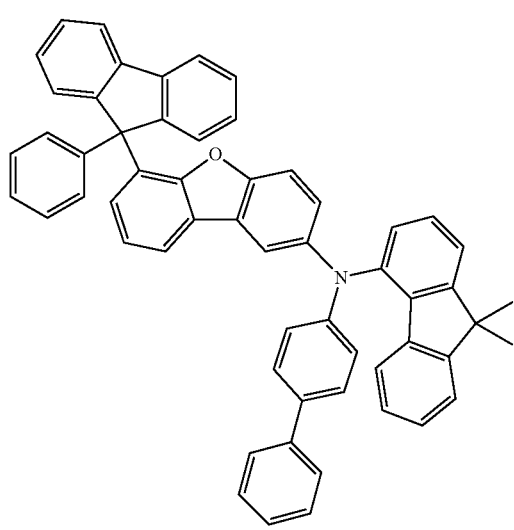
107
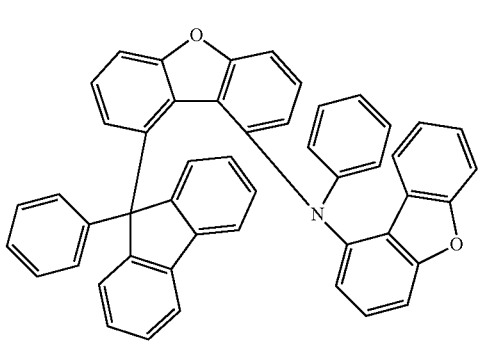
111

112
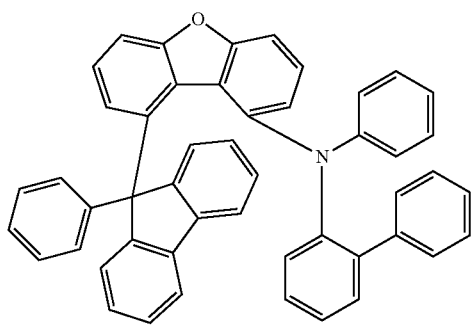
113
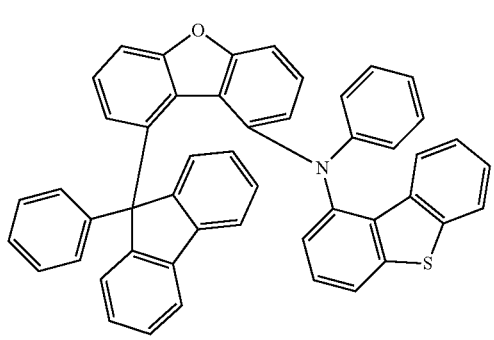
114
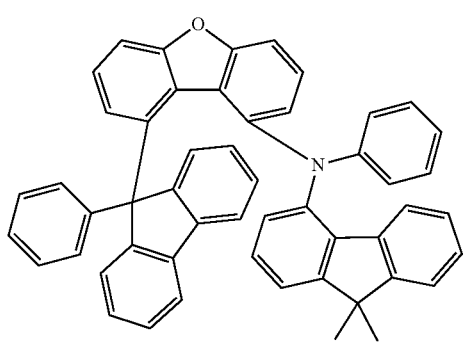
115
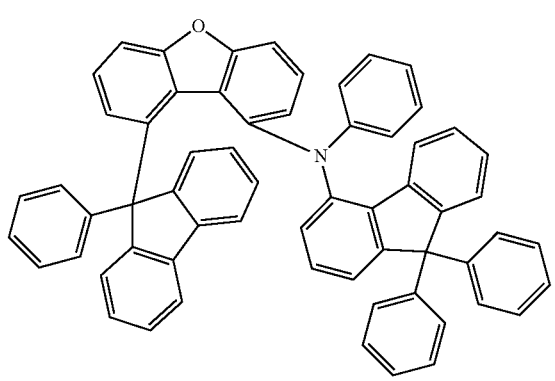
116
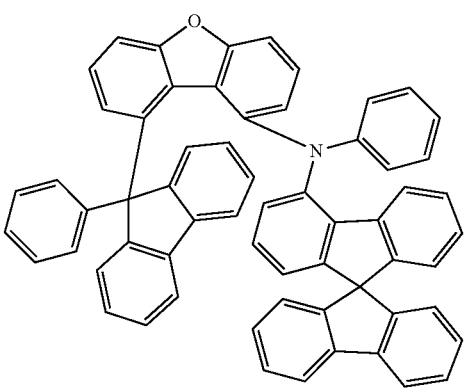
117
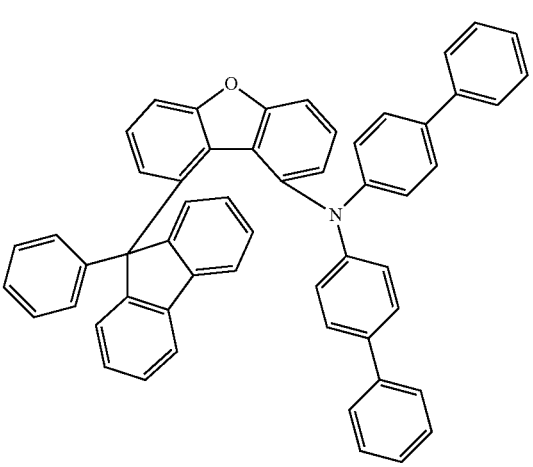
118
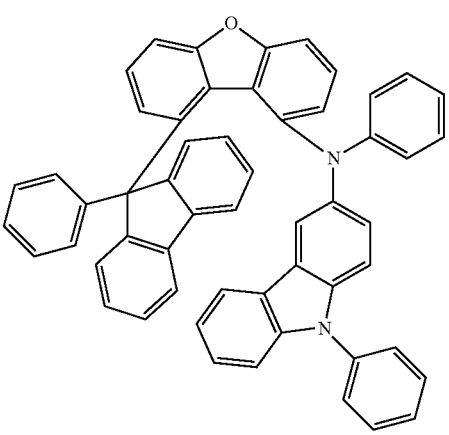
119
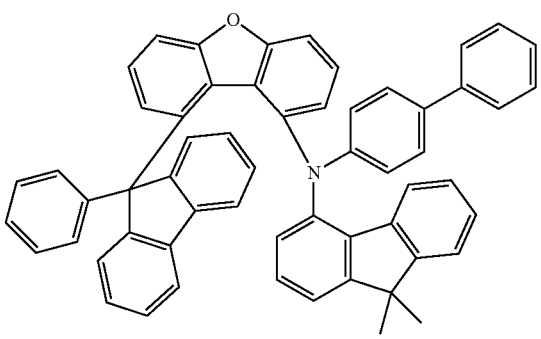

120
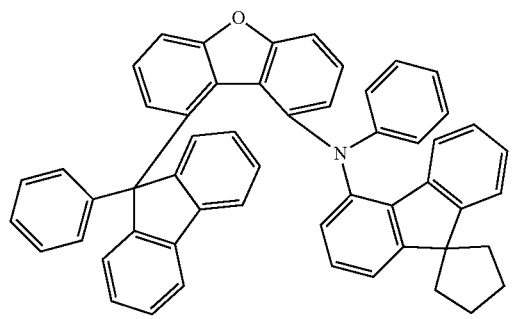
121
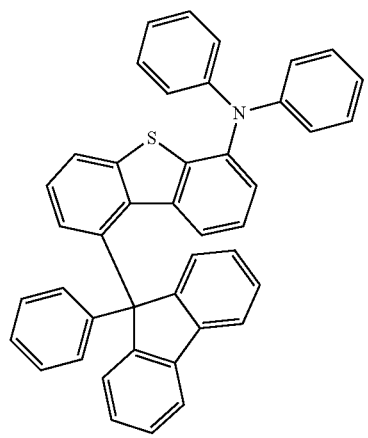
122
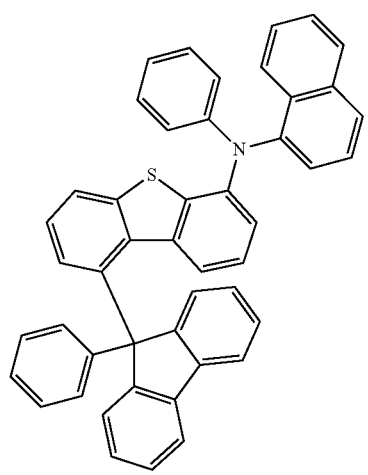
123
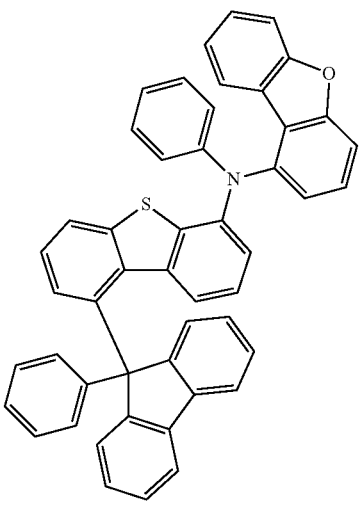
124
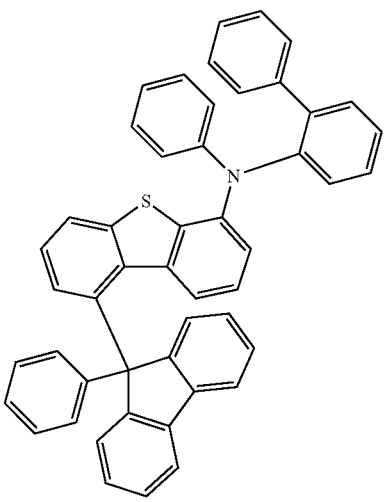
125
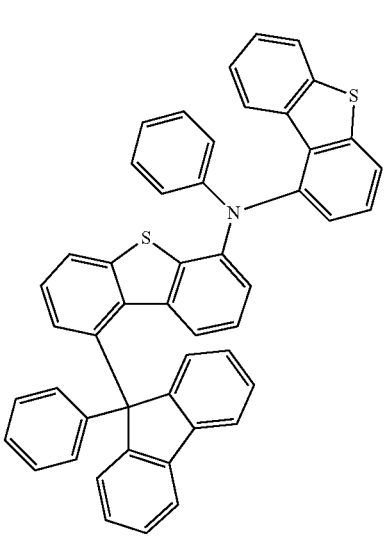

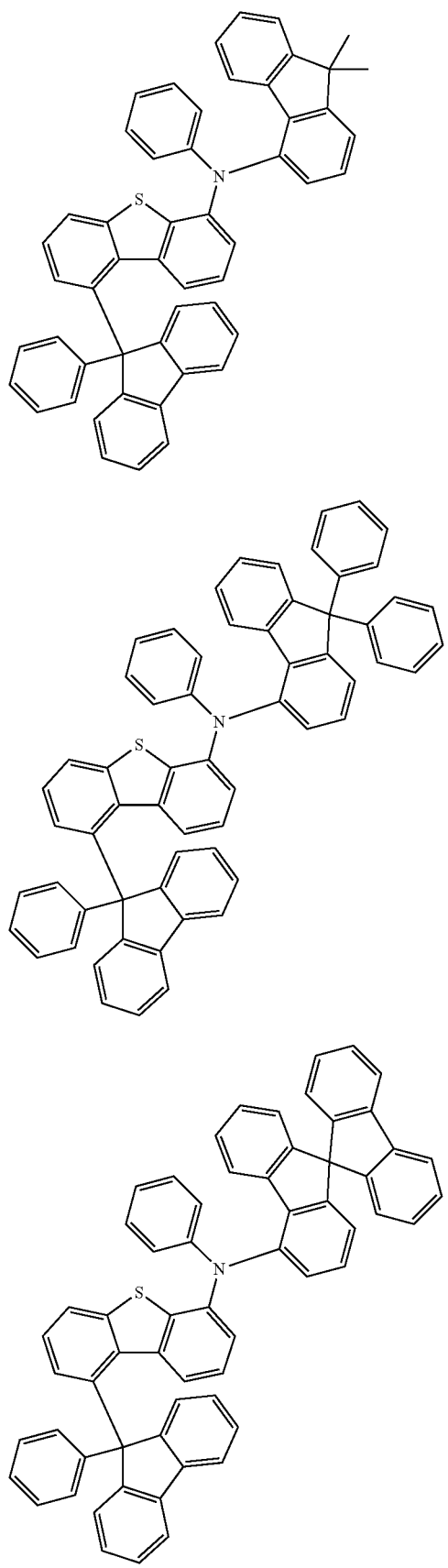
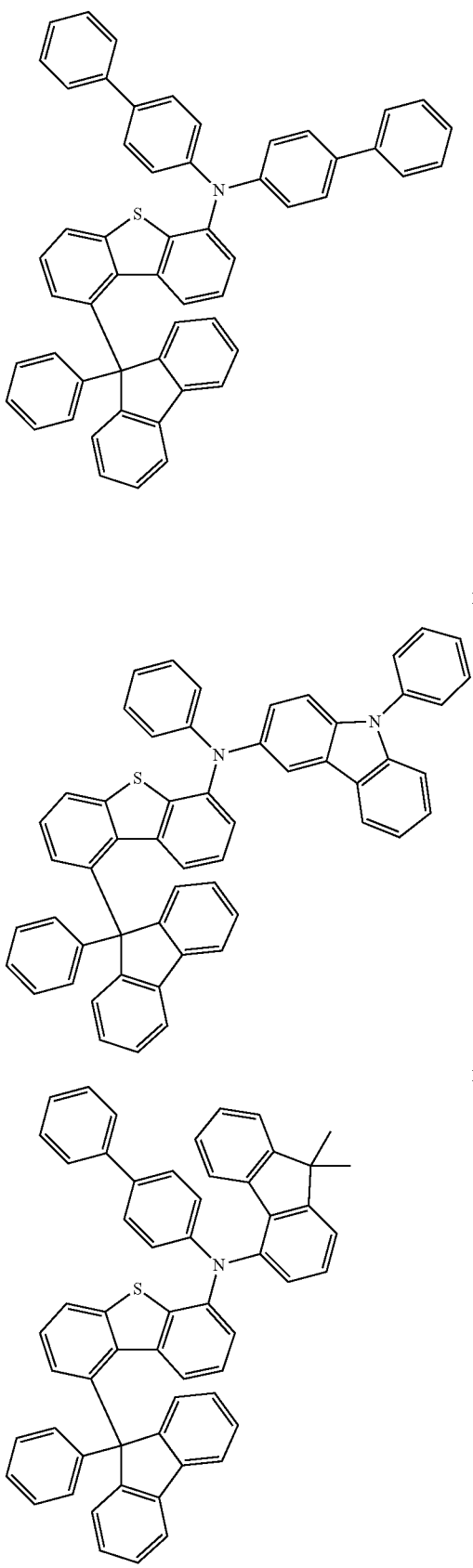

132
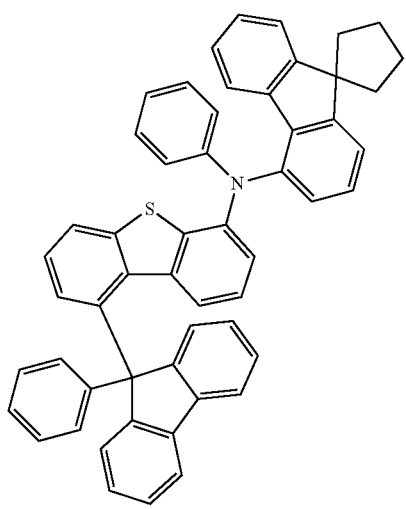
133
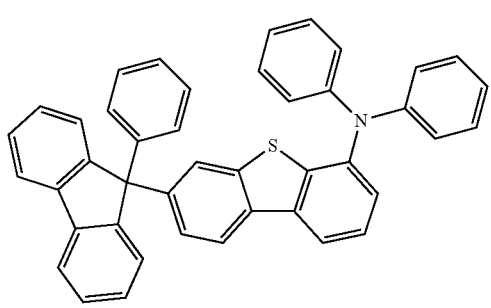
134
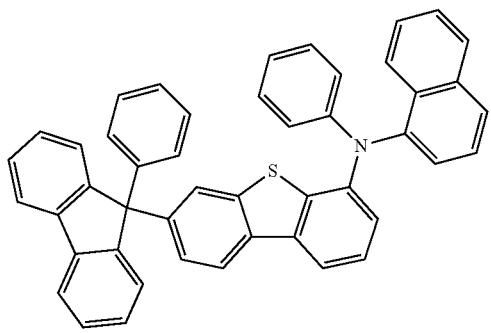
135
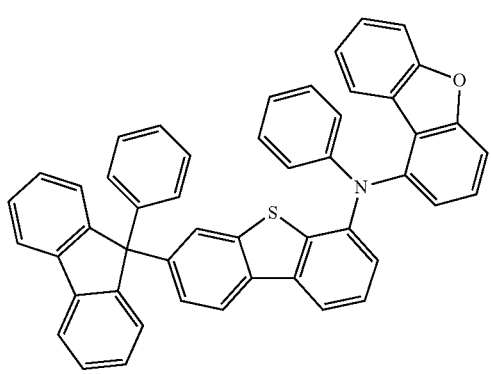
136
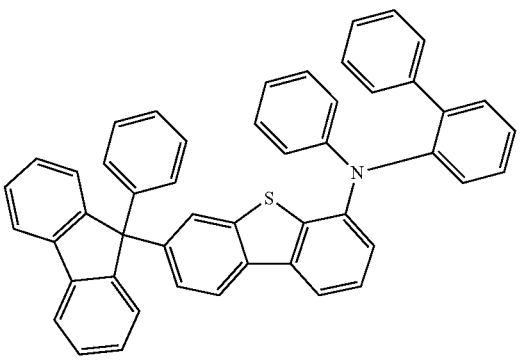
137
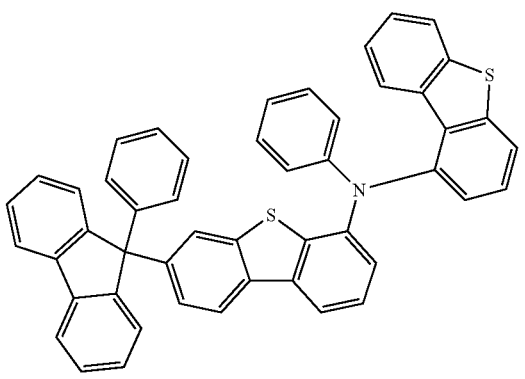
138
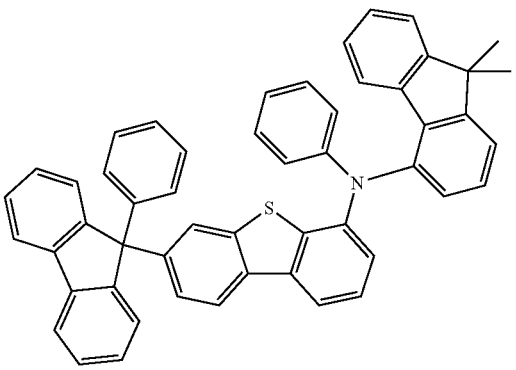
139
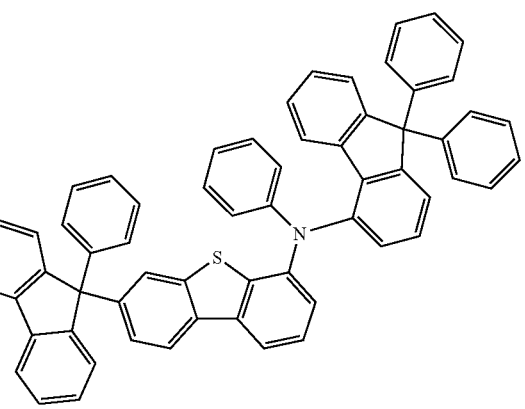

140
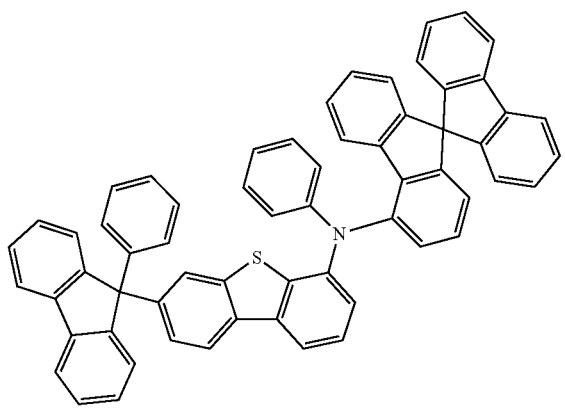
141
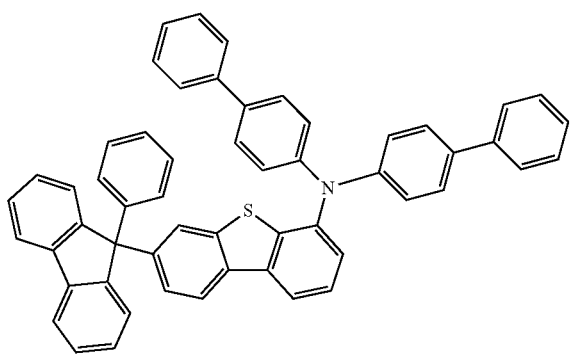
142
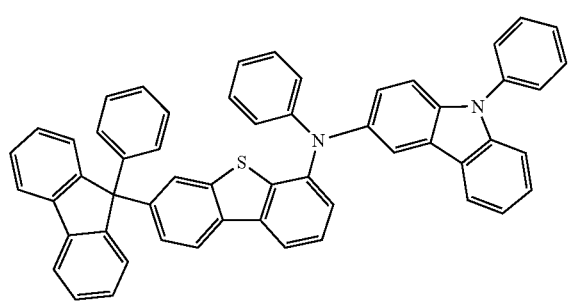
143
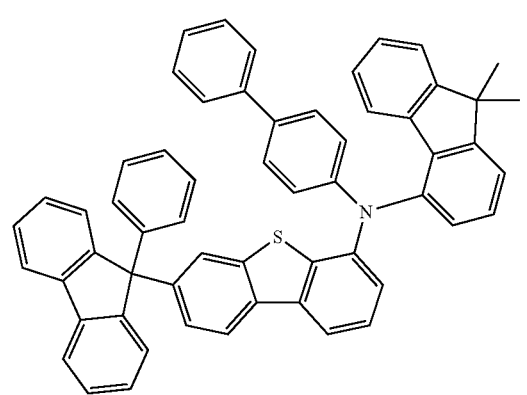
144
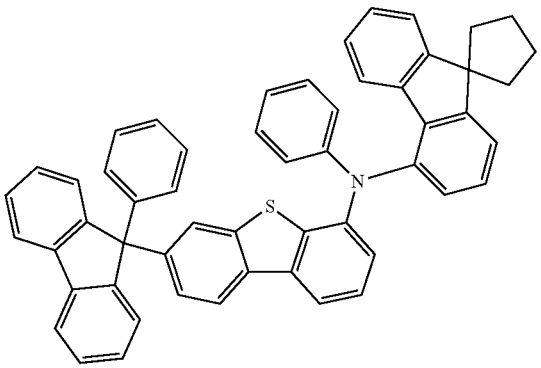
145
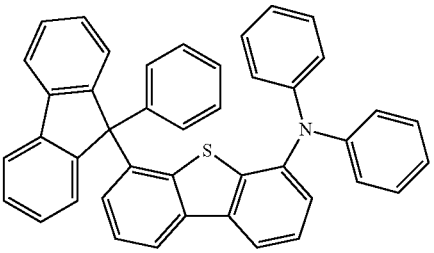
146
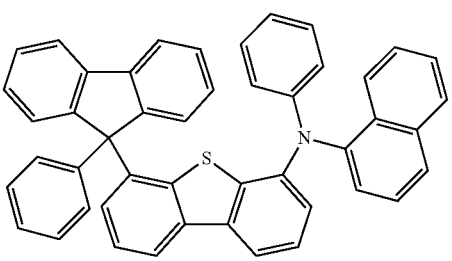
147
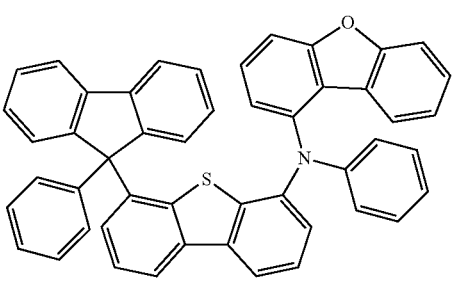
148
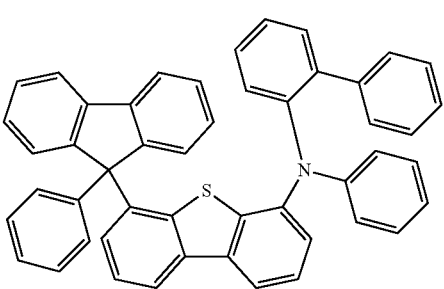

149
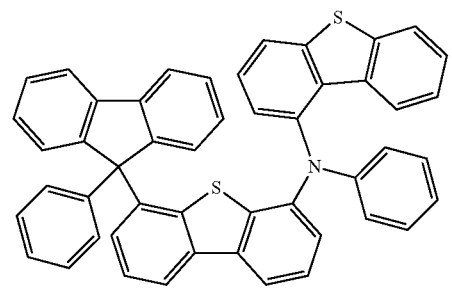
150
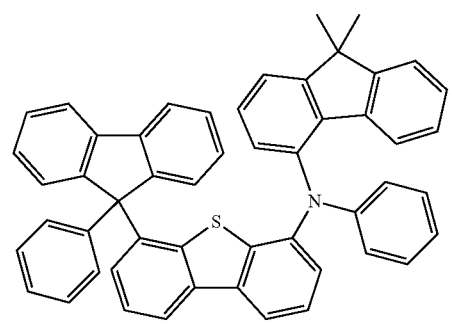
151
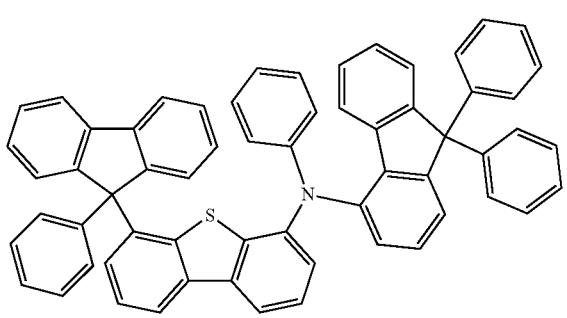
152
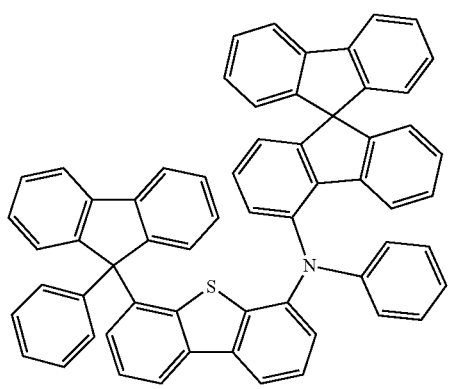
153
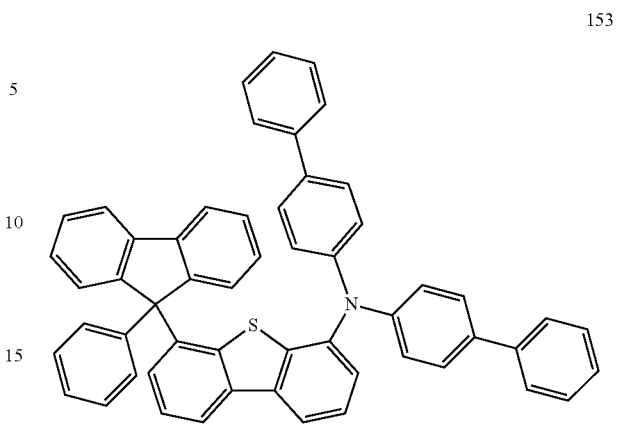
154
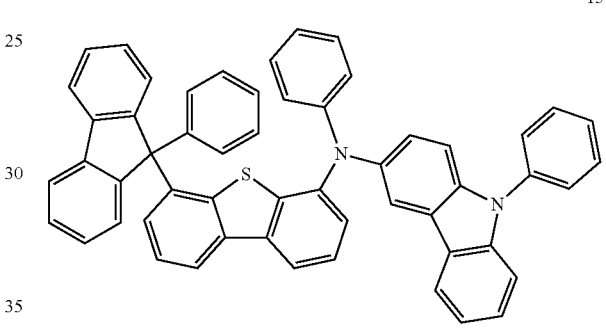
155
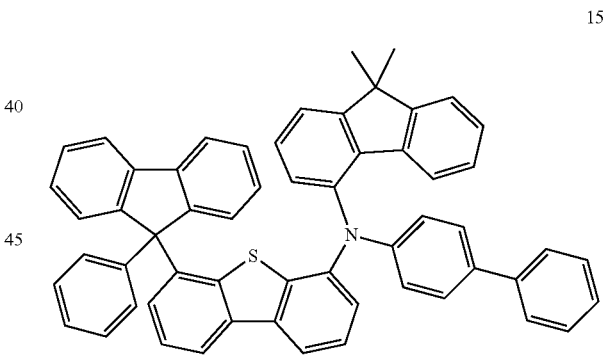
156
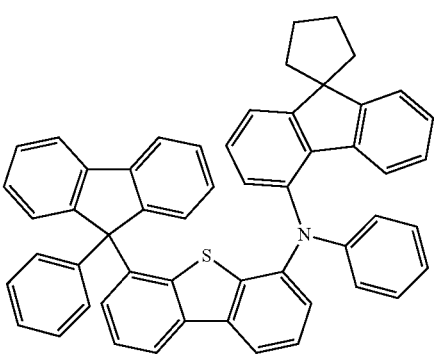

157 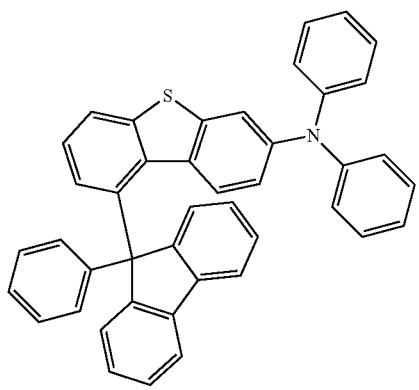
158 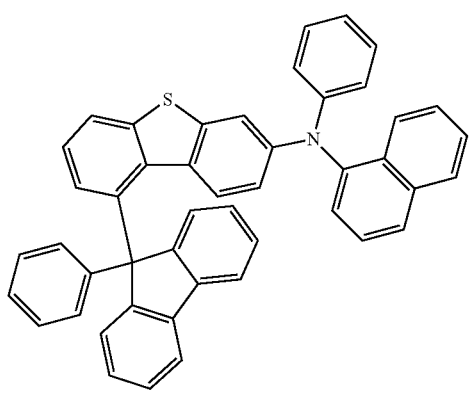
159 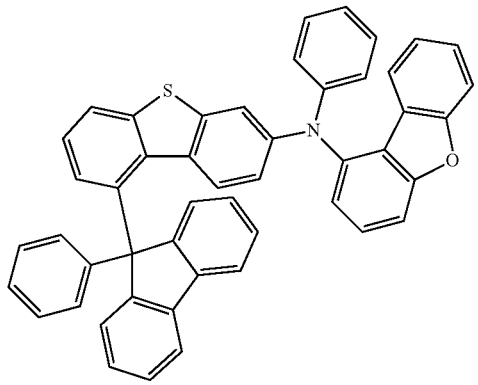
160 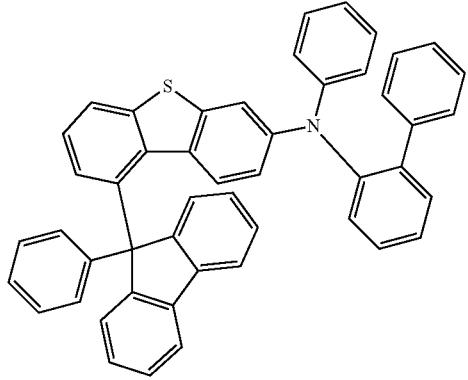
161 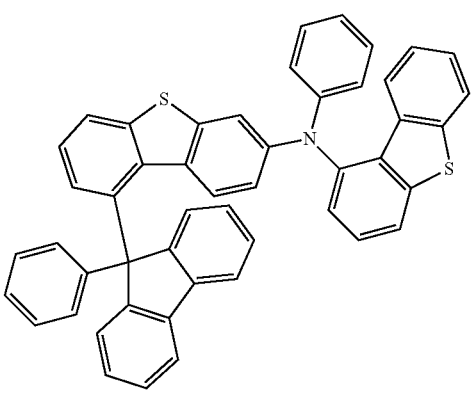
162 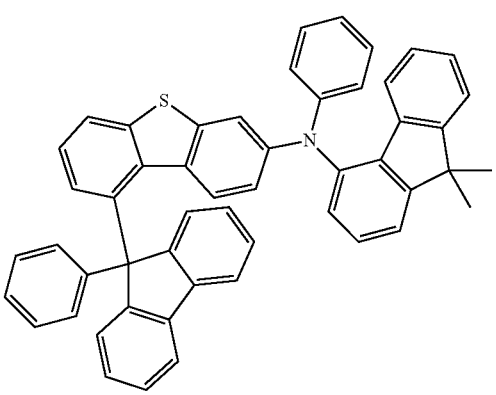
163 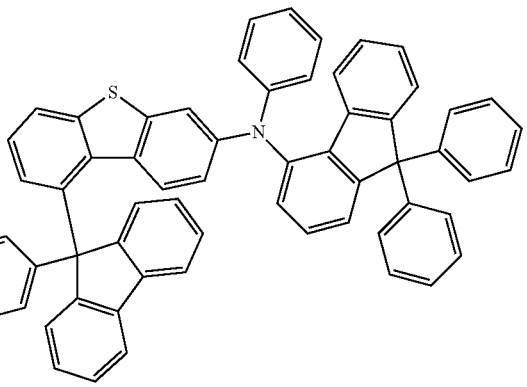
164 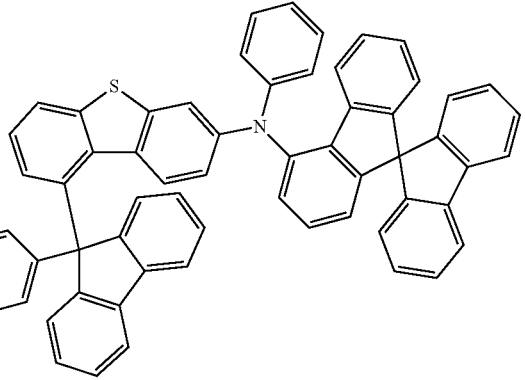

165
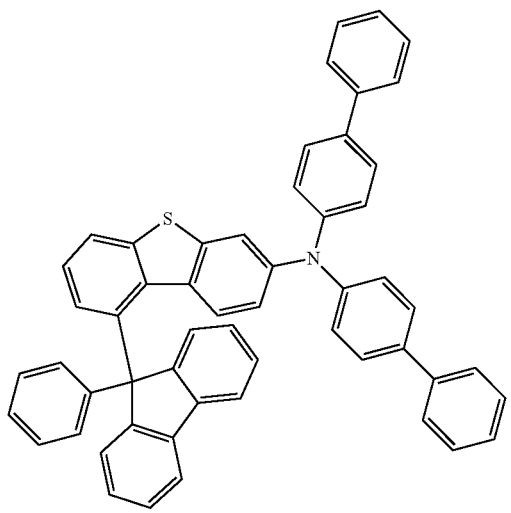
166
168
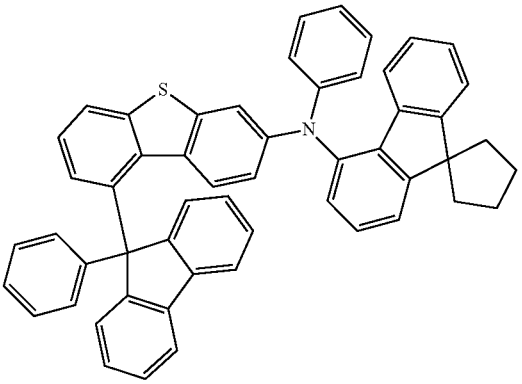
169
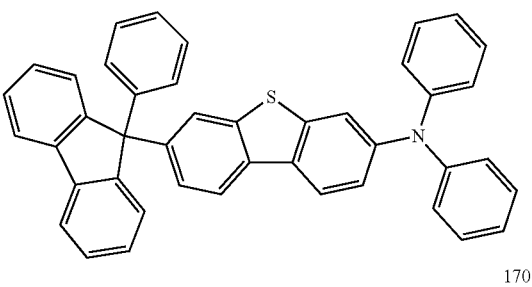
170
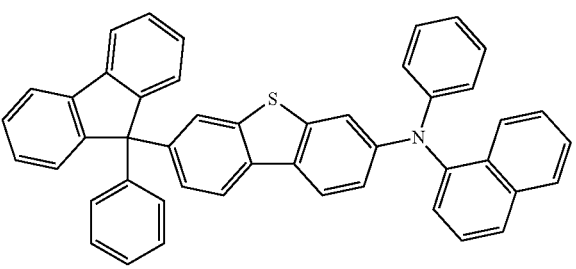
171
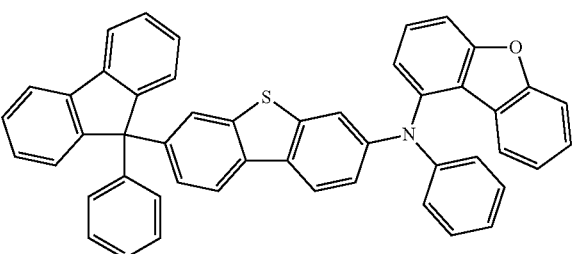
167
172
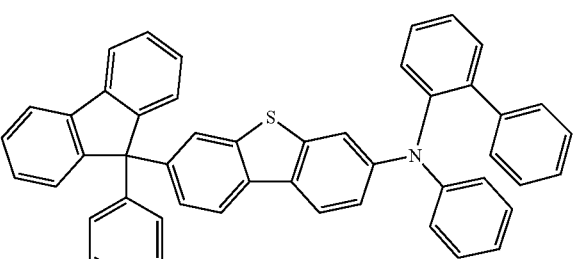

173
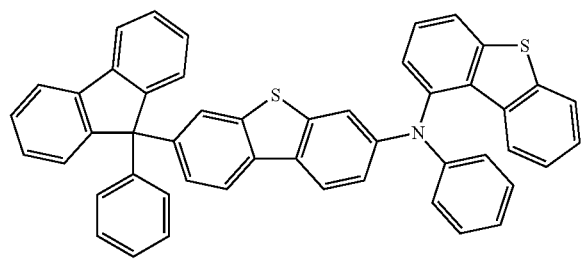
174
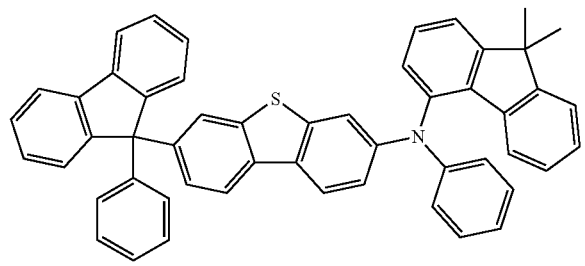
175
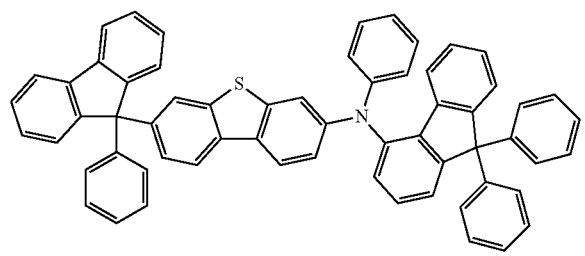
176
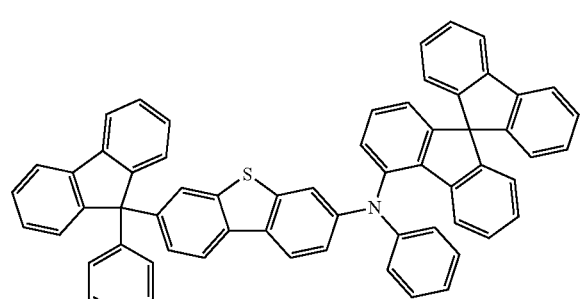
177
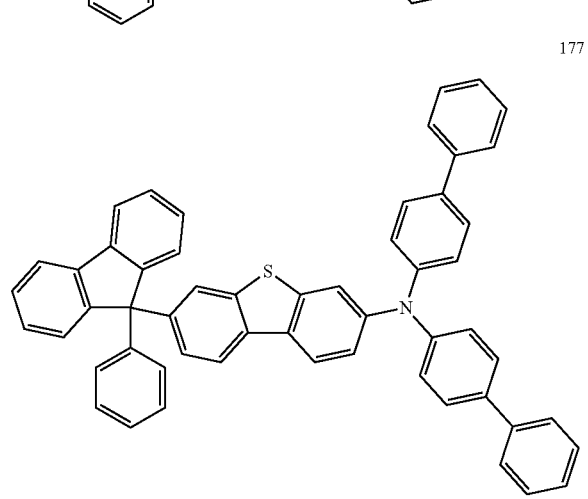
178
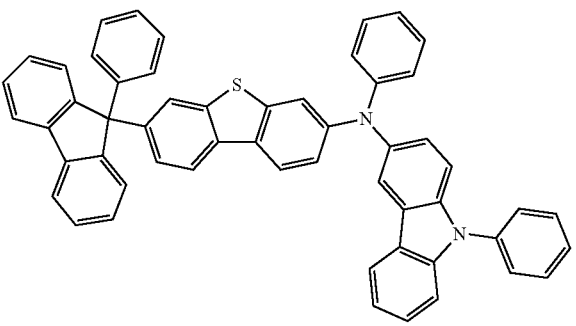
179
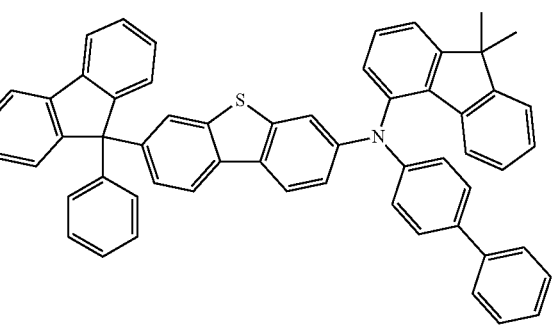
180
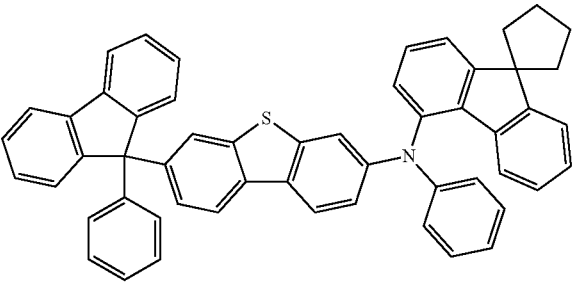
181
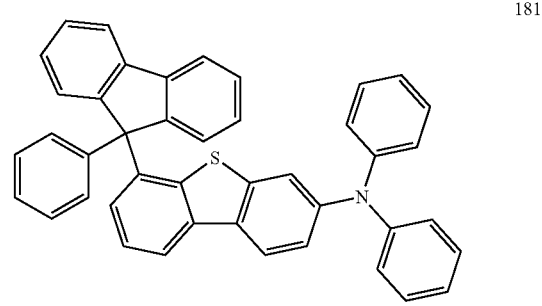
182
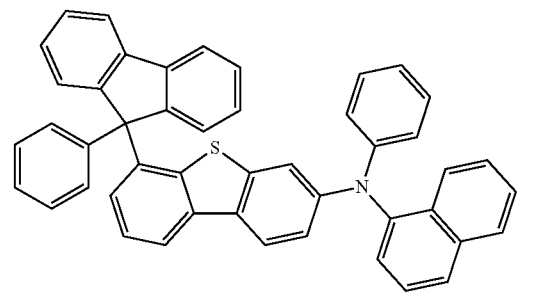

183
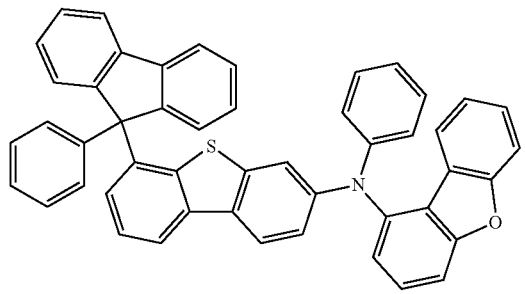
188
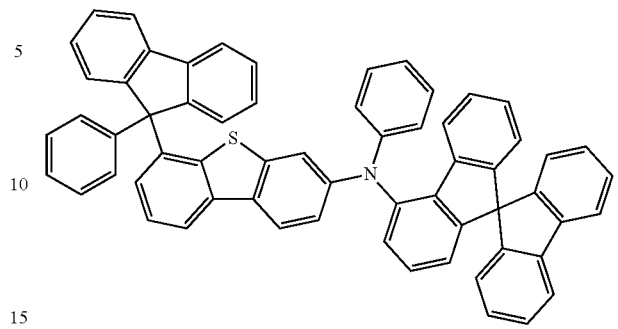
184
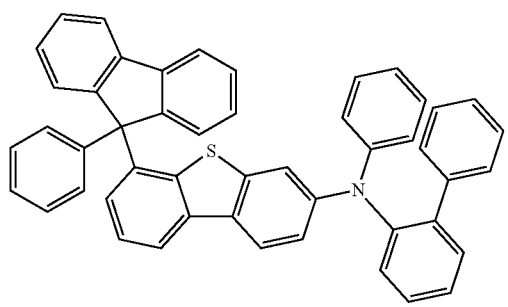
189
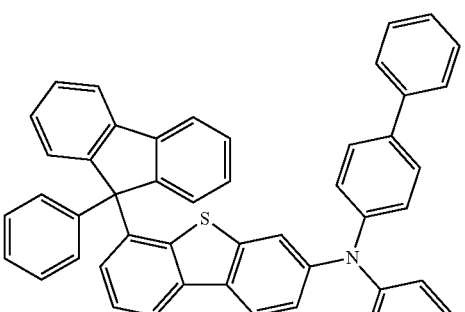
185
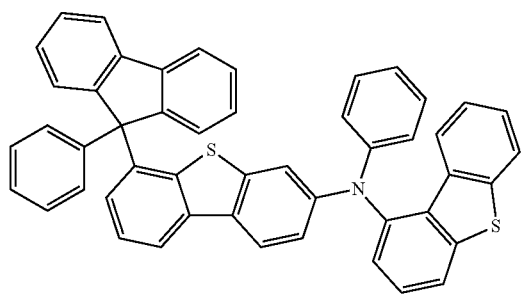
190
186
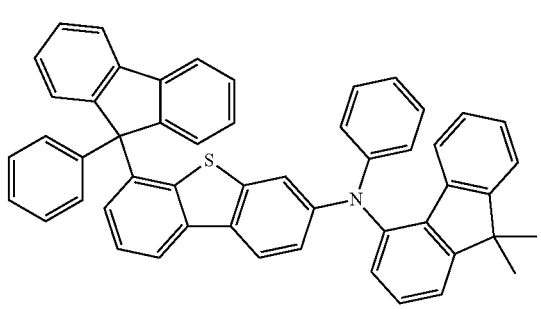
191
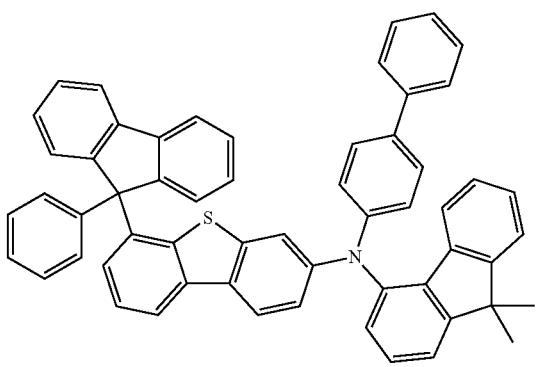
187
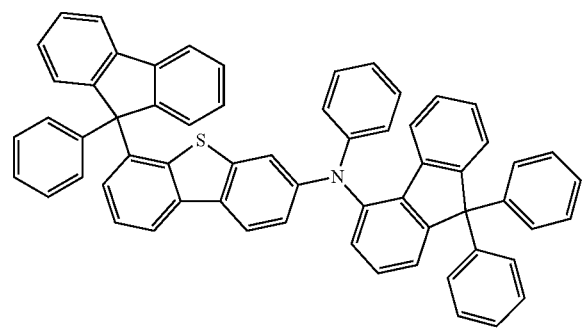

71
-continued
192
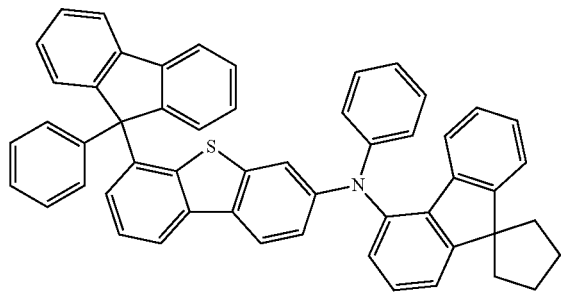
193
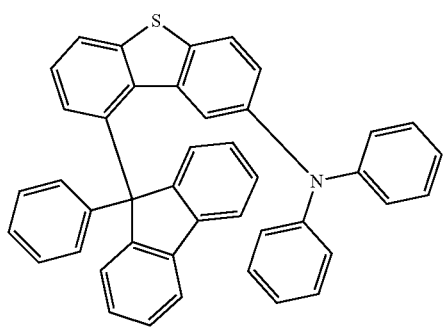
194
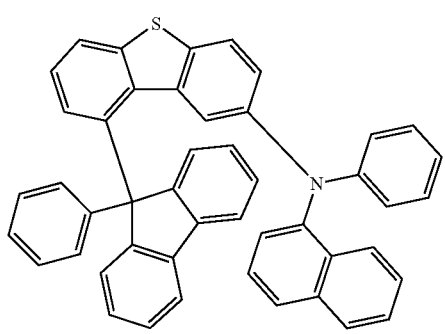
195
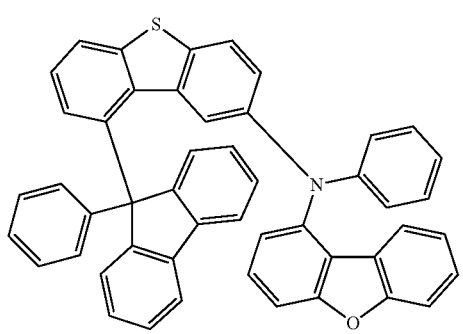
196
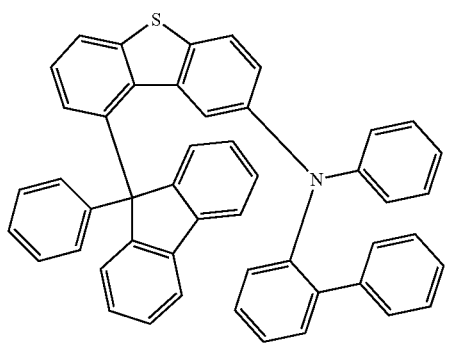
72
-continued
197
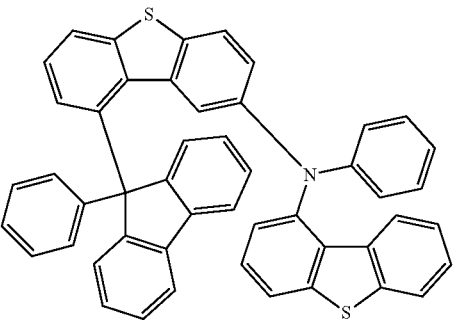
198
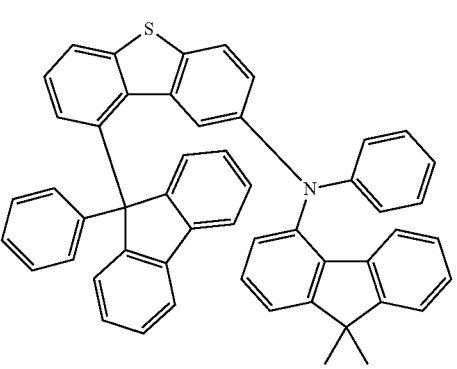
199
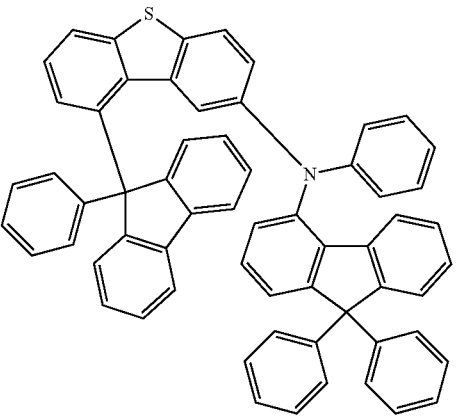
200
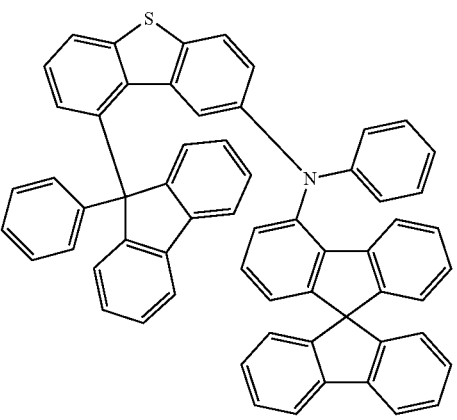

-continued
201
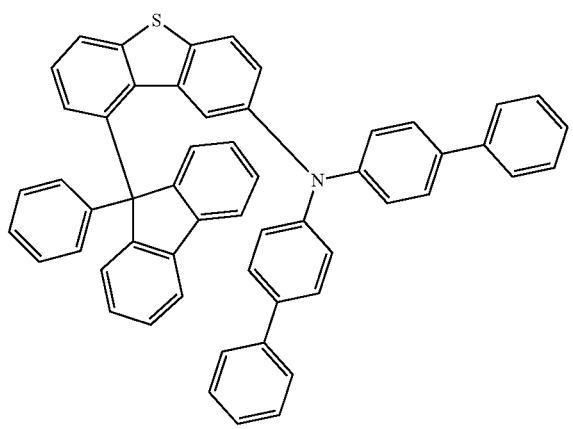
202
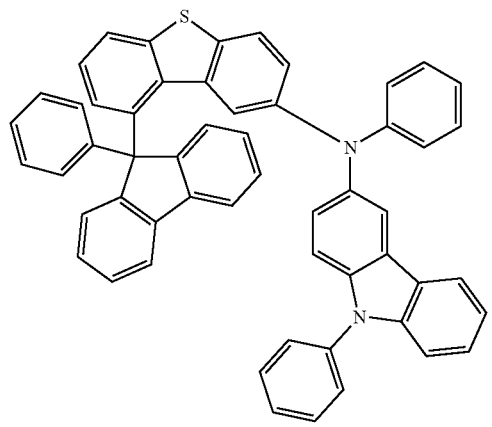
203
204
205
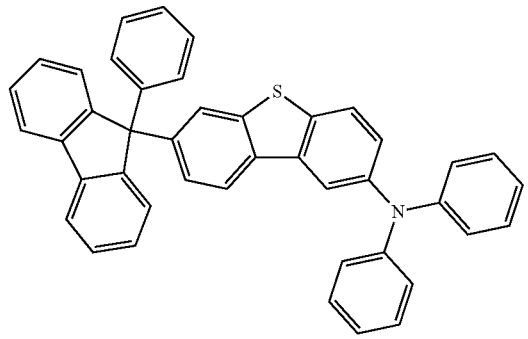
206
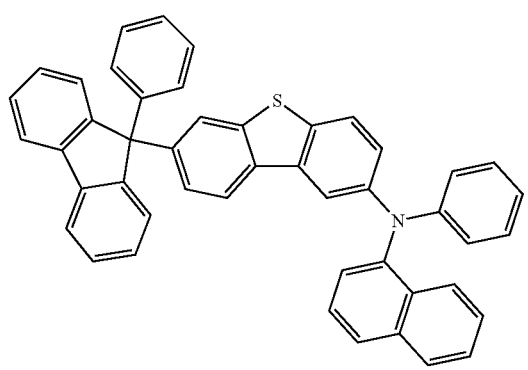
207
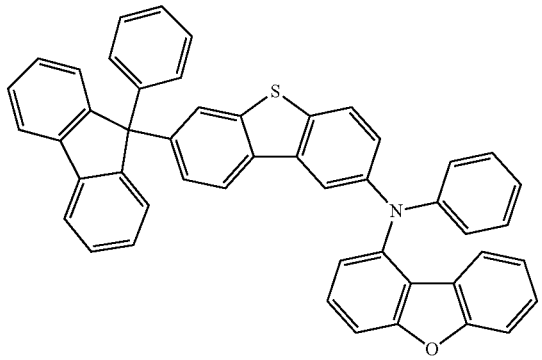
208
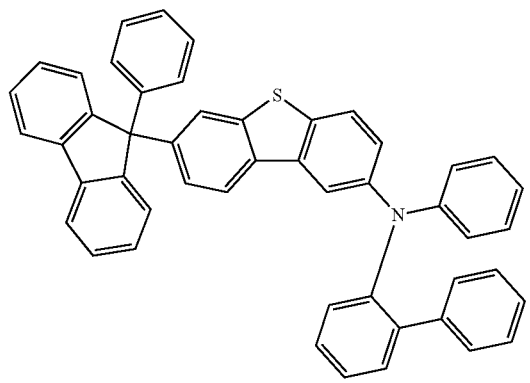

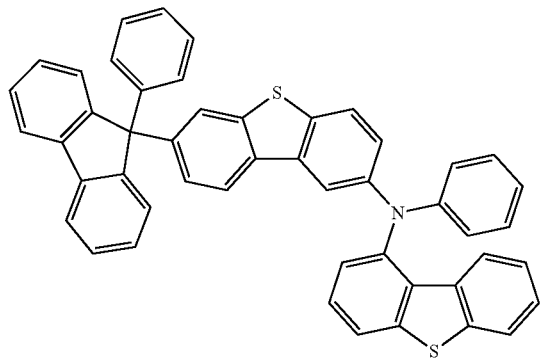
209
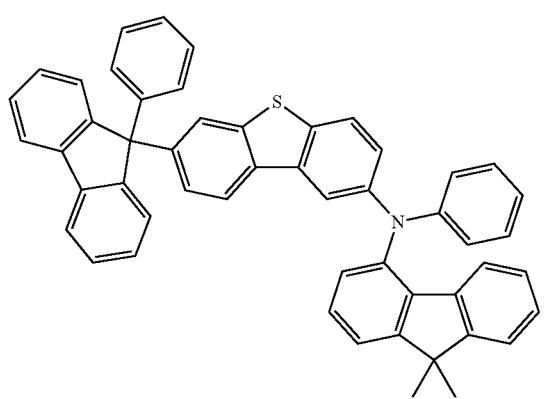
210
211
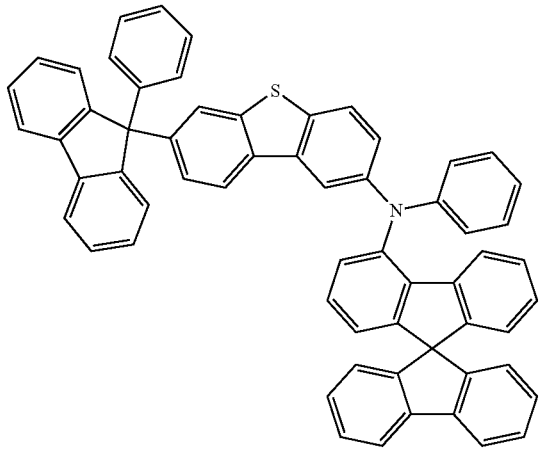
212
213
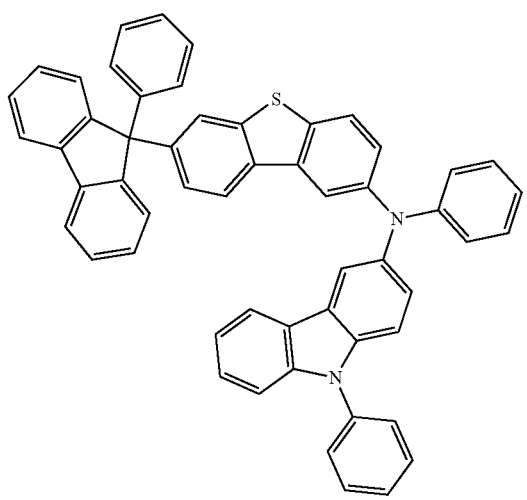
214

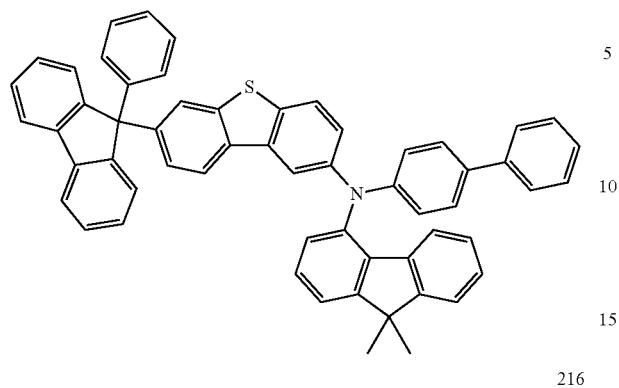
215
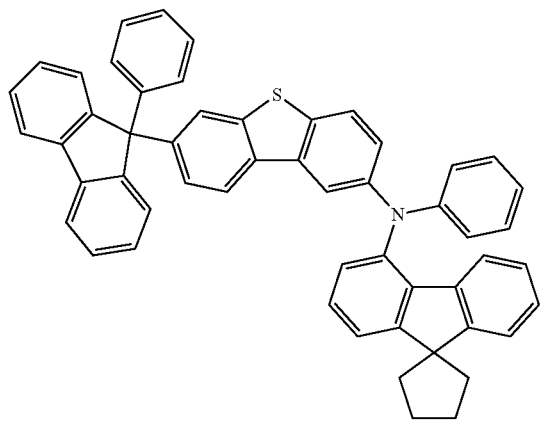
216
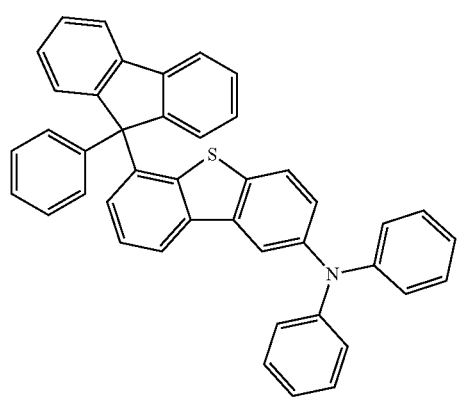
217
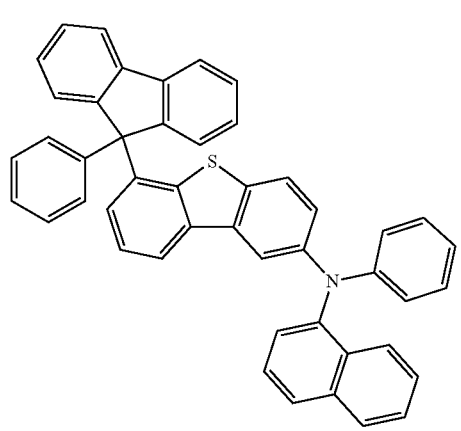
218
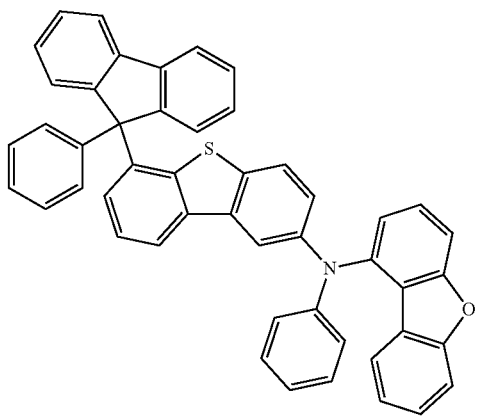
219
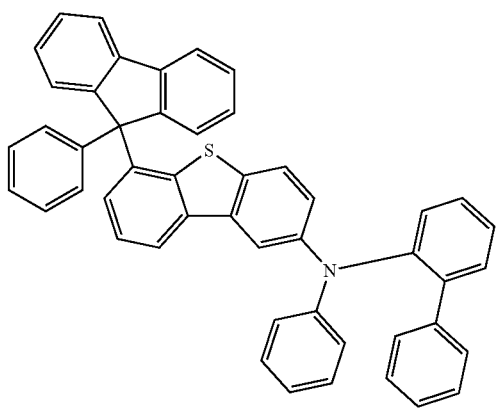
220
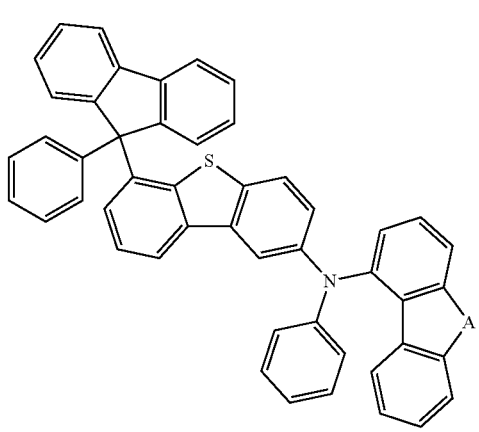
221

222
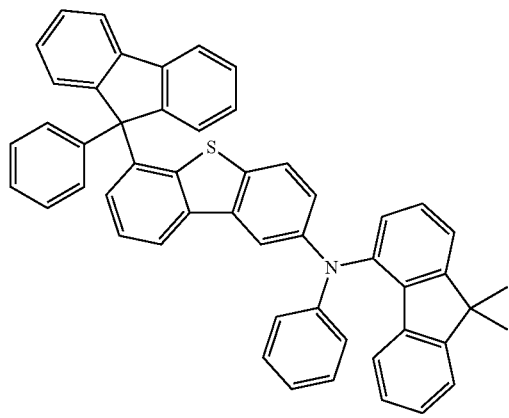
223
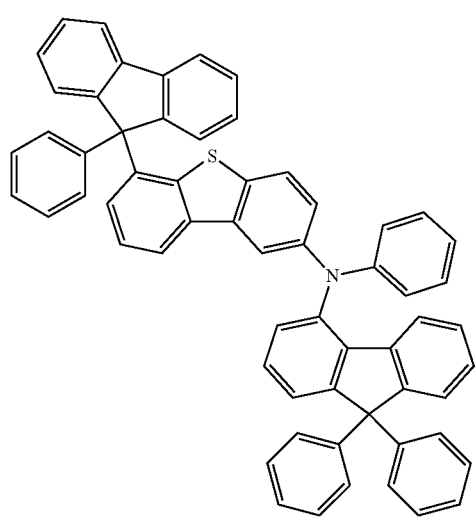
224
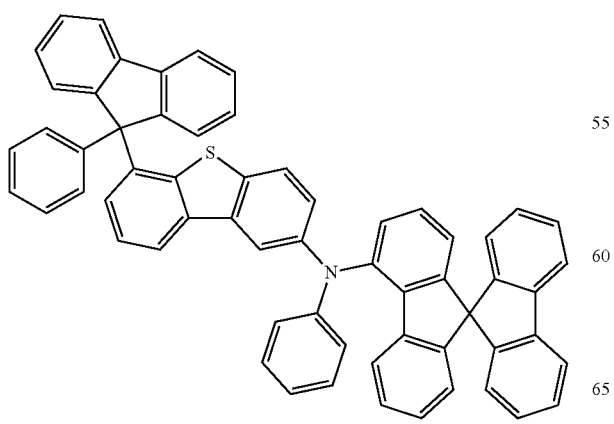
225
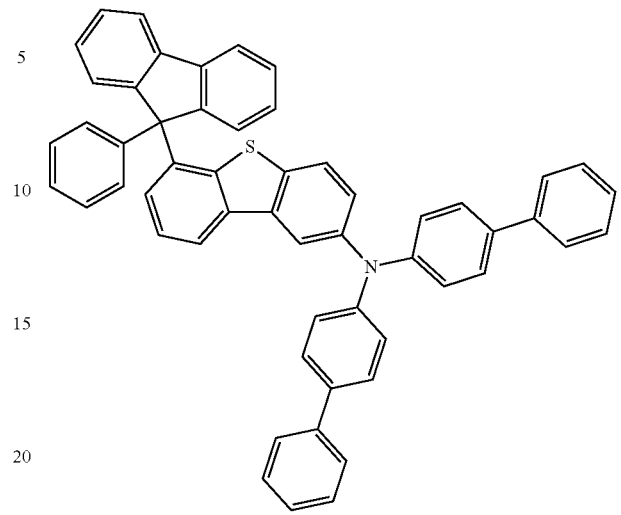
226
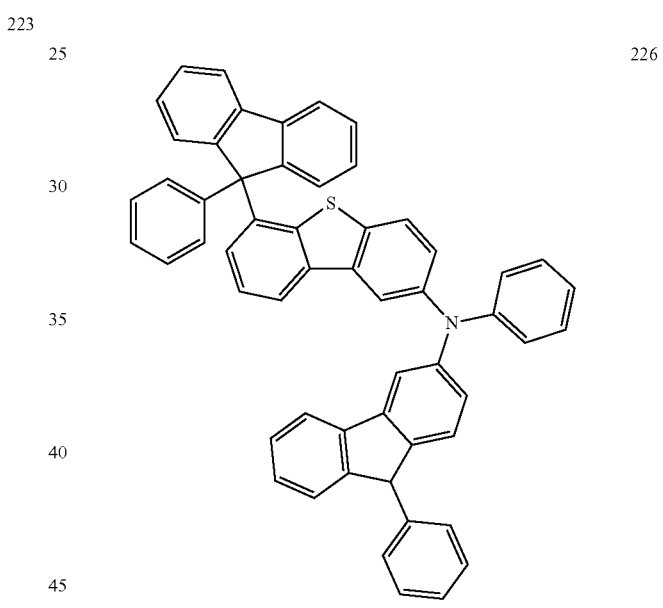
227
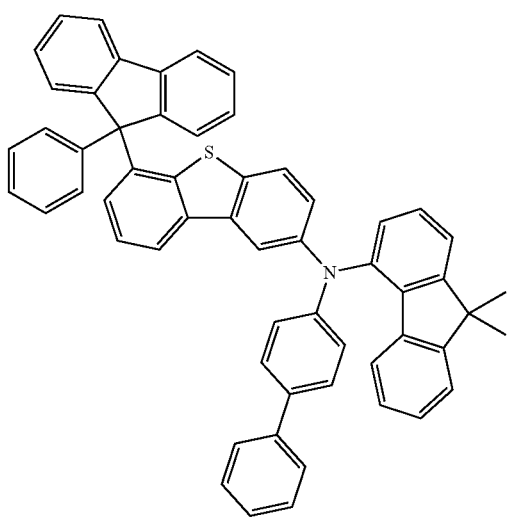

228
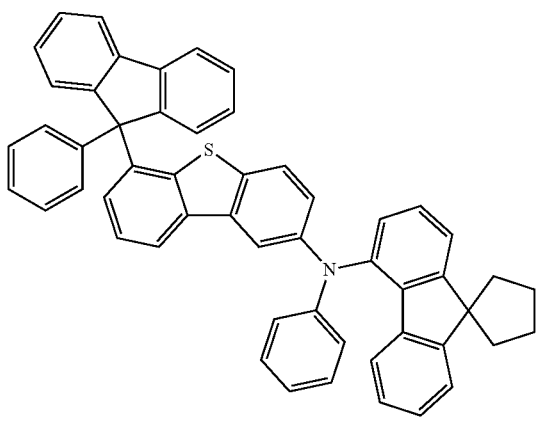
229
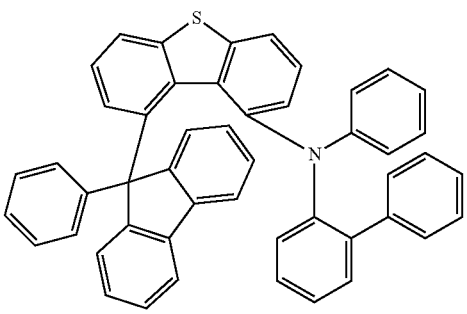
230
232
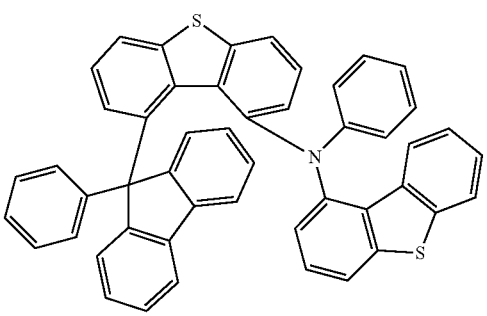
233
234
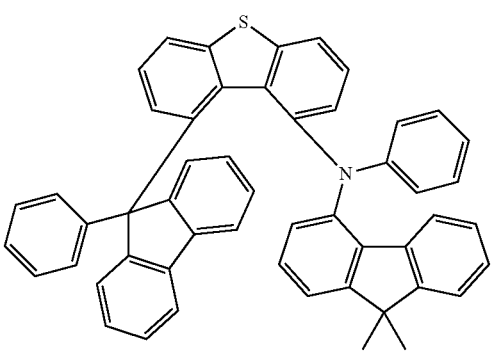
231
235
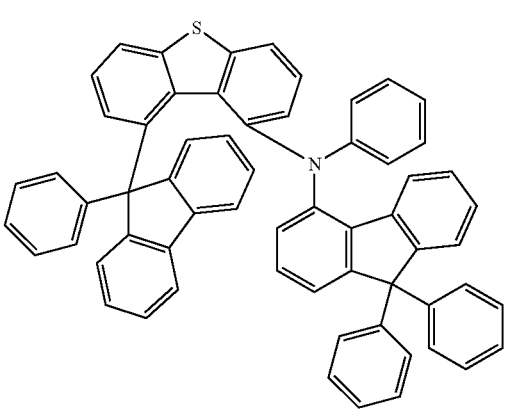

236
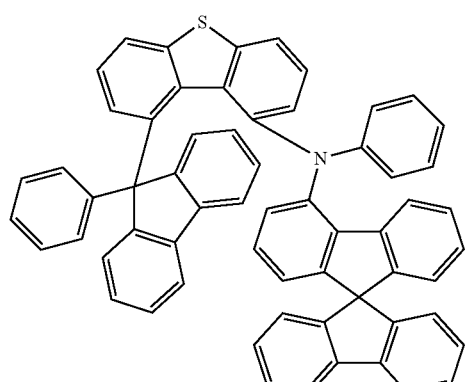
237
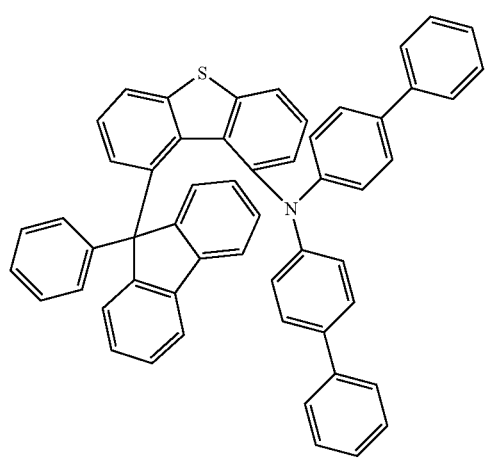
238
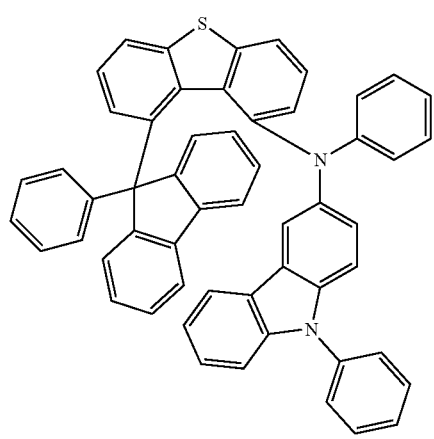
239
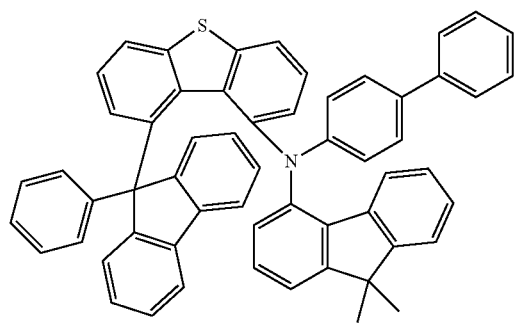
240
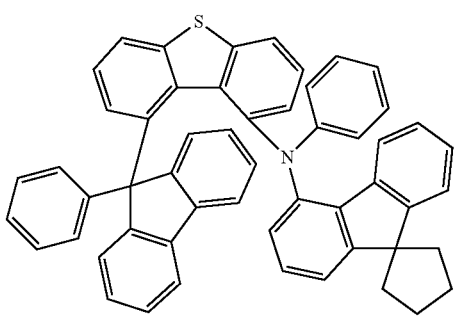
241
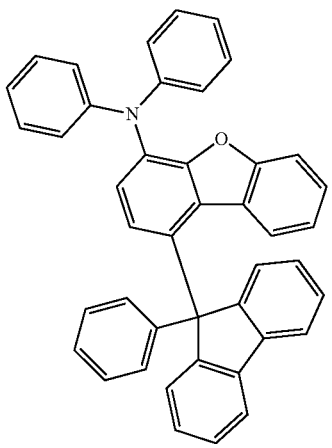
242
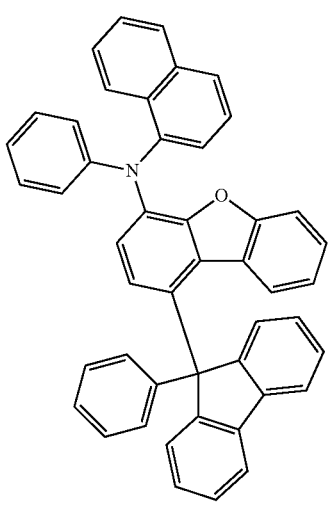

243
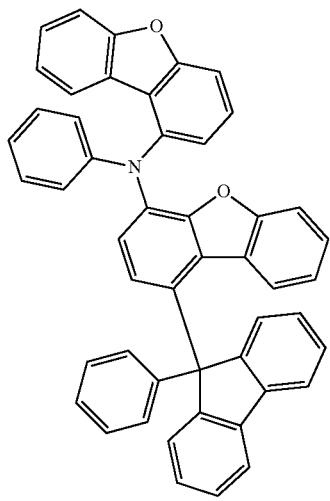
244
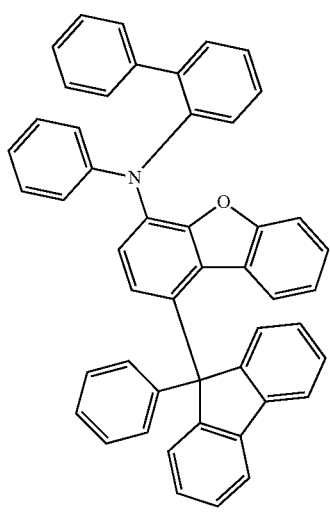
245
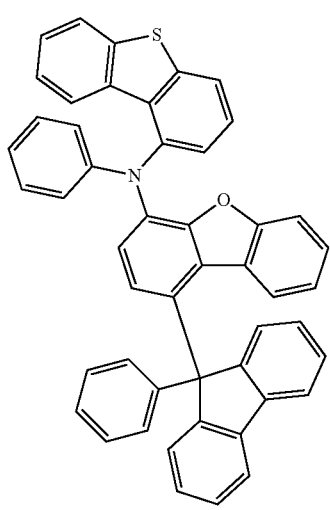
246
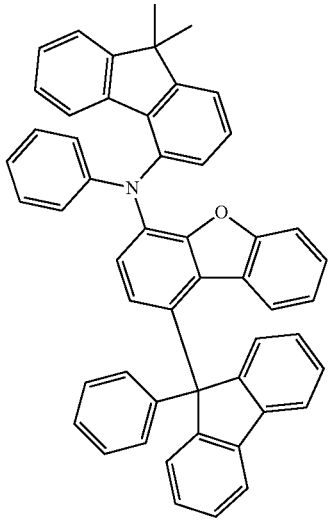
247
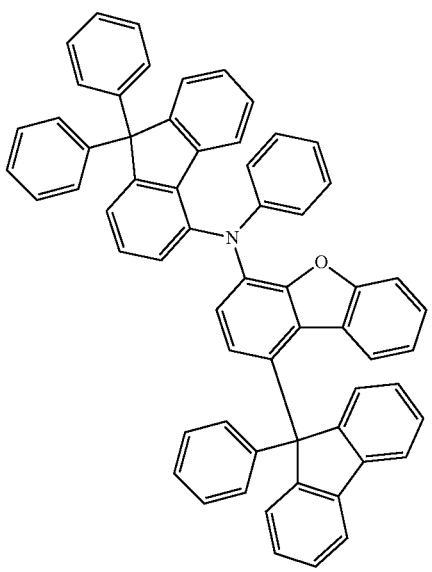

248
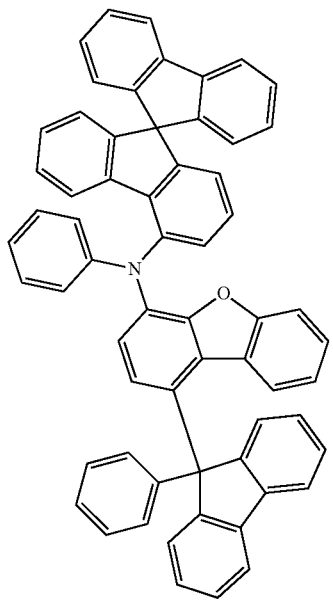
249
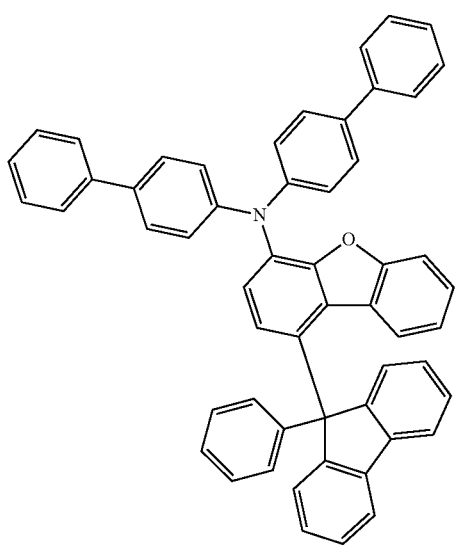
250
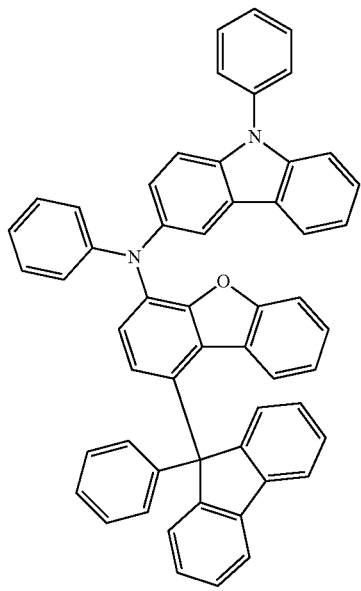
251
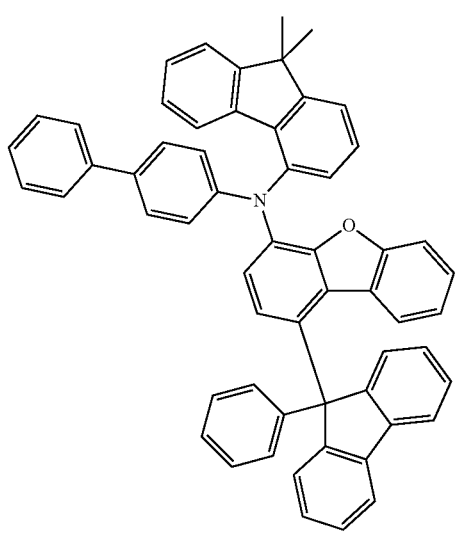
252
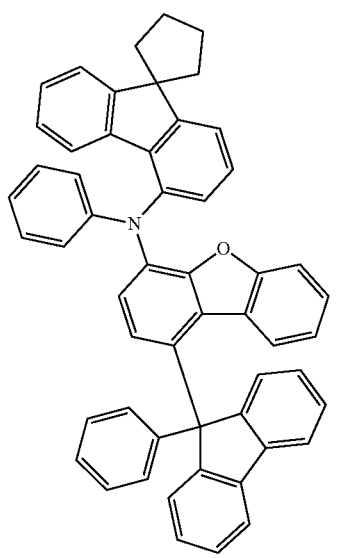

253 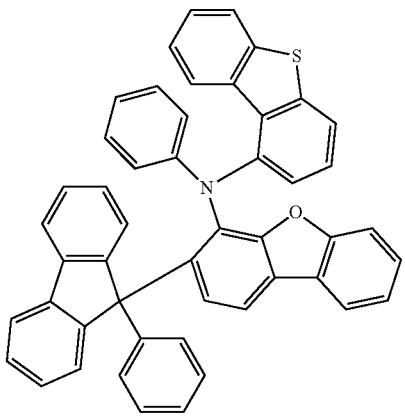
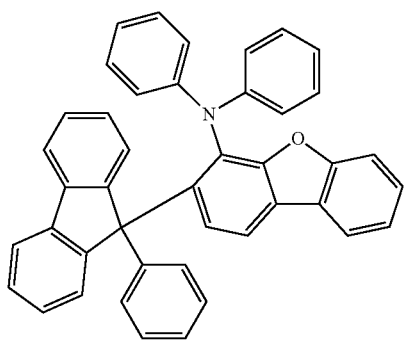
254
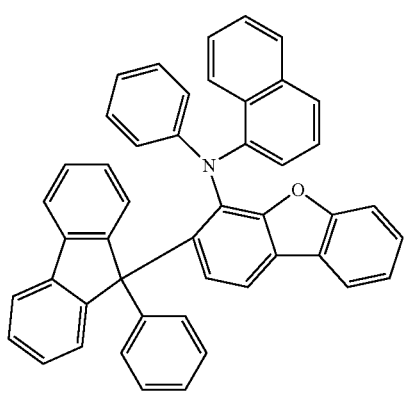
258 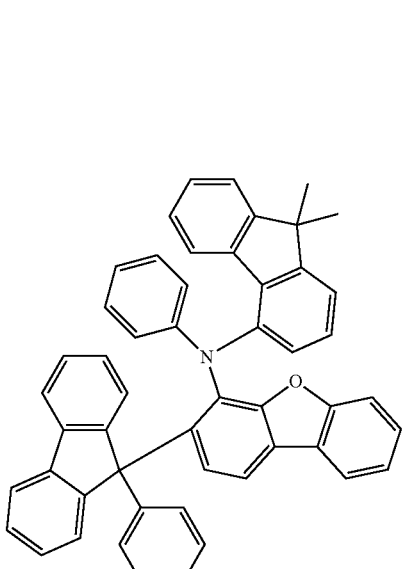
255
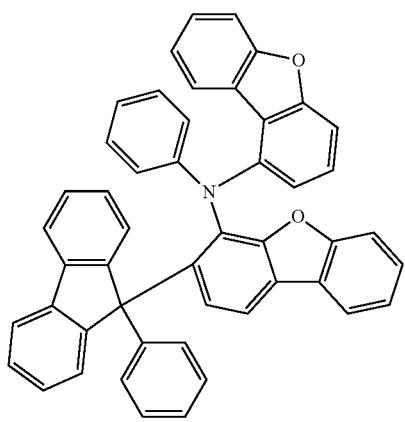
256
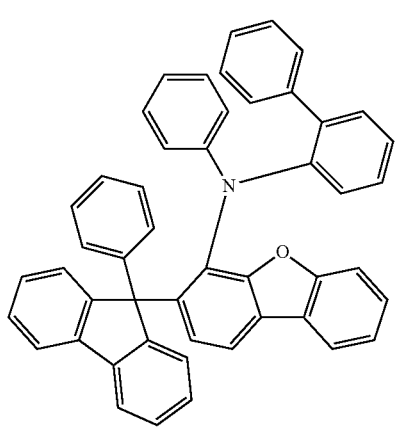
259 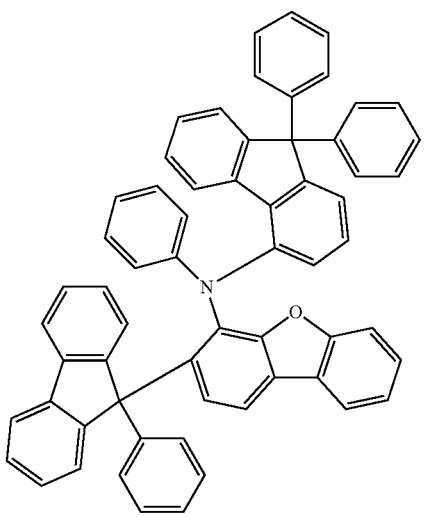

US 11,711,978 B2
260
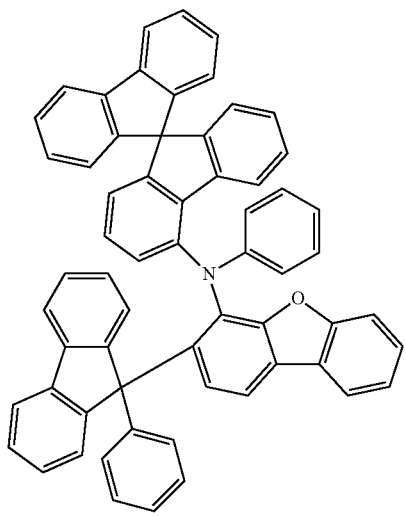
261
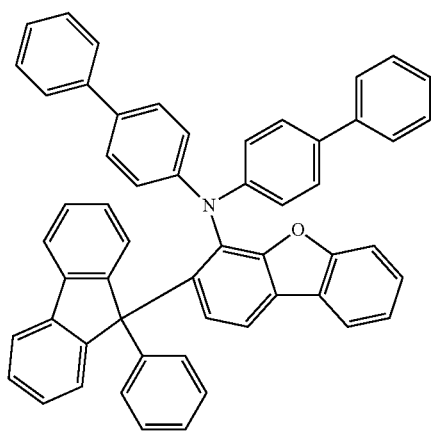
262
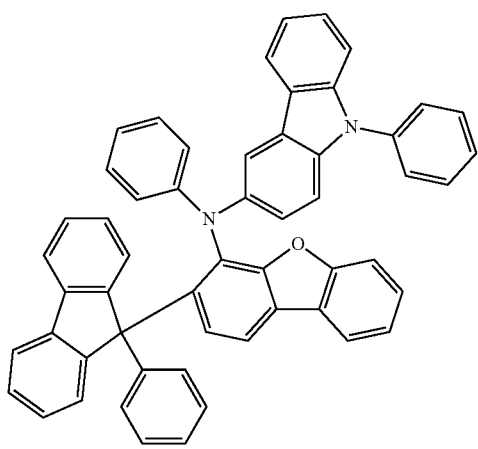
263
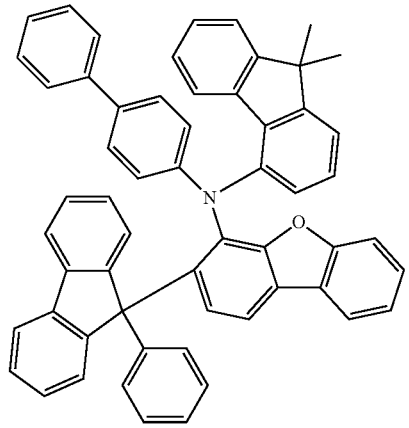
264
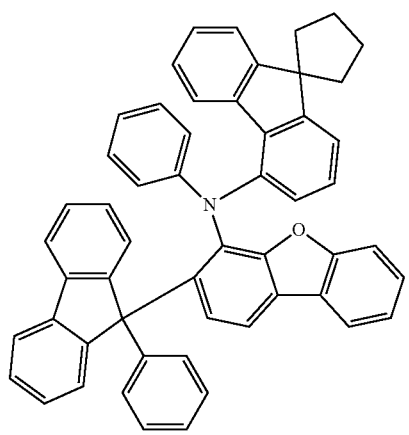
265
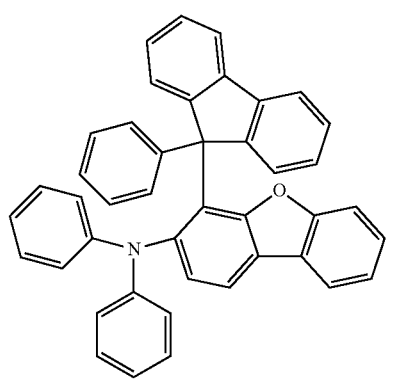
266
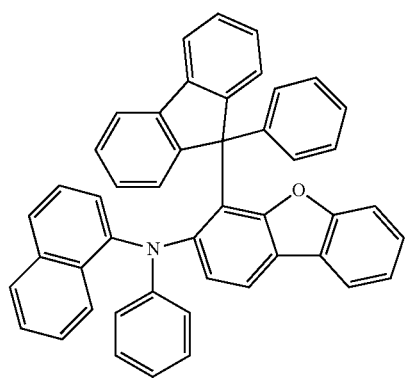

267
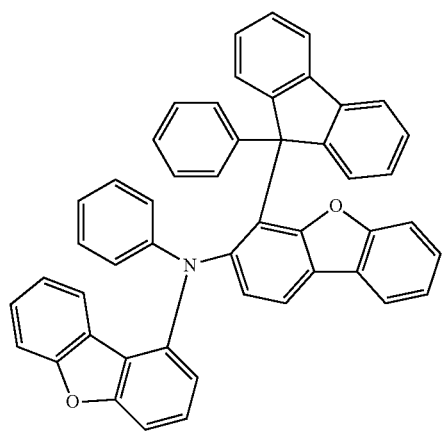
268
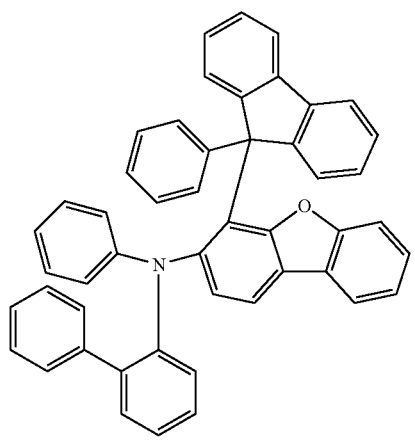
269
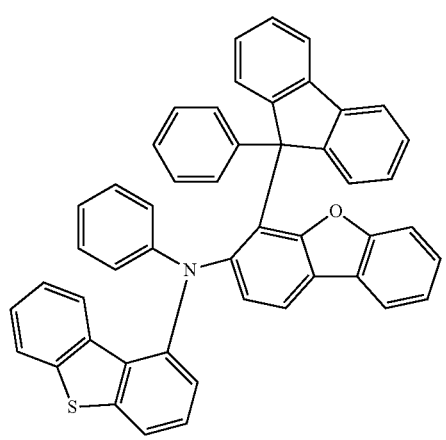
270
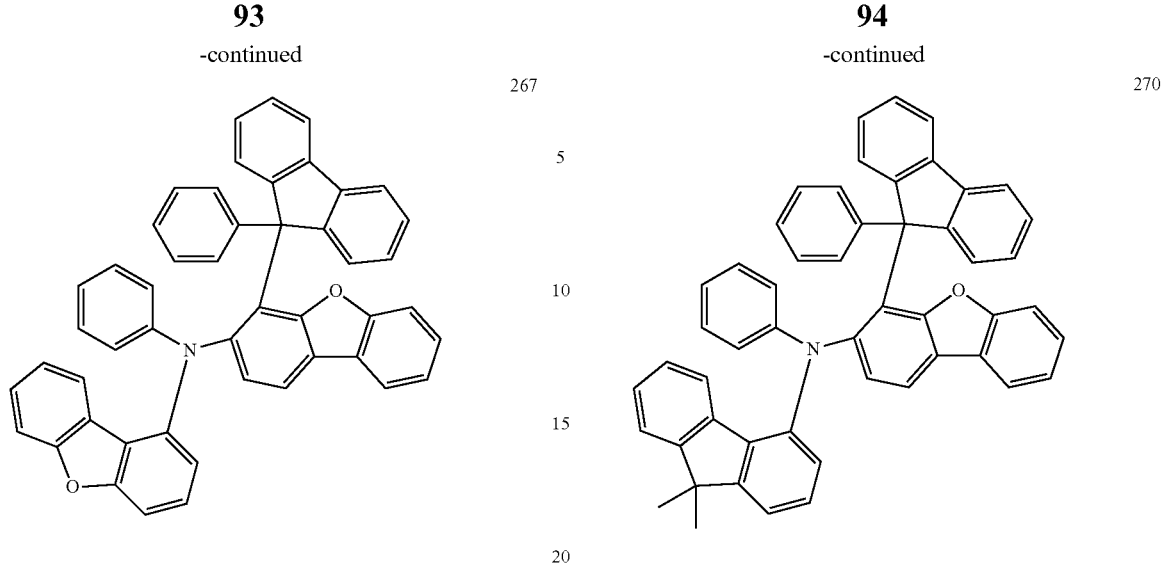
271
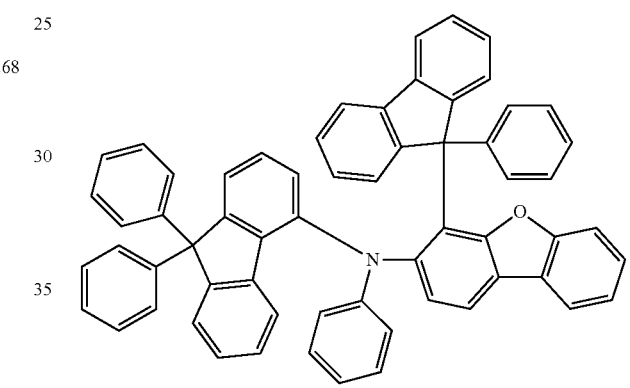
272
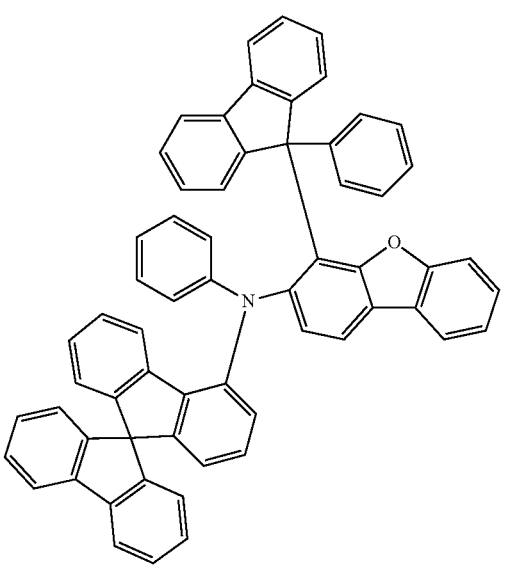

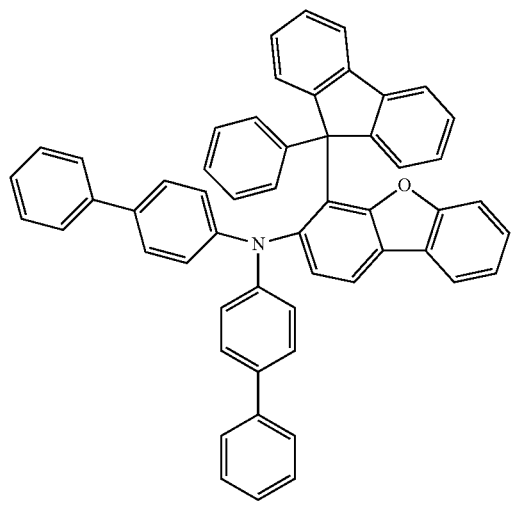
273
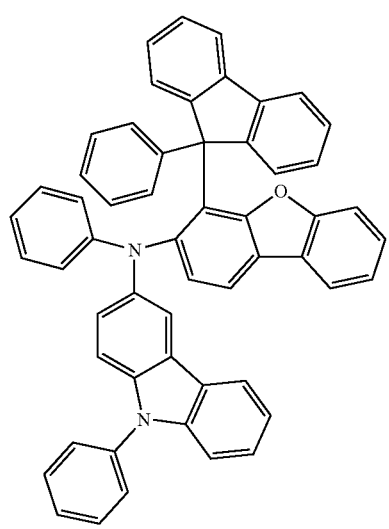
274
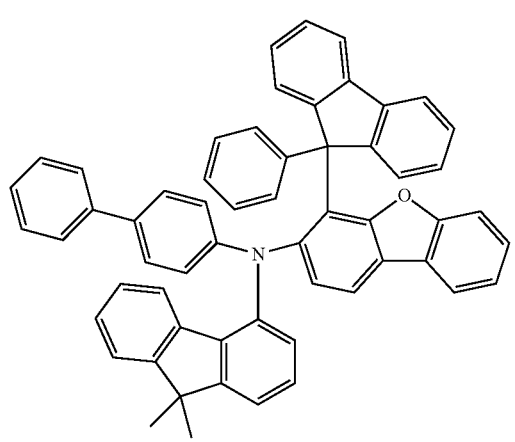
275
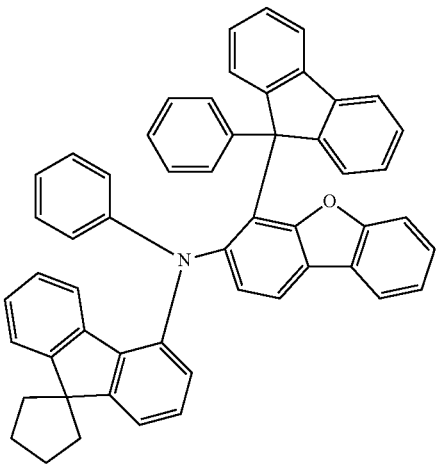
276
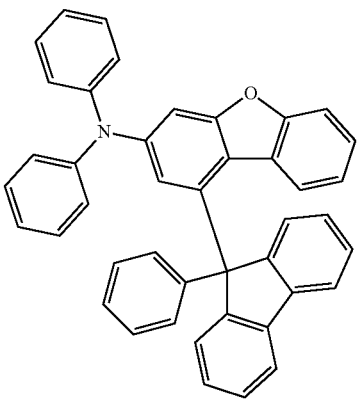
277
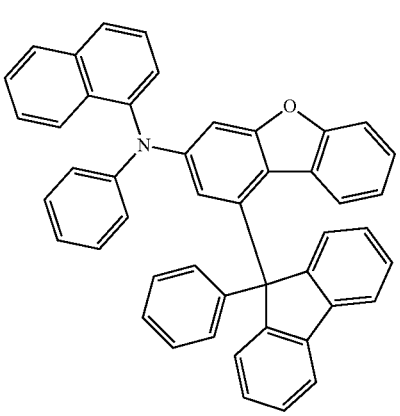
278

279
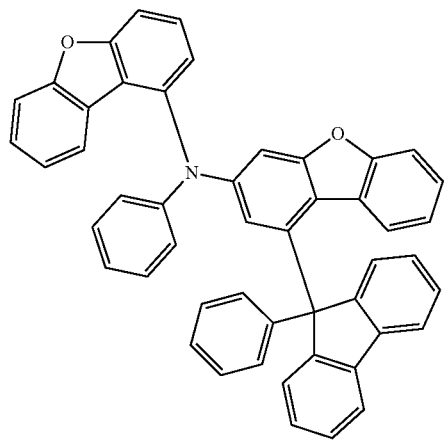
280
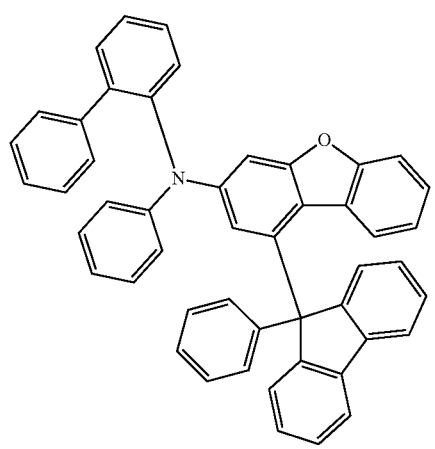
281
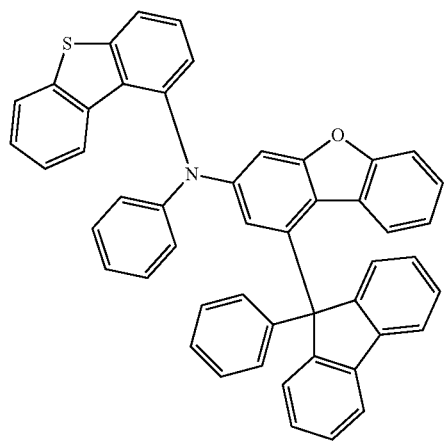
282
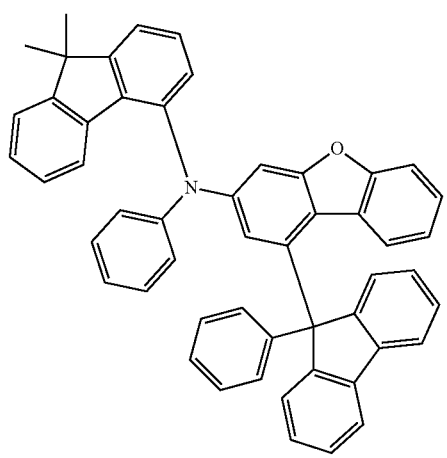
283
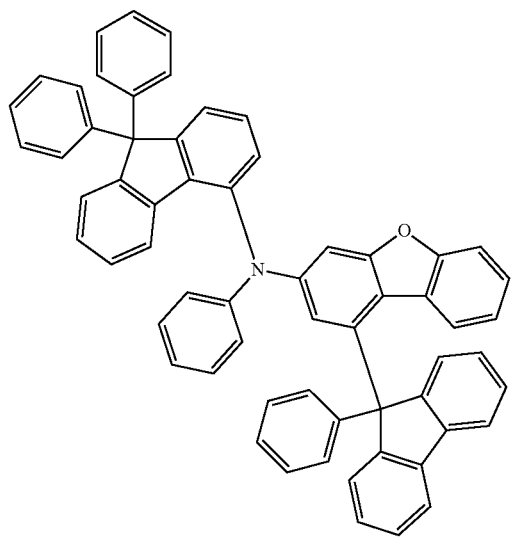
284
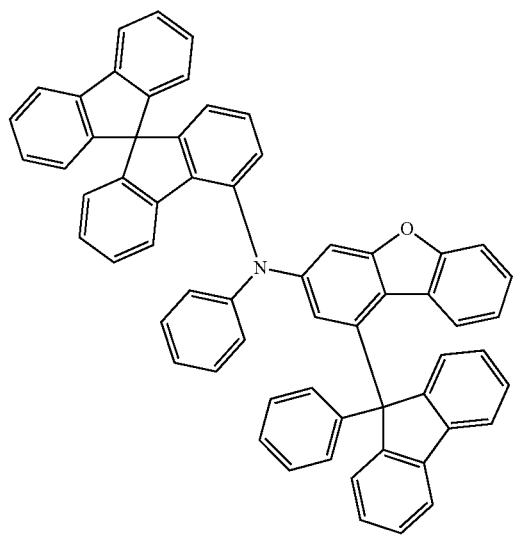

285
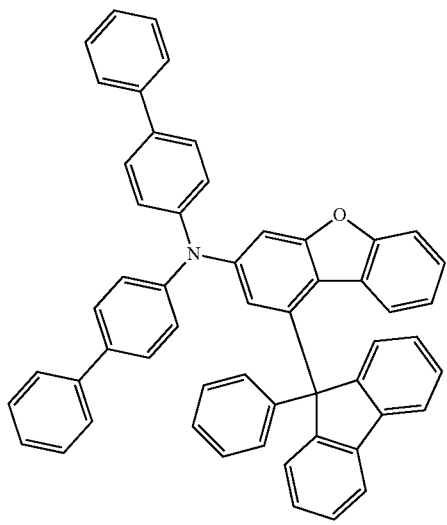
286
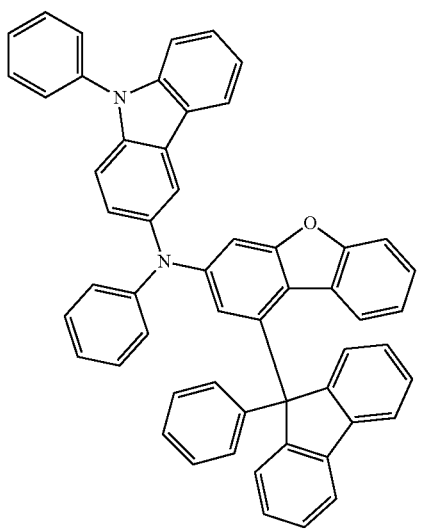
287
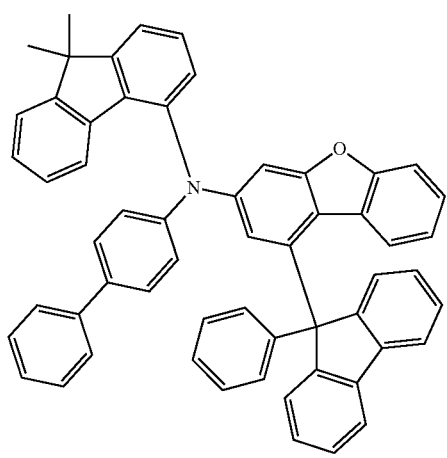
288
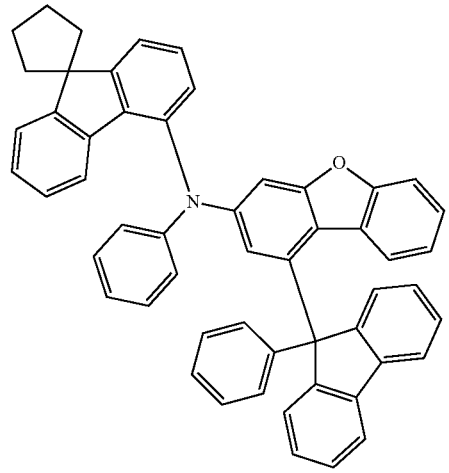
289
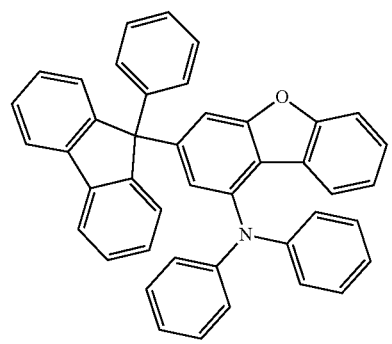
290
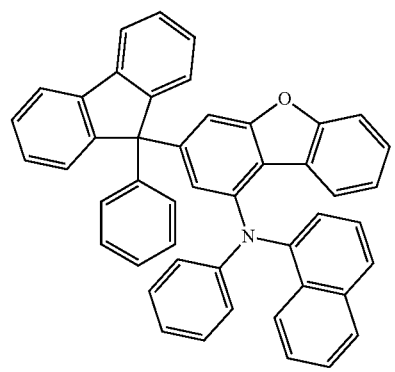
291
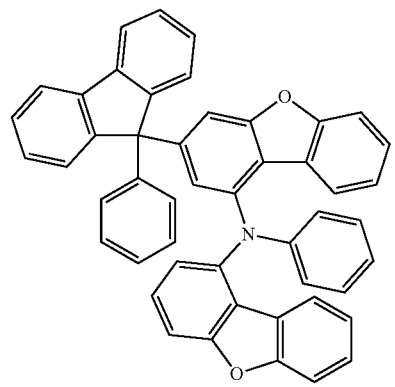

-continued
292
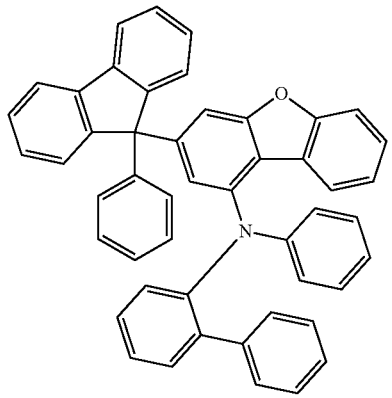
293
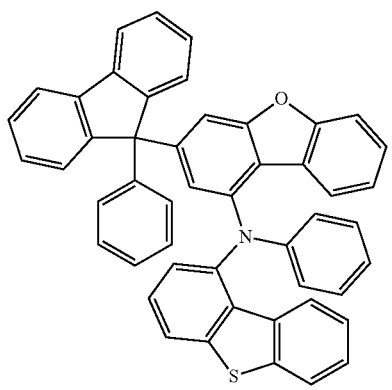
294
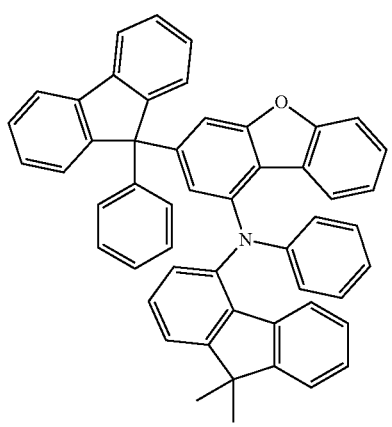
-continued
295
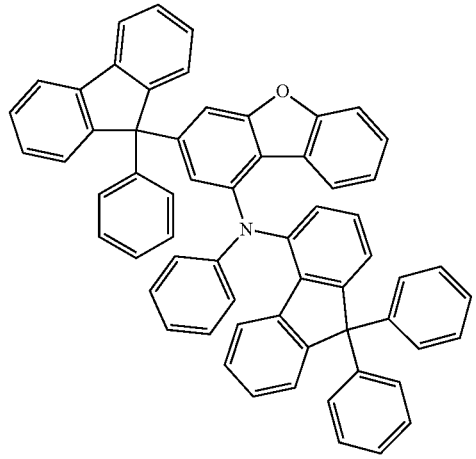
296
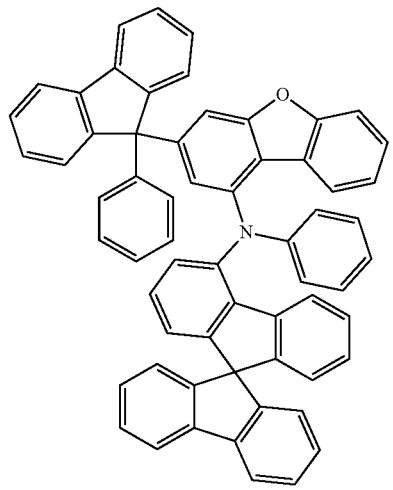
297
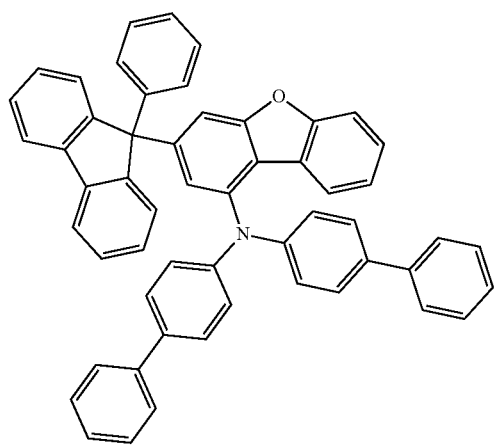

298
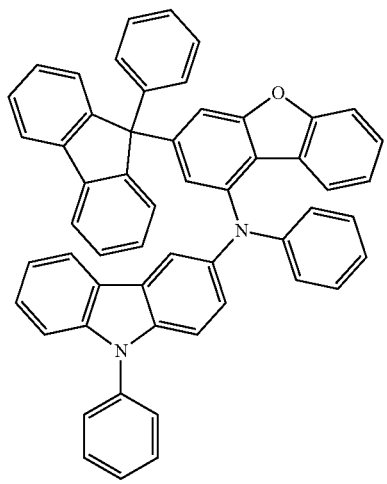
299
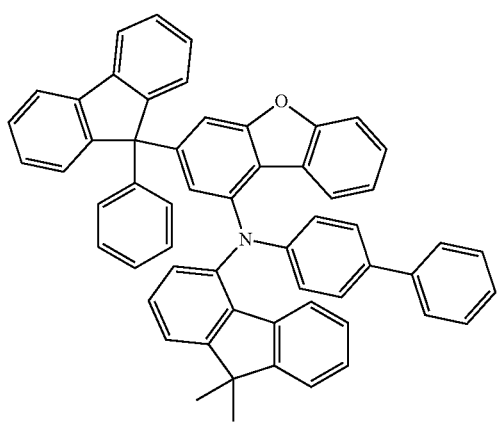
300
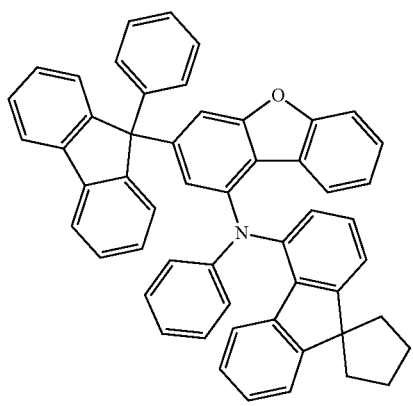
301
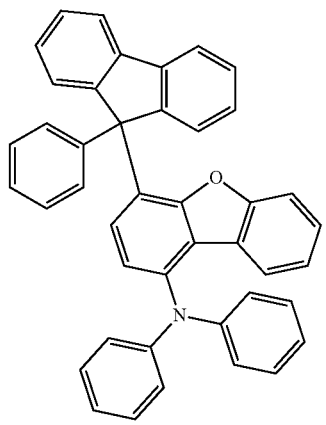
302
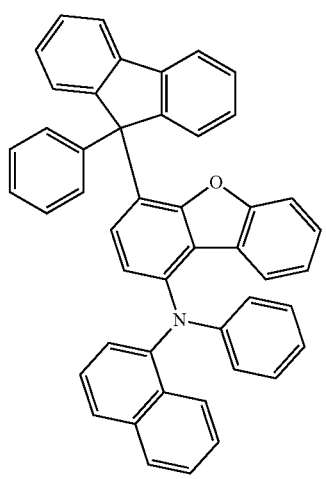
303
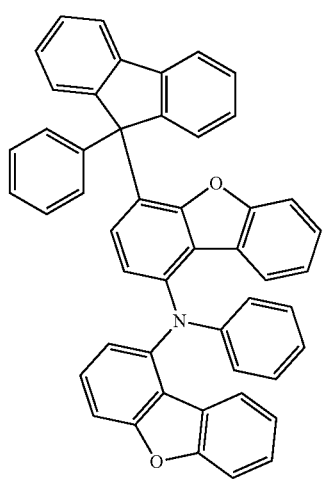

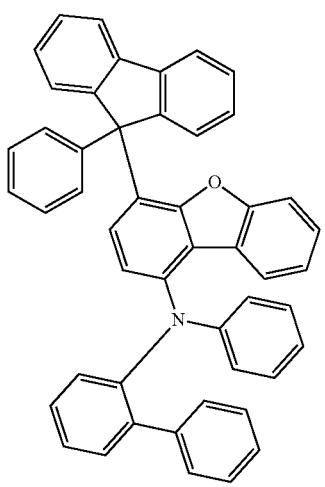
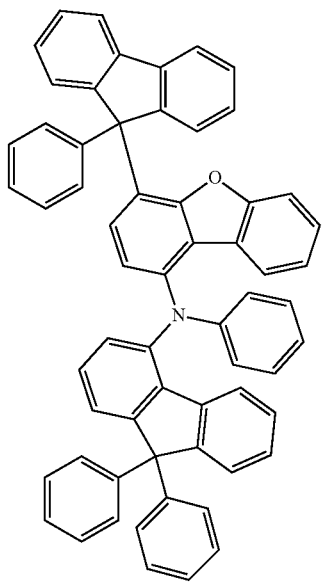
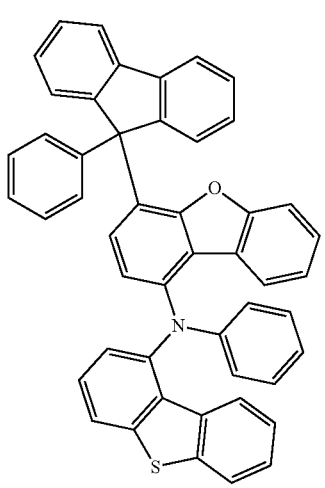
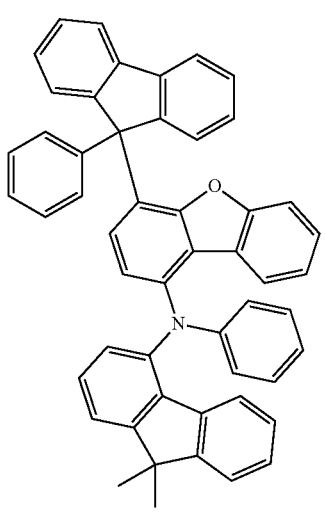
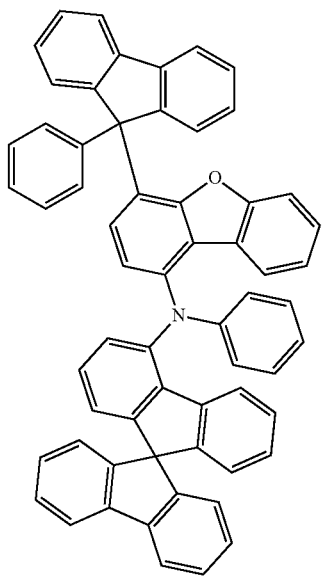

309
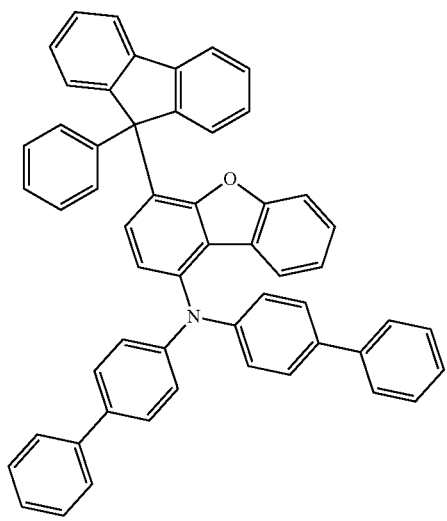
310
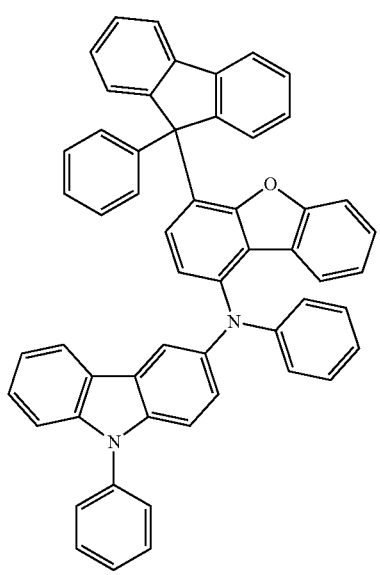
311
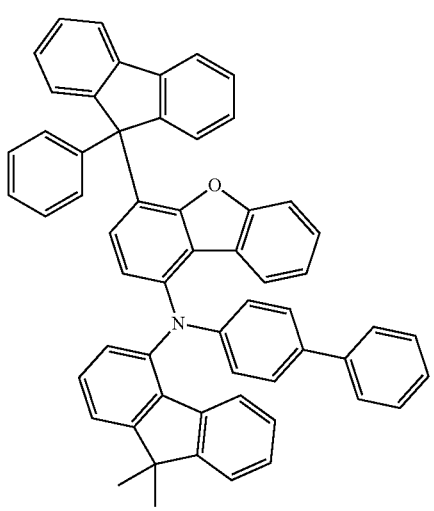
312
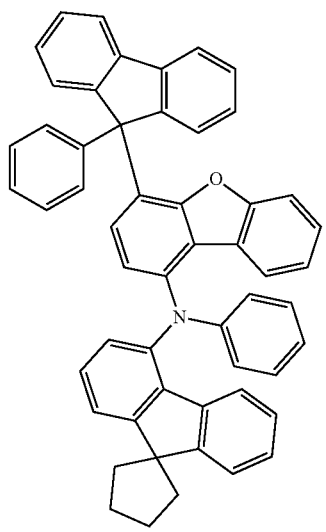
313
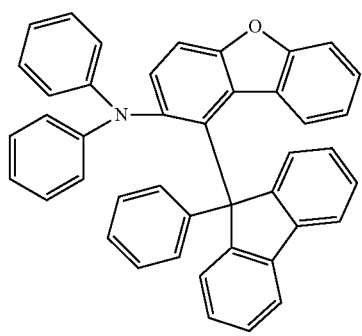
314
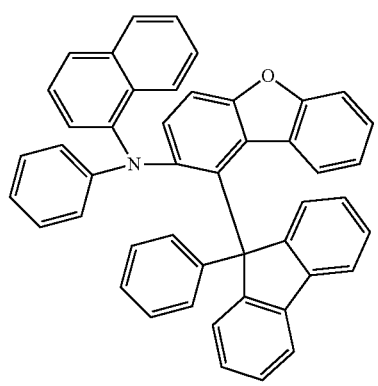
315
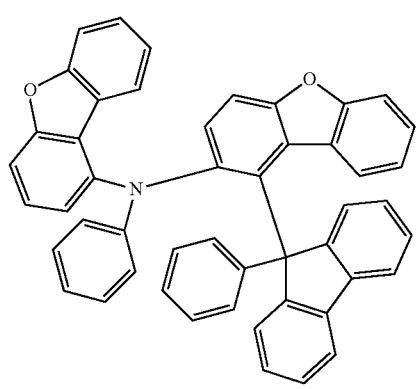

316 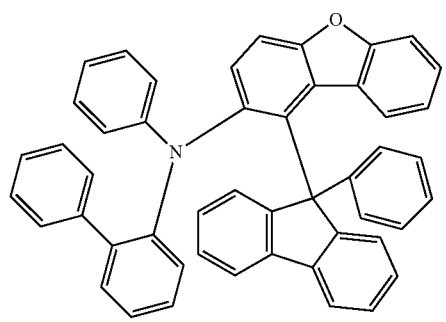
320 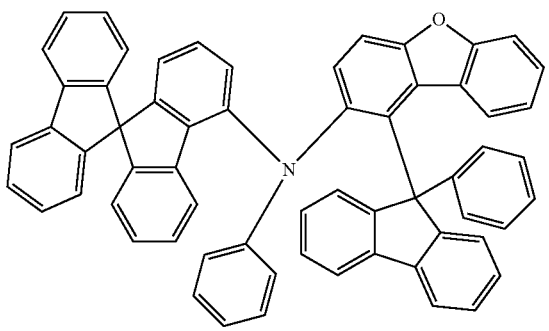
317 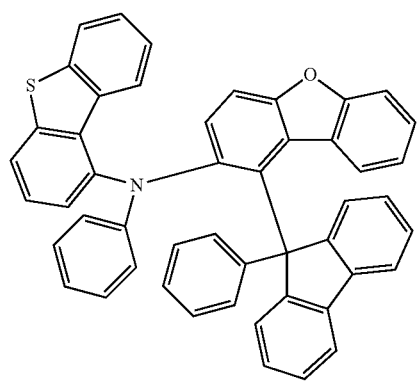
321 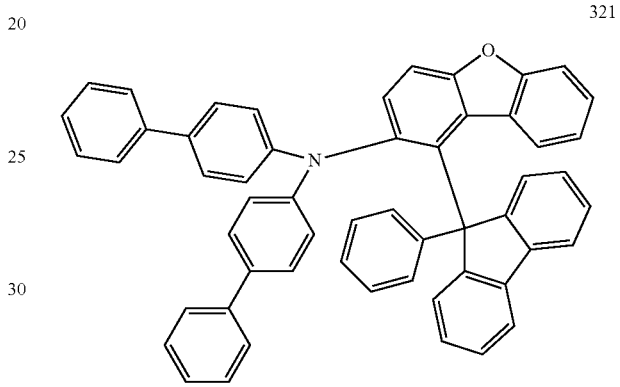
318 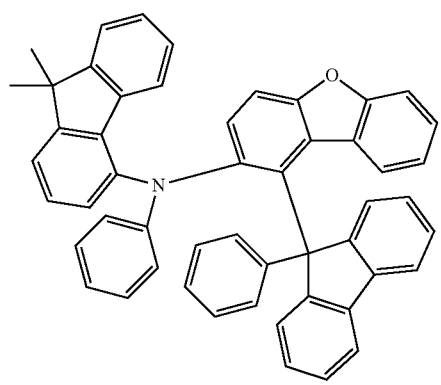
322 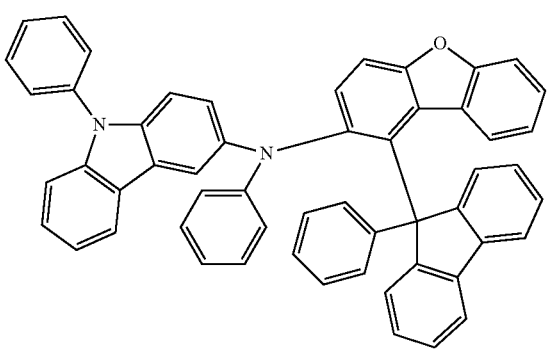
319 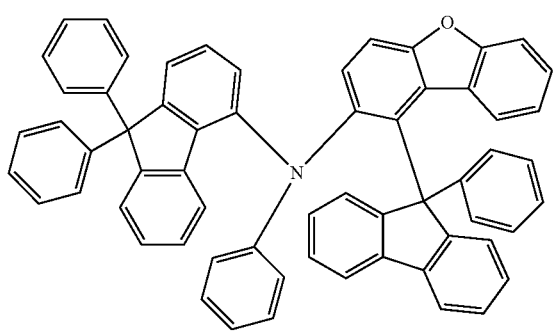
323 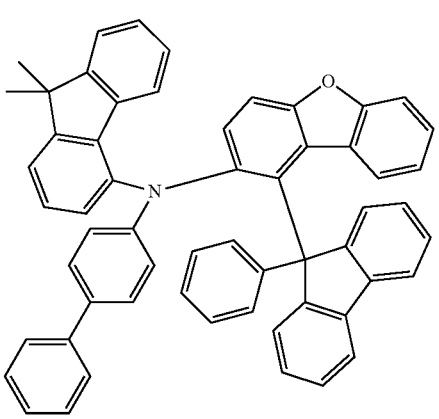

324
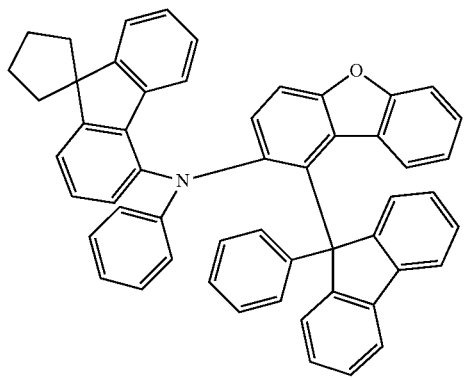
328
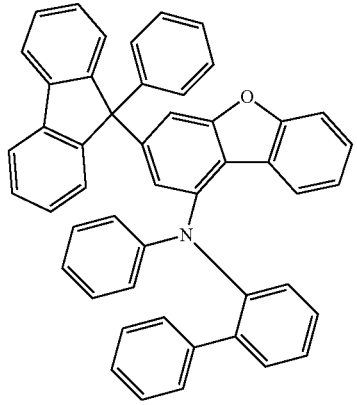
325
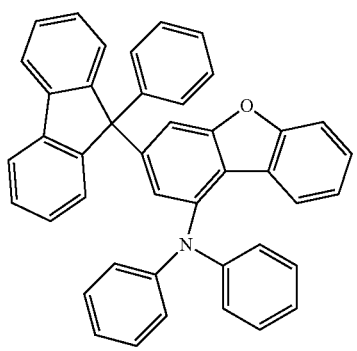
326
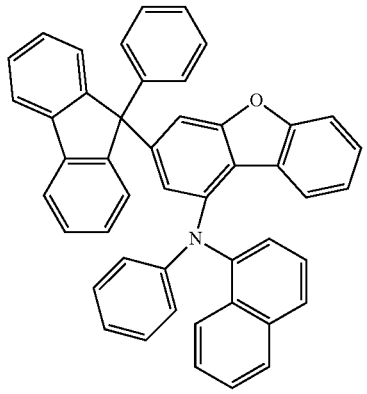
329
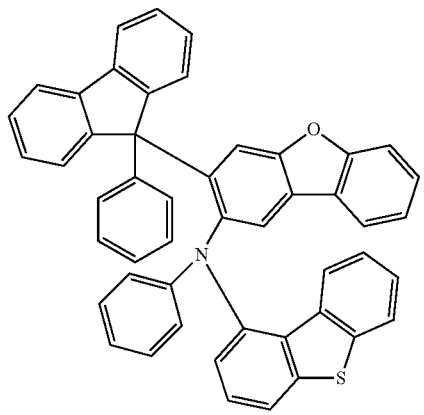
327
330
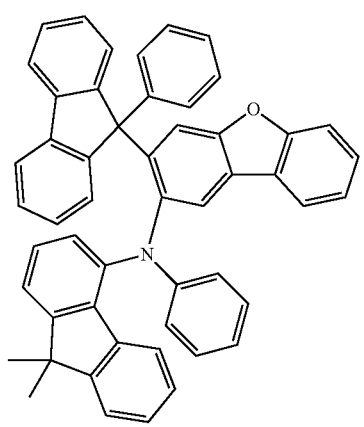

| 331 | 334 |
|---|---|
| 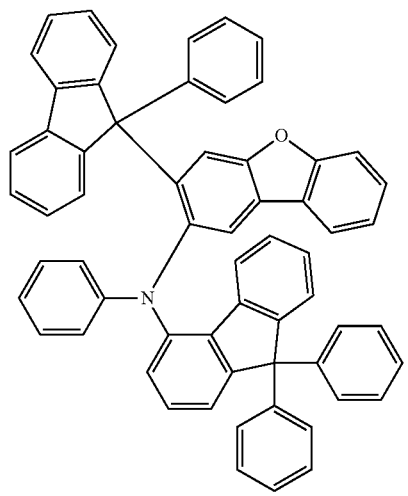 | 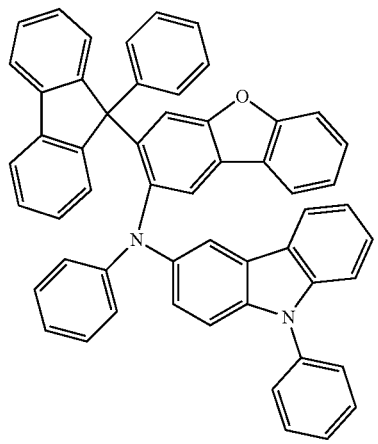 |
| 332 | 335 |
| 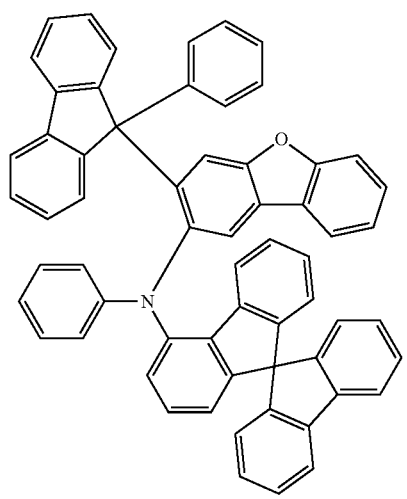 | 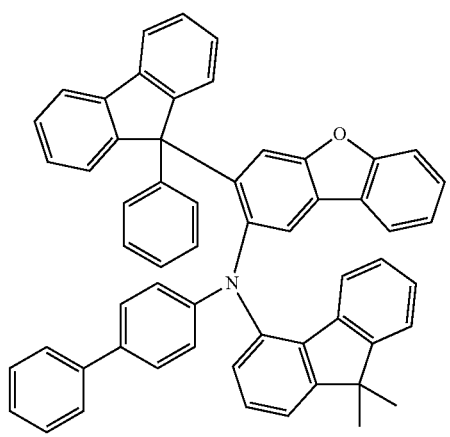 |
| 333 | 336 |
| 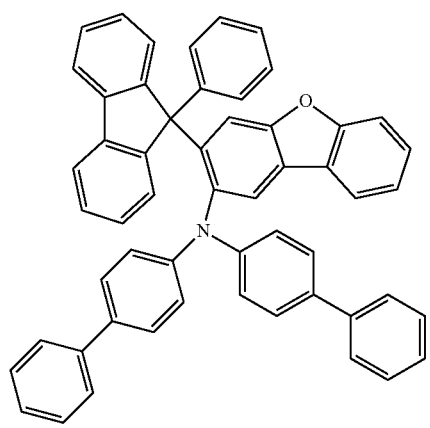 | 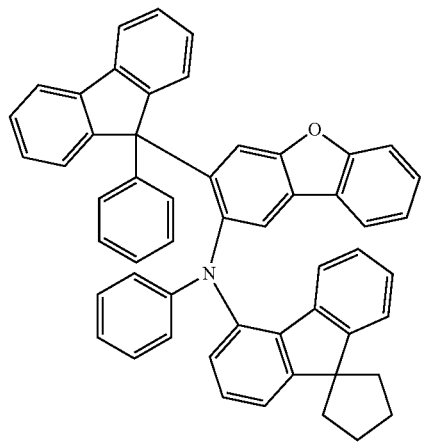 |

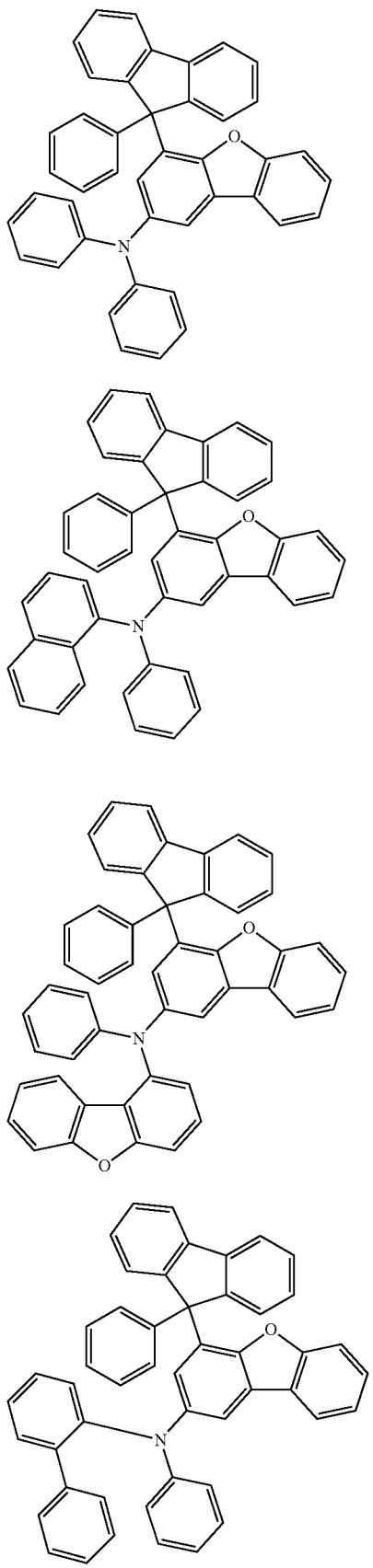
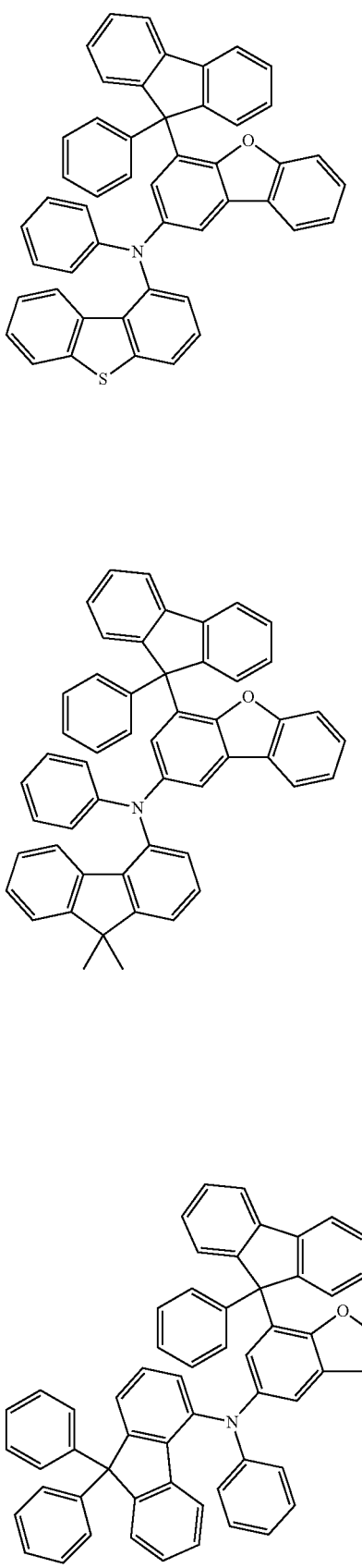

344

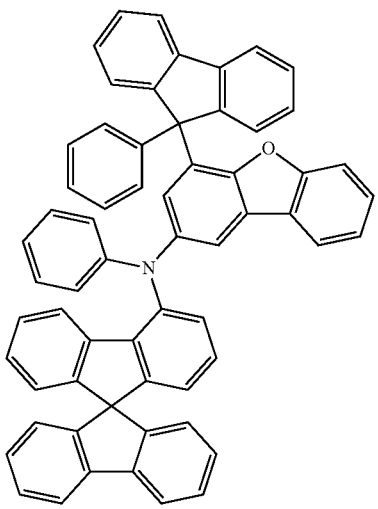

345

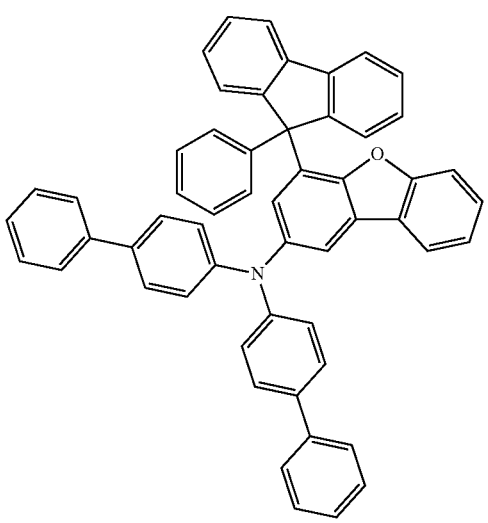

346

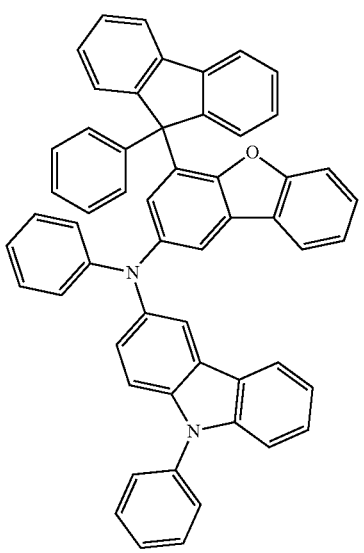

347

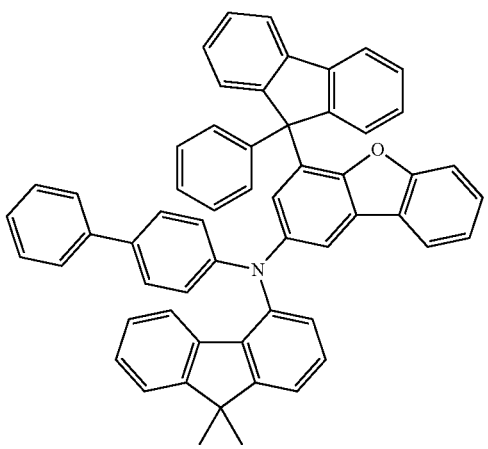

348

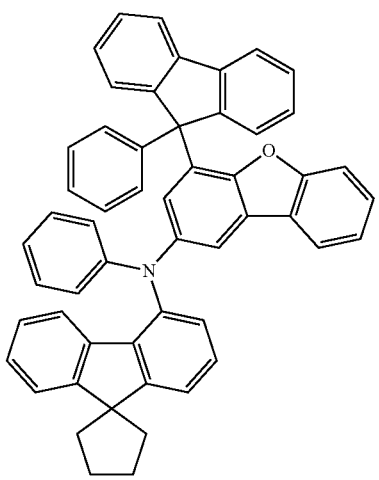

Because the heterocyclic compound represented by Formula 1 has excellent charge transporting capability, the heterocyclic compound represented by Formula 1 may be suitable for use as a hole transport material.

In addition, when the heterocyclic compound represented by Formula 1 has a structure in which a ninth carbon atom of a fluorene is linked to the first, second, or fourth position of a dibenzofuran or a dibenzothiophene, an intramolecular distance (e.g., between moieties) is narrowed, thereby obtaining a structurally stable effect.

Furthermore, because the heterocyclic compound represented by Formula 1 includes a dibenzofuran or dibenzothiophene structure, a glass transition temperature (Tg) of the compound may be relatively high. Therefore, the heat resistance of the compound to Joule heating when the organic light-emitting device including the heterocyclic compound is driven may be improved, thereby obtaining long lifespan characteristics.

In addition, because the heterocyclic compound represented by Formula 1 has a structure in which the ninth carbon atom of a fluorenyl group represented by Formula 2-1 is directly linked to a core (for example, a dibenzofuran or a dibenzothiophene core), the stability of the core may be improved and the thermal stability of the heterocyclic compound may be improved, thereby obtaining long lifespan characteristics.

Furthermore, because the heterocyclic compound represented by Formula 1 includes a group represented by Formula 2-1 and a group represented by Formula 2-2, the heterocyclic compound represented by Formula 1 may have an energy level suitable for hole transport from the first or second electrode to the emission layer, thereby obtaining high efficiency and long lifespan characteristics.

Suitable synthesis methods for the heterocyclic compound represented by Formula 1 will be apparent to those of ordinary skill in the art by referring to the following examples.

At least one of the heterocyclic compound represented by Formula 1 may be used between a pair of electrodes of an organic light-emitting device. For example, the heterocyclic compound may be included in an emission layer. In one or more embodiments, the heterocyclic compound represented by Formula 1 may be used as a material for a capping layer located outside a pair of electrodes of an organic light-emitting device.

One or more embodiments of the present disclosure provide an organic light-emitting device including: a first electrode; a second electrode facing the first electrode; and an organic layer between the first electrode and the second electrode, the organic layer including an emission layer and at least one heterocyclic compound represented by Formula 1.

The expression "(an organic layer) includes at least one heterocyclic compound" as used herein may refer to a case in which "(an organic layer) includes identical heterocyclic compounds (e.g., the same compound) represented by Formula 1" as well as a case in which "(an organic layer) includes two or more different heterocyclic compounds represented by Formula 1".

For example, the organic layer may include, as the heterocyclic compound, only Compound 1 (e.g., one compound). Here, Compound 1 may exist only in the emission layer of the organic light-emitting device. In one or more embodiments, the organic layer may include, as the heterocyclic compound, Compound 1 and Compound 2 (e.g., a first compound and a second compound). In this regard, Compound 1 and Compound 2 may exist in an identical (e.g., the same) layer (for example, Compound 1 and Compound 2 may both or simultaneously exist in an emission layer), or in different layers (for example, Compound 1 may exist in an emission layer and Compound 2 may exist in a hole transport layer).

In one embodiment,
the first electrode of the organic light-emitting device may be an anode,
the second electrode of the organic light-emitting device may be a cathode,
the organic layer may include at least one heterocyclic compound represented by Formula 1,
the organic layer may further include a hole transport region between the first electrode and the emission layer and an electron transport region between the emission layer and the second electrode,
the hole transport region may include a hole injection layer, a hole transport layer, an emission auxiliary layer, an electron blocking layer, or any combination thereof, and
the electron transport region may include a hole blocking layer, an electron transport layer, an electron injection layer, or any combination thereof.

In one embodiment, the hole transport region may include the heterocyclic compound.

In one or more embodiments, the hole transport region includes a hole transport layer, which includes the heterocyclic compound.

In one or more embodiments, the emission layer may include the heterocyclic compound.

In one embodiment, the hole transport region may include a p-dopant, which has a lowest unoccupied molecular orbital (LUMO) energy level of −3.5 eV or less.

For example, the p-dopant may include at least one selected from a quinone derivative, a metal oxide, and a cyano group-containing compound.

For example, the hole transport region may include a hole transport layer, and the hole transport layer may include the p-dopant, or the hole transport region may include a hole injection layer, and the hole injection layer may include the p-dopant.

In one embodiment, the electron transport region of the organic light-emitting device may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

In one embodiment, the emission layer may include at least one compound selected from a styryl-based compound, an anthracene-based compound, a pyrene-based compound, a spiro-bifluorene-based compound, a carbazole-based compound, a benzimidazole-based compound, a phosphine oxide-based compound, a dibenzofuran-based compound, a silicon-based compound, and a triazine-based compound.

In one embodiment, the emission layer may be a first emission layer to emit a first color light,
the organic light-emitting device may further include, between the first electrode and the second electrode, i) at least one second emission layer to emit a second color light or ii) at least one second emission layer to emit the second color light and at least one third emission layer to emit a third color light,
a maximum emission wavelength of the first color light, a maximum emission wavelength of the second color light, and a maximum emission wavelength of the third color light are identical to or different from each other, and
the first color light and the second color light may be emitted in the form of mixed light, or the first color light, the second color light, and the third color light may be emitted in the form of mixed light.

The term "an organic layer" as used herein may refer to a single layer and/or a plurality of layers disposed between the first electrode and the second electrode of an organic light-emitting device. Materials included in the "organic layer" are not limited to being organic materials.

For example, the organic light-emitting device may have i) a stacked structure including a first electrode, an organic layer, a second electrode, and a second capping layer sequentially stacked in this stated order, ii) a stacked structure including a first capping layer, a first electrode, an organic layer, and a second electrode sequentially stacked in this stated order, or iii) a stacked structure including a first capping layer, a first electrode, an organic layer, a second electrode, and a second capping layer sequentially stacked in this stated order, and at least one selected from the first capping layer and the second capping layer may include the heterocyclic compound.

[Description of FIG. 1]

Figure 1:
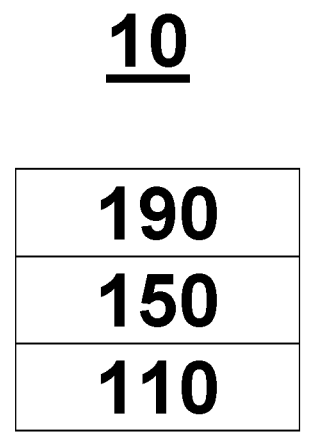

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate and/or a plastic substrate, each having excellent mechanical strength, thermal stability, transparency, surface smoothness, ease of handling, and/or water resistance.

The first electrode 110 may be formed by depositing or sputtering a material to form the first electrode 110 on the substrate. When the first electrode 110 is an anode, the material to form the first electrode 110 may be selected from materials with a high work function to facilitate hole injection.

The first electrode 110 may be a reflective electrode, a semi-reflective electrode, or a transmissive electrode. When the first electrode 110 is a transmissive electrode, a material to form a first electrode may be selected from indium tin oxide (ITO), indium zinc oxide (IZO), tin oxide ($SnO_2$), zinc oxide (ZnO), and combinations thereof, but embodiments of the present disclosure are not limited thereto. In one or more embodiments, when the first electrode 110 is a semi-transmissive electrode or a reflective electrode, a material to form a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein the constituting layers of each structure are sequentially stacked from the first electrode 110 in the stated order, but the structure of the hole transport region is not limited thereto.

The hole transport region may include the heterocyclic compound represented by Formula 1.

In one embodiment, the hole transport region may include at least one selected from m-MTDATA, TDATA, 2-TNATA, NPB(NPD), p-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

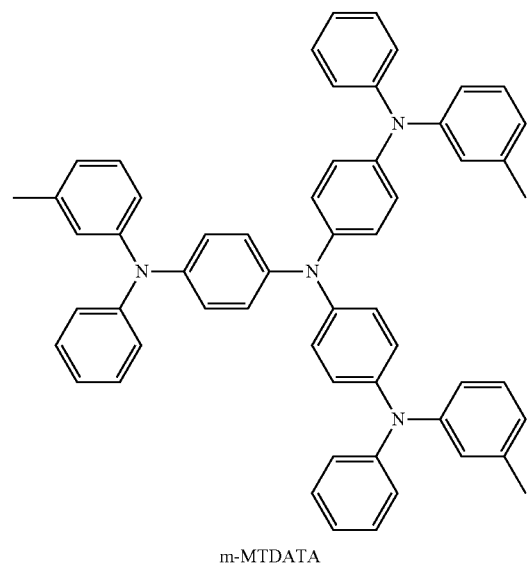

m-MTDATA

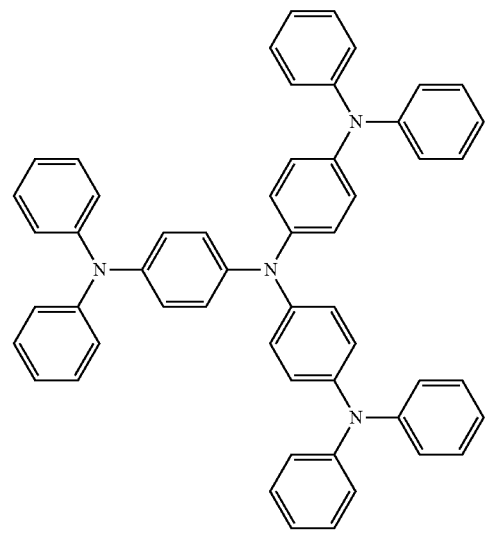

TDATA

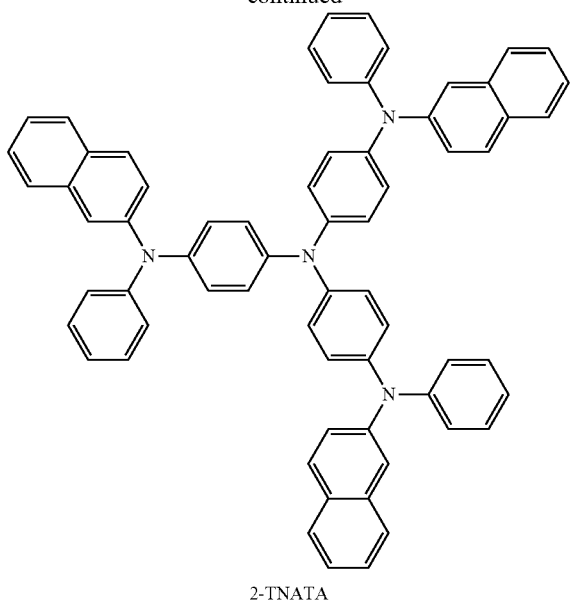
2-TNATA
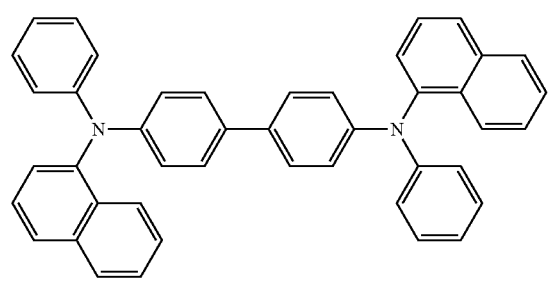
NPB
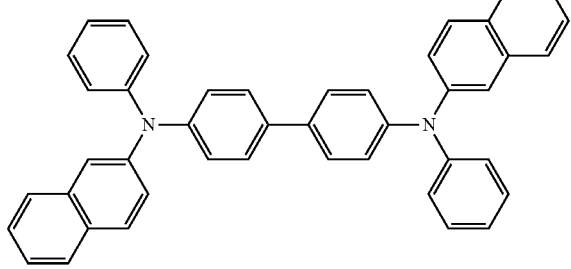
β-NPB
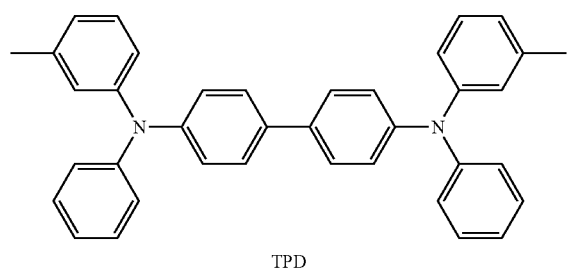
TPD
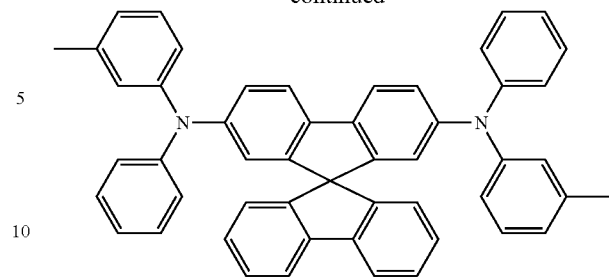
Spiro-TPD
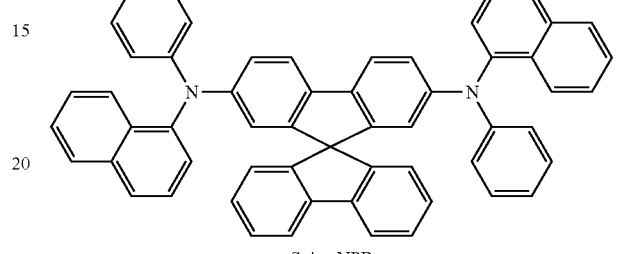
Spiro-NPB
methylated NPB
TAPC
HMTPD
Formula 201
$$R_{201}\!-\!(L_{201})_{xa1}\!-\!N\!\begin{array}{c}(L_{202})_{xa2}\!-\!R_{202}\\(L_{203})_{xa3}\!-\!R_{203},\end{array}$$

Formula 202

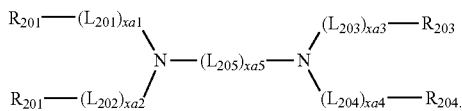

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202, $R_2$ and $R_{202}$ may optionally be linked to each other via a single bond, a dimethyl-methylene group, or a diphenyl-methylene group, and $R_{203}$ and $R_{204}$ may optionally be linked to each other via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_1$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked to each other via a single bond, and/or ii) $R_{203}$ and $R_{204}$ may be linked to each other via a single bond.

In one or more embodiments, at least one selected from $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

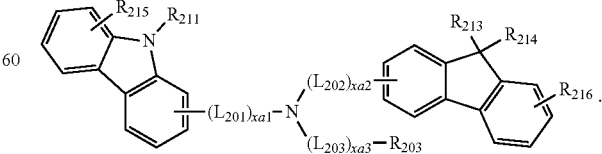

Formula 201A

In one embodiment, the compound represented by Formula 201 may be represented by Formula 201A(1), but embodiments of the present disclosure are not limited thereto:

Formula 201A(1)

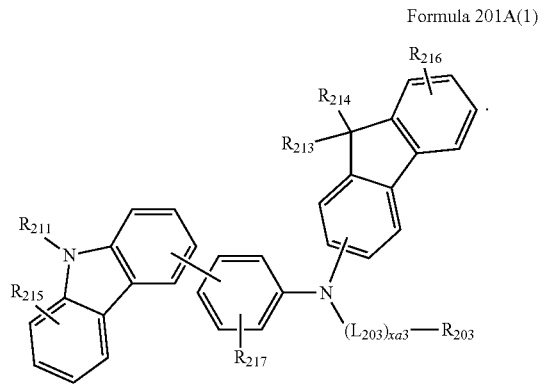

In one or more embodiments, the compound represented by Formula 201 may be represented by Formula 201A-1, but embodiments of the present disclosure are not limited thereto:

Formula 201A-1

In one embodiment, the compound represented by Formula 202 may be represented by Formula 202A:

Formula 202A

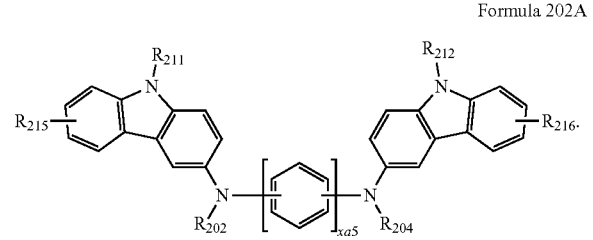

In one or more embodiments, the compound represented by Formula 202 may be represented by Formula 202A-1:

Formula 202A-1

In Formulae 201A, 201A(1), 201A-1, 202A, 202A-1, $L_{201}$ to $L_{203}$, xa1 to xa3, xa5, and $R_{202}$ to $R_{204}$ may each be understood by referring to the corresponding descriptions presented herein, $R_{211}$ and $R_{212}$ may each be understood by referring to the description presented in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

131 HT1
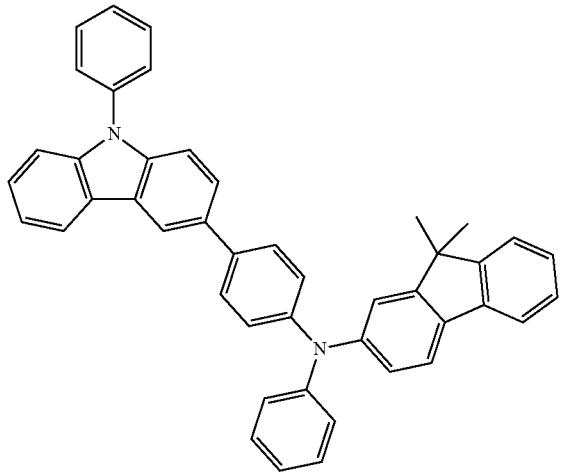
132 HT2
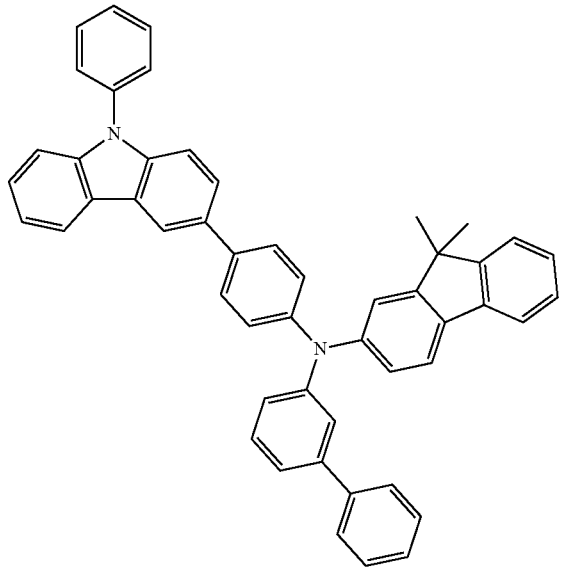
HT3
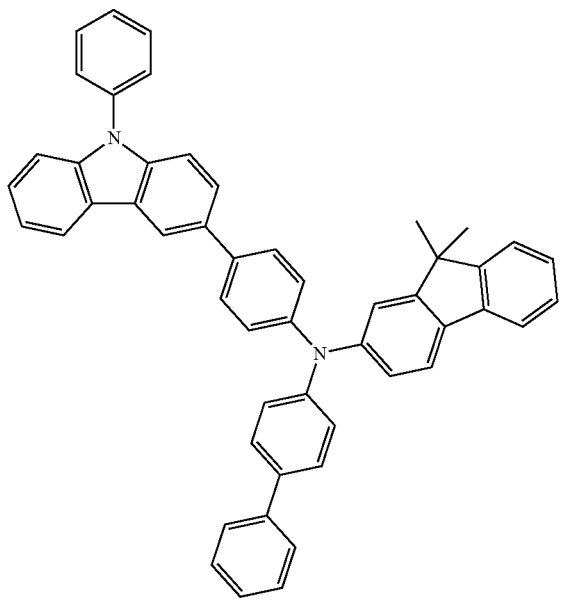
HT4
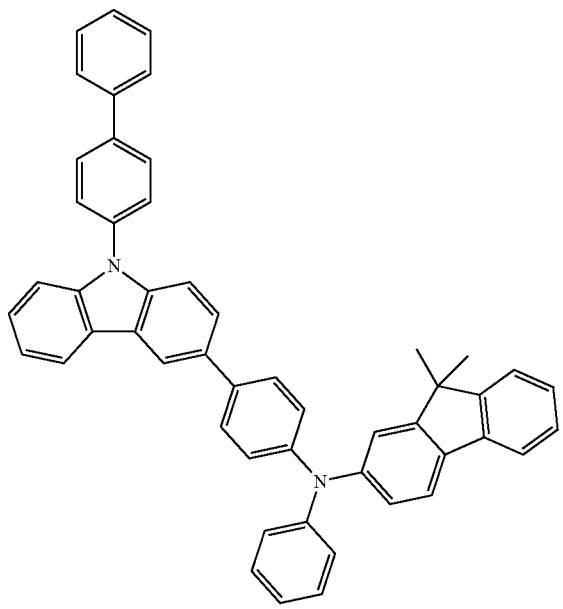

-continued
HT5
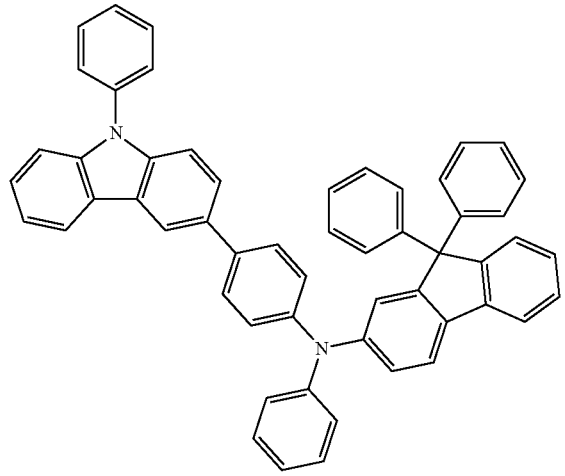
HT6
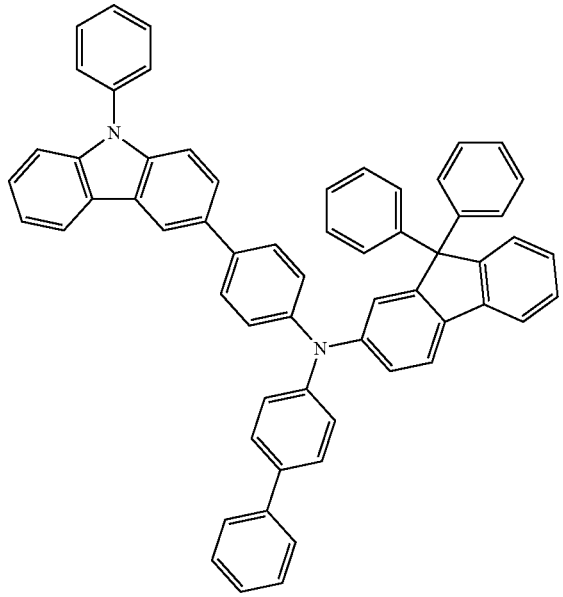
HT7
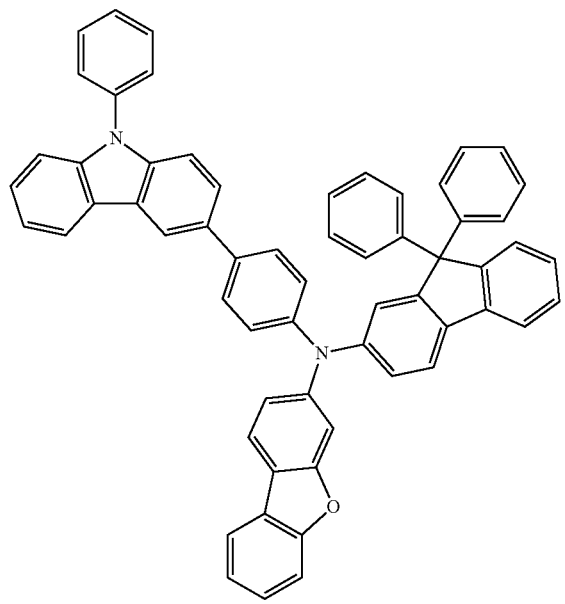
HT8
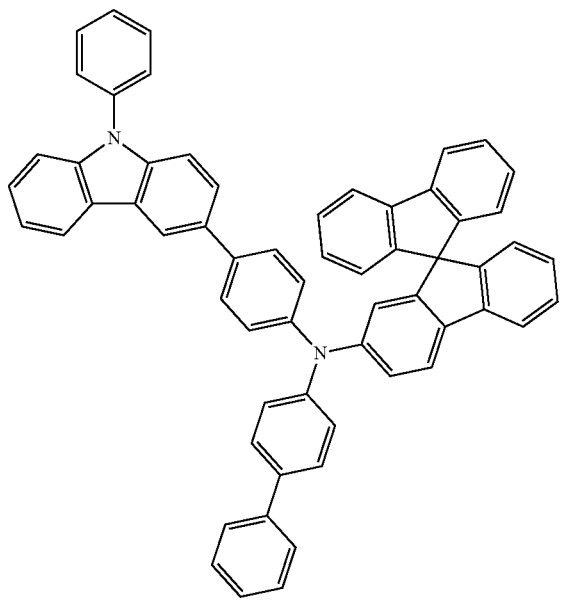

HT9
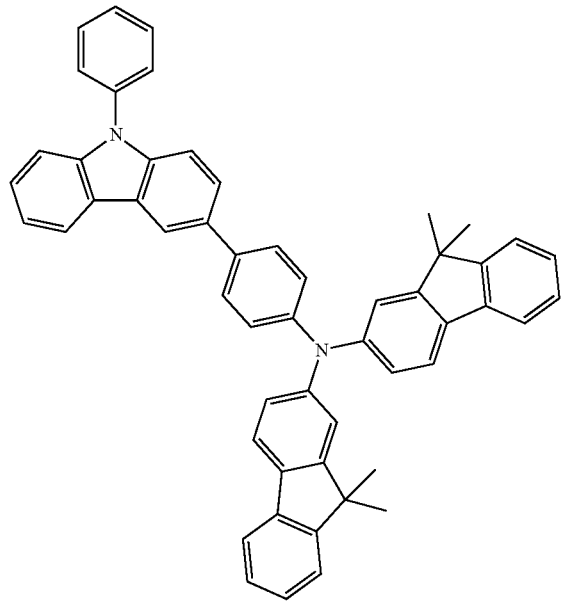
HT10
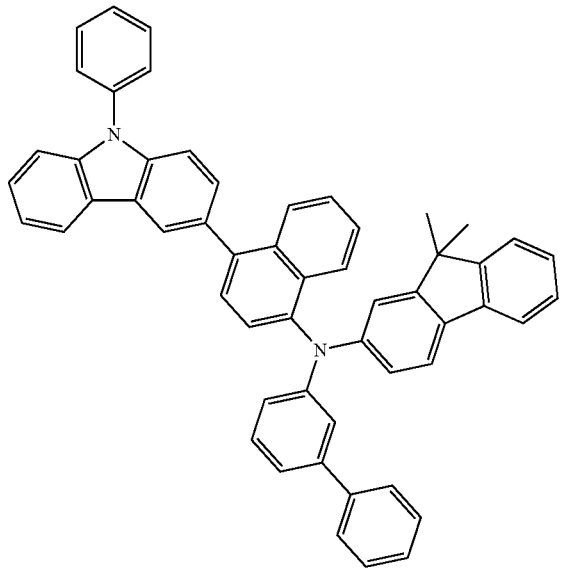
HT11
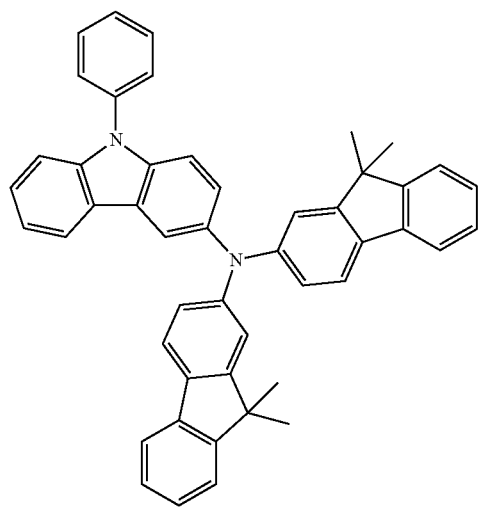
HT12
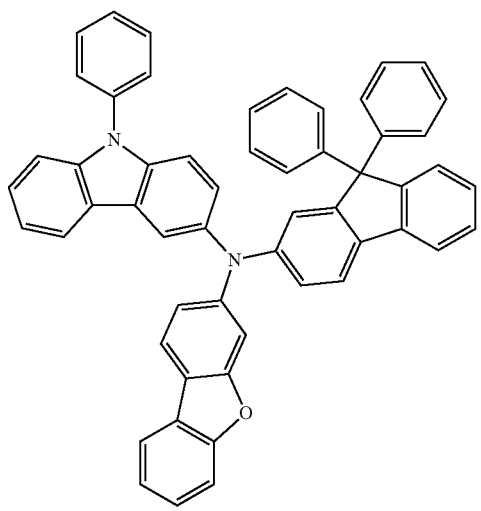

-continued
HT13
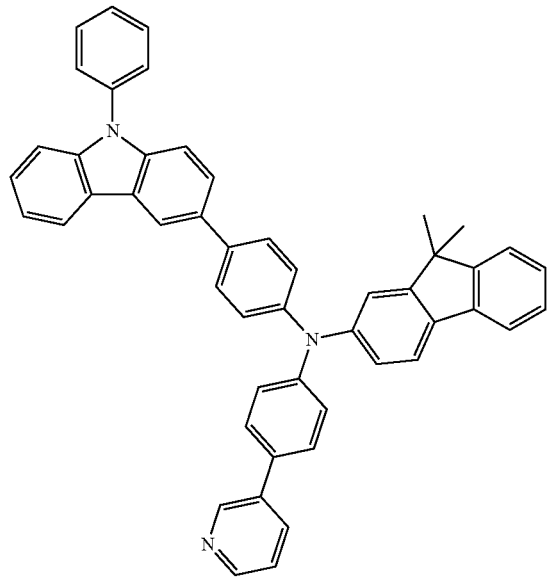
HT14
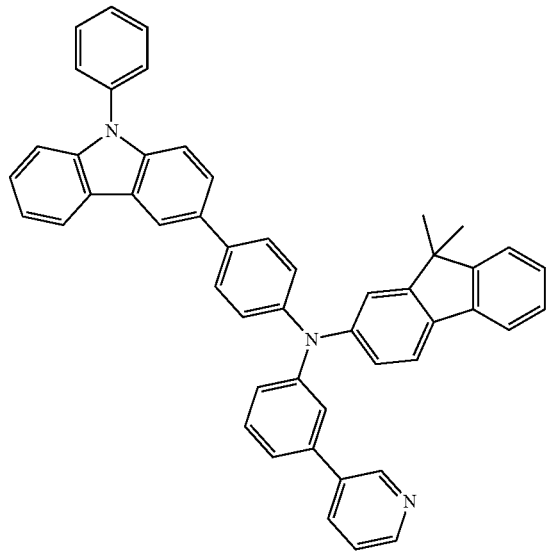
HT15
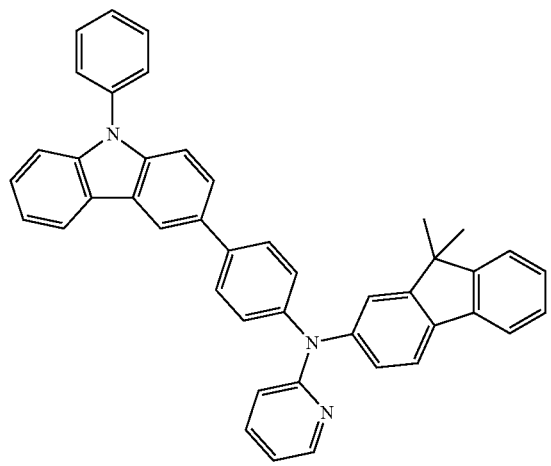
HT16
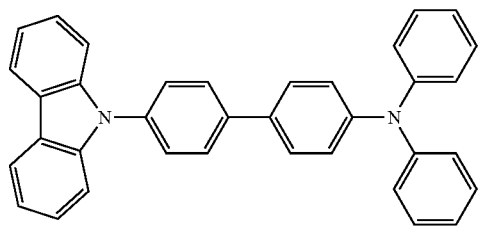
HT17
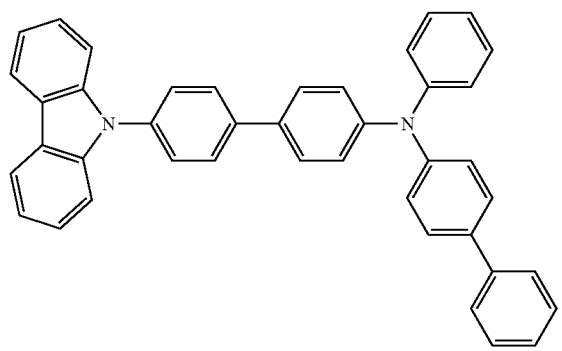
HT18
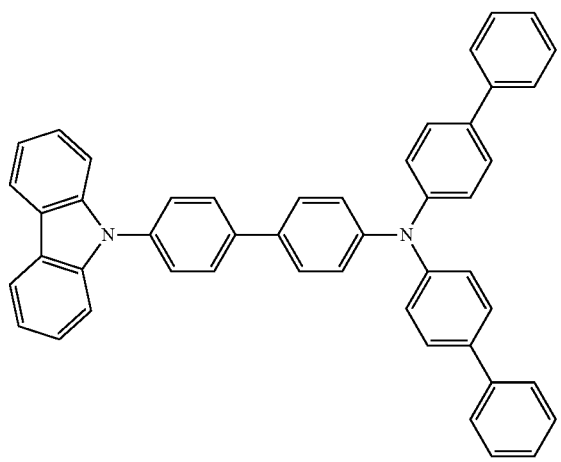

-continued
HT19
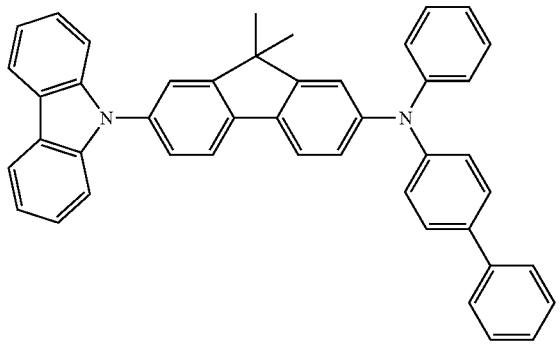
HT20
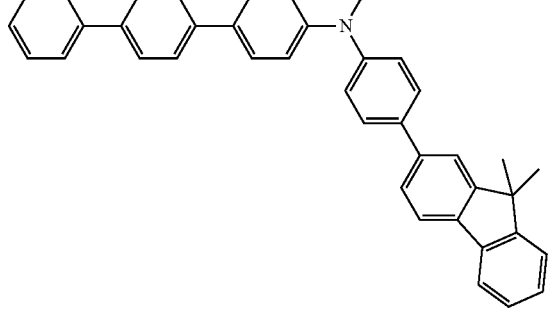
HT21
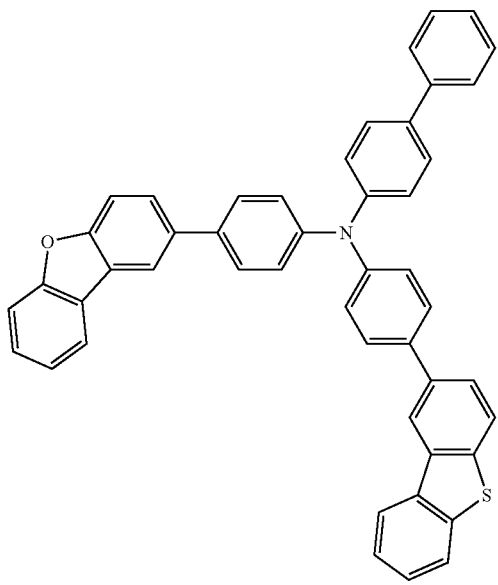
HT22
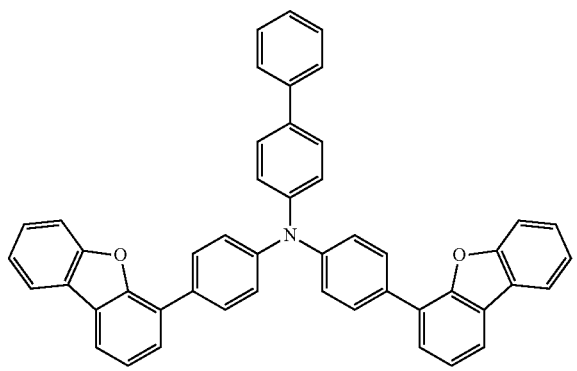

HT23
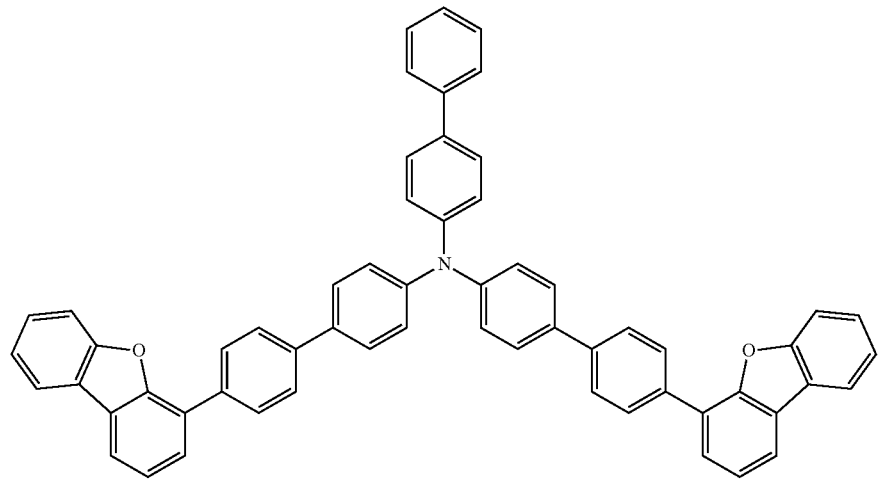
HT24
HT25
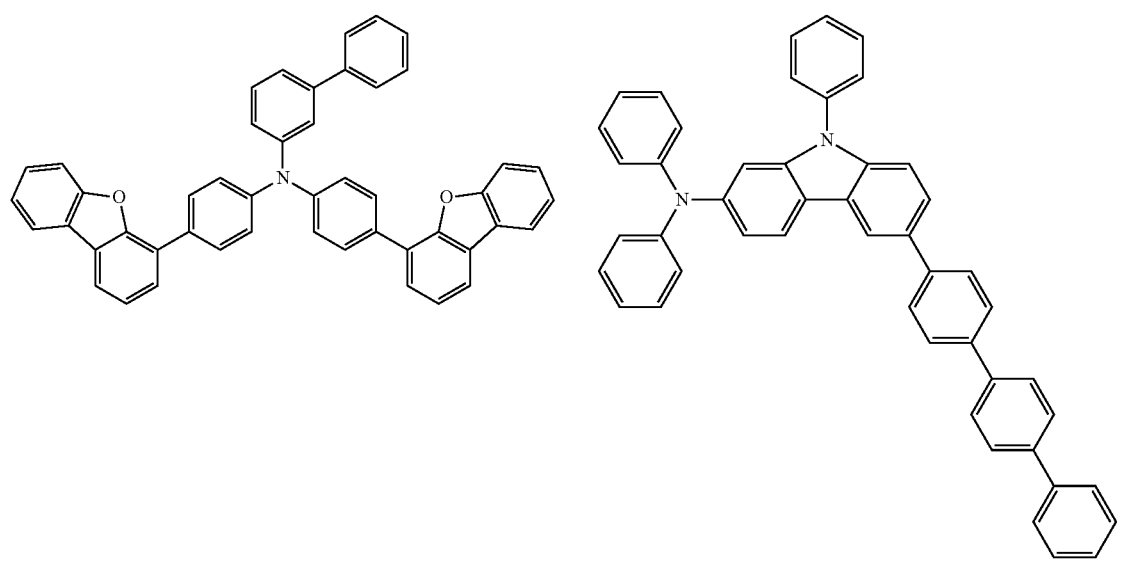
HT26
HT27
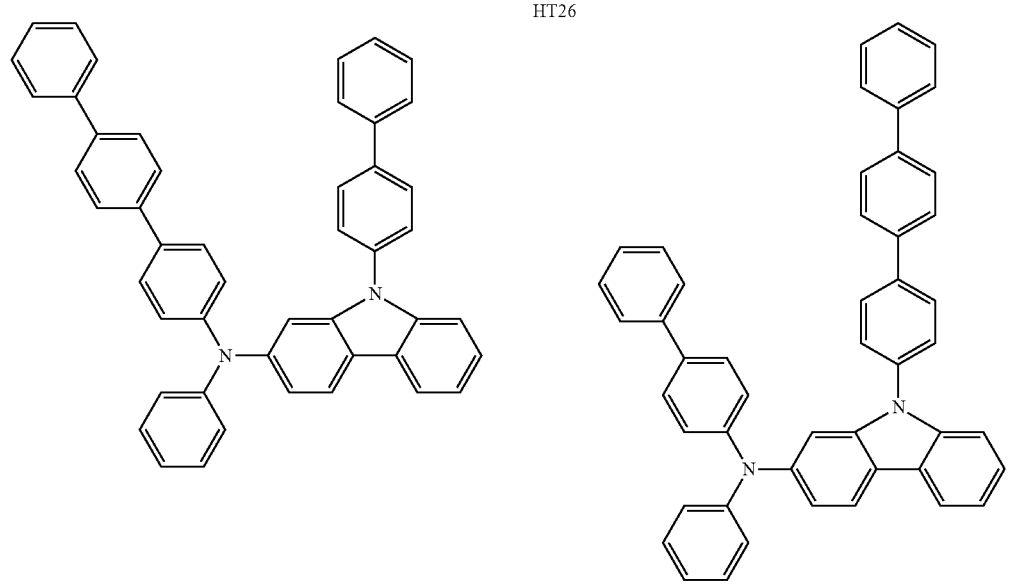

-continued
HT28
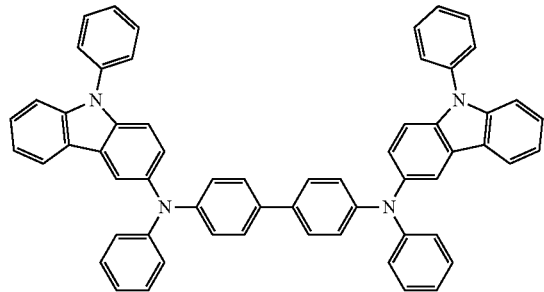
HT29
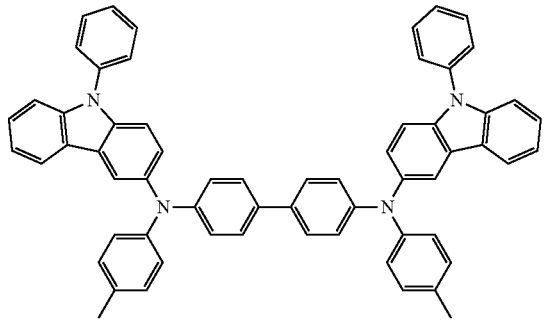
HT30
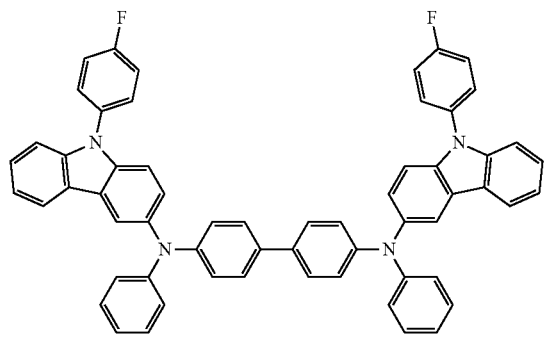
HT31
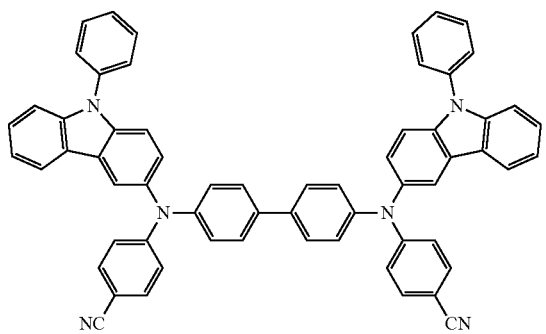
HT32
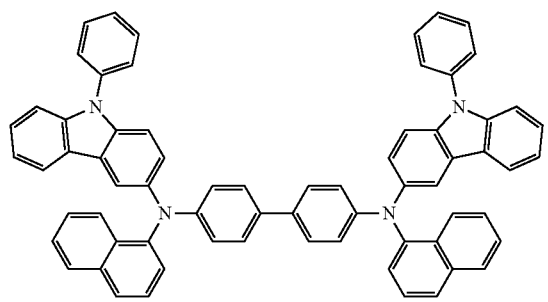
HT33
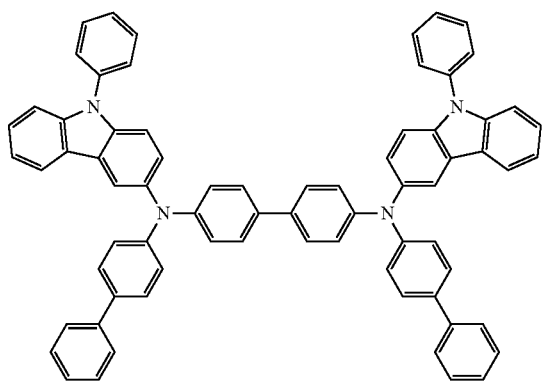
HT34
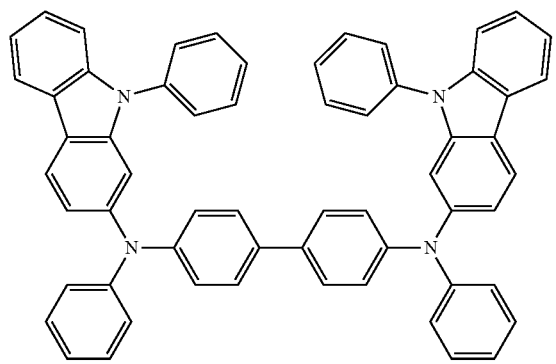
HT35
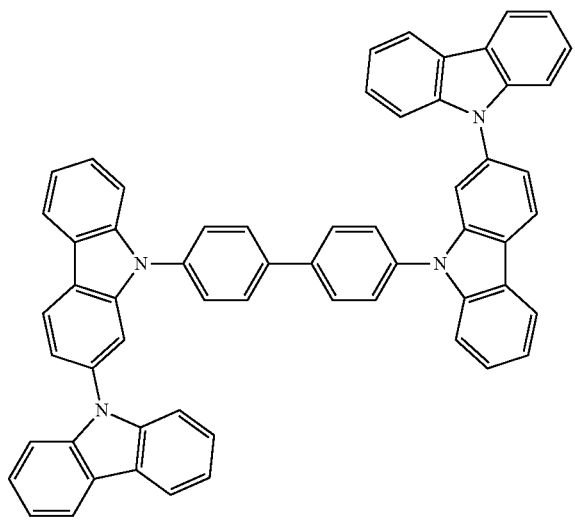

-continued

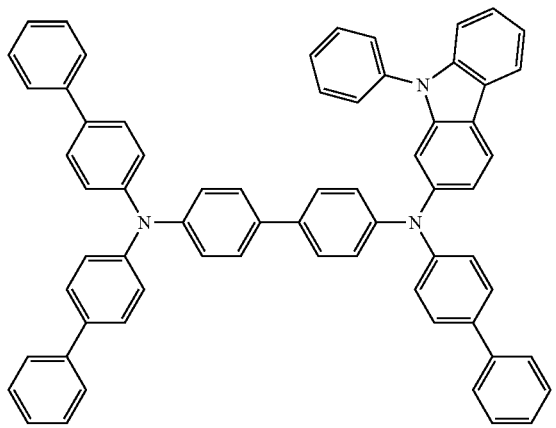

HT36

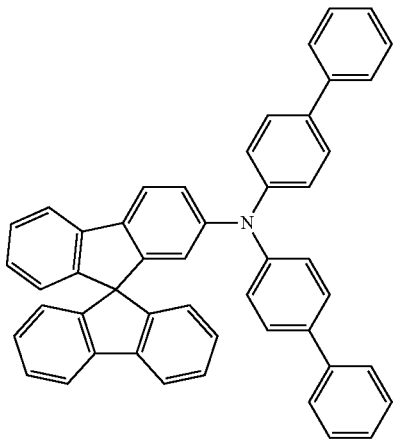

HT37

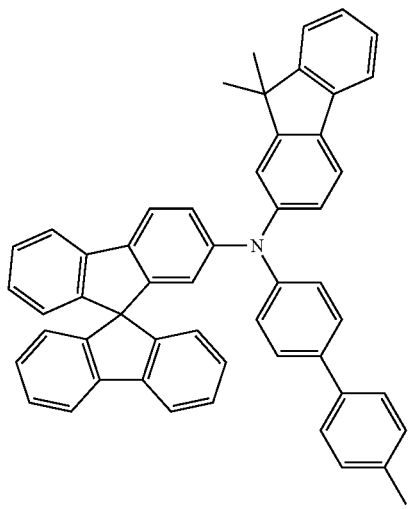

HT38

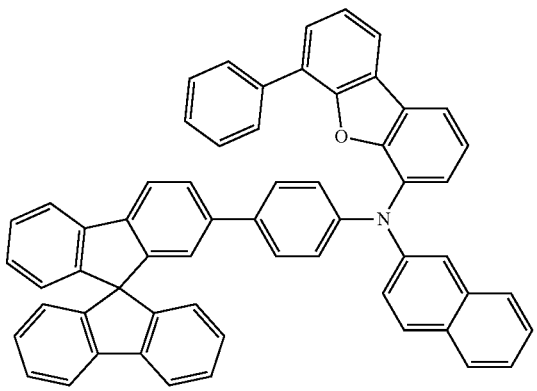

HT39

The hole transport region may have a thickness of about 100 Å to about 10,000 Å, for example, about 100 Å to about 3,000 Å. When the hole transport region includes at least one selected from a hole injection layer and a hole transport layer, the hole injection layer may have a thickness of about 100 Å to about 9,000 Å, for example, about 100 Å to about 1,000 Å, and the hole transport layer may have a thickness of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may include the materials described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a LUMO energy level of −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:

a quinone derivative (such as tetracyanoquinodimethane (TCNQ) and/or 2,3,5,6-tetrafluoro-7,7,8,8-tetracyanoquinodimethane (F4-TCNQ));

a metal oxide (such as tungsten oxide and/or molybdenum oxide);

1,4,5,8,9,12-hexaazatriphenylene-hexacarbonitrile (HAT-CN); and a compound represented by Formula 221:
but embodiments of the present disclosure are not limited thereto:

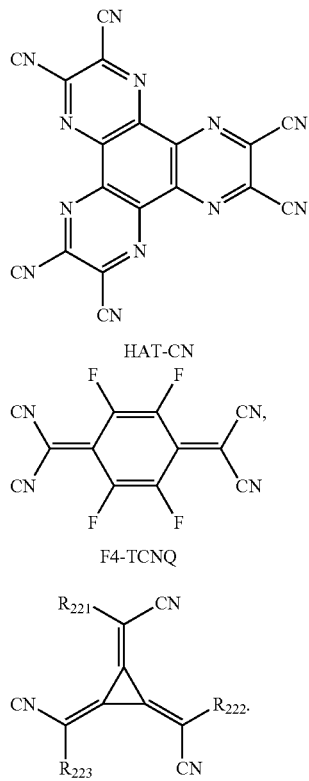

HAT-CN

F4-TCNQ

Formula 221

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers may contact each other or may be separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer the dopant may be included in an amount of about 0.01 parts by weight to about 15 parts by weight based on 100 parts by weight of the host, but embodiments of the present disclosure are not limited thereto.

The emission layer may have a thickness of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In one or more embodiments, the host may include a compound represented by Formula 301:

Formula 301

In Formula 301,
$Ar_{301}$ may be a substituted or unsubstituted $C_5$-$C_{60}$ carbocyclic group or a substituted or unsubstituted $C_1$-$C_{60}$ heterocyclic group,
xb11 may be 1, 2, or 3,
$L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
xb1 may be an integer from 0 to 5,
$R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$),
xb21 may be an integer from 1 to 5, and
$Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:
a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is 2 or more, two or more $Ar_{301}$(s) may be linked to each other via a single bond.

In one or more embodiments, the compound represented by Formula 301 may be represented by Formula 301-1 or Formula 301-2:

group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each be understood by referring to the corresponding descriptions presented herein, $L_{302}$ to $L_{304}$ may each be understood by referring to the description presented in connection with $L_{301}$, xb2 to xb4 may each be understood by referring to the description presented in connection with xb1, and $R_{302}$ to $R_{304}$ may each be understood by referring to the description presented in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a

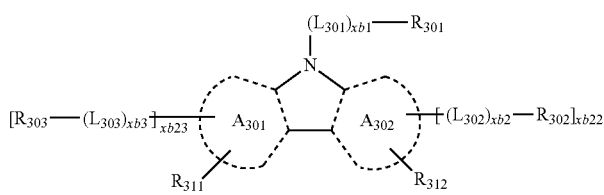

Formula 301-1

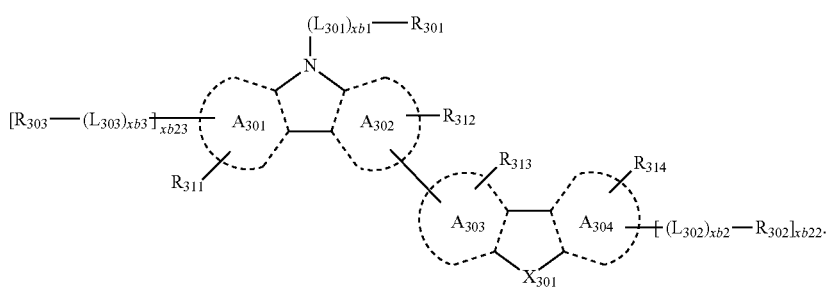

Formula 301-2

In Formulae 301-1 and 301-2, $A_{301}$ to $A_{304}$ may each independently be selected from a benzene, a naphthalene, a phenanthrene, a fluoranthene, a triphenylene, a pyrene, a chrysene, a pyridine, a pyrimidine, an indene, a fluorene, a spiro-bifluorene, a benzofluorene, a dibenzofluorene, an indole, a carbazole, benzocarbazole, dibenzocarbazole, a furan, a benzofuran, a dibenzofuran, a naphthofuran, a benzonaphthofuran, dinaphthofuran, a thiophene, a benzothiophene, a dibenzothiophene, a naphthothiophene, a benzonaphthothiophene, and a dinaphthothiophene, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be the same as described above.

In one or more embodiments, the host may include an alkaline earth metal complex. For example, the host may be selected from a Be complex (for example, Compound H55) and a Mg complex. In some embodiments, the host may include a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1

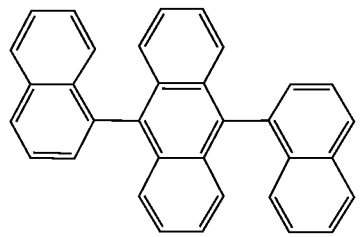

H2

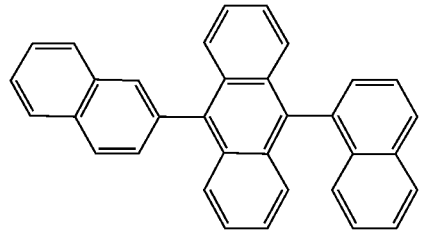

H3

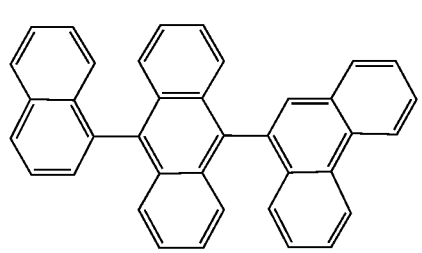

H4

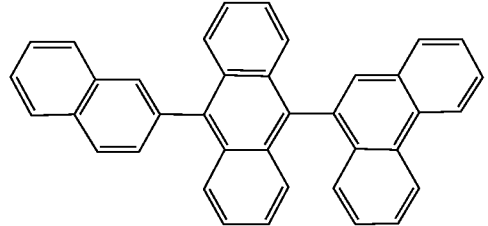

H5

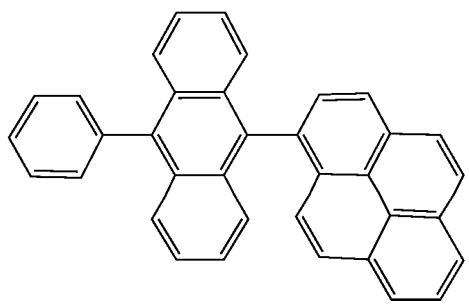

H6

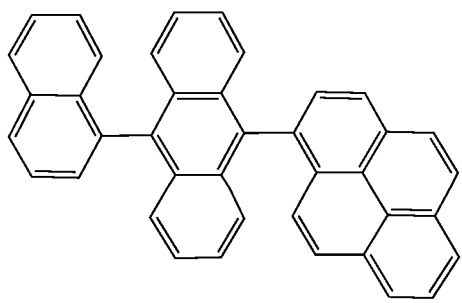

H7

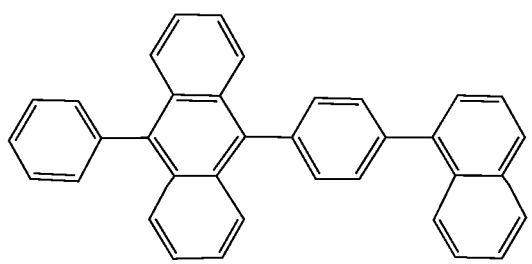

H8

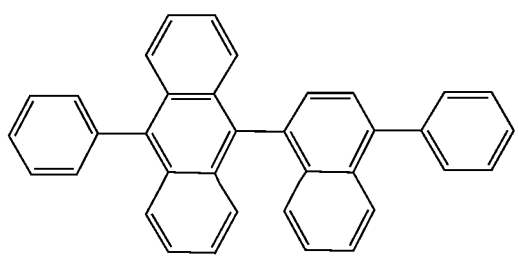

H9

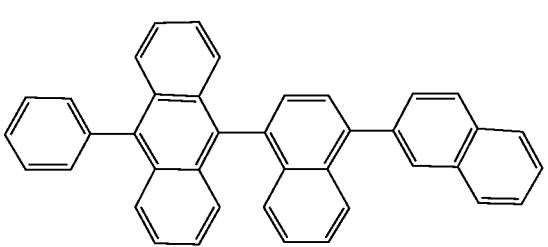

H10
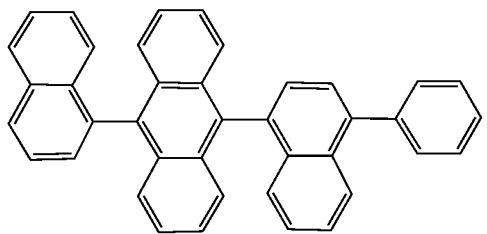
H15
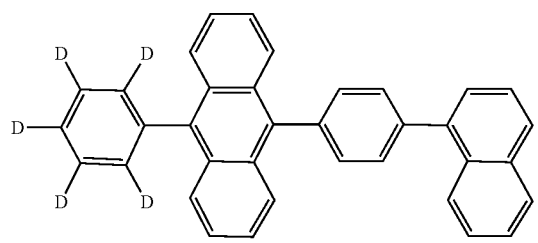
H11
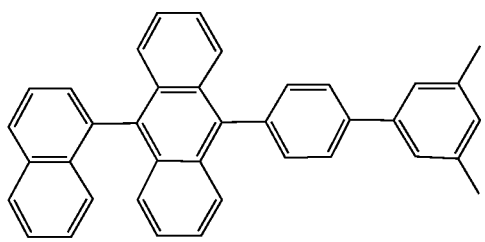
H16
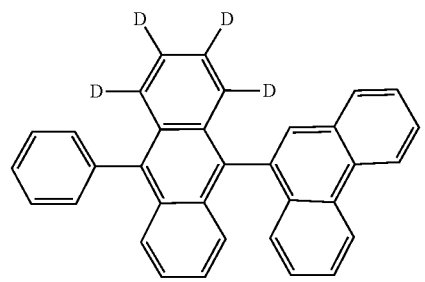
H12
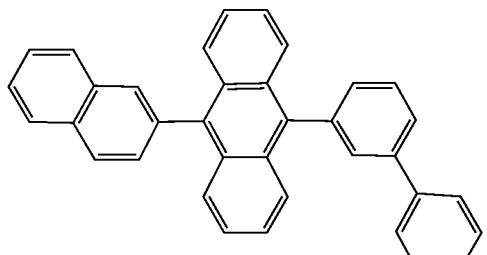
H17
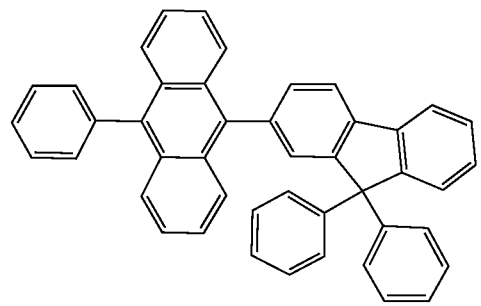
H13
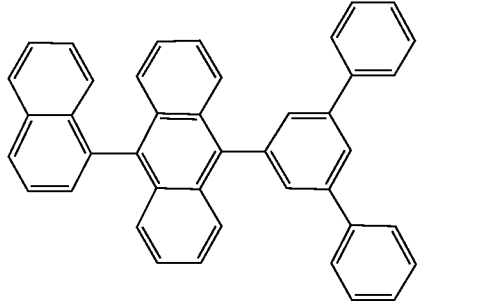
H18
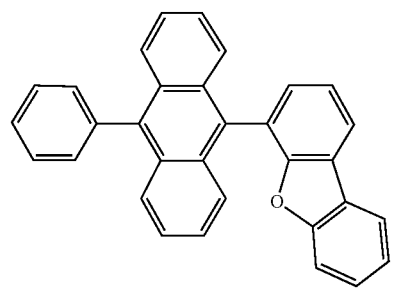
H14
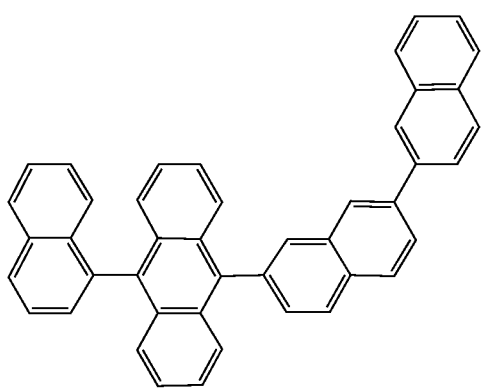
H19
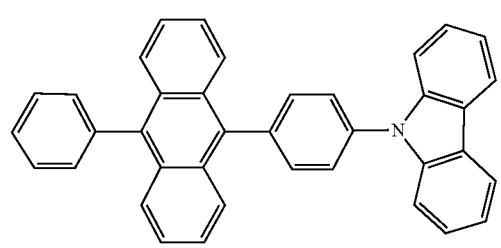

-continued
H20
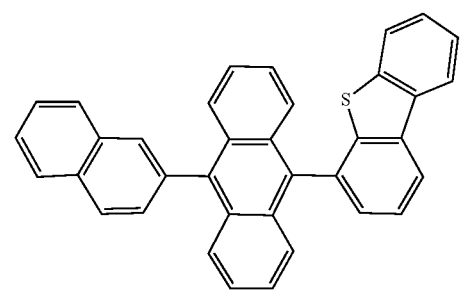
H21
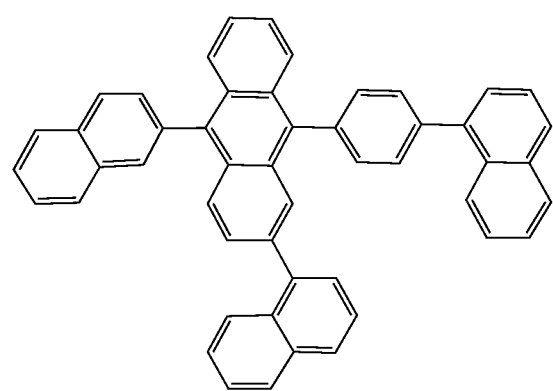
H22
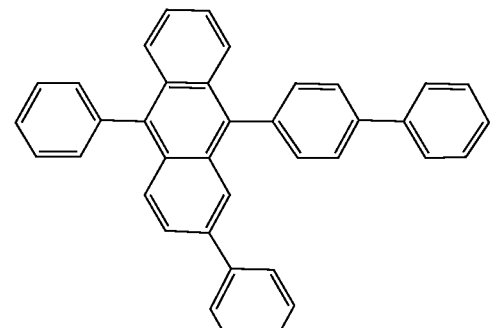
H23
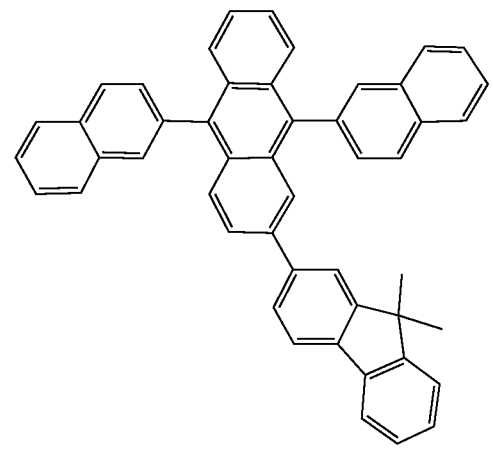
-continued
H24
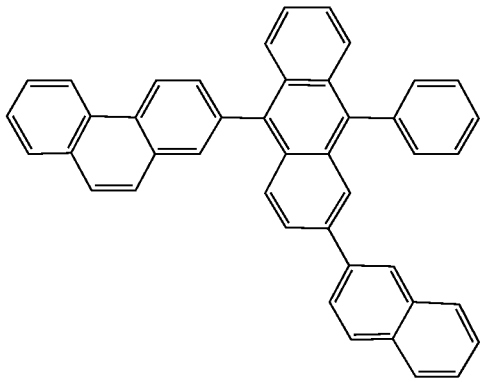
H25
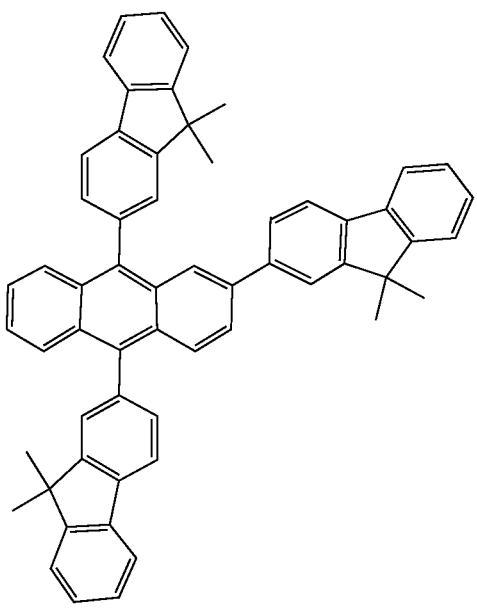
H26
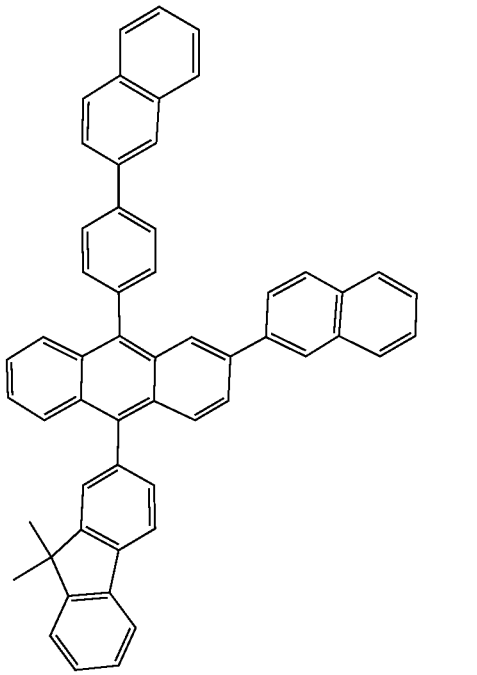

159
-continued
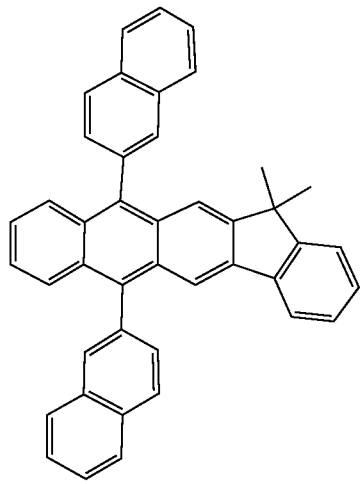
H27
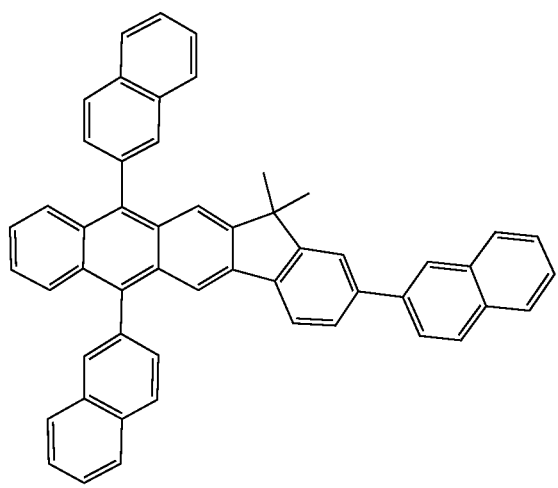
H28
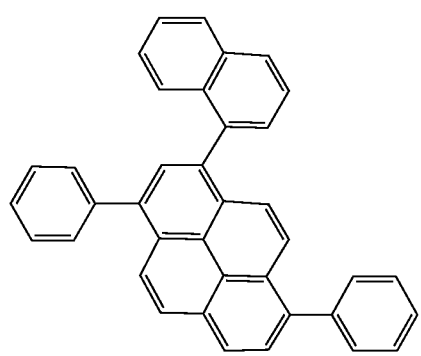
H29
160
-continued
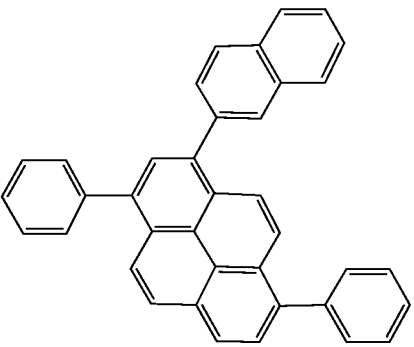
H30
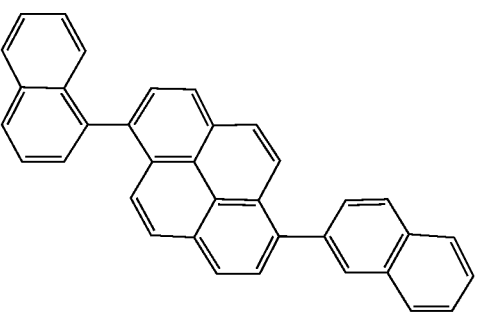
H31
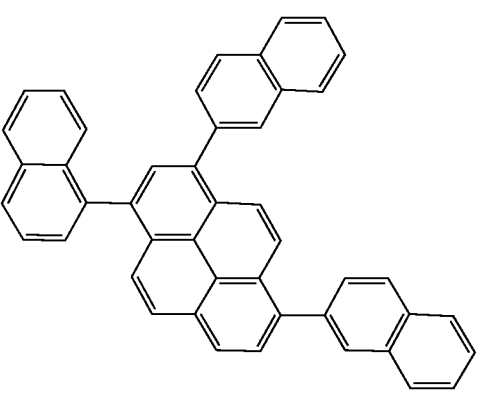
H32
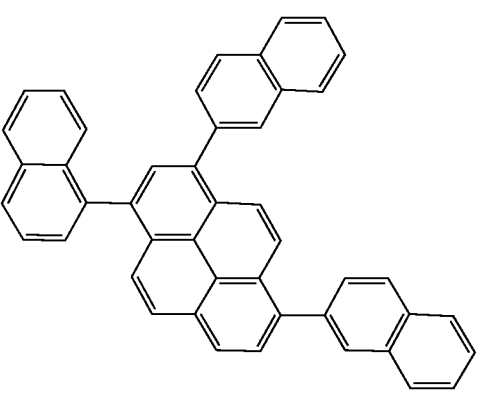
H33
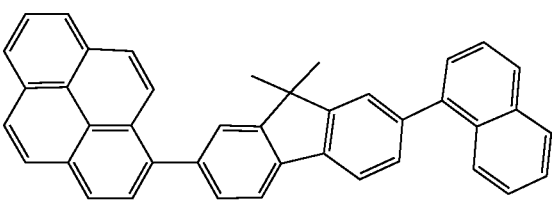
H34

-continued
H35
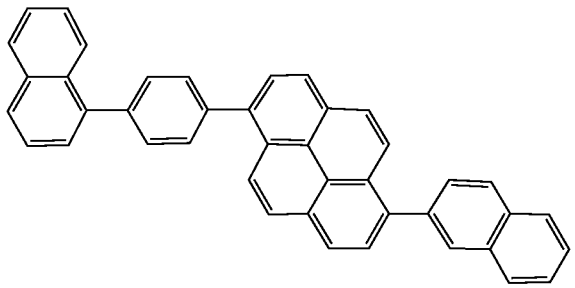
H36
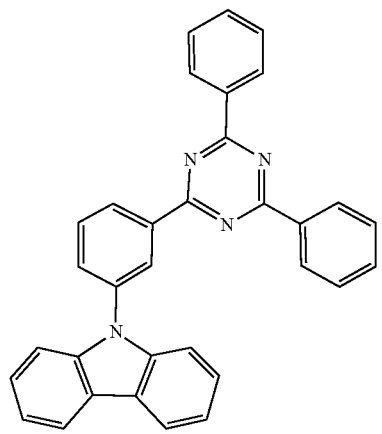
H37
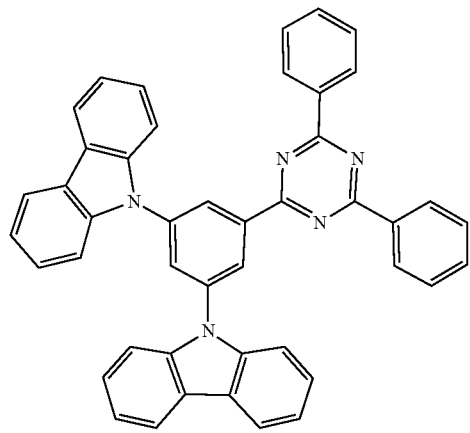
H38
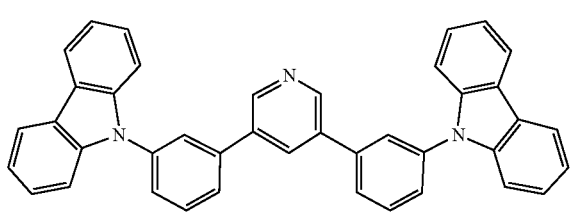
-continued
H39
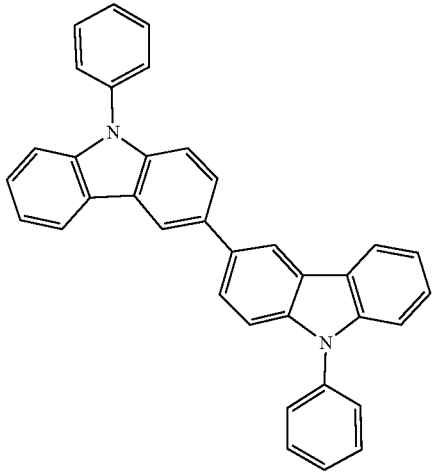
H40
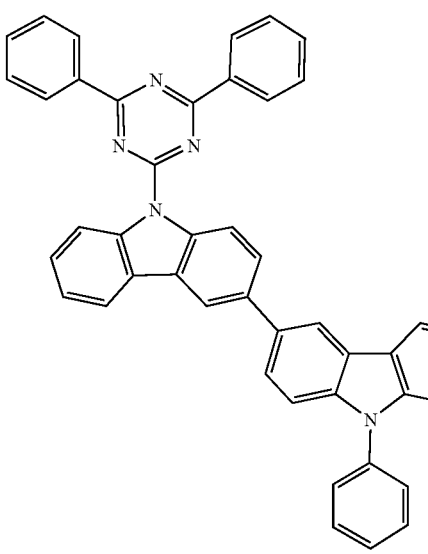
H41
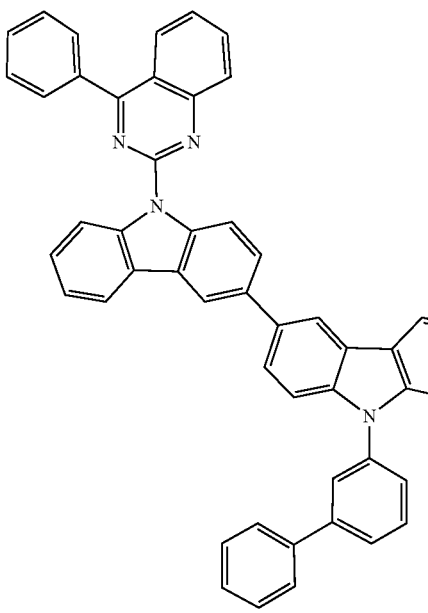

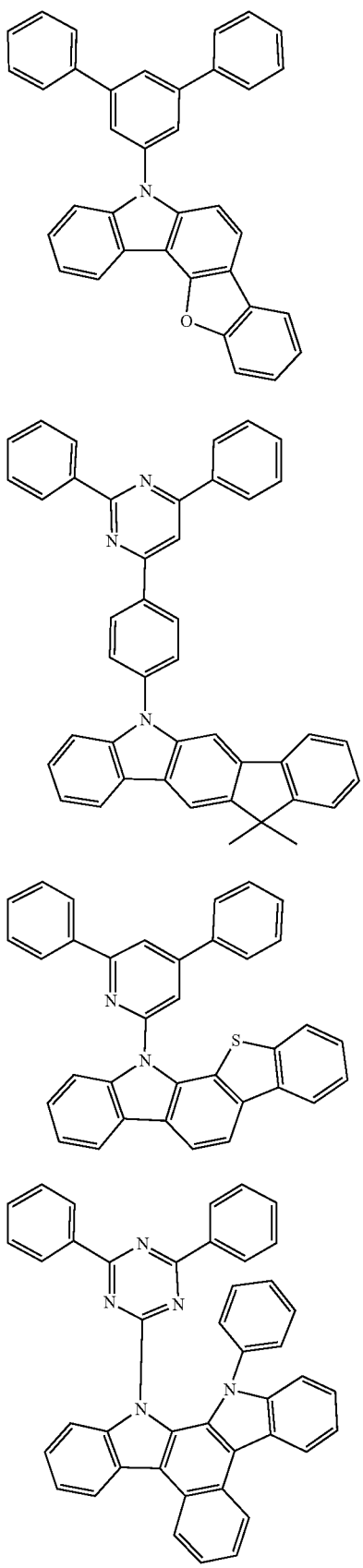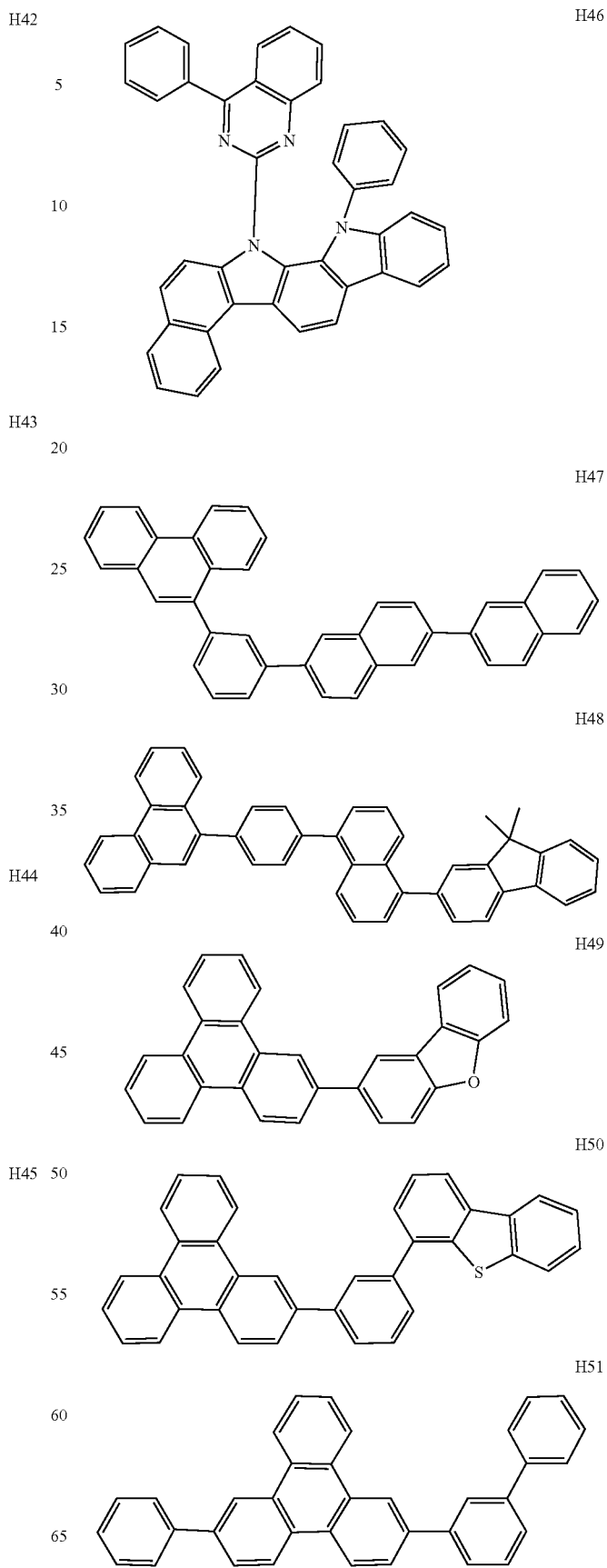

-continued

H52

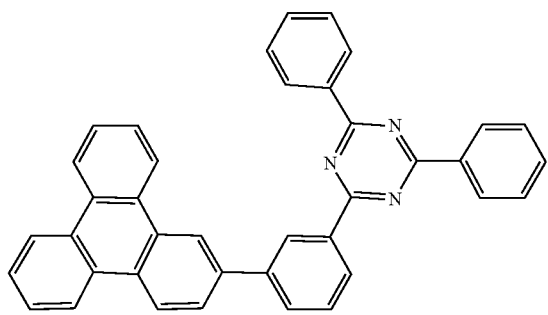

H53

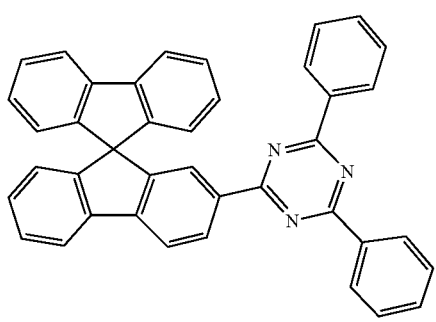

H54

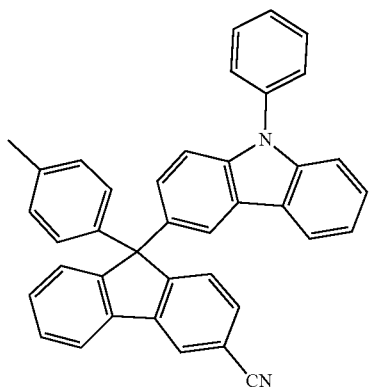

H55

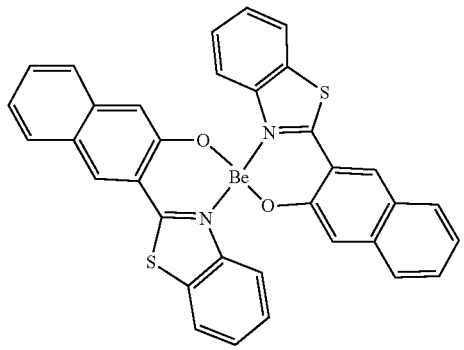

[Phosphorescent Dopant Included in Emission Layer in Organic Layer 150]

The phosphorescent dopant may include an organometallic complex represented by Formula 401:

Formula 401

$M(L_{401})_{xc1}(L_{402})_{xc2}$,

-continued

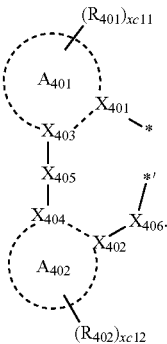

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein when xc1 is two or more, two or more $L_{401}$(s) may be identical to or different from each other, $L_{402}$ may be an organic ligand, and xc2 may be an integer from 0 to 4, wherein, when xc2 is 2 or more, two or more $L_{402}$(s) may be identical to or different from each other, $X_{401}$ to $X_{404}$ may each independently be nitrogen or carbon, $X_{401}$ and $X_{403}$ may be linked to each other via a single bond or a double bond, and $X_{402}$ and $X_{404}$ may be linked to each other via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)*', *—C($Q_{411}$)=C($Q_{412}$)-*, *—C($Q_{411}$)=*', or *=C($Q_{411}$)=*', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and \* and \*' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time (e.g., simultaneously).

In one or more embodiments, $R_{401}$ and $R_{402}$ in Formula 501 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanylgroup, and a norbornenylgroup;

a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantly group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantly group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is 2 or more, two $A_{401}$(s) in two or more $L_{401}$(s) may optionally be linked to each other via $X_{407}$, which is a linking group, or two $A_{402}$(s) in two or more $L_{401}$(s) may optionally be linked to each other via $X_{408}$, which is a linking group (see Compounds PD1 to PD4 and PD7). $X_{407}$ and $X_{408}$ may each independently be a single bond, *—O—*', *—S*', *—C(=O)—*' *—N($Q_{413}$)-*', *—C($Q_{413}$)($Q_{414}$)-*', or *—C($Q_{413}$)=C($Q_{414}$)*' (wherein 0413 and 0414 may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine or phosphite), but embodiments of the present disclosure are not limited thereto.

In one or more embodiments, the phosphorescent dopant may be selected from, for example, Compounds PD1 to PD25, but embodiments of the present disclosure are not limited thereto:

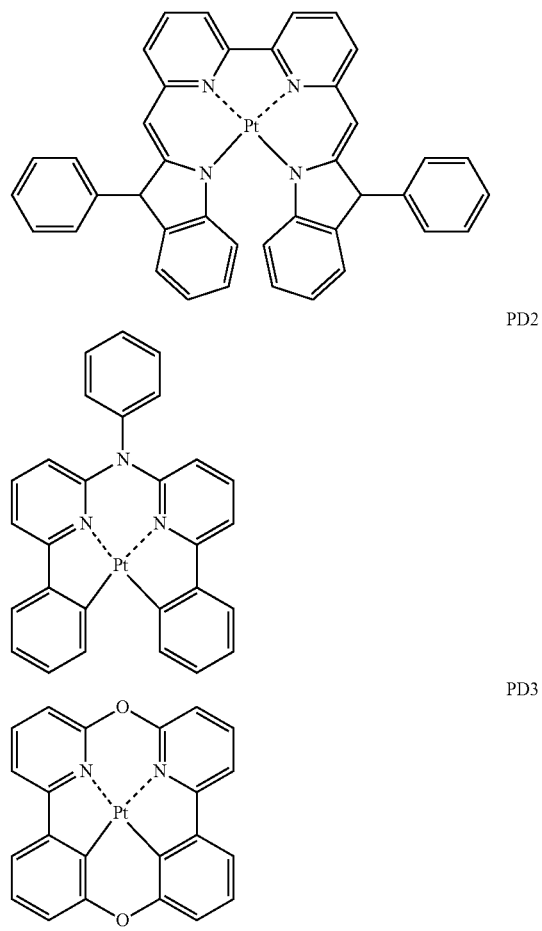

PD1

PD2

PD3

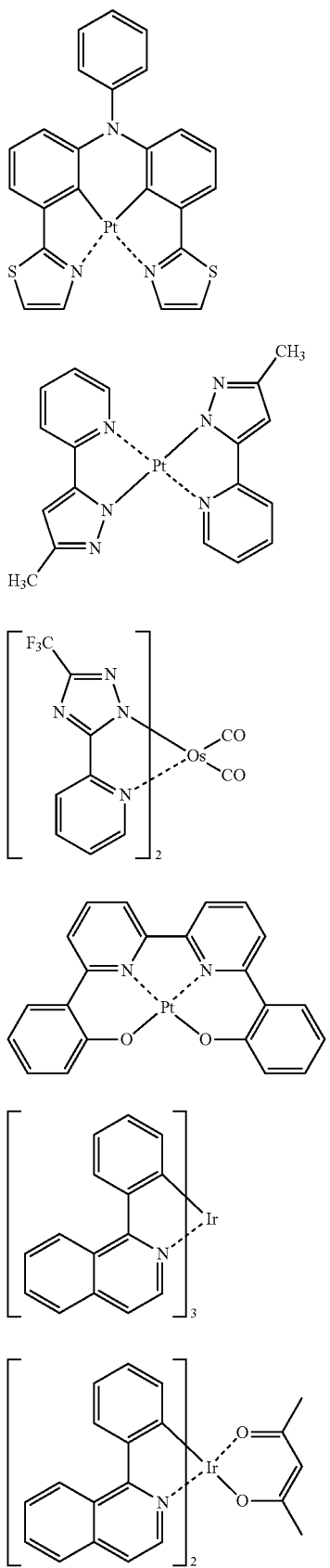

PD15 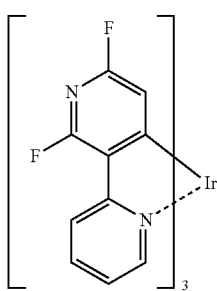
PD16 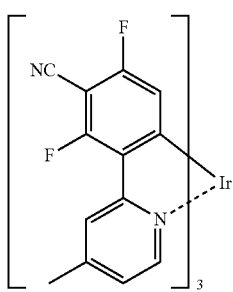
PD17 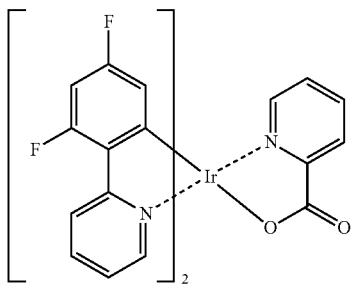
PD18 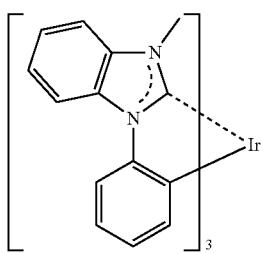
PD19 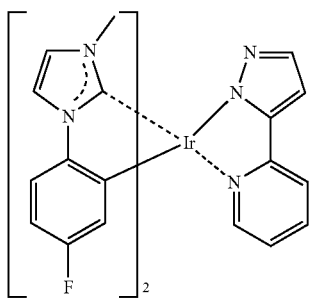
PD20 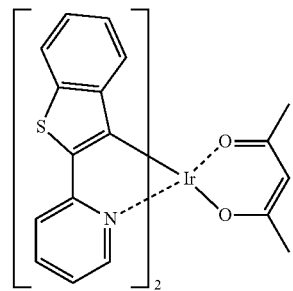
PD21 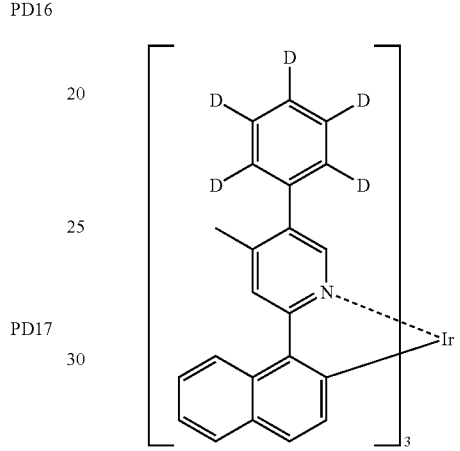
PD22 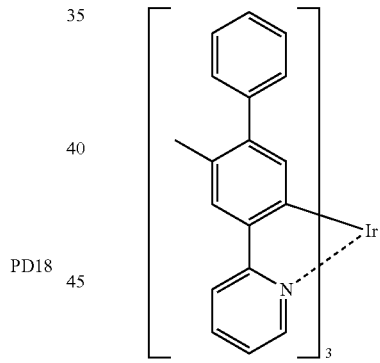
PD23 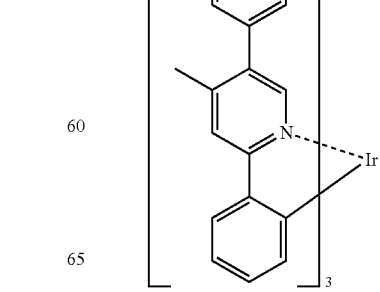

-continued

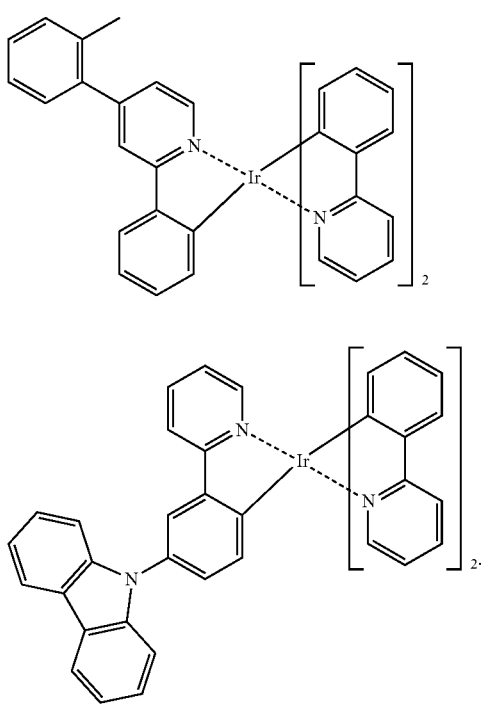

PD24

PD25

[Fluorescent Dopant in Emission Layer]

The fluorescent dopant may include an arylamine compound or a styrylamine compound.

The fluorescent dopant may include a compound represented by Formula 501:

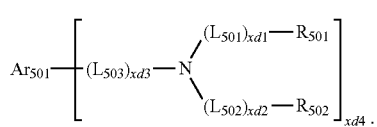

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

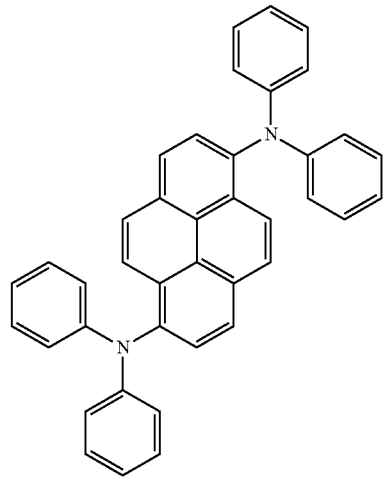

FD1

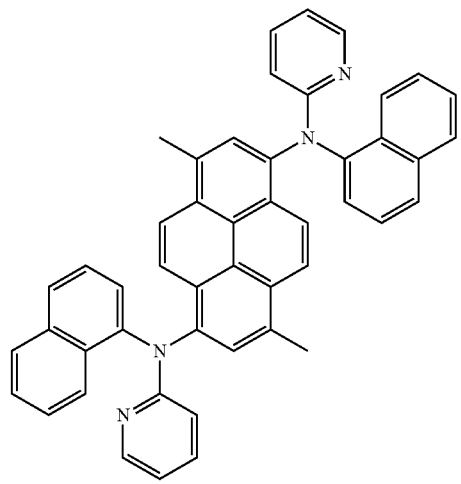

FD2

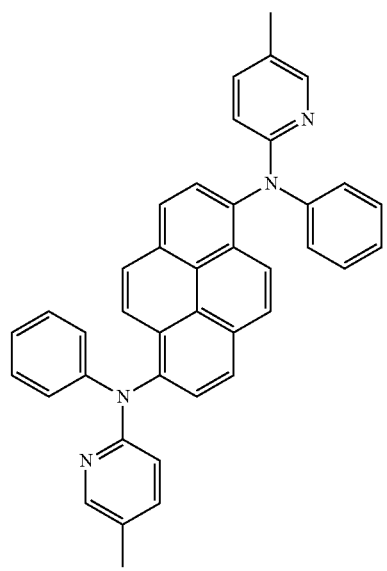

FD3

FD4
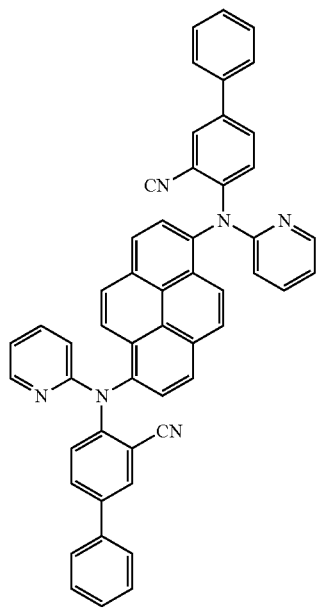
FD7
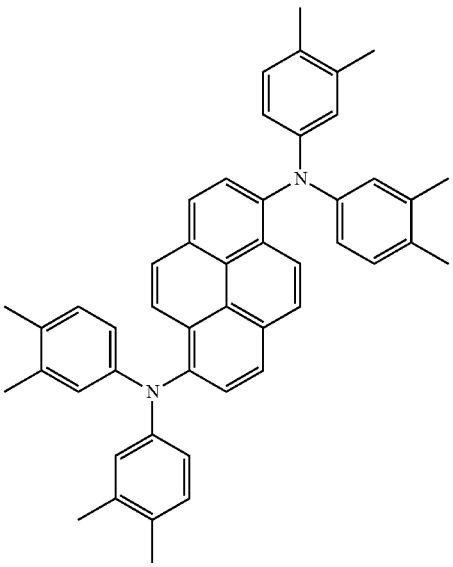
FD5
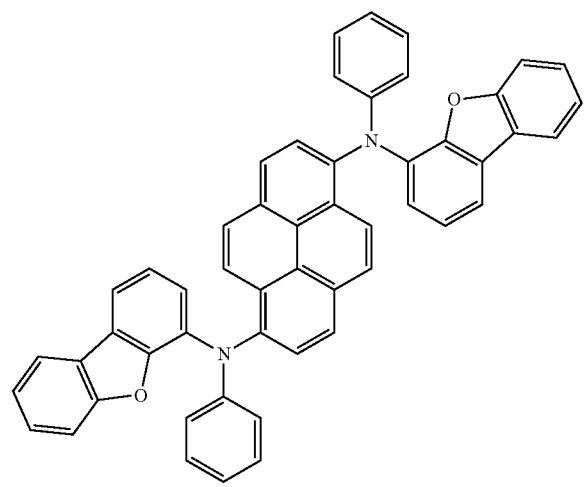
FD8
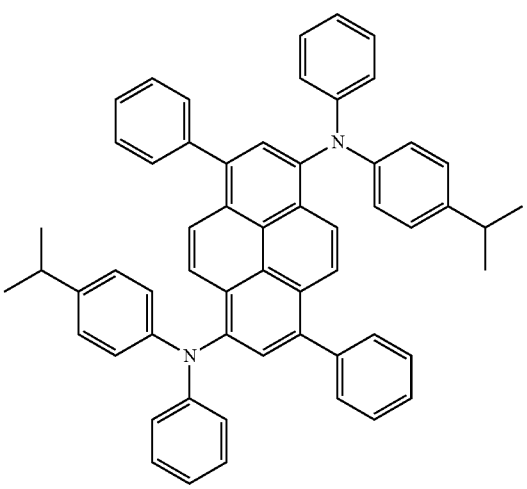
FD6
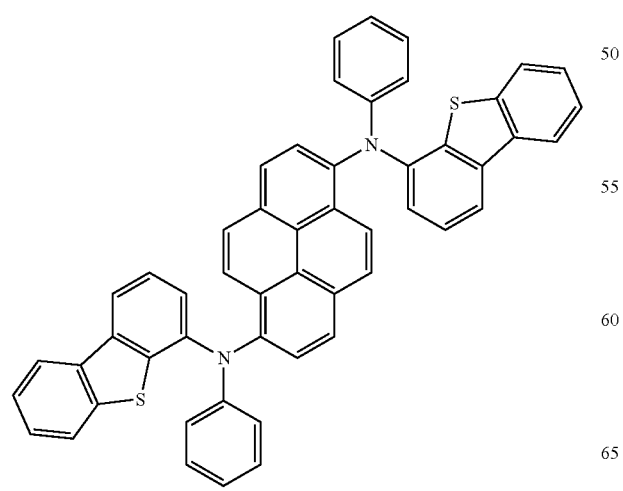
FD9
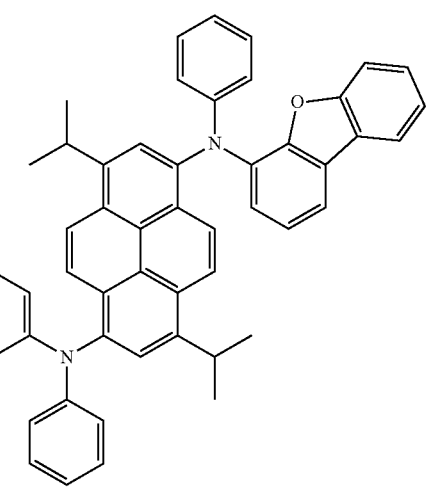

FD10
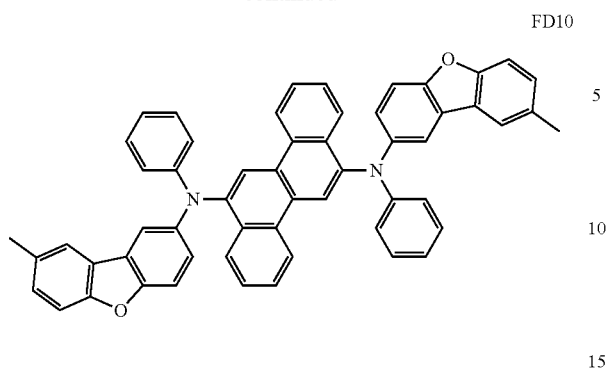
FD11
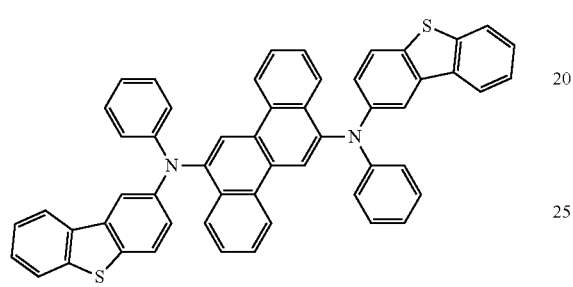
FD12
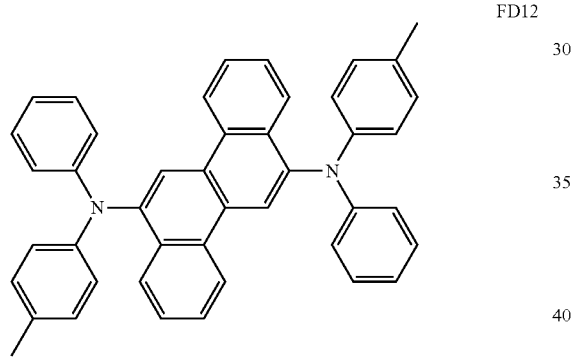
FD13
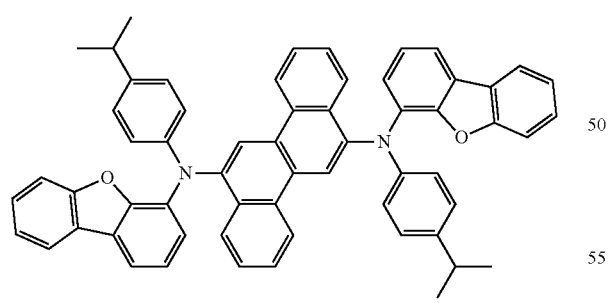
FD14
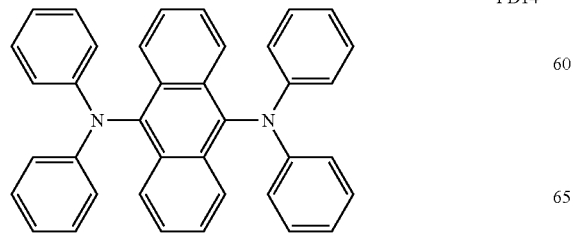
FD15
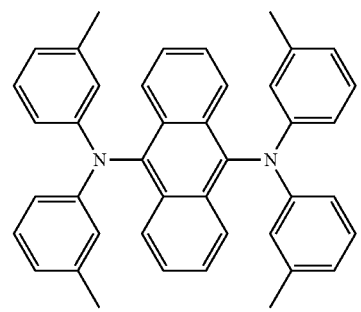
FD16
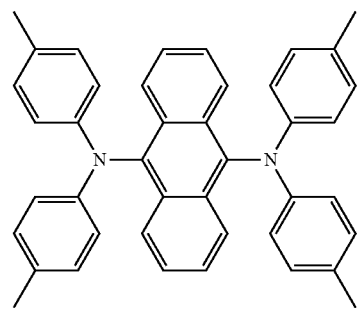
FD17
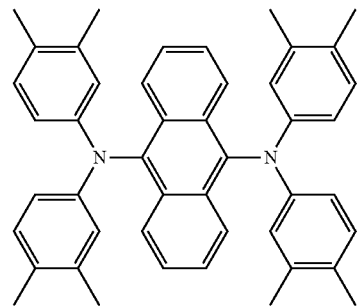
FD18
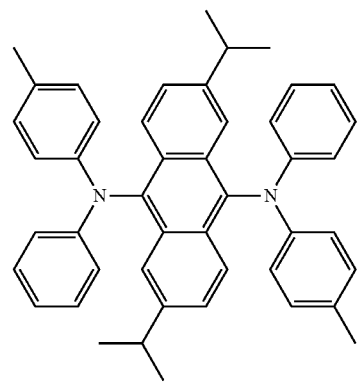

FD19
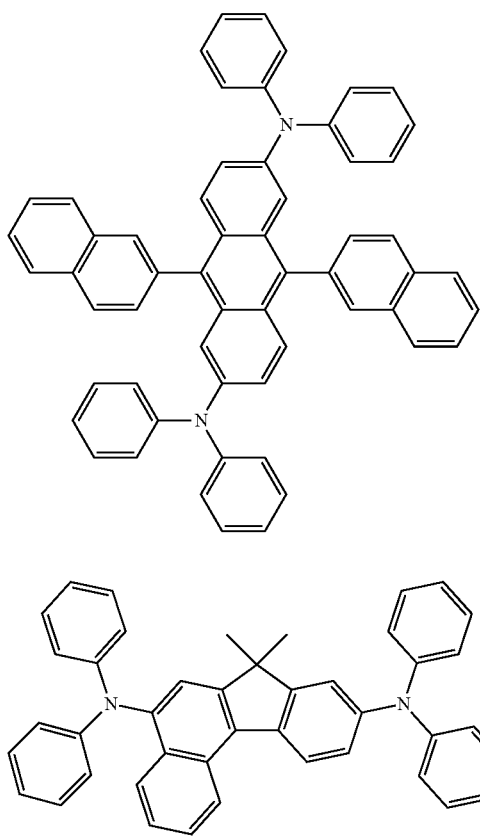
FD21
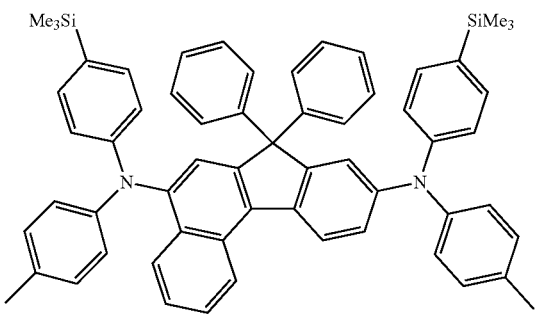
FD22
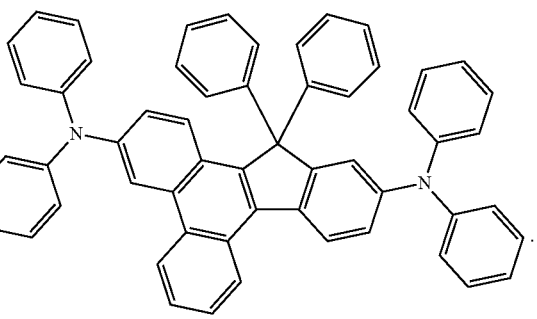
FD20
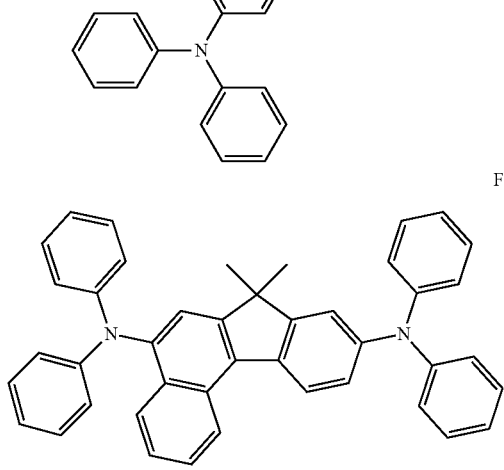
In one or more embodiments, the fluorescent dopant may be selected from the following compounds, but embodiments of the present disclosure are not limited thereto:
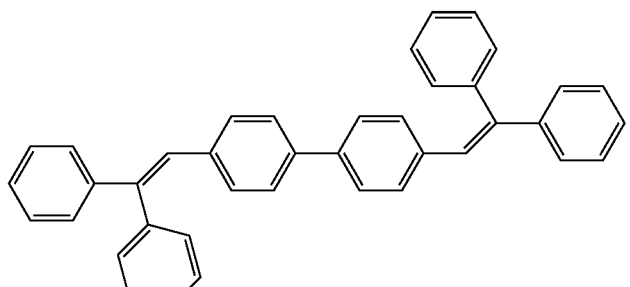
DPVBi
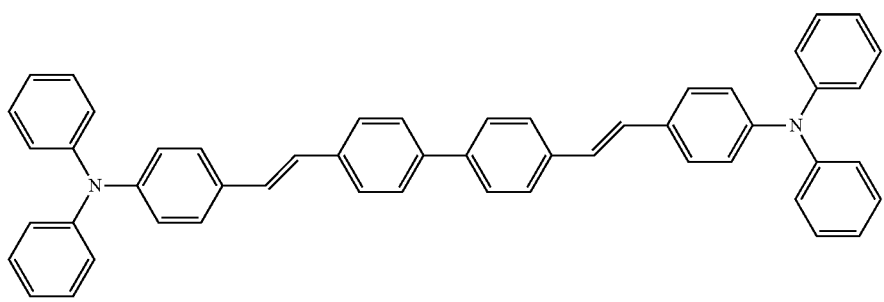
DPAVBi -continued

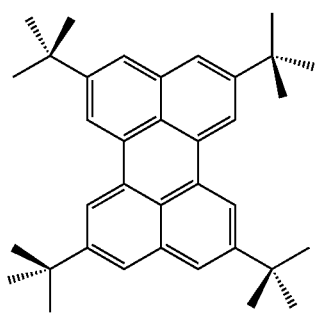
TBPe

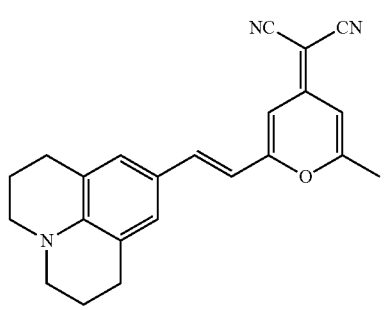
DCM

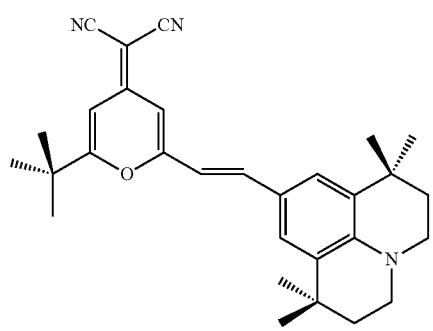
DCJTB

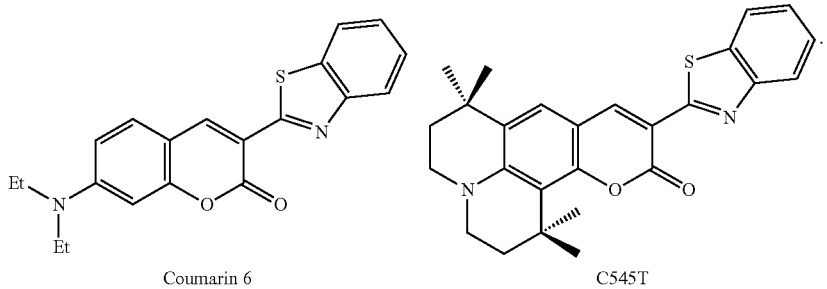
Coumarin 6          C545T

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein the constituting layers of each structure are sequentially stacked from the emission layer in the stated order. However, embodiments of the structure of the electron transport region are not limited thereto.

The electron transport region (for example, a buffer layer, a hole blocking layer, an electron control layer, and/or an electron transport layer in the electron transport region) may include a metal-free compound containing at least one π electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups having at least one *—N=*' moiety each are condensed with each other, or iii) a heteropolycyclic group in which at least one 5-membered to 7-membered heteromonocyclic group, having at least one *—N=*' moiety, is condensed with at least one $C_5$-$C_{60}$ carbocyclic group.

Non-limiting examples of the π electron-depleted nitrogen-containing ring include an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, but are not limited thereto.

For example, the electron transport region may include a compound represented by Formula 601:

$$[Ar_{601}]_{xe11}-[(L_{601})_{xe1}-R_{601}]_{xe21}.$$  Formula 601

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of the xe11 $Ar_{601}$ groups and xe21 $R_{601}$ groups may include the π electron-depleted nitrogen-containing ring.

In one embodiment, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or more, the two or more $Ar_{601}$ groups may be linked to each other via a single bond.

In one or more embodiments, $Ar_{601}$ in Formula 601 may be an anthracene group.

In one or more embodiments, a compound represented by Formula 601 may be represented by Formula 601-1:

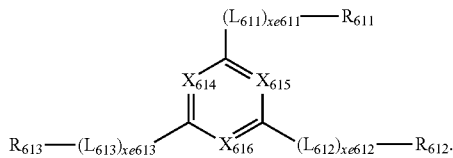

Formula 601-1

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each be understood by referring to the description presented in connection with $L_{601}$, xe611 to xe613 may each be understood by referring to the description presented in connection with xe1, $R_{611}$ to $R_{613}$ may each be understood by referring to the description presented in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may each independently be the same as described above.

The electron transport region may include at least one compound selected from Compounds ET1 to ET36, but embodiments of the present disclosure are not limited thereto:

ET1

ET3

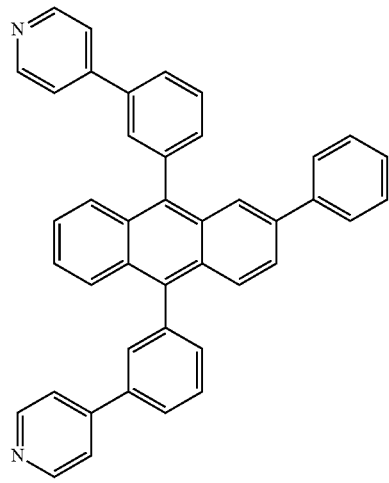

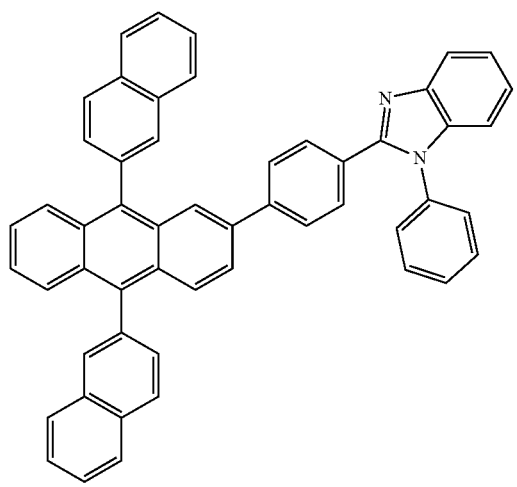

ET4

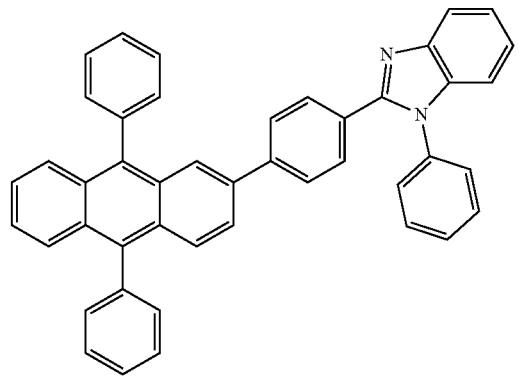

ET2

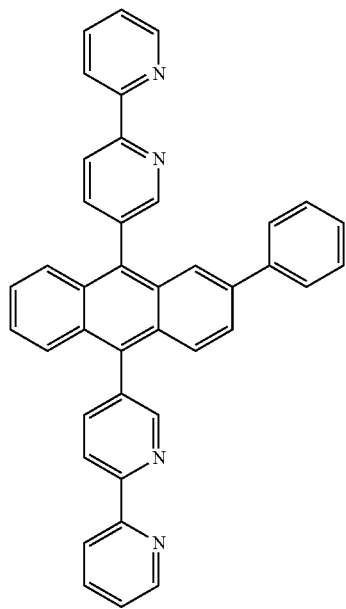

ET5

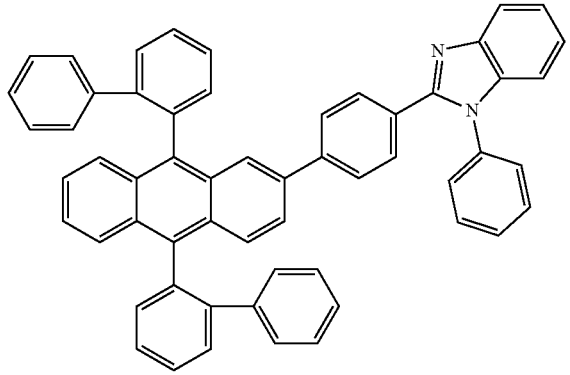

ET6
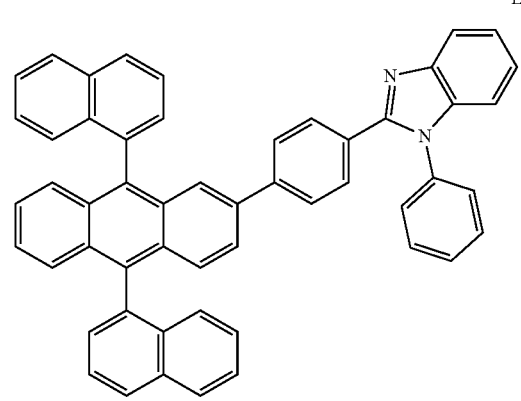
ET7
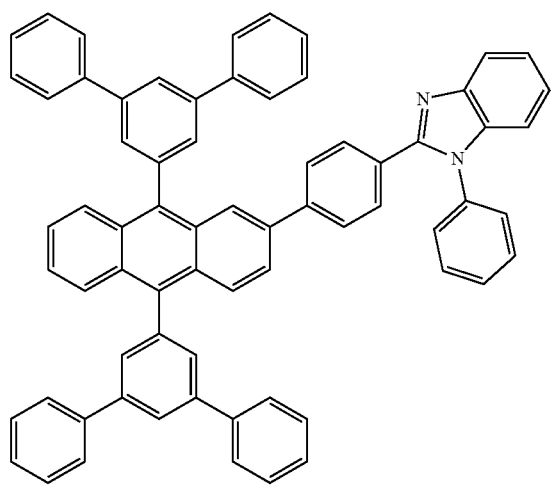
ET8
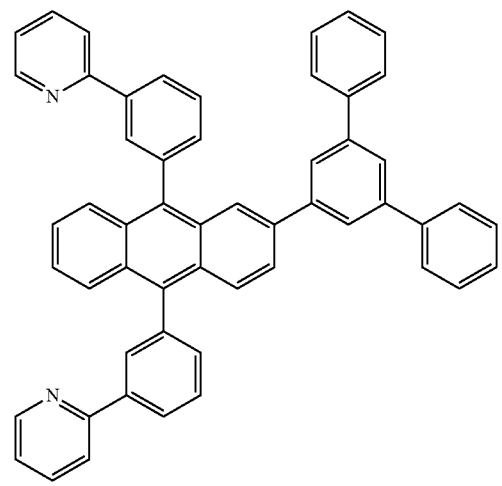
ET9
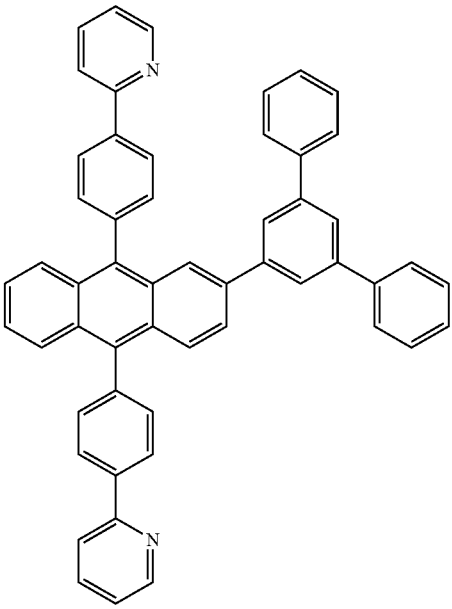
ET10
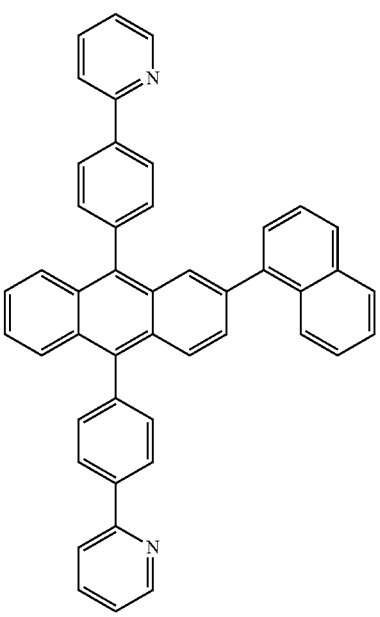

ET11
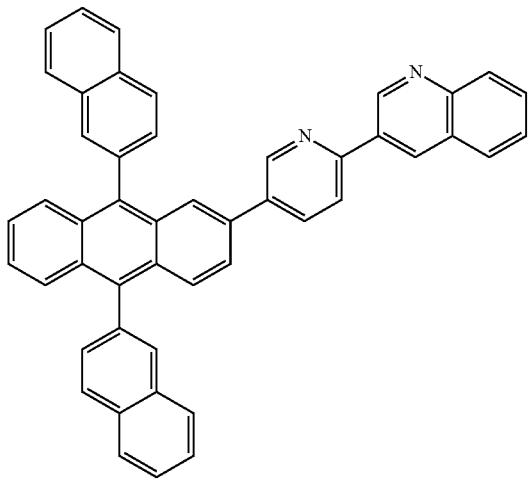
ET12
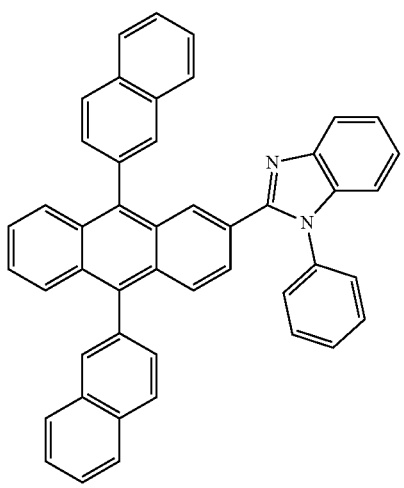
ET13
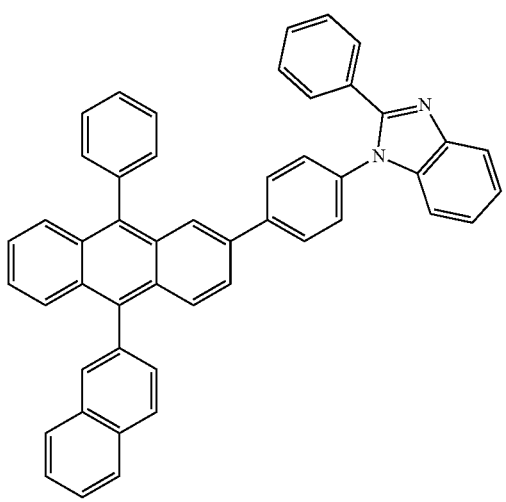
ET14
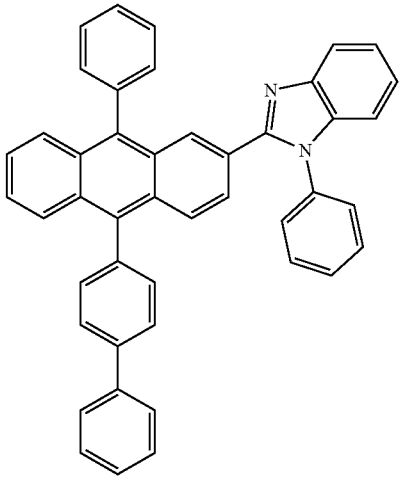
ET15
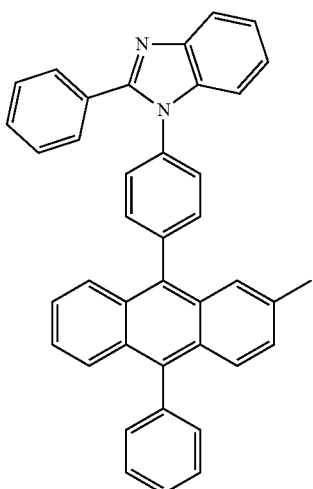
ET16
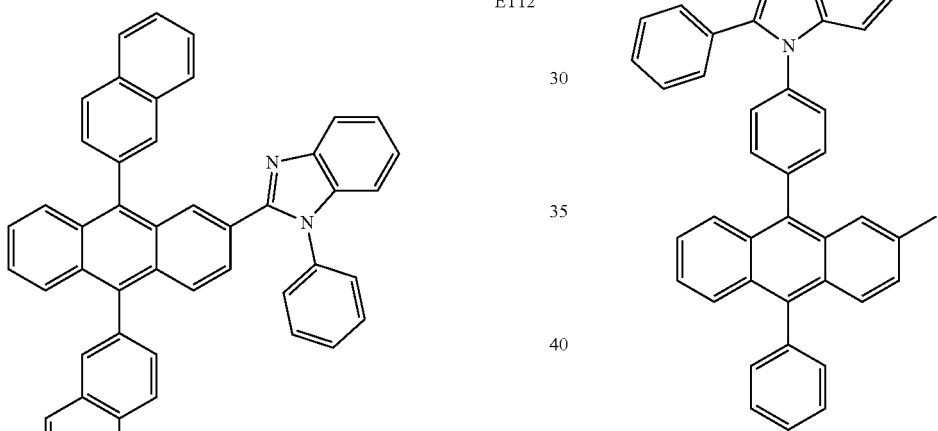

ET17
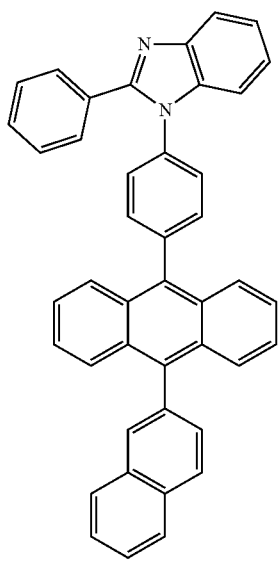
ET20
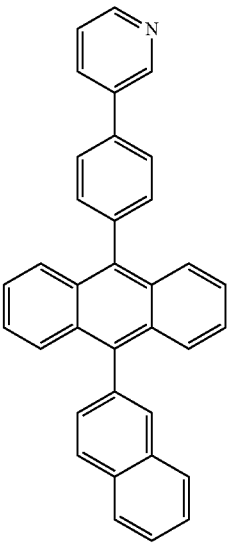
ET18
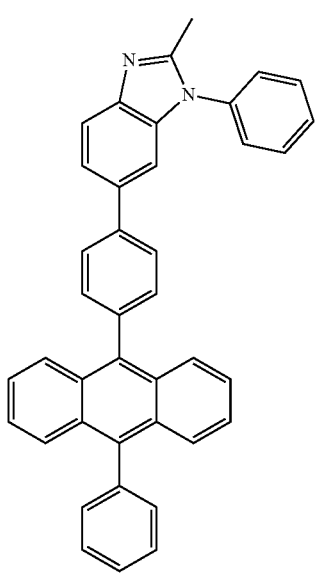
ET21
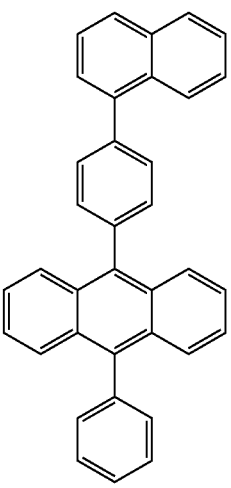
ET19
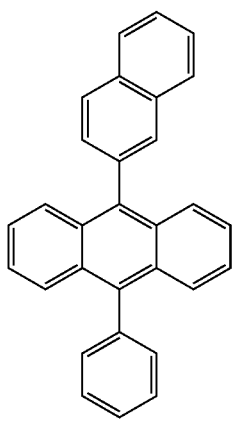
ET22
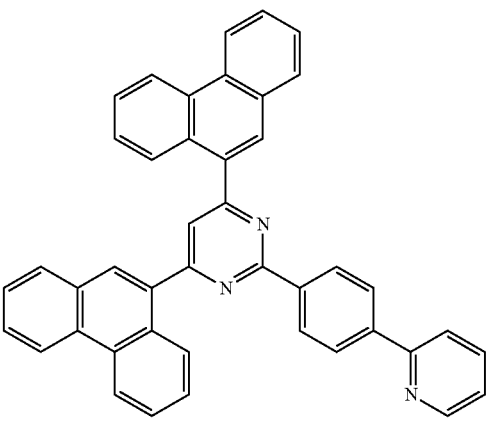

ET23
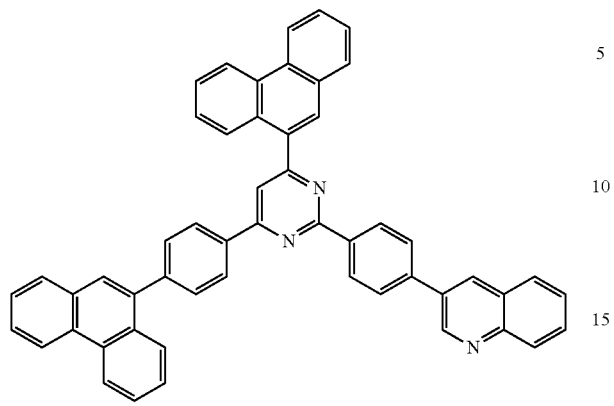
ET24
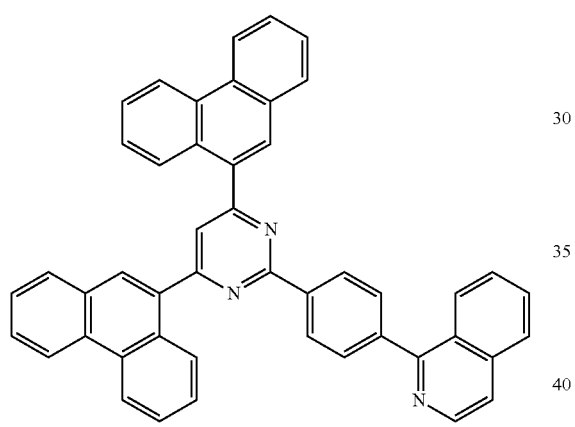
ET25
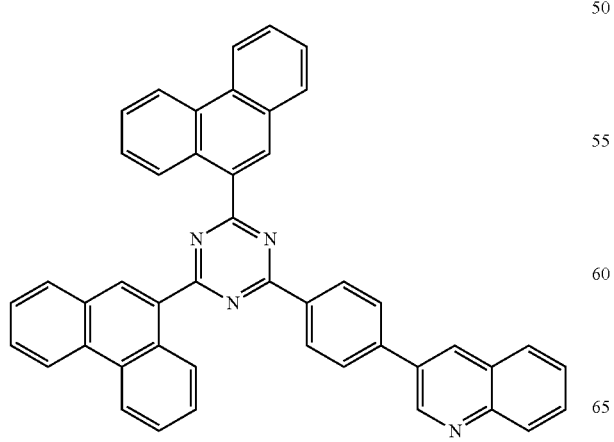
ET26
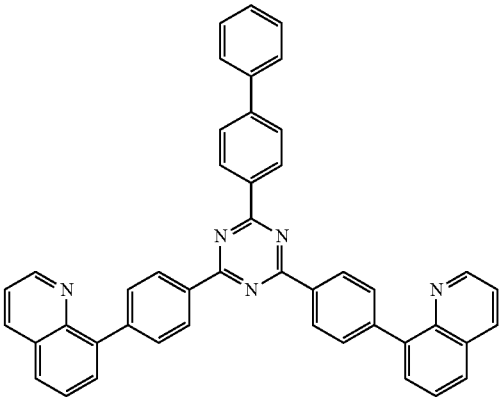
ET27
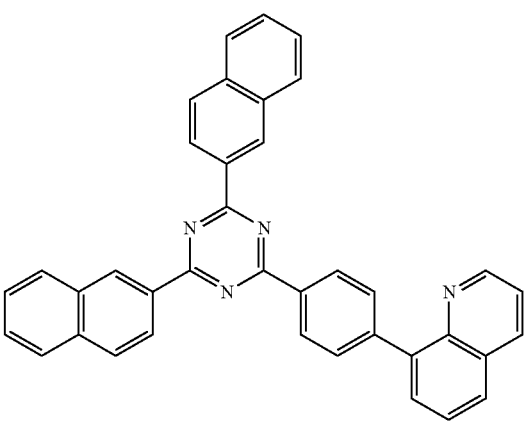
ET28
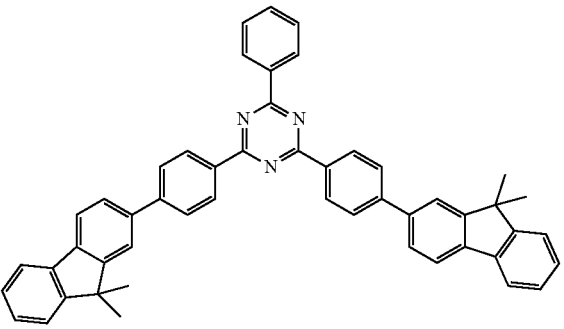
ET29
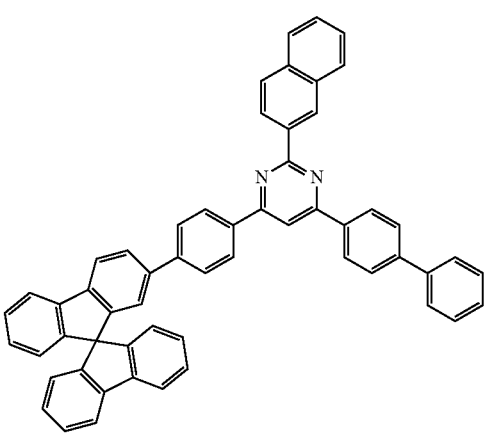

ET30
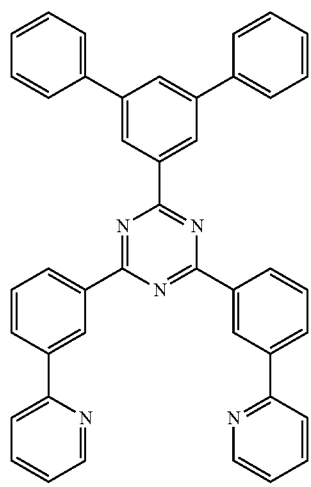
ET31
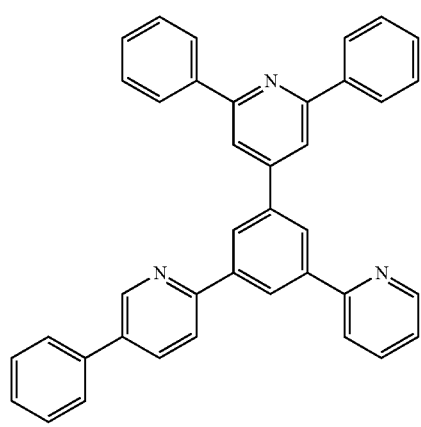
ET32
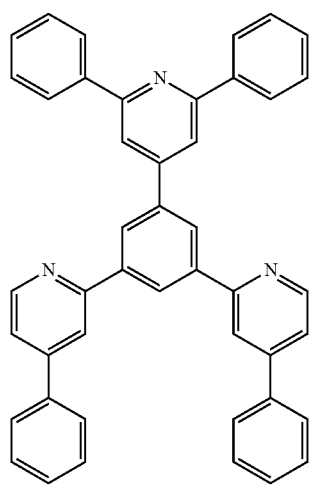
ET33
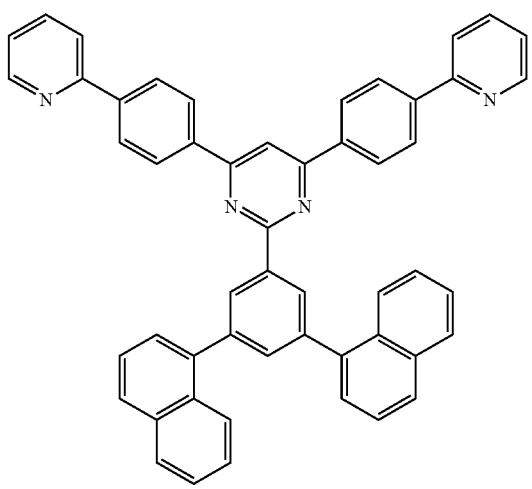
ET34
ET35
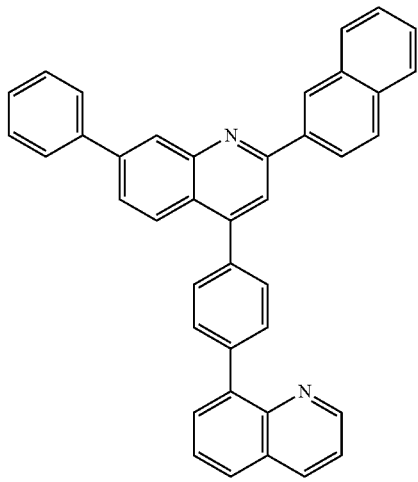

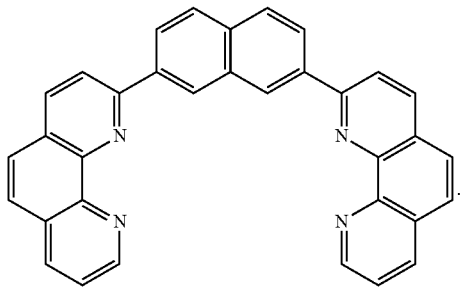

ET36

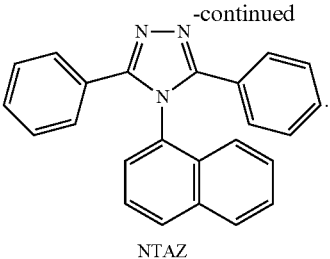

NTAZ

In one or more embodiments, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

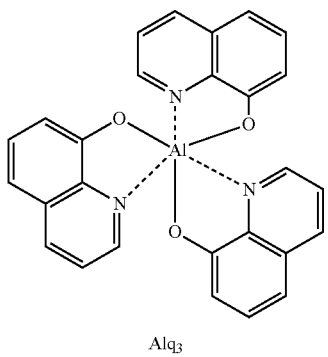

Alq₃

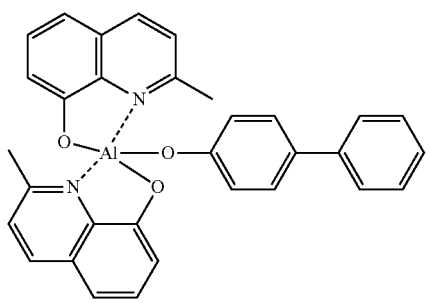

BAlq

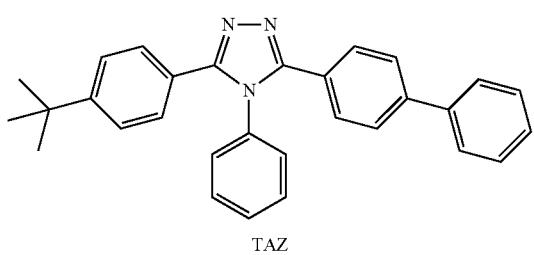

TAZ

The buffer layer, the hole blocking layer, and the electron control layer may each have a thickness of about 20 Å to about 1,000 Å, for example, about 30 Å to about 300 Å. When the thicknesses of the buffer layer, the hole blocking layer, and the electron control layer are each within these ranges, the electron blocking layer may have excellent electron blocking characteristics or electron control characteristics without a substantial increase in driving voltage.

The electron transport layer may have a thickness of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from a lithium (Li) ion, a sodium (Na) ion, a potassium (K) ion, a rubidium (Rb) ion, and a cesium (Cs) ion, and the alkaline earth-metal complex may include a metal ion selected from a beryllium (Be) ion, a magnesium (Mg) ion, a calcium (Ca) ion, a strontium (Sr) ion, and a barium (Ba) ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2:

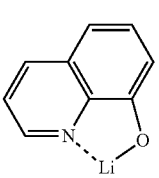

ET-D1

ET-D2

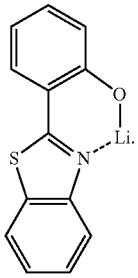

The electron transport region may include an electron injection layer to facilitate electron injection from the second electrode 190. The electron injection layer may be in direct contact with the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from scandium (Sc), yttrium (Y), cerium (Ce), terbium (Tb), ytterbium (Yb), and gadolinium (Gd).

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides (such as $Li_2O$, $Cs_2O$, and/or $K_2O$), and alkali metal halides (such as LiF, NaF, CsF, KF, LiI, NaI, CsI, and/or KI). In one embodiment, the alkali metal compound may be selected from LiF, $Li_2$, NaF, LiI, NaI, CsI, and KI, but embodiments of the present disclosure are not limited thereto.

The alkaline earth-metal compound may be selected from alkaline earth-metal oxides (such as BaO, SrO, CaO, $Ba_xSr_{1-x}$ O ($0<x<1$), and/or $Ba_xCa_{1-x}O$ ($0<x<1$)). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$ and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may respectively include an metal ion selected from an alkali metal, alkaline earth-metal, and rare earth metal, as described above, and a ligand coordinated with the metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include (e.g., consist of) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof, as described above. In one or more embodiments, the electron injection layer may further include an organic material. When the electron injection layer further includes an organic material, the alkali metal, the alkaline earth metal, the rare earth metal, the alkali metal compound, the alkaline earth-metal compound, the rare earth metal compound, the alkali metal complex, the alkaline earth-metal complex, the rare earth metal complex, or combination thereof may be homogeneously or non-homogeneously dispersed in a matrix including the organic material.

The electron injection layer may have a thickness of about 1 Å to about 100 Å, for example, about 3 Å to about 90 Å. When the thickness of the electron injection layer is within these ranges, satisfactory electron injection characteristics may be obtained without a substantial increase in driving voltage.

[Second Electrode 190]

The second electrode 190 may be disposed on the organic layer 150 having the above-described structure. The second electrode 190 may be a cathode, which is an electron injection electrode, and in this regard, a material to form the second electrode 190 may be selected from metal, an alloy, an electrically conductive compound, and combinations thereof, each having a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
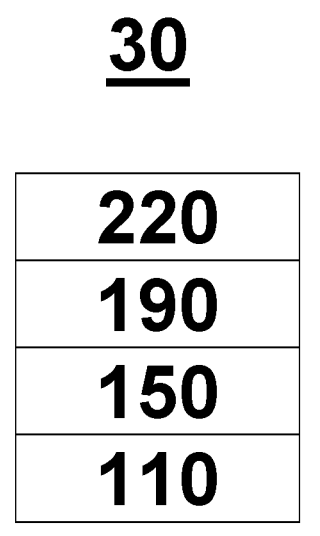
Figure 4:
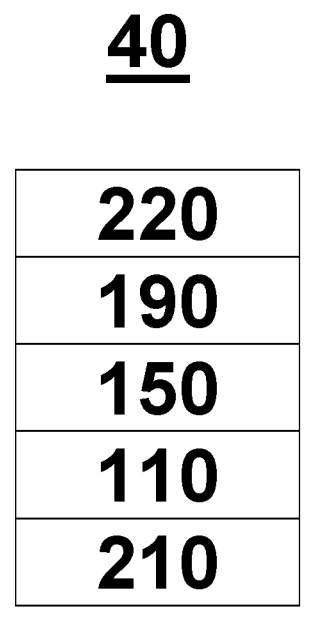

[Description of FIGS. 2 to 4]

Figure 2:
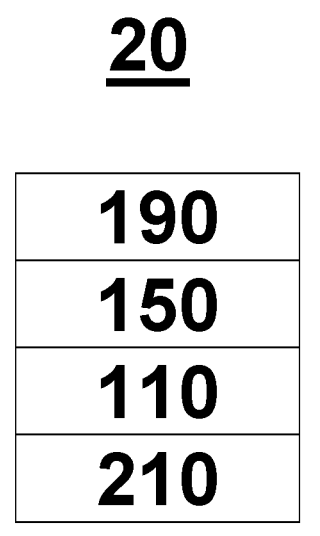

FIG. 2 is a schematic view of an organic light-emitting device 20 according to an embodiment. The organic light-emitting device 20 includes a first capping layer 210, the first electrode 110, the organic layer 150, and the second electrode 190 sequentially stacked in this stated order. FIG. 3 is a schematic view of an organic light-emitting device 30 according to an embodiment. The organic light-emitting device 30 includes the first electrode 110, the organic layer 150, the second electrode 190, and a second capping layer 220 sequentially stacked in this stated order. FIG. 4 is a schematic view of an organic light-emitting device 40 according to an embodiment. The organic light-emitting device 40 includes the first capping layer 210, the first electrode 110, the organic layer 150, the second electrode 190, and the second capping layer 220 sequentially stacked in this stated order.

Regarding FIGS. 2 to 4, the first electrode 110, the organic layer 150, and the second electrode 190 may each be understood by referring to the descriptions presented in connection with FIG. 1.

In the organic layer 150 of each of the organic light-emitting devices 20 and 40, light generated in the emission layer may pass through the first electrode 110 and the first capping layer 210 toward the outside, wherein the first electrode 110 is a semi-transmissive electrode or a transmissive electrode. In the organic layer 150 of each of the organic light-emitting devices 30 and 40, light generated in the emission layer may pass through the second electrode 190 and the second capping layer 220 toward the outside, wherein the second electrode 190 is a semi-transmissive electrode or a transmissive electrode.

The first capping layer 210 and the second capping layer 220 may increase the external luminescence efficiency of the device according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrin derivatives, phthalocyanine derivatives, naphthalocyanine derivatives, alkali metal complexes, and alkaline earth-based complexes. The carbocyclic compound, the heterocyclic compound, and the amine-based compound may optionally be substituted with a substituent containing at least one element selected from O, N, S, Se, Si, F, Cl, Br, and I. In one embodiment, at least one selected from the first capping layer 210 and the second capping layer 220 may each independently include a heterocyclic compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

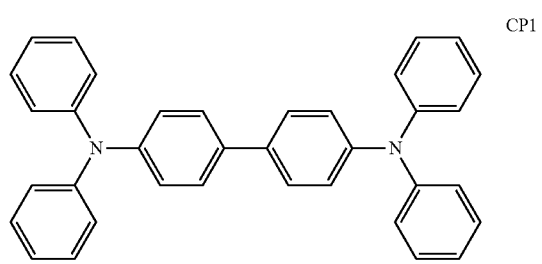

CP1

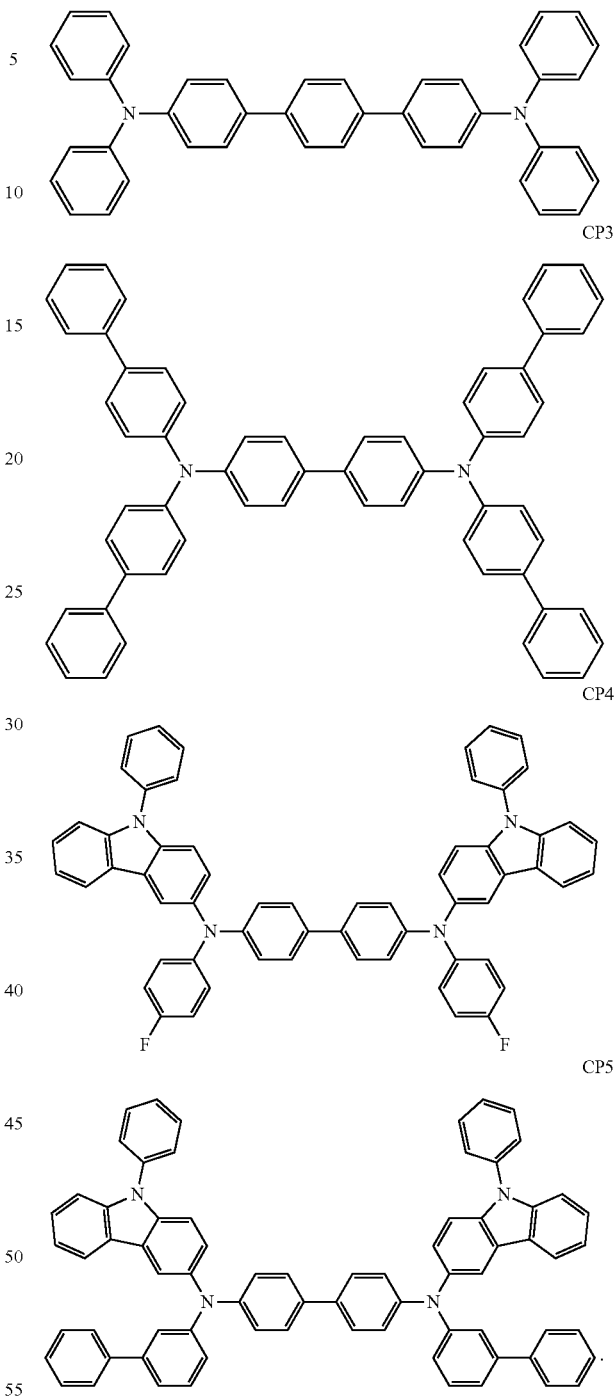

Hereinbefore, the organic light-emitting device according to an embodiment has been described in connection with FIGS. 1 to 4, but embodiments of the present disclosure are not limited thereto.

The layers constituting the hole transport region, the emission layer, and the layers constituting the electron transport region may each be formed in a certain (e.g., set or predetermined) region using one or more suitable methods selected from vacuum deposition, spin coating, casting, Langmuir-Blodgett (LB) deposition, ink-jet printing, laser-printing, and laser-induced thermal imaging.

When the layers constituting the hole transport region, the emission layer, and the layers constituting the electron transport region are formed by vacuum deposition, the deposition may be performed at a deposition temperature of about 100° C. to about 500° C., a vacuum degree of about 10-8 torr to about 10-3 torr, and a deposition speed of about 0.01 Å/sec to about 100 Å/sec, depending on the material to be included in the layer, and the structure of the layer to be formed.

When the layers constituting the hole transport region, the emission layer, and the layers constituting the electron transport region are formed by spin coating, the spin coating may be performed at a coating speed of about 2,000 rpm to about 5,000 rpm and at a heat treatment temperature of about 80° C. to 200° C., depending on the material to be included in the layer, and the structure of the layer to be formed.

[Apparatus]

The organic light-emitting device may be included in any suitable apparatus. For example, the apparatus may be a light-emitting apparatus, an authentication apparatus, or an electronic apparatus.

The light-emitting apparatus may further include, in addition to the organic light-emitting device, a thin-film transistor. Here, the thin-film transistor may include a source electrode, an activation layer, and a drain electrode, wherein the first electrode of the organic light-emitting device may be electrically connected the source electrode or the drain electrode of the thin-film transistor. The light-emitting apparatus may be used in various suitable displays, light sources, and/or the like.

The authentication apparatus may be, for example, a biometric authentication apparatus to authenticate an individual using biometric information of a biometric body (for example, a finger tip, a pupil, or the like).

The authentication apparatus may further include, in addition to the organic light-emitting device, a biometric information collector.

The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, or endoscope displays), fish finders, various measuring instruments, meters (for example, meters for a vehicle, an aircraft, and a vessel), projectors, and/or the like, but embodiments of the present disclosure are not limited thereto.

[General Definition of Substituents]

The term "$C_1$-$C_{60}$ alkyl group" as used herein refers to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having substantially the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and non-limiting examples thereof include an ethynyl group, and a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is a $C_1$-$C_{60}$ alkyl group), and non-limiting examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms, at least one carbon-carbon double bond in the ring thereof, and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_1$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group or the $C_6$-$C_{60}$ arylene group include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group include two or more rings, the rings may be condensed with each other.

The term "$C_6$-$C_{60}$ aryloxy group" as used herein refers to —$OA_{102}$ (wherein $A_{102}$ is a $C_6$-$C_{60}$ aryl group), and the term "$C_6$-$C_{60}$ arylthio group" as used herein refers to —$SA_{103}$ (wherein $A_{103}$ is a $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. A non-limiting example of the monovalent non-aromatic condensed polycyclic group is a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S as a ring-forming atom, and no aromaticity in its entire molecular structure. A non-limiting example of the monovalent non-aromatic condensed heteropolycyclic group is a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The term "$C_5$-$C_{60}$ carbocyclic group" as used herein refers to an aromatic carbocyclic group or a non-aromatic carbocyclic group. The $C_5$-$C_{60}$ carbocyclic group may be a ring (such as benzene), a monovalent group (such as a phenyl group), or a divalent group (such as a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having substantially the same structure as the $C_5$-$C_{60}$ carbocyclic group, except that at least one heteroatom selected from N, O, Si, P, and S is used as a ring-forming atom in addition to carbon (the number of carbon atoms may be 1 to 60).

In the present specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein refers to a phenyl group, the term "Me" as used herein refers to a methyl group, the term "Et" as used herein refers to an ethyl group, the term "ter-Bu" or "Bu'" as used herein refers to a tert-butyl group, and the term "OMe" as used herein refers to a methoxy group.

The term "biphenyl group" as used herein may refer to "a phenyl group substituted with a phenyl group". In other words, a "biphenyl group" is a substituted phenyl group having a $C_6$-$C_{60}$ aryl group (phenyl group) as a substituent.

The term "terphenyl group" as used herein may refer to "a phenyl group substituted with a biphenyl group". In other words, a "terphenyl group" is a phenyl group having, as a substituent, a $C_6$-$C_{60}$ aryl group substituted with a $C_6$-$C_{60}$ aryl group (biphenyl group).

* and *' as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples indicates that an identical molar equivalent of B was used in place of A.

EXAMPLES

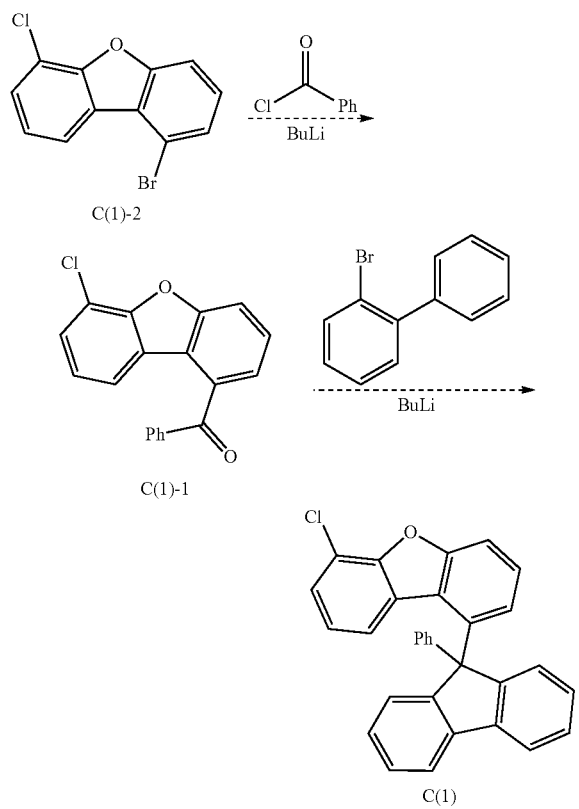

Synthesis of Intermediate C(1)-1:

1-bromo-6-chlorodibenzo[b,d]furan (2.81 g, 1 eq) was dissolved in tetrahydrofuran (THF) and stirred at a temperature of −78° C. After 30 minutes, 1 eq of n-BuLi was added dropwise thereto and stirred for 1 hour. Benzoyl chloride (1.4 g, 1 eq) was added dropwise thereto and stirred for 4 hours. The reaction was quenched using dilute hydrochloric acid and extraction was performed thereon using methylene chloride (MC). 1.8 g of Intermediate C(1)-1 was obtained through column separation. (Yield: 60%).

Synthesis of Intermediate C(1):

2-bromo-1,1'-biphenyl (1.4 g, 1 eq) was dissolved in THF and stirred at a temperature of −78° C. After 30 minutes, 1 eq of n-BuLi was added dropwise thereto and stirred for 1 hour. Intermediate C(1)-1 (1.8 g, 1 eq) was added dropwise thereto and stirred for 3 hours. The reaction was quenched using dilute hydrochloric acid and extraction was performed thereon using MC. 1 g of Intermediate C(1) was obtained through column separation. (Yield: 40%).

Synthesis of Intermediate C(2):

Intermediate C(2) was synthesized in substantially the same manner as in Synthesis of Intermediate C(1), except that 3-bromo-6-chlorodibenzo[b,d]furan was used instead of Compound C(1)-2.

Synthesis of Intermediate C(3):

Intermediate C(3) was synthesized in substantially the same manner as in Synthesis of Intermediate C(1), except that 4-bromo-6-chlorodibenzo[b,d]furan was used instead of Compound C(1)-2.

Synthesis of Intermediate C(4):

Intermediate C(4) was synthesized in substantially the same manner as in Synthesis of Intermediate C(1), except that 1-bromo-7-chlorodibenzo[b,d]furan was used instead of Compound C(1)-2.

Synthesis of Intermediate C(5):

Intermediate C(5) was synthesized in substantially the same manner as in Synthesis of Intermediate C(1), except that 3-bromo-7-chlorodibenzo[b,d]furan was used instead of Compound C(1)-2.

Synthesis of Intermediate C(6):

Intermediate C(6) was synthesized in substantially the same manner as in Synthesis of Intermediate C(1), except that 4-bromo-7-chlorodibenzo[b,d]furan was used instead of Compound C(1)-2.

Synthesis of Intermediate C(7):

Intermediate C(7) was synthesized in substantially the same manner as in Synthesis of Intermediate C(1), except that 1-bromo-8-chlorodibenzo[b,d]furan was used instead of Compound C(1)-2.

Synthesis of Intermediate C(8):

Intermediate C(8) was synthesized in substantially the same manner as in Synthesis of Intermediate C(1), except that 3-bromo-8-chlorodibenzo[b,d]furan was used instead of Compound C(1)-2.

Synthesis of Intermediate C(9):

Intermediate C(9) was synthesized in substantially the same manner as in Synthesis of Intermediate C(1), except that 4-bromo-8-chlorodibenzo[b,d]furan was used instead of Compound C(1)-2.

Synthesis Example 1: Synthesis of Compound 1

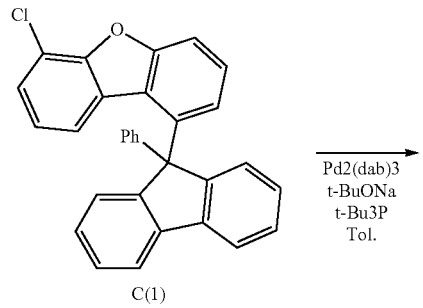

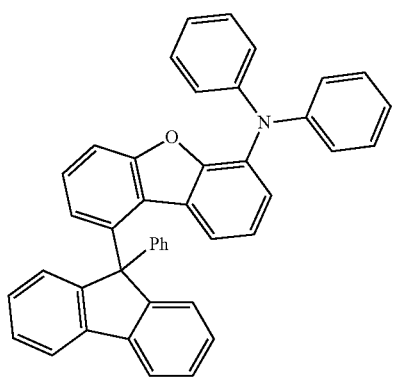

Intermediate C(1) (1 g, 1 eq), diphenylamine (0.42 g, 1.1 eq), Pd$_2$(dba)$_3$ (0.1 g, 0.05 eq), t-BuONa (0.65 g, 3 eq), t-Bu$_3$P (0.08 mL), and toluene (50 ml) were added to a 1-neck round bottom flask and stirred at a temperature of 90° C. for 3 hours. The mixture was worked up with MC/H$_2$O and 0.96 g of Compound 1 was obtained through column separation. (Yield: 74%).

Synthesis Example 2: Synthesis of Compound 2

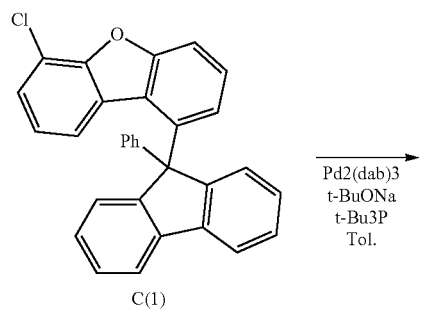

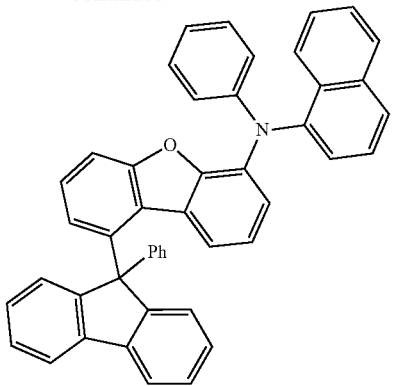

Intermediate C(1) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.99 g of Compound 2 was obtained through column separation. (Yield: 70%).

Synthesis Example 3: Synthesis of Compound 6

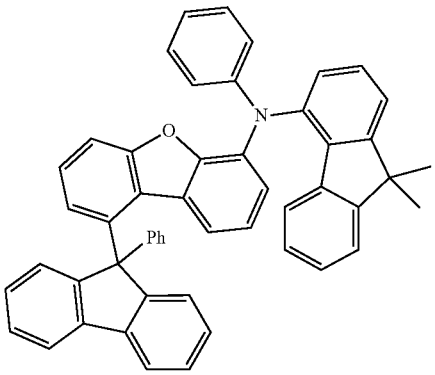

Intermediate C(1) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu$_3$P (0.08 ml), and toluene (50 mL) were added to a 1-neck round bottom flask and stirred at a temperature of 90° C. for 3 hours. The mixture was worked up with MC/H$_2$O and 1.06 g of Compound 6 was obtained through column separation. (Yield: 68%).

Synthesis Example 4: Synthesis of Compound 13

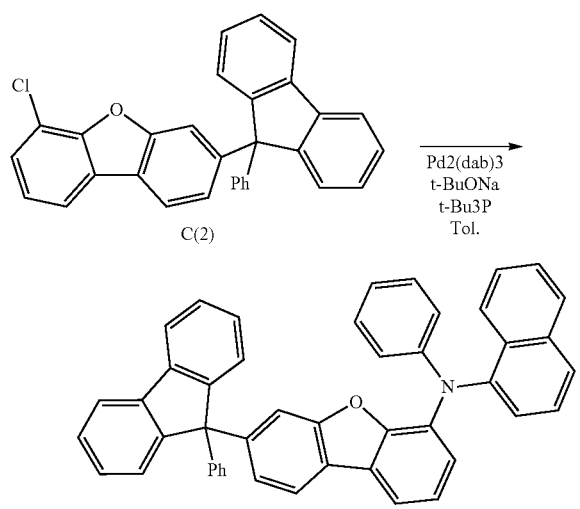

Intermediate C(2) (1 g, 1 eq), diphenylamine (0.42 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.99 g of Compound 13 was obtained through column separation. (Yield: 77%).

Synthesis Example 5: Synthesis of Compound 14

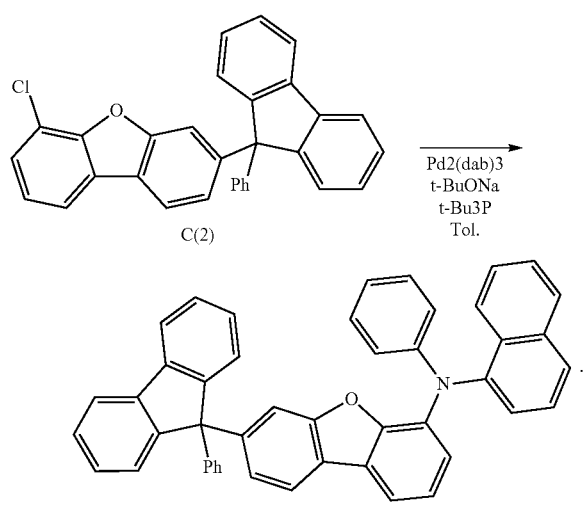

Intermediate C(2) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.93 g of Compound 14 was obtained through column separation. (Yield: 66%).

Synthesis Example 6: Synthesis of Compound 18

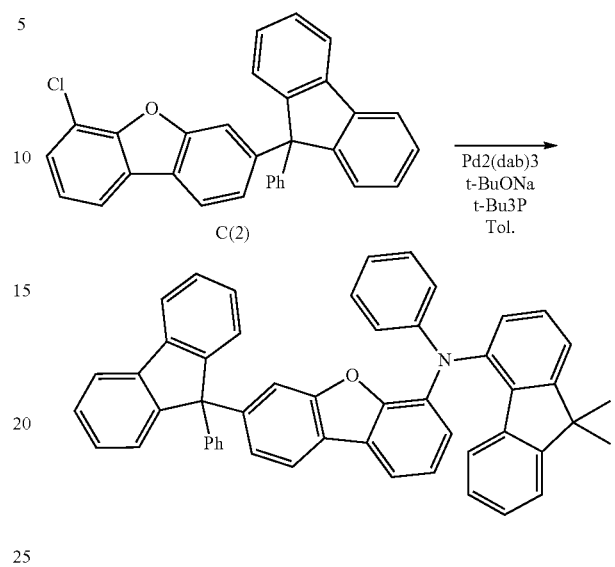

Intermediate C(2) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 1.1 g of Compound 18 was obtained through column separation. (Yield: 71%).

Synthesis Example 7: Synthesis of Compound 25

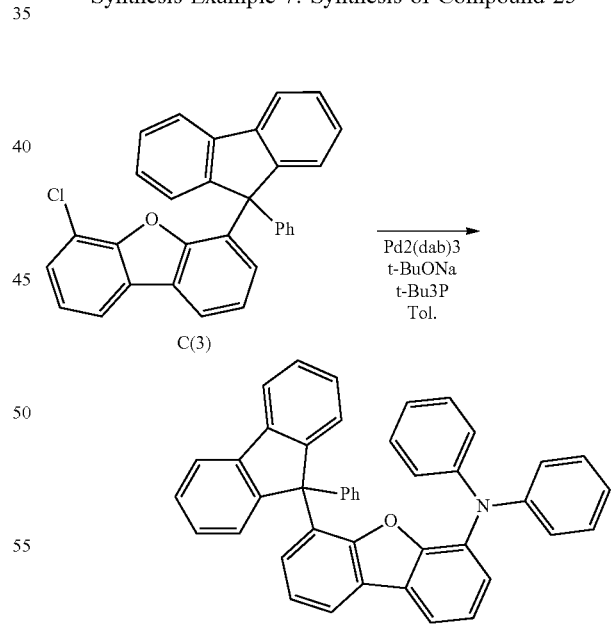

Intermediate C(3) (1 g, 1 eq), diphenylamine (0.42 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.99 g of Compound 25 was obtained through column separation. (Yield: 77%).

Synthesis Example 8: Synthesis of Compound 26

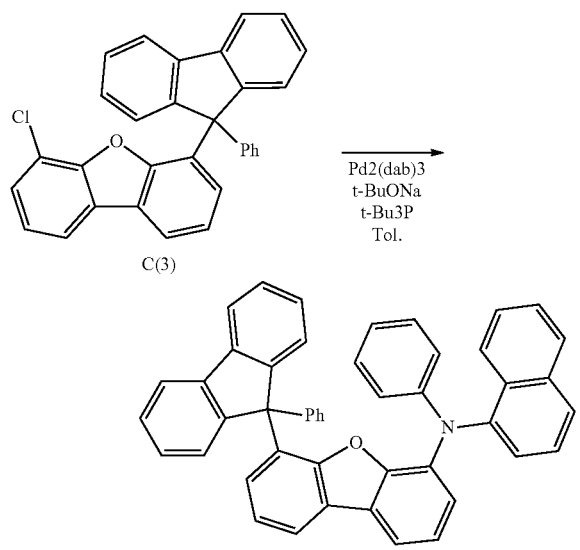

Intermediate C(3) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.83 g of Compound 26 was obtained through column separation. (Yield: 59%).

Synthesis Example 9: Synthesis of Compound 30

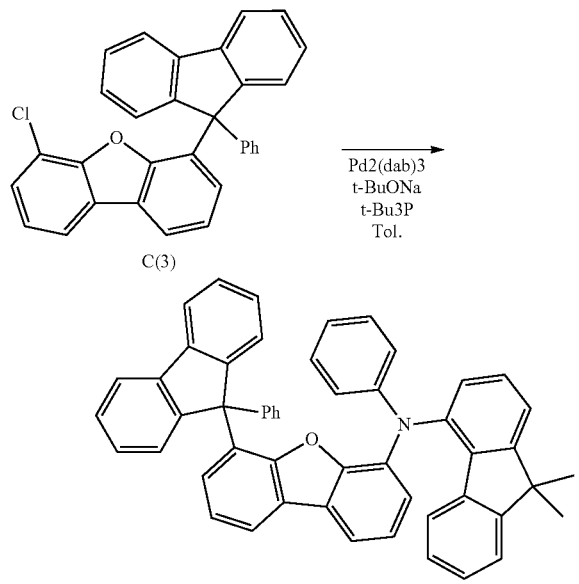

Intermediate C(3) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 1.13 g of Compound 30 was obtained through column separation. (Yield: 73%).

Synthesis Example 10: Synthesis of Compound 37

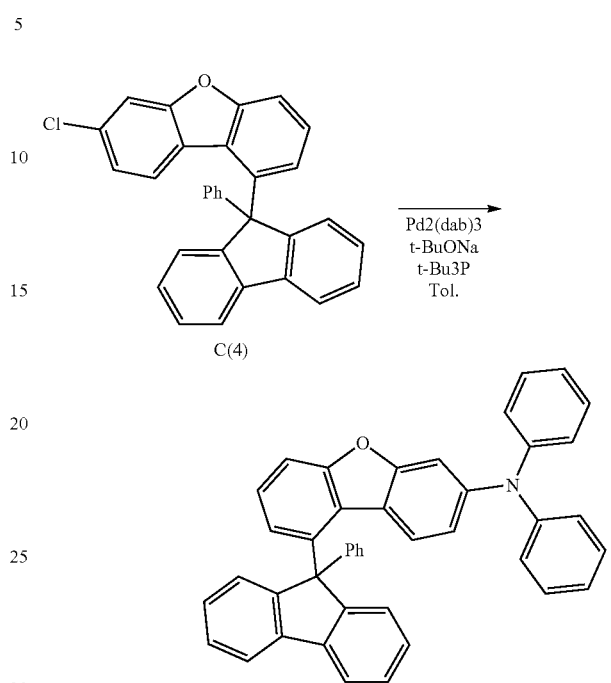

Intermediate C(4) (1 g, 1 eq), diphenylamine (0.42 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 1.03 g of Compound 37 was obtained through column separation. (Yield: 80%).

Synthesis Example 11: Synthesis of Compound 38

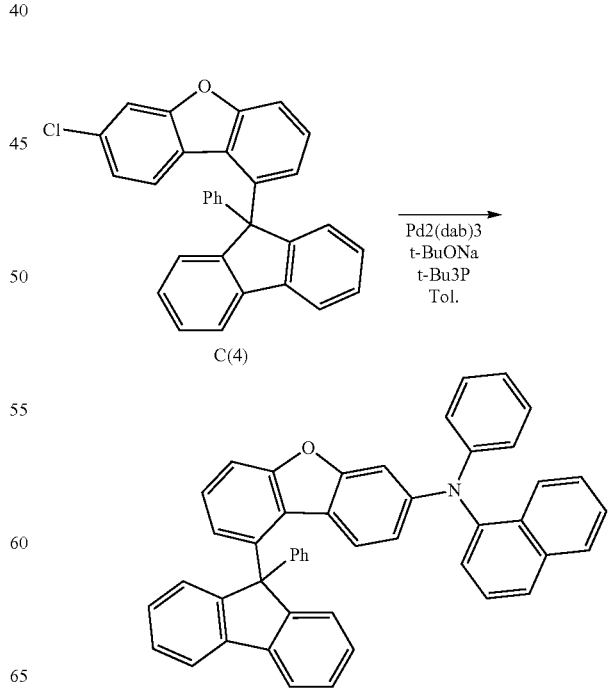

Intermediate C(4) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.99 g of Compound 38 was obtained through column separation. (Yield: 70%).

Synthesis Example 12: Synthesis of Compound 42

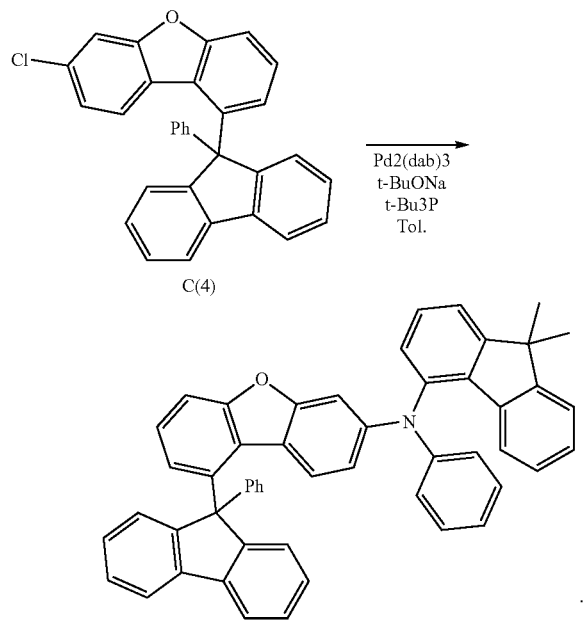

Intermediate C(4) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 1.01 g of Compound 42 was obtained through column separation. (Yield: 65%).

Synthesis Example 13: Synthesis of Compound 49

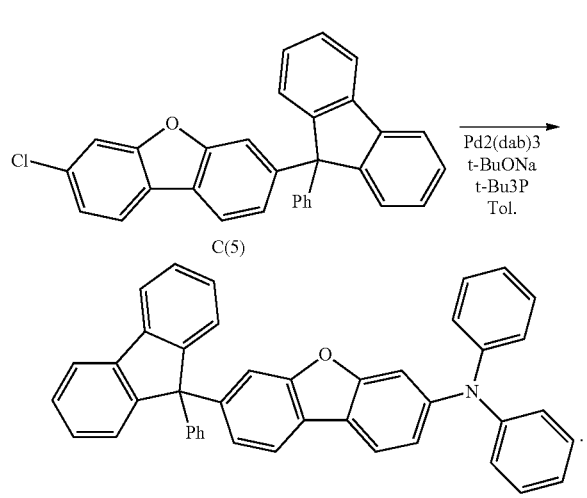

Intermediate C(5) (1 g, 1 eq), diphenylamine (0.42 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.95 g of Compound 49 was obtained through column separation. (Yield: 74%).

Synthesis Example 14: Synthesis of Compound 50

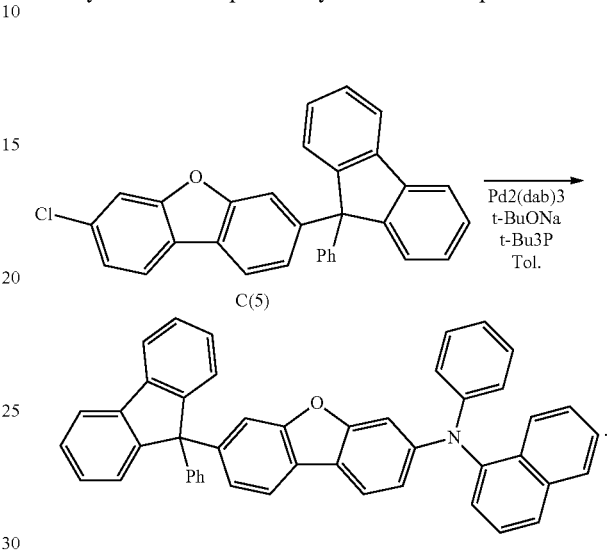

Intermediate C(5) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.97 g of Compound 50 was obtained through column separation. (Yield: 70%).

Synthesis Example 15: Synthesis of Compound 54

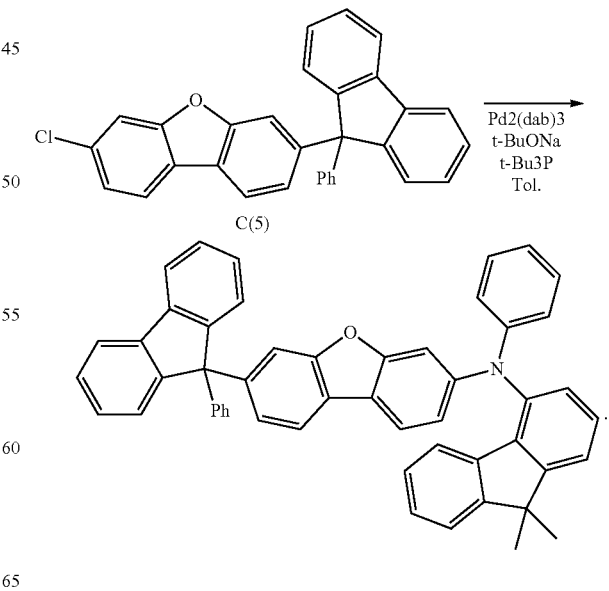

Intermediate C(5) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 1.1 g of Compound 54 was obtained through column separation. (Yield: 71%).

Synthesis Example 16: Synthesis of Compound 61

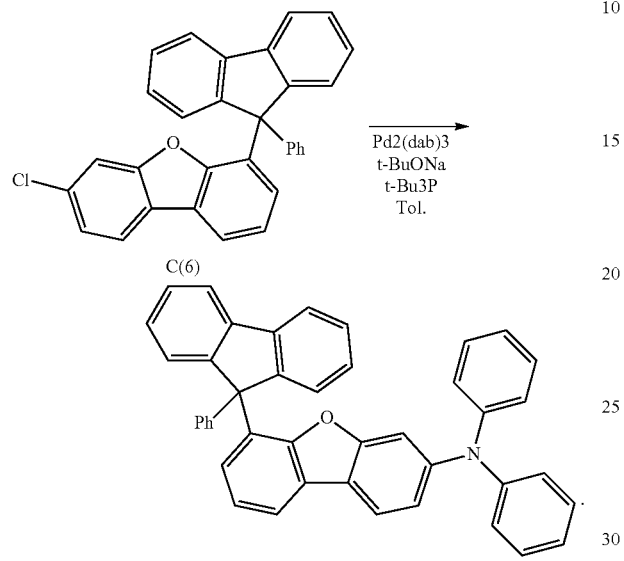

Intermediate C(6) (1 g, 1 eq), diphenylamine (0.42 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 0.92 g of Compound 61 was obtained through column separation. (Yield: 72%).

Synthesis Example 17: Synthesis of Compound 62

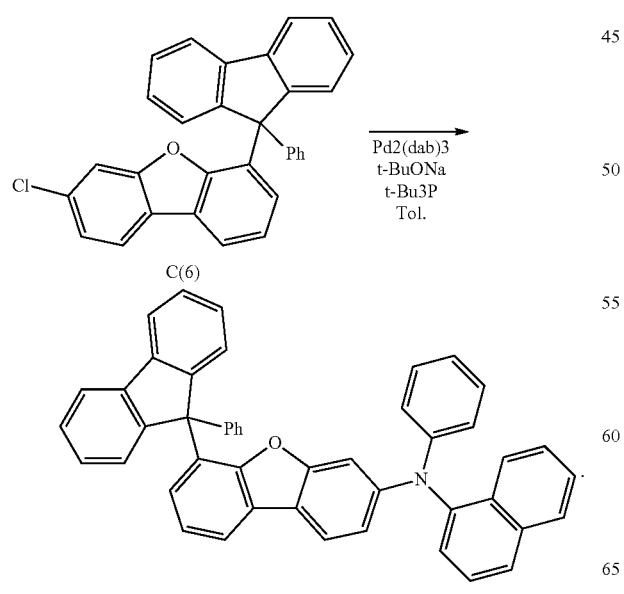

Intermediate C(6) (1 g, 1 eq), N-phenylnaphthalene-1-amine (0.54 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 0.88 g of Compound 62 was obtained through column separation. (Yield: 64%).

Synthesis Example 18: Synthesis of Compound 66

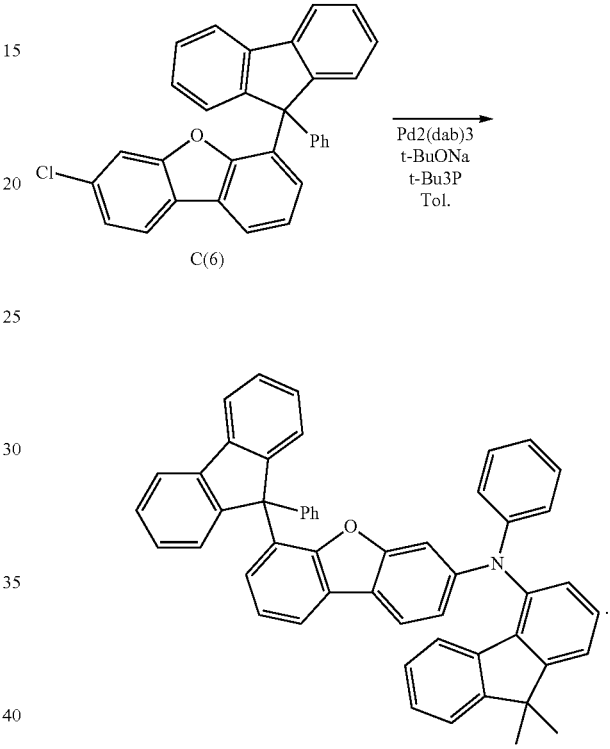

Intermediate C(6) (1 g, 1 eq), 9,9-dimethyl-N-phenyl-9H-fluorene-4-amine (0.71 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 1.07 g of Compound 66 was obtained through column separation. (Yield: 69%).

Synthesis Example 19: Synthesis of Compound 73

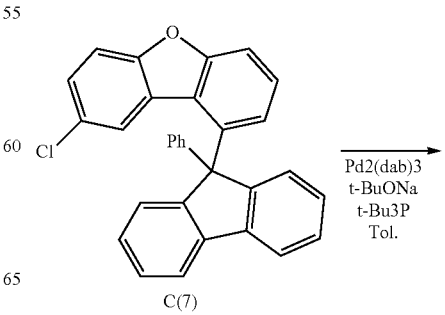

-continued

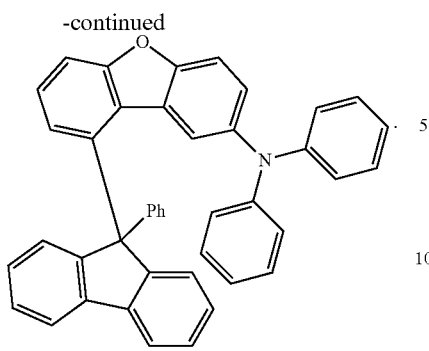

Intermediate C(7) (1 g, 1 eq), diphenylamine (0.42 g, 1.1 eq), $Pd_2(dba)_3$ (0.1 g, 0.05 eq), t-BuONa (0.65 g, 3 eq), t-$Bu_3P$ (0.08 mL), and toluene (50 mL) were added to a 1-neck round bottom flask and stirred at a temperature of 90° C. for 3 hours. The mixture was worked up with MC/$H_2O$ and 1.03 g of Compound 73 was obtained through column separation. (Yield: 80%).

Synthesis Example 20: Synthesis of Compound 74

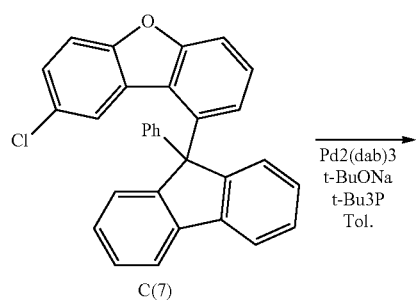

Intermediate C(7) (1 g, 1 eq), N-phenylnaphthalene-1-amine (0.54 g, 1.1 eq), $Pd_2(dba)_3$ (0.1 g, 0.05 eq), t-BuONa (0.65 g, 3 eq), t-$Bu_3P$ (0.08 mL), and toluene (50 mL) were added to a 1-neck round bottom flask and stirred at a temperature of 90° C. for 3 hours. The mixture was worked up with MC/$H_2O$ and 1.02 g of Compound 74 was obtained through column separation. (Yield: 72%).

Synthesis Example 21: Synthesis of Compound 78

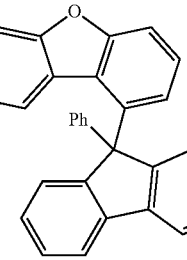

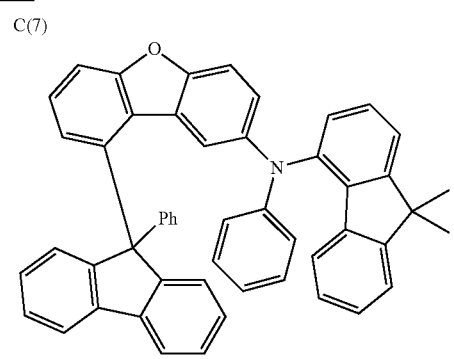

Intermediate C(7) (1 g, 1 eq), 9,9-dimethyl-N-phenyl-9H-fluorene-4-amine (0.71 g, 1.1 eq), $Pd_2(dba)_3$ (0.1 g, 0.05 eq), t-BuONa (0.65 g, 3 eq), t-$Bu_3P$ (0.08 mL), and toluene (50 mL) were added to a 1-neck round bottom flask and stirred at a temperature of 90° C. for 3 hours. The mixture was worked up with MC/$H_2O$ and 1.08 g of Compound 78 was obtained through column separation. (Yield: 70%).

Synthesis Example 22: Synthesis of Compound 85

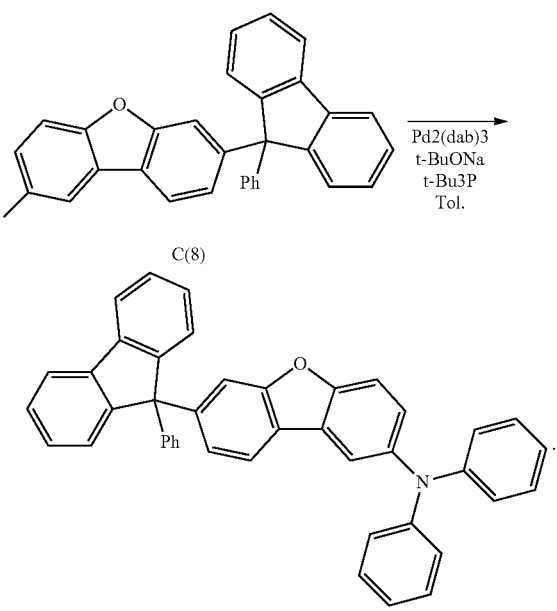

Intermediate C(8) (1 g, 1 eq), diphenylamine (0.42 g, 1.1 eq), $Pd_2(dba)_3$ (0.1 g, 0.05 eq), t-BuONa (0.65 g, 3 eq), t-$Bu_3P$ (0.08 mL), and toluene (50 mL) were added to a 1-neck round bottom flask and stirred at a temperature of 90° C. for 3 hours. The mixture was worked up with MC/H₂O and 1.01 g of Compound 85 was obtained through column separation. (Yield: 79%).

Synthesis Example 23: Synthesis of Compound 86

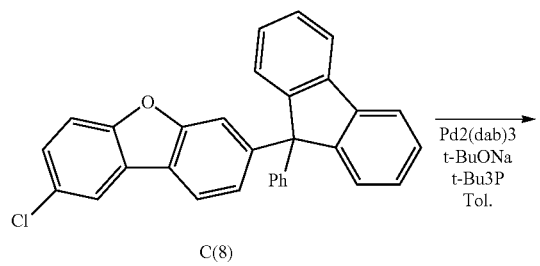

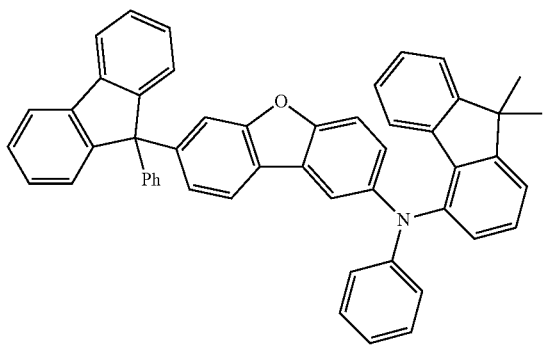

Intermediate C(8) (1 g, 1 eq), 9,9-dimethyl-N-phenyl-9H-fluorene-4-amine (0.71 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 1.1 g of Compound 89 was obtained through column separation. (Yield: 71%).

Synthesis Example 25: Synthesis of Compound 97

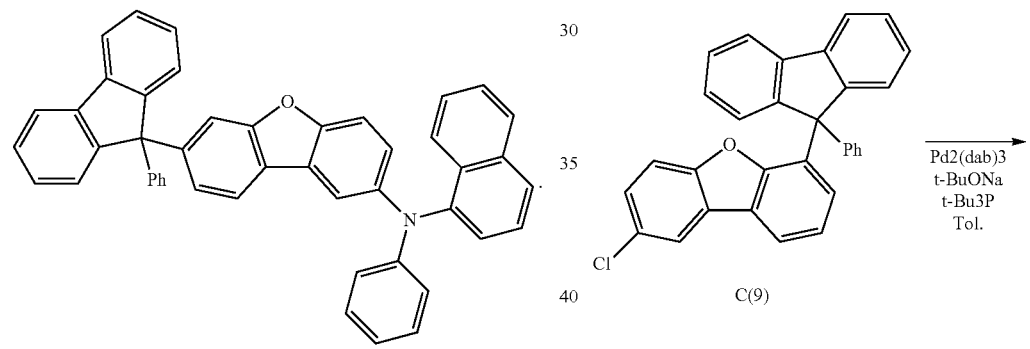

Intermediate C(8) (1 g, 1 eq), N-phenylnaphthalene-1-amine (0.54 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 0.97 g of Compound 86 was obtained through column separation. (Yield: 69%).

Synthesis Example 24: Synthesis of Compound 89

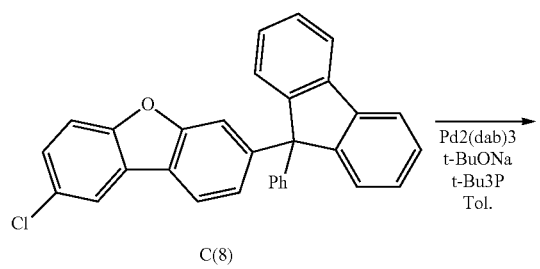

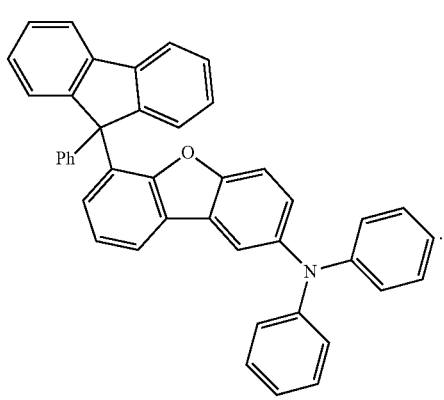

Intermediate C(9) (1 g, 1 eq), dimethylamine (0.42 g, 1.1 eq), Pd₂(dba)₃ (0.1 g, 0.05 eq), t-BuONa (0.65 g, 3 eq), t-Bu₃P (0.08 mL), and toluene (50 mL) were added to a 1-neck round bottom flask and stirred at a temperature of 90° C. for 3 hours. The mixture was worked up with MC/H₂O and 0.99 g of Compound 97 was obtained through column separation. (Yield: 77%).

Synthesis Example 26: Synthesis of Compound 98

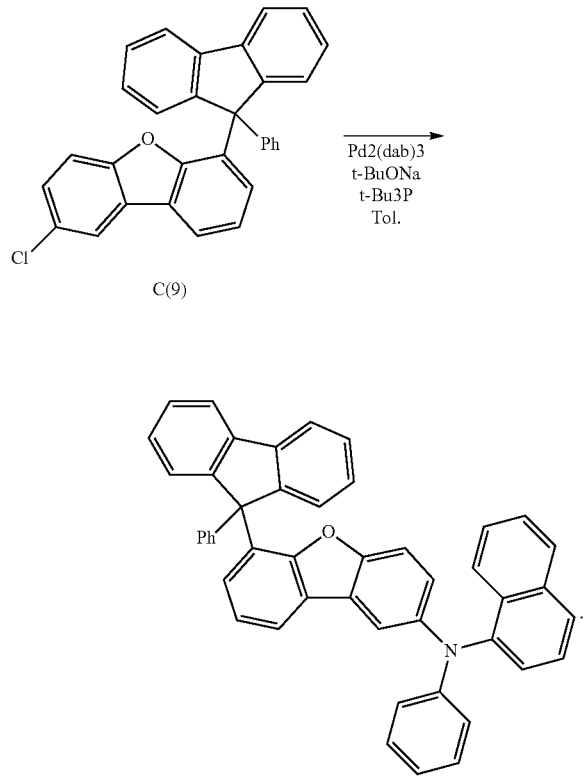

Intermediate C(9) (1 g, 1 eq), N-phenylnaphthalene-1-amine (0.54 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 0.83 g of Compound 98 was obtained through column separation. (Yield: 59%).

Synthesis Example 27: Synthesis of Compound 102

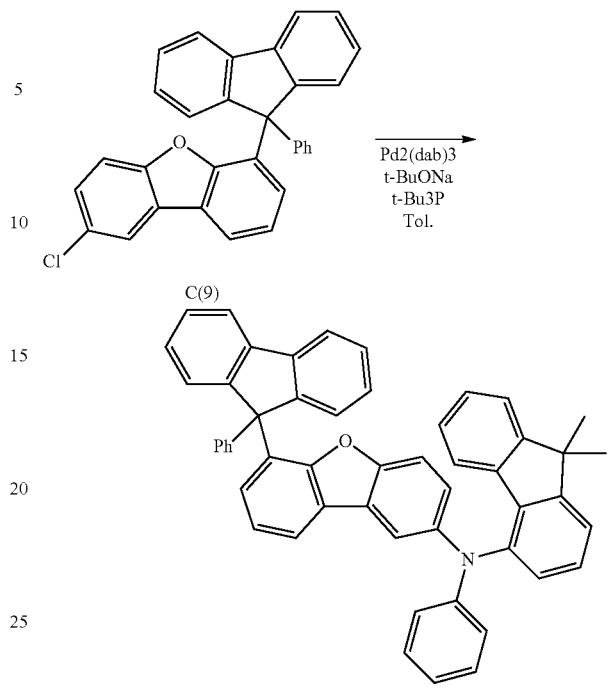

Intermediate C(9) (1 g, 1 eq), 9,9-dimethyl-N-phenyl-9H-fluorene-4-amine (0.71 g, 1.1 eq), Pd$_2$(dba)$_3$ (0.1 g, 0.05 eq), t-BuONa (0.65 g, 3 eq), t-Bu$_3$P (0.08 mL), and toluene (50 mL) were added to a 1-neck round bottom flask and stirred at a temperature of 90° C. for 3 hours. The mixture was worked up with MC/H$_2$O and 1.13 g of Compound 102 was obtained through column separation. (Yield: 73%).

$^1$H NMR and MS/FAB of the Compounds synthesized according to Synthesis Examples 1 to 27 are shown in Table 1.

Synthesis methods of compounds other than the Compounds shown in Table 1 may be easily recognized by those of ordinary skill in the art by referring to the synthesis mechanisms and source materials described above.

TABLE 1

| Compound | $^1$H NMR (CDCl$_3$, 400 MHz) | MS/FAB found | MS/FAB calc. |
|---|---|---|---|
| 1 | | 575.71 | 575.22 |
| 2 | | 625.77 | 625.24 |
| 6 | δ = 7.90(d, 3H), 7.64(d, 1H), 7.55~7.49(d, 4H), 7.38~7.00(m, 23H), 1.69(s, 6H) | 691.87 | 691.29 |
| 13 | δ = 7.90~7.83(d, 3H), 7.64(d, 1H), 7.55 (d, 2H), 7.38~7.00(m, 23H) | 575.71 | 575.22 |
| 14 | δ = 8.22~8.15(d, 2H), 7.90~7.81(d, 4H), 7.64~7.49(d, 7H), 7.38~7.00(m, 18H) | 625.77 | 625.24 |
| 18 | δ = 7.90~7.83(d, 4H), 7.64(d, 1H), 7.55~7.49(d, 3H), 7.38~7.00 (m, 23H), 1.69(s, 6H) | 691.87 | 691.29 |
| 25 | δ = 7.90~7.88(d, 3H), 7.64(d, 1H), 7.55 (d, 2H), 7.38~7.00(m, 23H) | 575.71 | 575.22 |
| 26 | | 625.77 | 625.24 |
| 30 | δ = 7.90~7.88(d, 4H), 7.64(d, 1H), 7.55~7.49(d, 3H), 7.38~7.00 (m, 23H), 1.69(s, 6H) | 691.87 | 691.29 |
| 37 | δ = 8.03(s, 1H), 7.90(d, 2H), 7.80(d, 1H), 7.55~7.49(d, 3H), 7.38~7.00(m, 23H), 6.91(d, 1H | 575.71 | 575.22 |
| 38 | | 625.77 | 625.24 |
| 42 | | 691.87 | 691.29 |
| 49 | δ = 8.03(s, 1H), 7.90~7.80(d, 4H), 7.55 (d, 2H), 7.38(m, 2H), 7.28~7.00(m, 20H) | 575.71 | 575.22 |
| 50 | δ = 8.22~8.15(d, 2H), 8.03(s, 1H), 7.90~7.80(m, 4H), 7.63~7.49(d, 6H), 7.38~7.00(d, 17H), 6.91(d, 1H) | 625.77 | 625.24 |

TABLE 1-continued

| Compound | $^1$H NMR (CDCl$_3$, 400 MHz) | MS/FAB found | MS/FAB calc. |
|---|---|---|---|
| 54 | δ = 8.03(s, 1H), 7.90~7.80(d, 5H), 7.55 (d, 3H), 7.38~7.00(m, 22H), 6.91(d, 1H), 1.69(s, 6H) | 691.87 | 691.29 |
| 61 | δ = 8.03(s, 1H), 7.90~7.88(d, 3H), 7.80(d, 1H), 7.55 (d, 2H), 7.38~7.00(m, 22H), 6.91(d, 1H) | 575.71 | 575.22 |
| 62 | δ = 8.22~8.15(d, 2H), 8.03(s,1H), 7.90~7.80(m, 5H), 7.63~7.49(d, 6H), 7.38~7.00(d, 16H), 6.91(d, 1H) | 625.77 | 625.24 |
| 66 | δ = 8.03(s, 1H), 7.90~7.88(d, 4H), 7.80(d, 1H), 7.55 (d, 3H), 7.38~7.00(m, 21H), 6.91(d,1H), 1.69(s, 6H) | 691.87 | 691.29 |
| 73 | δ = 8.22(s, 1H), 7.90(d, 2H), 7.56~7.49 (d, 4H), 7.38~7.00(m, 22H) | 575.71 | 575.22 |
| 74 | | 625.77 | 625.24 |
| 78 | δ = 8.22(s, 1H), 7.90(d, 3H), 7.56~7.49 (d, 5H), 7.38~7.00(m, 21H), 6.91(d, 1H), 1.69(s, 6H) | 691.87 | 691.29 |
| 85 | δ = 8.22(s, 1H), 7.90~7.83(d, 3H), 7.56~7.55 (d, 3H), 7.38(m, 2H), 7.28~7.00(m, 20H) | 575.71 | 575.22 |
| 86 | δ = 8.22~8.15(d, 3H), 7.90~7.81(m, 4H), 7.63~7.49(m, 7H), 7.38~7.00(d, 17H) | 625.77 | 625.24 |
| 89 | δ = 8.22(s, 1H), 7.90~7.83(d, 4H), 7.56~7.55 (d, 4H), 7.38~7.00(m, 22H), 1.69(s, 6H) | 691.87 | 691.29 |
| 97 | δ = 8.22(s, 1H), 7.90~7.88(d, 3H), 7.56~7.55 (d, 3H), 7.38~7.00(m, 22H) | 575.71 | 575.22 |
| 98 | δ = 8.22~8.15(d, 3H), 7.90~7.81(m, 4H), 7.63~7.49(m, 7H), 7.38~7.00(d, 17H) | 625.77 | 625.24 |
| 102 | δ = 8.22(s, 1H), 7.90~7.83(d, 4H), 7.56~7.55 (d, 4H), 7.38~7.00(m, 22H), 1.69(s, 6H) | 691.87 | 691.29 |

Example 1

As an anode, a Corning 15 Ω/cm$^2$ (1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. The ITO glass substrate was provided to a vacuum deposition apparatus.

2-TNATA was vacuum-deposited on the ITO glass substrate to form a hole injection layer having a thickness of 600 Å, and a hole transport compound, Compound 1, was vacuum-deposited on the hole injection layer to form a hole transport layer having a thickness of 300 Å.

9,10-di(naphthalene-2-yl)anthracene (DNA) and 4,4'-bis [2-(4-(N,N'-diphenylamino)phenyl)vinyl]biphenyl (DPAVBi) were co-deposited on the hole transport layer at a weight ratio of 98:2 to form an emission layer having a thickness of 300 Å.

Then, Alq$_3$ was deposited on the emission layer to form an electron transport layer having a thickness of 300 Å, an alkali metal halide LiF was deposited on the electron transport layer to form an electron injection layer having a thickness of 10 Å, and Al was vacuum-deposited to a thickness of 3,000 Å to form a LiF/A electrode, thereby completing the manufacture of an organic light-emitting device.

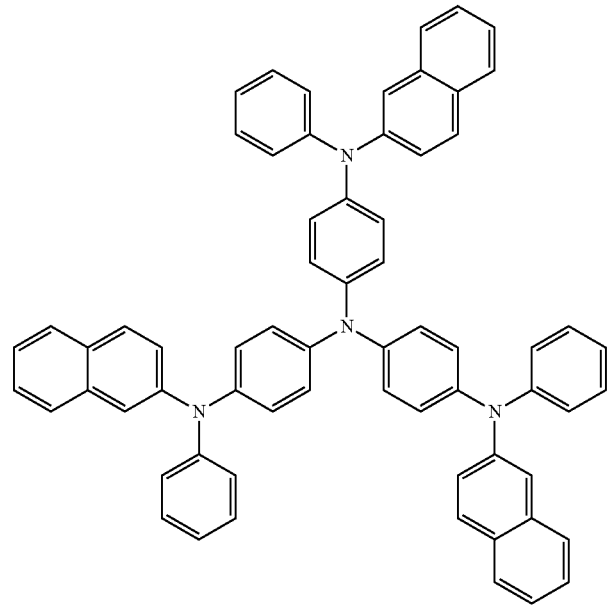

2-TNATA

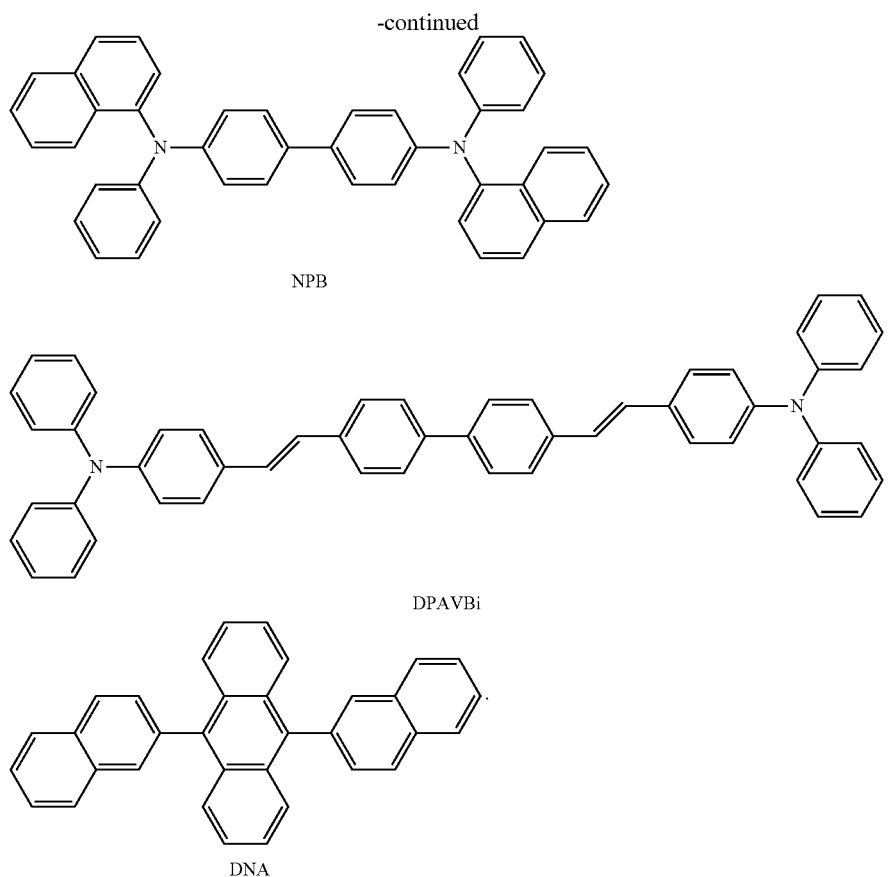

Examples 2 to 27 and Comparative Examples 1 to 5

Organic light-emitting devices were manufactured in substantially the same manner as in Example 1, except that Compounds shown in Table 2 were each used instead of Compound 1 in forming an emission layer.

Evaluation Example 1

The device performance (driving voltage, luminance, efficiency, and color coordinates) of each of the organic light-emitting devices manufactured according to Examples 1 to 27 and Comparative Example 1 to 5 was measured at a current density of 50 mA/cm$^2$, and an amount of time (half lifespan) elapsed when luminance was 50% of initial luminance (100%) was measured at a current density of 100 mA/cm$^2$. Results thereof are shown in Table 2.

Luminance measurement: Power was supplied from a current-voltage meter (Keithley SMU 236), and luminance was measured using a luminance meter PR650.

Efficiency measurement: Power was supplied from a current-voltage meter (Keithley SMU 236), and efficiency was measured using a luminance meter PR650.

TABLE 2

| | Hole transport material | Driving voltage (V) | Current density (mA/cm$^2$) | Luminance (cd/m$^2$) | Efficiency (cd/A) | Emission color | Half lifespan (hr @ 100 mA/cm$^2$) |
|---|---|---|---|---|---|---|---|
| Comparative Example 1 | NPB | 7.01 | 50 | 2645 | 5.29 | Blue | 258 |
| Comparative Example 2 | Compound A | 5.99 | 50 | 3122 | 6.20 | Blue | 300 |
| Comparative Example 3 | Compound B | 6.66 | 50 | 2867 | 5.88 | Blue | 283 |
| Comparative Example 4 | Compound C | 6.91 | 50 | 2622 | 5.54 | Blue | 228 |
| Comparative Example 5 | Compound D | 4.66 | 50 | 3155 | 6.37 | Blue | 320 |

TABLE 2-continued

|  | Hole transport material | Driving voltage (V) | Current density (mA/cm$^2$) | Luminance (cd/m$^2$) | Efficiency (cd/A) | Emission color | Half lifespan (hr @ 100 mA/cm$^2$) |
|---|---|---|---|---|---|---|---|
| Example 1 | Compound 1 | 4.32 | 50 | 3670 | 7.34 | Blue | 362 |
| Example 2 | Compound 2 | 4.21 | 50 | 3715 | 7.43 | Blue | 353 |
| Example 3 | Compound 6 | 4.22 | 50 | 3665 | 7.33 | Blue | 372 |
| Example 4 | Compound 13 | 4.26 | 50 | 3730 | 7.46 | Blue | 374 |
| Example 5 | Compound 14 | 4.26 | 50 | 3730 | 7.46 | Blue | 374 |
| Example 6 | Compound 18 | 4.25 | 50 | 3630 | 7.26 | Blue | 384 |
| Example 7 | Compound 25 | 4.21 | 50 | 3725 | 7.45 | Blue | 343 |
| Example 8 | Compound 26 | 4.16 | 50 | 3770 | 7.46 | Blue | 374 |
| Example 9 | Compound 30 | 4.18 | 50 | 3693 | 7.36 | Blue | 364 |
| Example 10 | Compound 37 | 4.31 | 50 | 3688 | 7.56 | Blue | 389 |
| Example 11 | Compound 38 | 4.23 | 50 | 3711 | 7.46 | Blue | 377 |
| Example 12 | Compound 42 | 4.24 | 50 | 3735 | 7.41 | Blue | 372 |
| Example 13 | Compound 49 | 4.21 | 50 | 3691 | 7.43 | Blue | 380 |
| Example 14 | Compound 50 | 4.22 | 50 | 3750 | 7.42 | Blue | 378 |
| Example 15 | Compound 54 | 4.30 | 50 | 3703 | 7.39 | Blue | 374 |
| Example 16 | Compound 61 | 4.19 | 50 | 3698 | 7.50 | Blue | 386 |
| Example 17 | Compound 62 | 4.27 | 50 | 3730 | 7.48 | Blue | 373 |
| Example 18 | Compound 66 | 4.23 | 50 | 3724 | 7.51 | Blue | 371 |
| Example 19 | Compound 73 | 4.21 | 50 | 3751 | 7.43 | Blue | 390 |
| Example 20 | Compound 74 | 4.19 | 50 | 3800 | 7.46 | Blue | 384 |
| Example 21 | Compound 78 | 4.20 | 50 | 3710 | 7.38 | Blue | 374 |
| Example 22 | Compound 85 | 4.30 | 50 | 3699 | 7.56 | Blue | 386 |
| Example 23 | Compound 86 | 4.27 | 50 | 3716 | 7.40 | Blue | 371 |
| Example 24 | Compound 89 | 4.33 | 50 | 3735 | 7.45 | Blue | 372 |
| Example 25 | Compound 97 | 4.19 | 50 | 3770 | 7.45 | Blue | 374 |
| Example 26 | Compound 98 | 4.15 | 50 | 3720 | 7.39 | Blue | 384 |
| Example 27 | Compound 102 | 4.22 | 50 | 3718 | 7.51 | Blue | 389 |

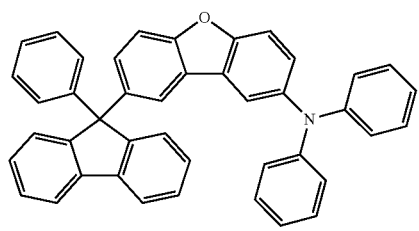

[Compound A]

TABLE 2-continued

| Hole transport material | Driving voltage (V) | Current density (mA/cm²) | Luminance (cd/m²) | Efficiency (cd/A) | Emission color | Half lifespan (hr @ 100 mA/cm²) |
| --- | --- | --- | --- | --- | --- | --- |

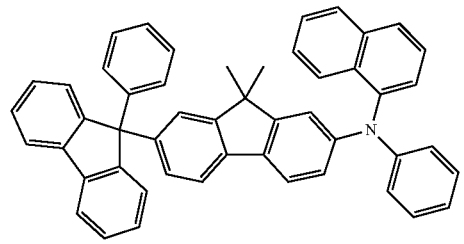

[Compound B]

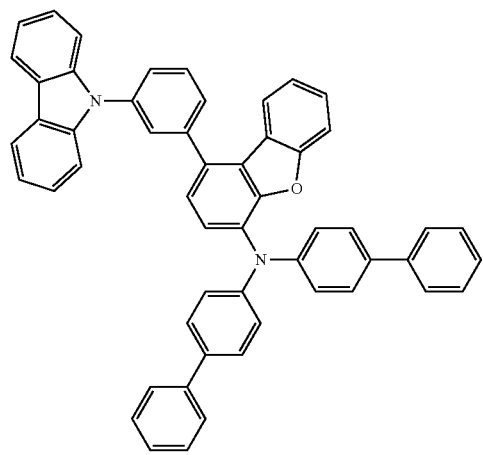

[Compound C]

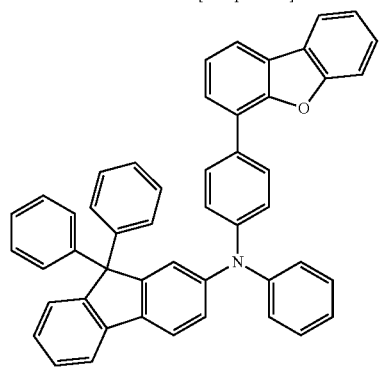

[Compound D]

From Table 2, it is confirmed that when the Example Compounds are used as the material to form the hole transport layer, the organic light-emitting devices have excellent characteristics (such as a low driving voltage, high luminescence efficiency, high luminance, and/or along lifespan), compared to when the Comparative Examples 1 to 5 were used.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the drawings, it will be understood by those of ordinary skill in the art that various changes in form and details may be made therein without departing from the spirit and scope as defined by the following claims and equivalents thereof.

What is claimed is:
1. An organic light-emitting device comprising:
a first electrode;
a second electrode facing the first electrode; and
an organic layer between the first electrode and the second electrode and comprising an emission layer; and
at least one heterocyclic compound represented by Formula 1:

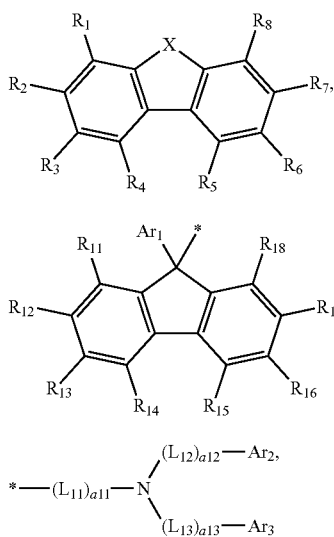

<Formula 1>

<Formula 2-1>

<Formula 2-2> wherein, in Formulae 1, 2-1, and 2-2,

X is O or S, $R_1$ to $R_8$ are each independently selected from a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein, when X is O or S, one selected from $R_1$, $R_2$, $R_4$, $R_5$, $R_7$, and $R_8$ is a group represented by Formula 2-1, and one selected from the remaining $R_1$ to $R_8$ groups is a group represented by Formula 2-2, $R_{11}$ to $R_{18}$ are each independently selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), two adjacent groups among $R_1$ to $R_8$ and two adjacent groups among $R_{11}$ to $R_{18}$ are optionally linked to each other to form a ring, $Ar_1$ to $Ar_3$ are each independently a substituted or unsubstituted $C_5$-$C_{60}$ carbocyclic group or a substituted or unsubstituted $C_1$-$C_{60}$ heterocyclic group, $Ar_2$ and $Ar_3$ are optionally linked to each other via a single bond, —C($Q_4$)($Q_5$)-, —Si($Q_4$)($Q_5$)-, —O—, —S—, —N($Q_4$)-, —B($Q_4$)-, C(=O)—, —S(=O)$_2$—, —S(=O)($Q_4$)-, or —P(=O)($Q_4$)- to form a condensed heteroring, $L_{11}$ to $L_{13}$ are each independently a substituted or unsubstituted $C_5$-$C_{60}$ carbocyclic group or a substituted or unsubstituted $C_1$-$C_{60}$ heterocyclic group, a11 to a13 are each independently an integer from 0 to 3, when a11 is 0, *-($L_{11}$)$_{a11}$-*' indicates a single bond, when a12 is 0, *-($L_{12}$)$_{a12}$-*' indicates a single bond, and when a13 is 0, *-($L_{13}$)$_{a13}$-*' indicates a single bond, at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_5$, $Q_{11}$ to $Q_{13}$, $Q_{21}$ to $Q_{23}$, and $Q_{31}$ to $Q_{33}$ are each independently selected from hydrogen, deuterium, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a group represented by Formula 1.

2. The organic light-emitting device of claim 1, wherein:
the first electrode is an anode,
the second electrode is a cathode,
the organic layer comprises the at least one heterocyclic compound,
the organic layer further comprises a hole transport region between the first electrode and the emission layer, and an electron transport region between the emission layer and the second electrode,
the hole transport region comprises a hole injection layer, a hole transport layer, an emission auxiliary layer, an electron blocking layer, or any combination thereof, and
the electron transport region comprises a hole blocking layer, an electron transport layer, an electron injection layer, or any combination thereof.

3. The organic light-emitting device of claim 2, wherein the hole transport region comprises the at least one heterocyclic compound.

4. The organic light-emitting device of claim 2, wherein the hole transport region comprises a hole transport layer, and the hole transport layer comprises the at least one heterocyclic compound.

5. The organic light-emitting device of claim 2, wherein:
the hole transport region comprises a p-dopant, and
the p-dopant has a lowest unoccupied molecular orbital (LUMO) energy level of −3.5 eV or less.

6. The organic light-emitting device of claim 1, wherein the emission layer comprises at least one compound selected from a styryl-based compound, an anthracene-based compound, a pyrene-based compound, a spiro-bifluorene-based compound, a carbazole-based compound, a benzimidazole-based compound, a phosphine oxide-based compound, a dibenzofuran-based compound, a silicon-based compound, and a triazine-based compound.

7. The organic light-emitting device of claim 1, wherein:
the emission layer is a first emission layer to emit a first color light,
the organic light-emitting device further comprises, between the first electrode and the second electrode, i) at least one second emission layer to emit a second color light or ii) at least one second emission layer for emitting second color light and at least one third emission layer to emit a third color light,
a maximum emission wavelength of the first color light, a maximum emission wavelength of the second color light, and a maximum emission wavelength of the third color light are identical to or different from each other, and
the first color light and the second color light are emitted in the form of mixed light, or the first color light, the second color light, and the third color light are emitted in the form of mixed light.

8. A heterocyclic compound represented by Formula 1:

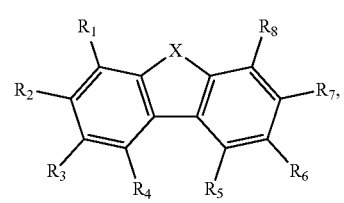

<Formula 1>

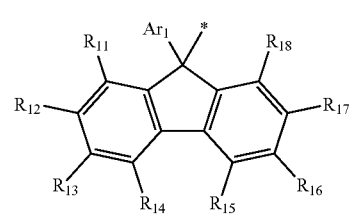

<Formula 2-1>

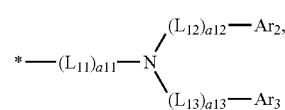

<Formula 2-2> wherein, in Formulae 1, 2-1, and 2-2,
X is O or S,
$R_1$ to $R_8$ are each independently selected from a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein, when X is O or S, one selected from $R_1$, $R_2$, $R_4$, $R_5$, $R_7$, and $R_8$ is a group represented by Formula 2-1, and one selected from the remaining $R_1$ to $R_8$ groups is a group represented by Formula 2-2, $R_{11}$ to $R_{18}$ are each independently selected from hydrogen, deuterium, —F, —Cl, —Br, —I, a hydroxyl group, a cyano group, a nitro group, an amino group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), two adjacent groups among $R_1$ to $R_8$ and two adjacent groups among $R_{11}$ to $R_{18}$ are optionally linked to each other to form a ring, $Ar_1$ to $Ar_3$ are each independently a substituted or unsubstituted $C_5$-$C_{60}$ carbocyclic group or a substituted or unsubstituted $C_1$-$C_{60}$ heterocyclic group, $Ar_2$ and $Ar_3$ are optionally linked to each other via a single bond, —C($Q_4$)($Q_5$)-, —Si($Q_4$)($Q_5$)-, —O—, —S—, —N($Q_4$)-, —B($Q_4$)-, C(=O)—, —S(=O)$_2$—, —S(=O)($Q_4$)-, or —P(=O)($Q_4$)- to form a condensed heteroring, $L_{11}$ to $L_{13}$ are each independently a substituted or unsubstituted $C_5$-$C_{60}$ carbocyclic group or a substituted or unsubstituted $C_1$-$C_{60}$ heterocyclic group, a11 to a13 are each independently an integer from 0 to 3, when a11 is 0, *-($L_{11}$)$_{a11}$-*' indicates a single bond, when a12 is 0, *-($L_{12}$)$_{a12}$-*' indicates a single bond, and when a13 is 0, *-($L_{13}$)$_{a13}$-*' indicates a single bond, at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_5$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group substituted $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a group represented by Formula 1.

9. The heterocyclic compound of claim 8, wherein:
X is O, one selected from $R_1$, $R_2$, and $R_4$ is a group represented by Formula 2-1, and one selected from $R_5$ to $R_8$ is a group represented by Formula 2-2, or
X is S, one selected from $R_1$ to $R_4$ is a group represented by Formula 2-1, and one selected from $R_5$ to $R_8$ is a group represented by Formula 2-2.

10. The heterocyclic compound of claim 8, wherein:
X is O, one selected from $R_1$, $R_2$, and $R_4$ is a group represented by Formula 2-1, and one selected from $R_1$ to $R_4$ that is not a group represented by Formula 2-1 is a group represented by Formula 2-2; or
X is S, one selected from $R_1$ to $R_4$ is a group represented by Formula 2-1, and one selected from the remaining groups is a group represented by Formula 2-2.

11. The heterocyclic compound of claim 8, wherein $R_1$ to $R_8$ are each independently selected from:
a group represented by Formula 2-1, a group represented by Formula 2-2, hydrogen, deuterium, —F, —Cl, —Br, —I, a hydroxyl group, a cyano group, a nitro group, an amino group, an amidino group, a hydrazino group, a hydrazono group, a methyl group, an ethyl group, an n-propyl group, an isopropyl group, an n-butyl group, an isobutyl group, a sec-butyl group, a tert-butyl group, an n-pentyl group, a tert-pentyl group, a neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group; and
a methyl group, an ethyl group, an n-propyl group, an isopropyl group, an n-butyl group, an isobutyl group, a sec-butyl group, a tert-butyl group, an n-pentyl group, a tert-pentyl group, a neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from deuterium, —F, —Cl, —Br, and —I.

12. The heterocyclic compound of claim 8, wherein, among $R_1$ to $R_8$, the groups not represented by Formula 2-1 or Formula 2-2 are each hydrogen.

13. The heterocyclic compound of claim 8, wherein $R_{11}$ to $R_{18}$ are each independently selected from:
hydrogen, deuterium, —F, —Cl, —Br, —I, a hydroxyl group, a cyano group, a nitro group, an amino group, an amidino group, a hydrazino group, a hydrazono group, a methyl group, an ethyl group, an n-propyl group, an isopropyl group, an n-butyl group, an isobutyl group, a sec-butyl group, a tert-butyl group, an n-pentyl group, a tert-pentyl group, a neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group; and
a methyl group, an ethyl group, an n-propyl group, an isopropyl group, an n-butyl group, an isobutyl group, a sec-butyl group, a tert-butyl group, an n-pentyl group, a tert-pentyl group, a neo-pentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isoctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from deuterium, —F, —Cl, —Br, and —I.

14. The heterocyclic compound of claim 8, wherein $L_{11}$ to $L_{13}$ are each independently selected from:
a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group;
a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

15. The heterocyclic compound of claim 8, wherein:

$L_{11}$ to $L_{13}$ are each independently a group represented by one selected from Formulae 3-1 to 3-39:

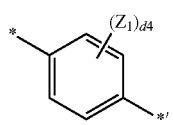

3-1

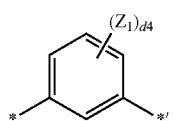

3-2

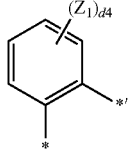

3-3

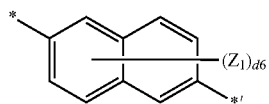

3-4

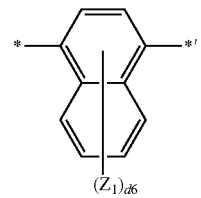

3-5

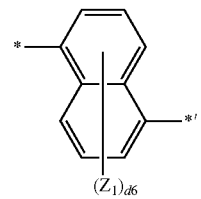

3-6

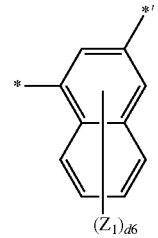

3-7

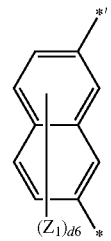

3-8

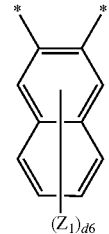

3-9

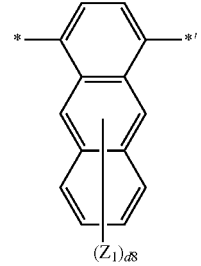

3-10

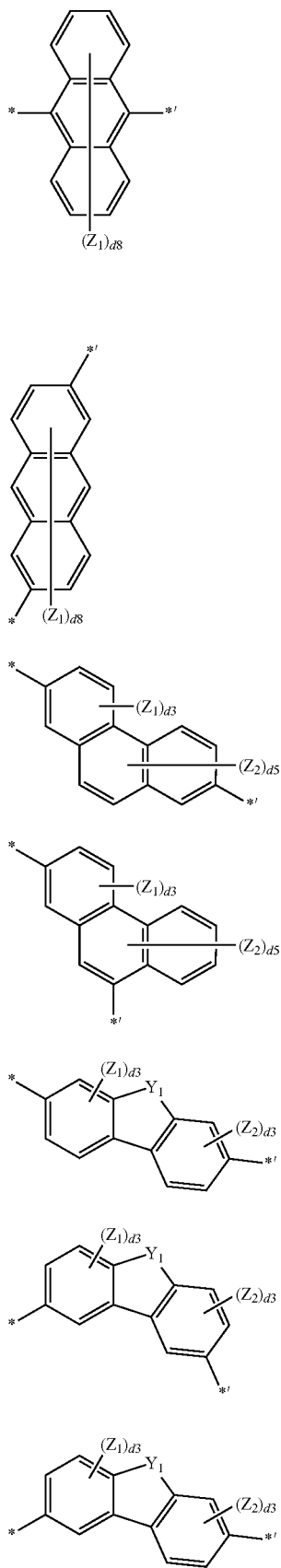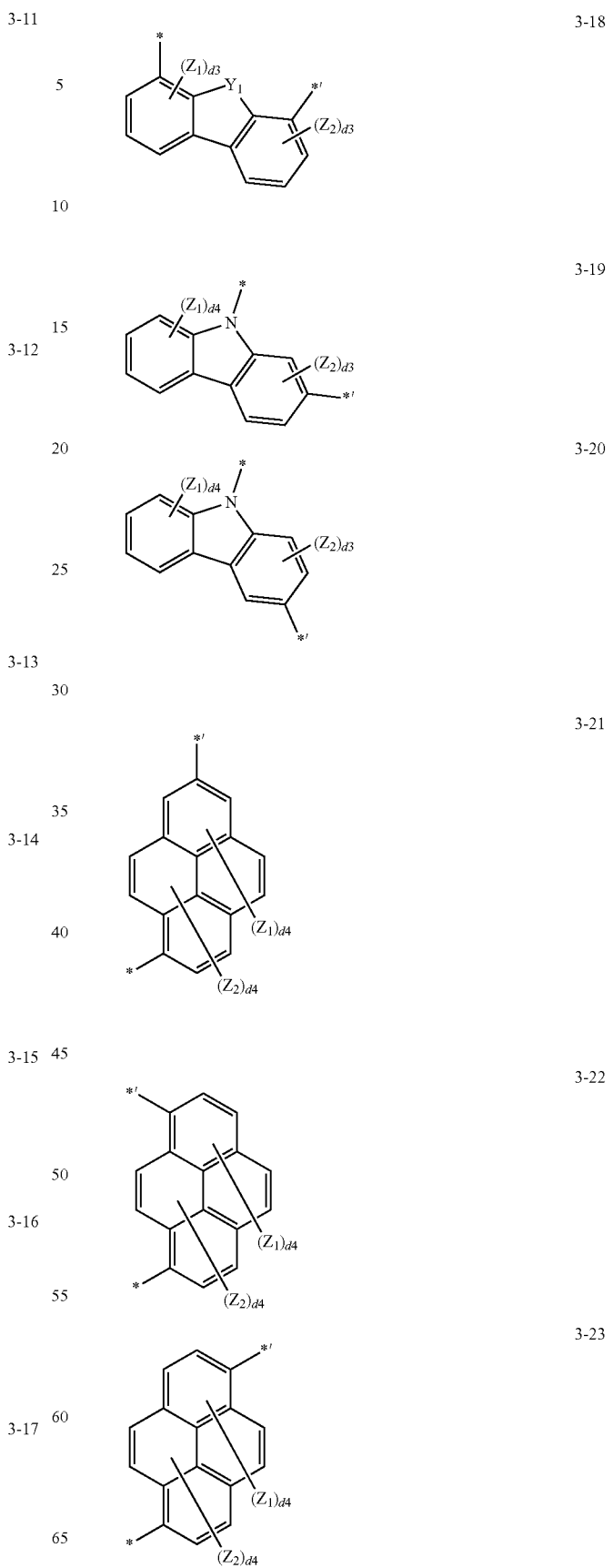

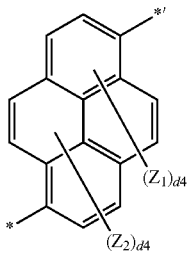
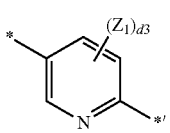
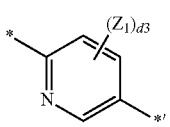
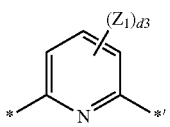
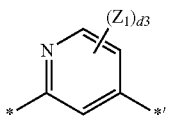
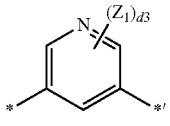
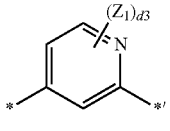
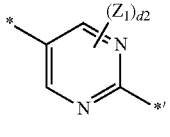
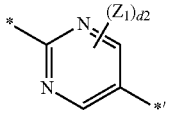
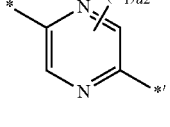
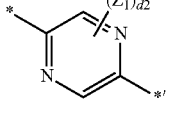

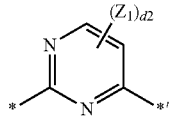
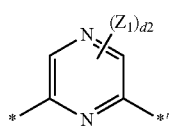
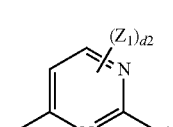
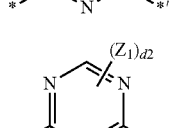
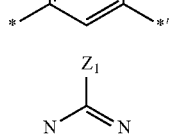
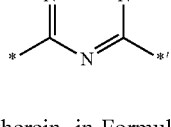
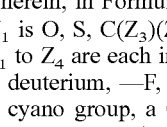
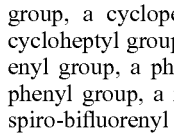
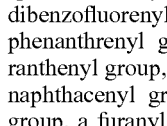
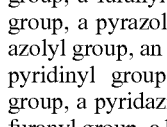
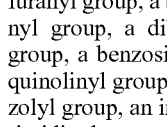

wherein, in Formulae 3-1 to 3-39, $Y_1$ is O, S, $C(Z_3)(Z_4)$, $N(Z_3)$, or $Si(Z_3)(Z_4)$, $Z_1$ to $Z_4$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, and —$Si(Q_{31})(Q_{32})(Q_{33})$, $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, $Z_3$ and $Z_4$ are optionally linked to each other to form a substituted or unsubstituted $C_5$-$C_{10}$ carbocyclic group or a substituted or unsubstituted $C_1$-$C_{10}$ heterocyclic group, d2 is an integer from 0 to 2, d3 is an integer from 0 to 3, d4 is an integer from 0 to 4, d5 is an integer from 0 to 5, d6 is an integer from 0 to 6,
d8 is an integer from 0 to 8, and
* and *' each indicate a binding site to a neighboring atom.

16. The heterocyclic compound of claim 8, wherein a11 is 0.

17. The heterocyclic compound of claim 8, wherein $Ar_1$ to $Ar_3$ are each independently selected from:
- a benzene group, a pentalene group, an indene group, a naphthalene group, an azulene group, a heptalene group, an indacene group, an acenaphthalene group, a fluorene group, a spiro-cyclopentane-fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group; and
- a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, and an imidazopyrimidine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-cyclopentane-fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and
- $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group.

18. The heterocyclic compound of claim 8, wherein $Ar_1$ to $Ar_3$ are each independently a group represented by one selected from Formulae 4-1 to 4-24:

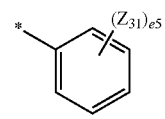

4-1

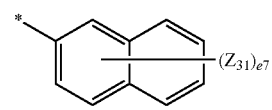

4-2

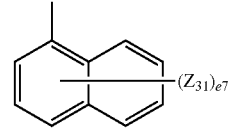

4-3

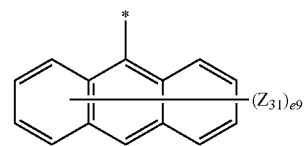

4-4

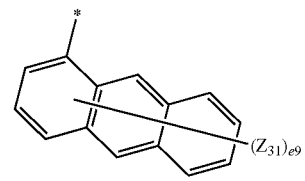

4-5

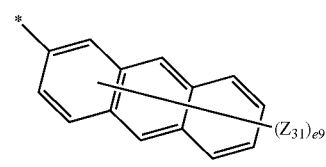

4-6

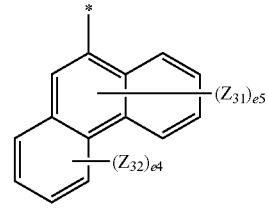

4-7

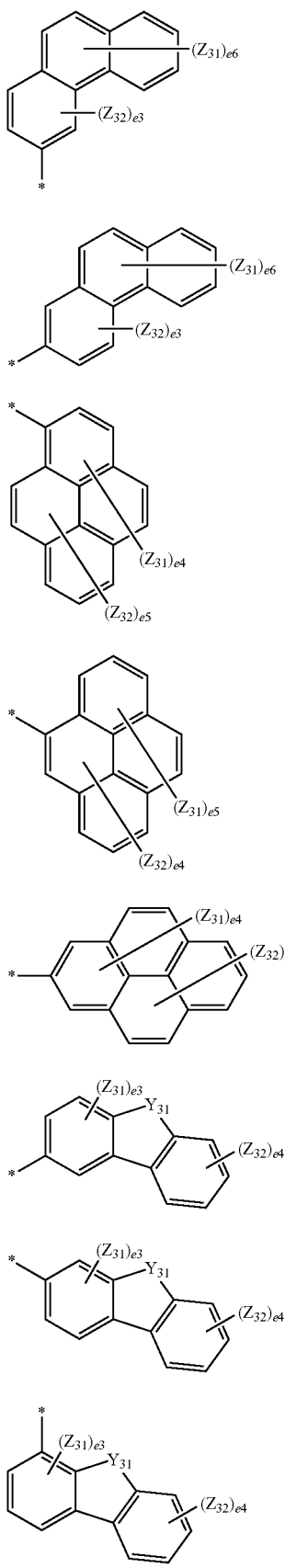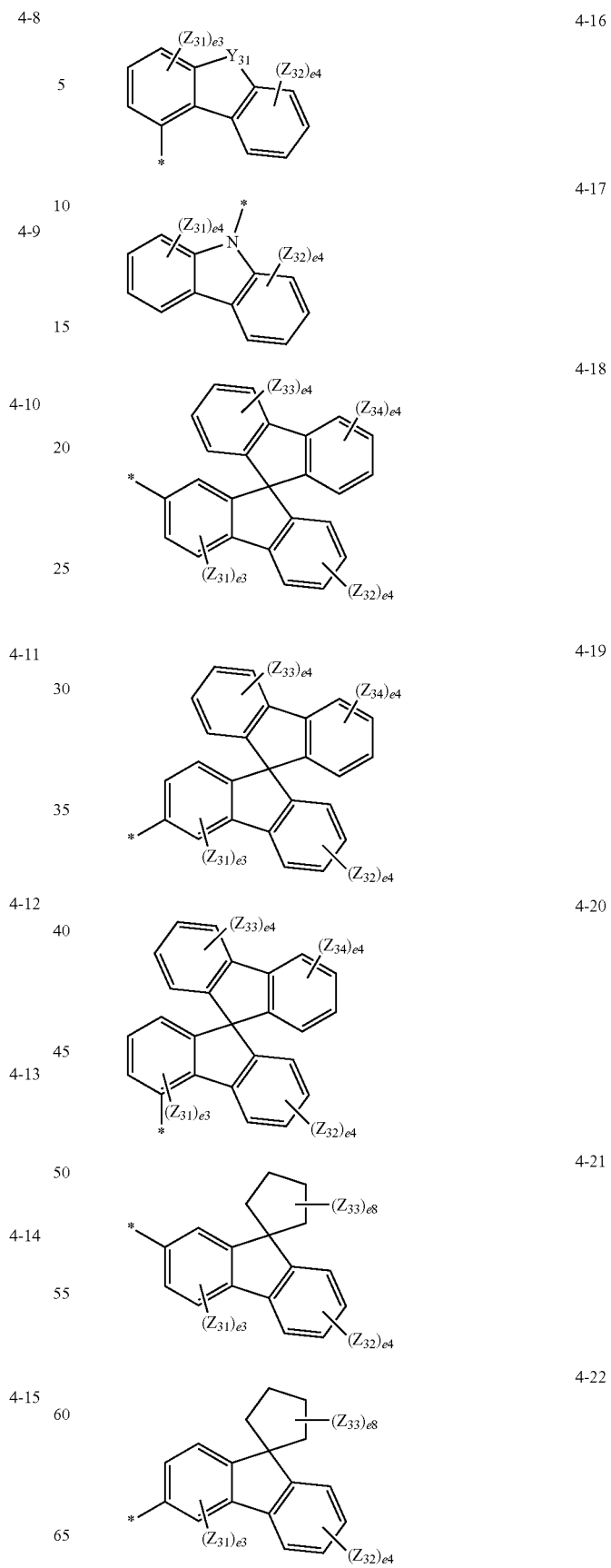

-continued

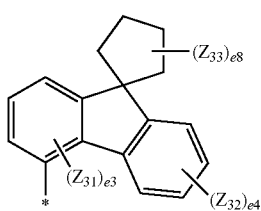

4-23

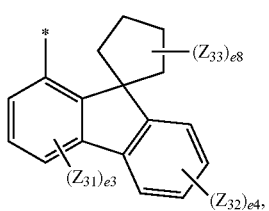

4-24 wherein, in Formulae 4-1 to 4-24, $Y_{31}$ is O, S, $C(Z_{35})(Z_{36})$, $N(Z_{35})$, or $Si(Z_{35})(Z_{36})$, $Z_{31}$ to $Z_{36}$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-cyclopentane-fluorenyl group, a spiro-bifluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, and —$Si(Q_{31})(Q_{32})(Q_{33})$, $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, and a pyridinyl group, e3 is an integer from 0 to 3, e4 is an integer from 0 to 4, e5 is an integer from 0 to 5, e6 is an integer from 0 to 6, e7 is an integer from 0 to 7, e8 is an integer from 0 to 8, e9 is an integer from 0 to 9, and

* indicates a binding site to a neighboring atom.

19. The heterocyclic compound of claim 8, wherein:
$Ar_1$ is a benzene group, and
$Ar_2$ and $Ar_3$ are each independently selected from:
a benzene group, a naphthalene group, a fluorene group, a spiro-cyclopentane-fluorene group, a spiro-bifluorene group, a benzofluorene group, a dibenzofluorene group, a dibenzofuran group, a dibenzothiophene group, a carbazole group, and a dibenzosilole group; and
a benzene group, a naphthalene group, a fluorene group, a spiro-bifluorene group, a benzofluorene group, a dibenzofluorene group, a dibenzofuran group, a dibenzothiophene group, a carbazole group, and a dibenzosilole group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a phenyl group, a biphenyl group, a terphenyl group, a naphthyl group, a spiro-cyclopentane-fluorenyl group, a spiro-bifluorenyl group, a benzofluorenyl group, a dibenzofluorenyl group, a dibenzofuranyl group, a dibenzothiophenyl group, a carbazolyl group, a dibenzosilolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$.

20. The heterocyclic compound of claim 8, wherein the heterocyclic compound is selected from Compounds 1 to 348:

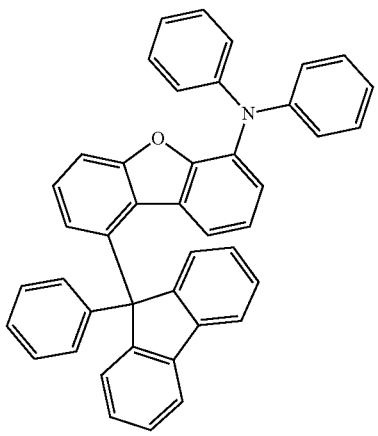

1

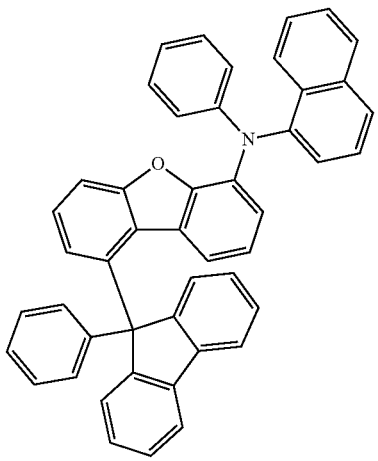

2

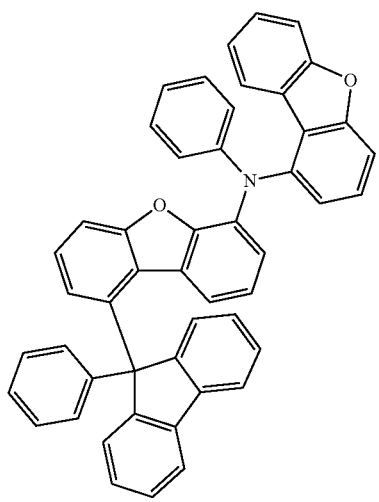
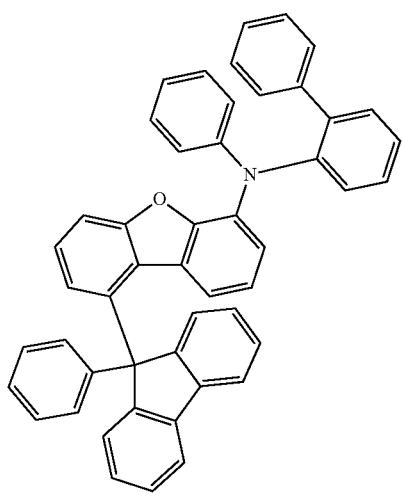
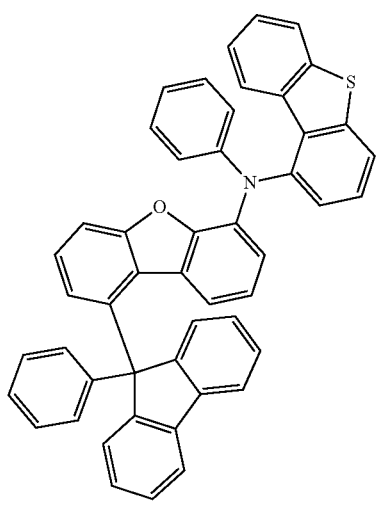
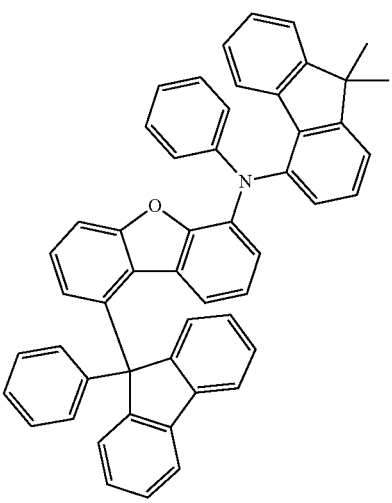
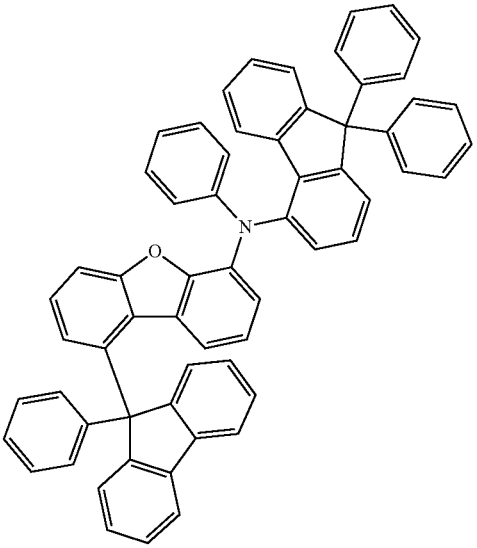
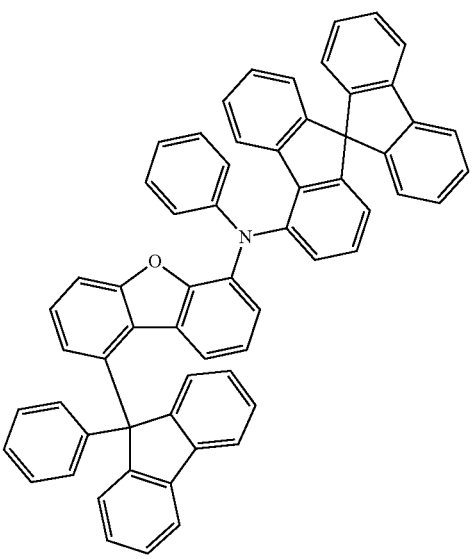

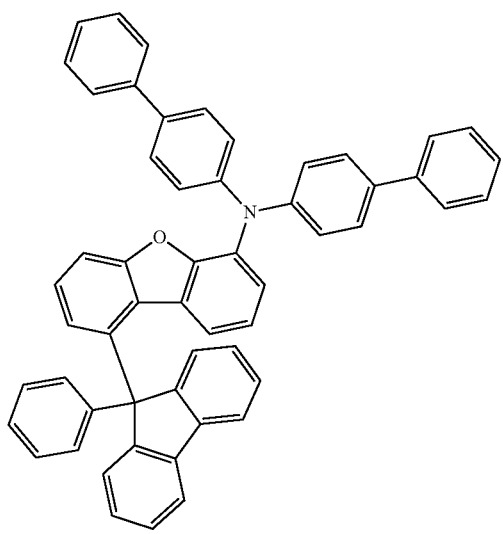
9
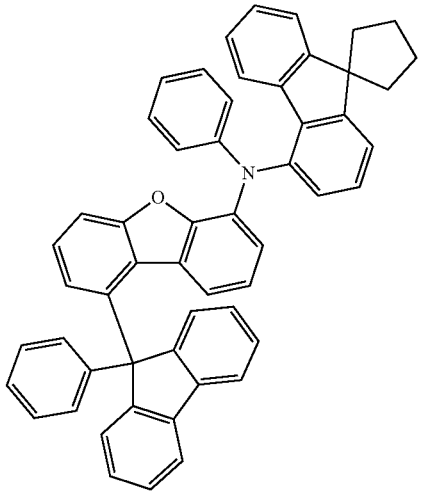
12
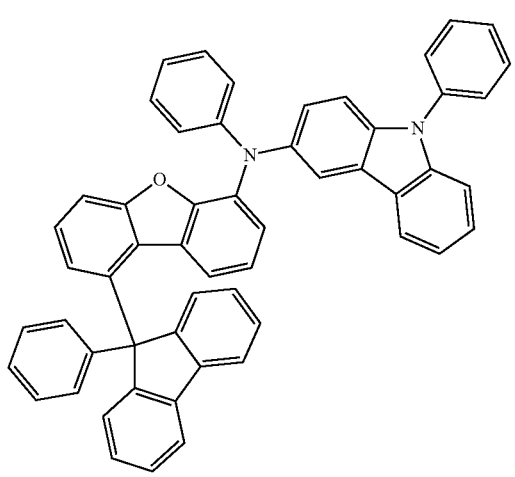
10
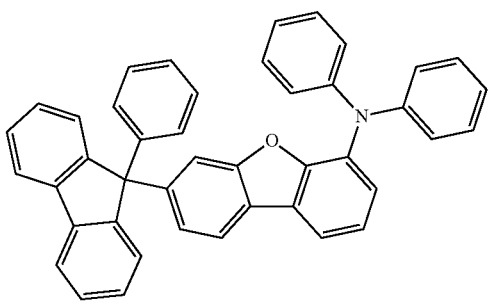
13
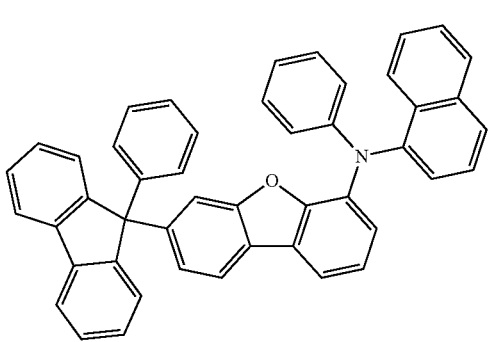
14
11
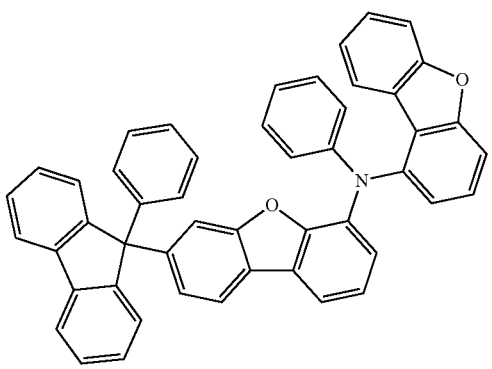
15

261
-continued
16
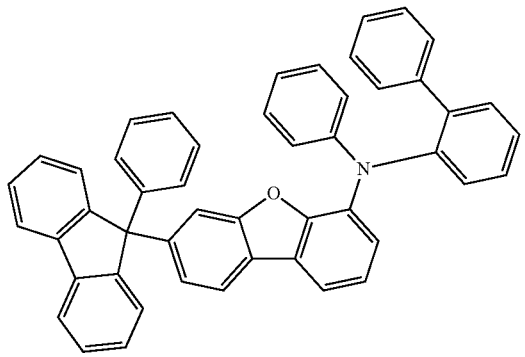
17
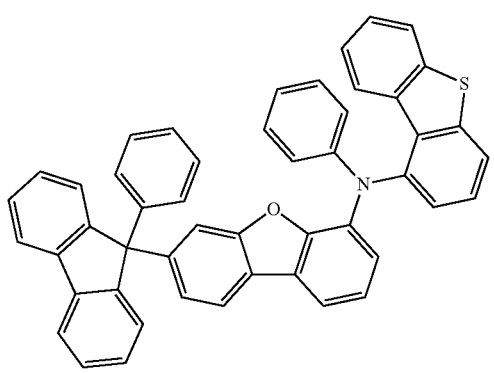
18
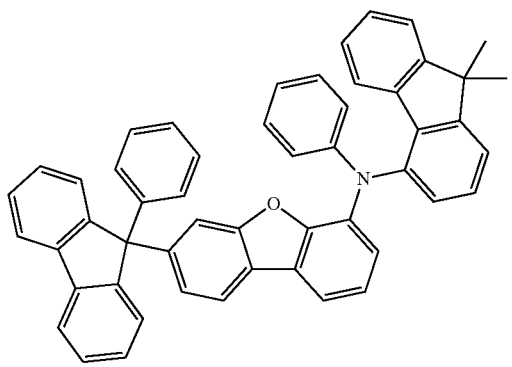
19
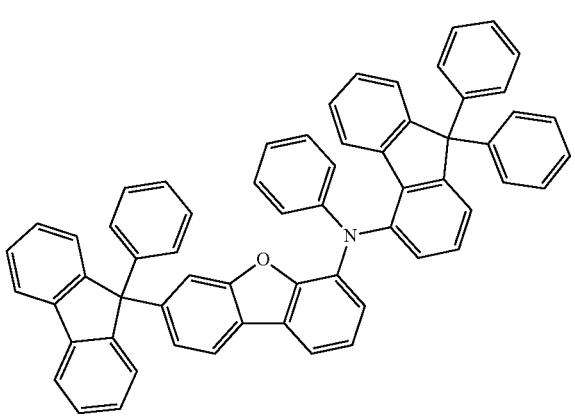
262
-continued
20
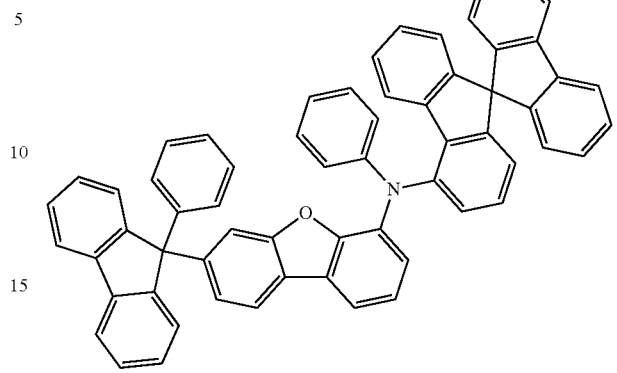
21
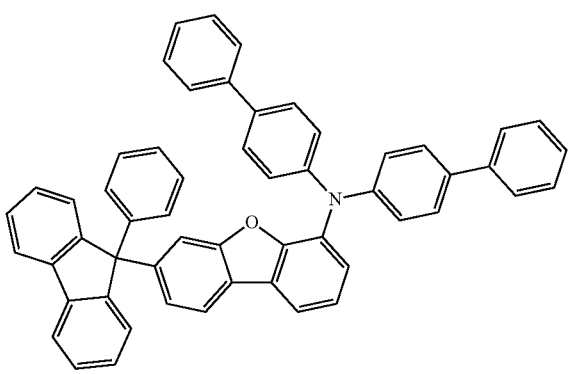
22
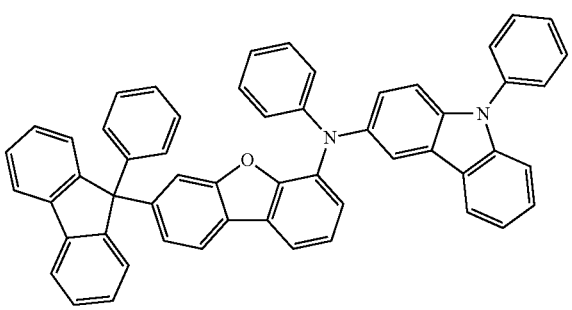
23
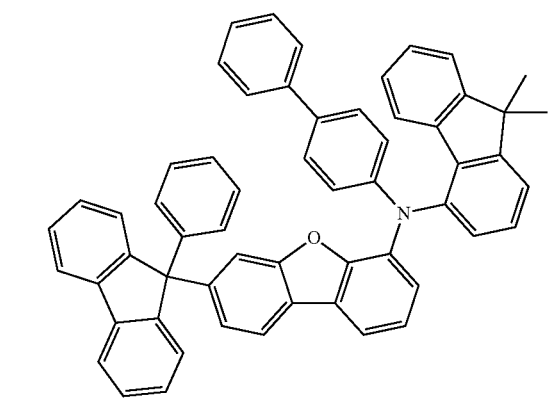

263
-continued
24
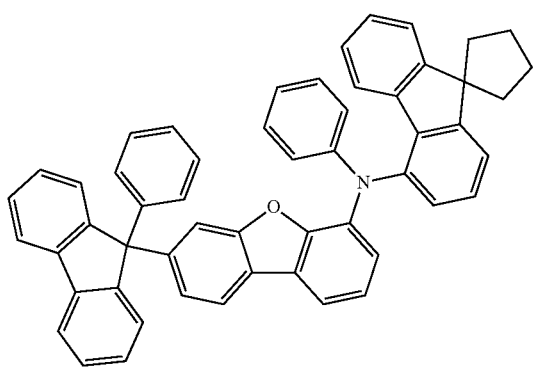
25
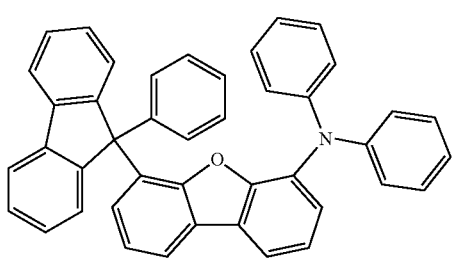
26
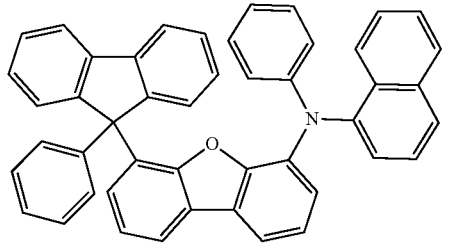
27
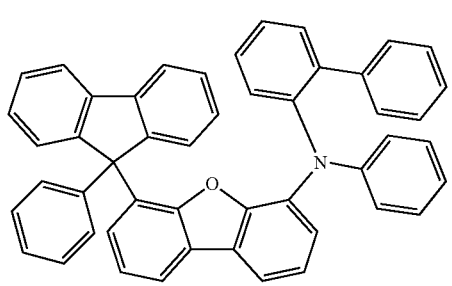
28
264
-continued
29
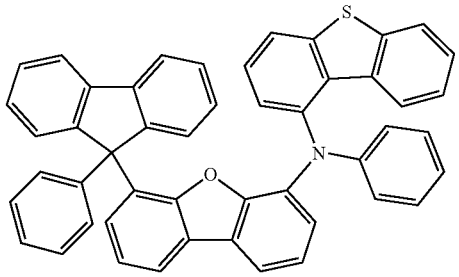
30
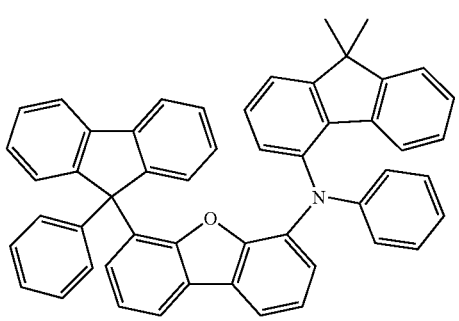
31
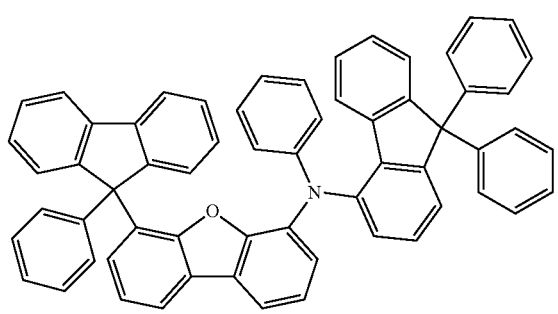
32
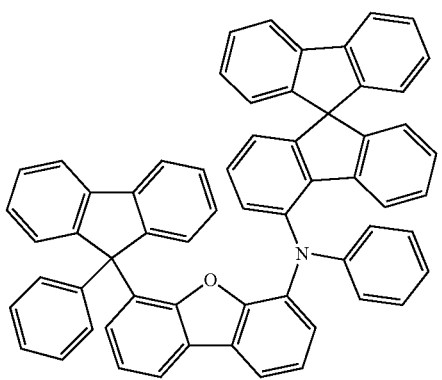

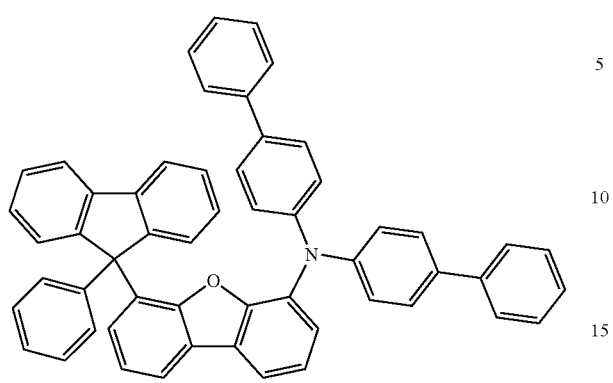
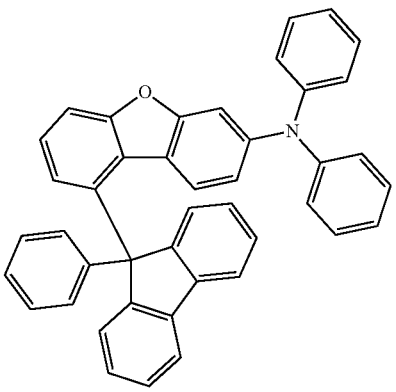
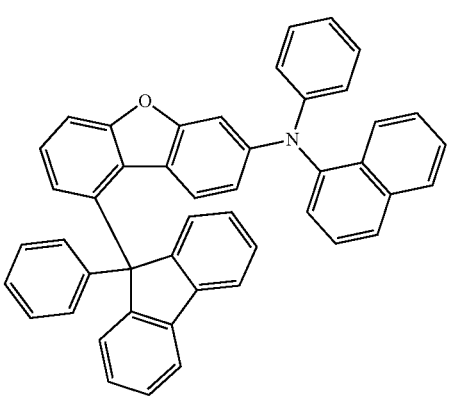
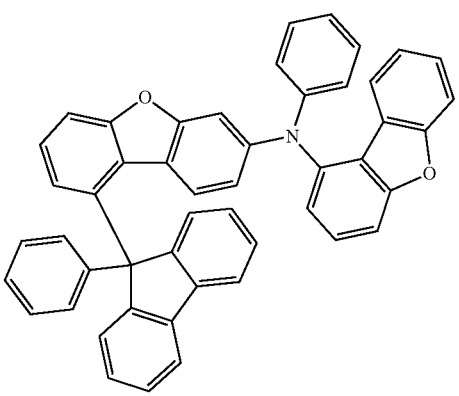
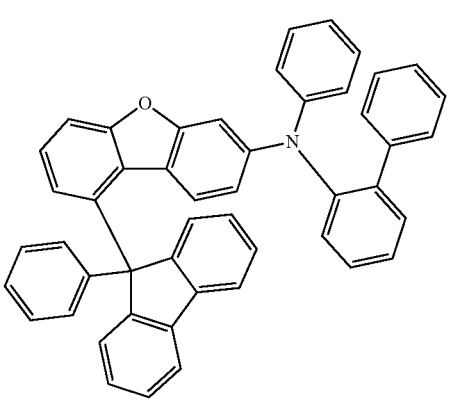

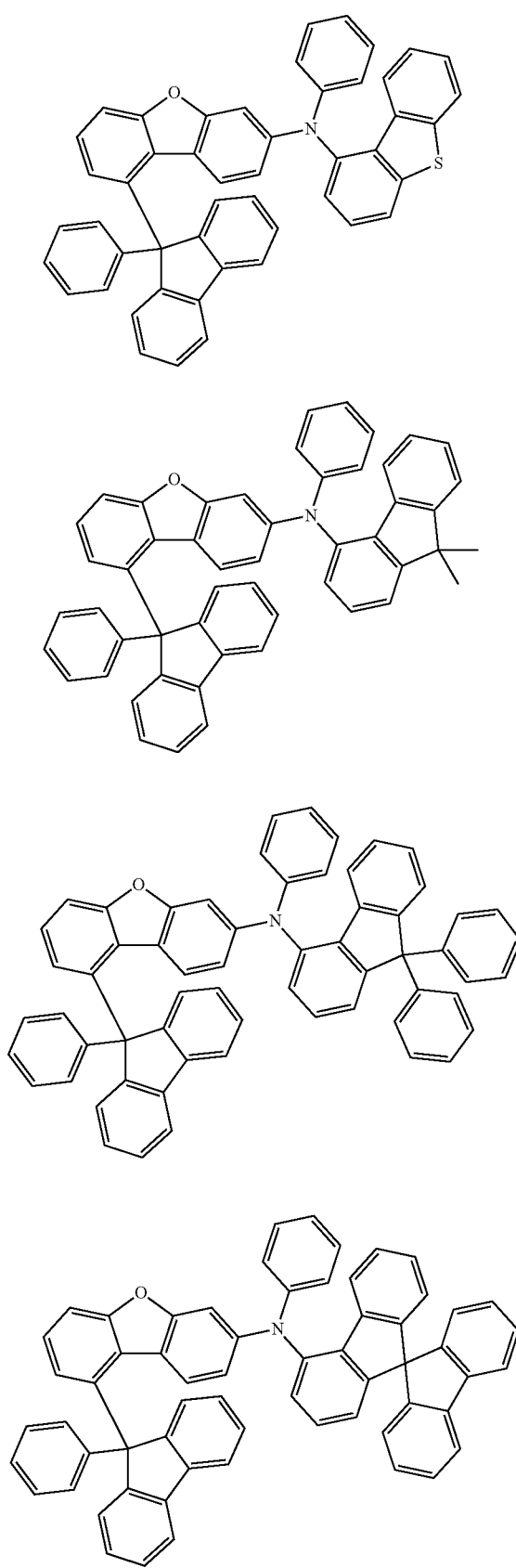
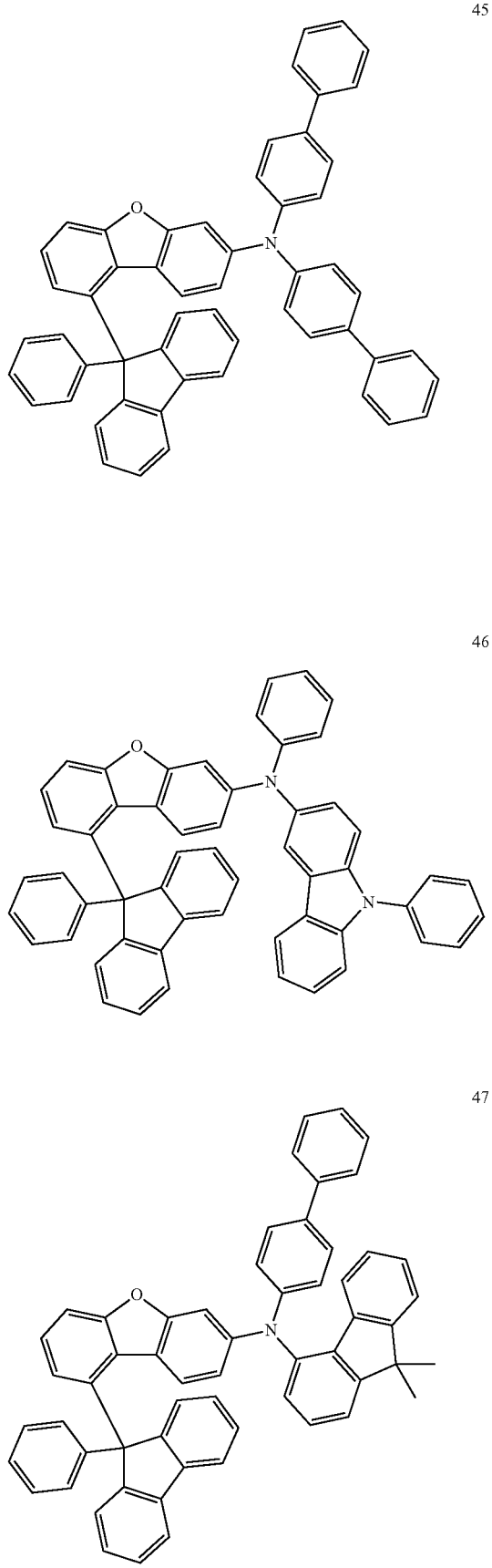

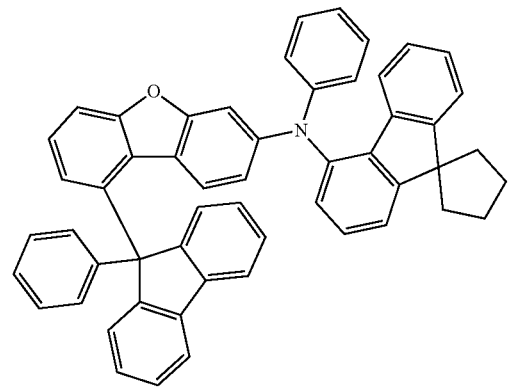
48
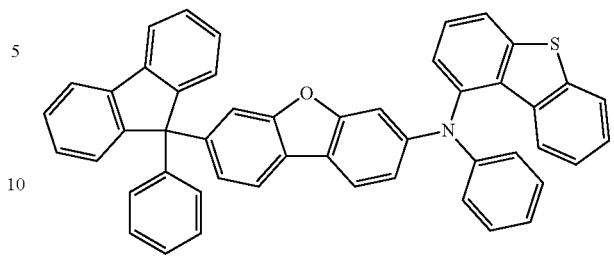
49
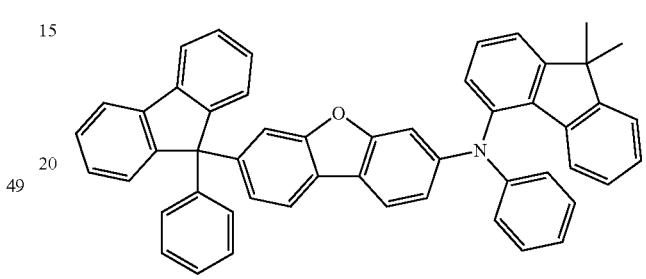
50
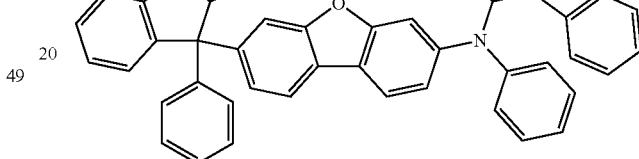
51
52
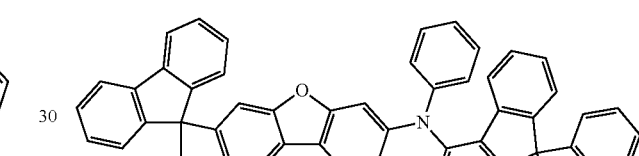
53
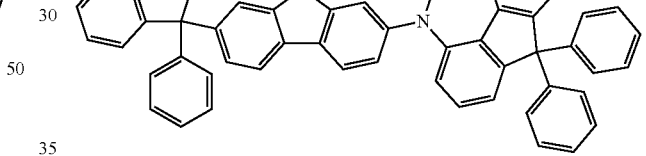
54
55
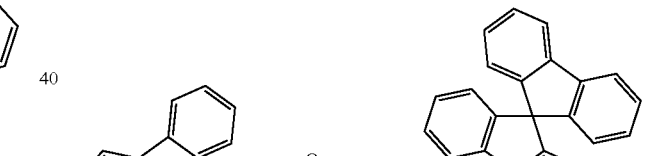
56
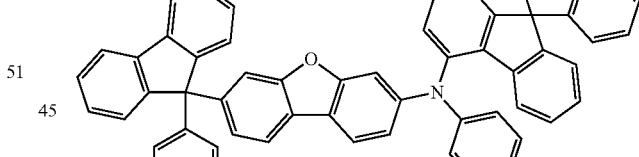
57
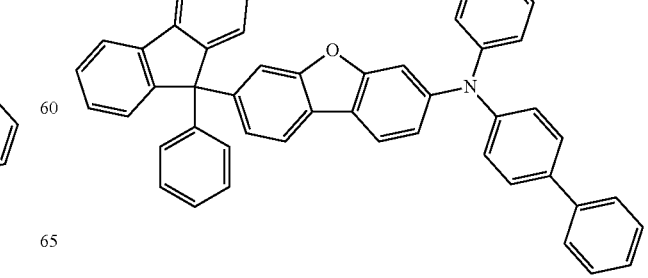

58
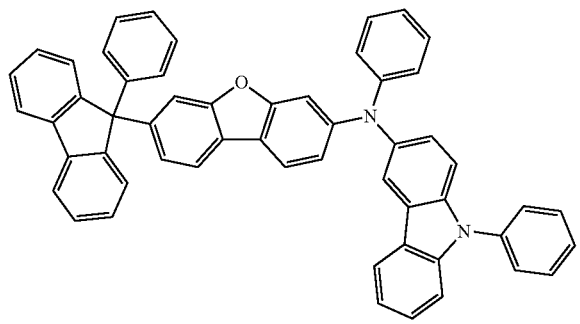
59
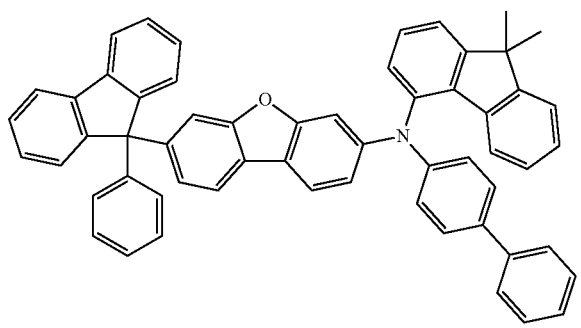
60
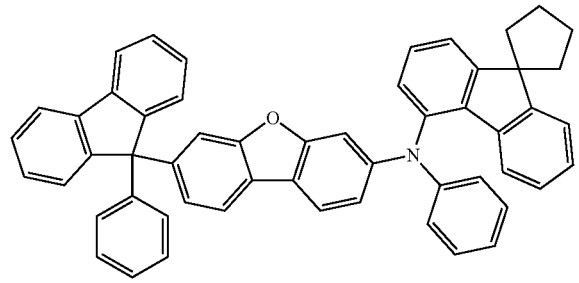
61
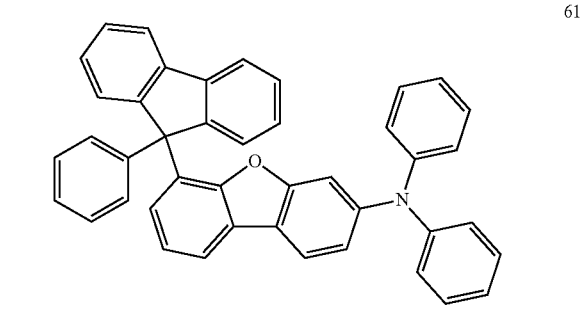
62
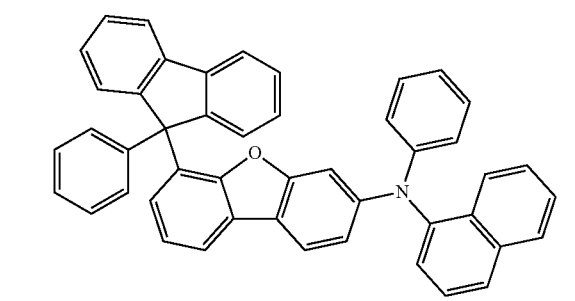
63
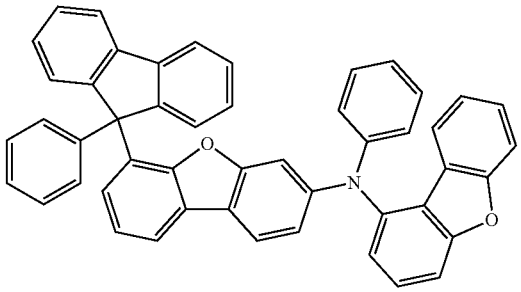
64
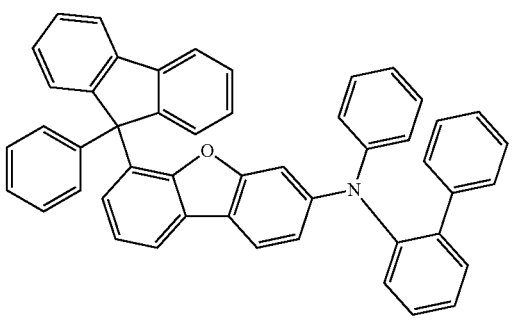
65
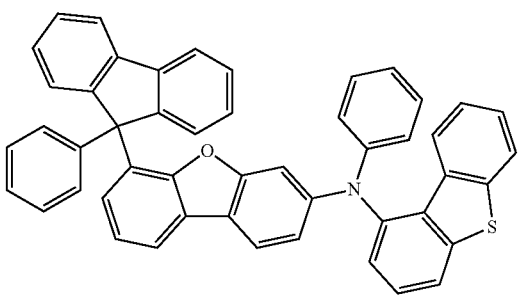
66
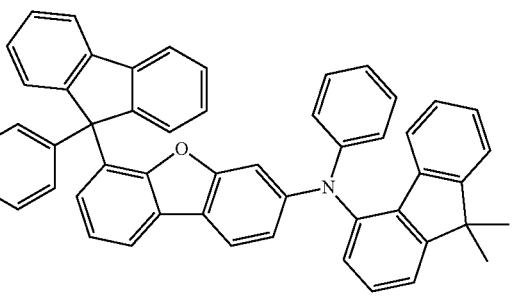
67
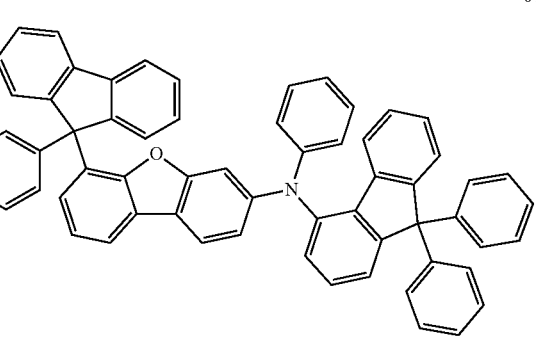

68
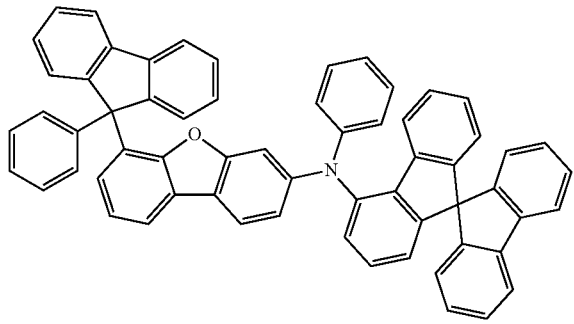
72
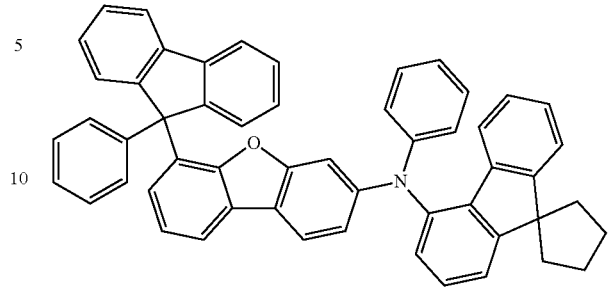
69
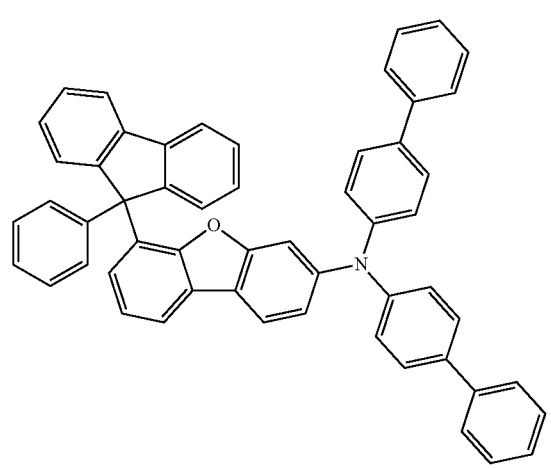
73
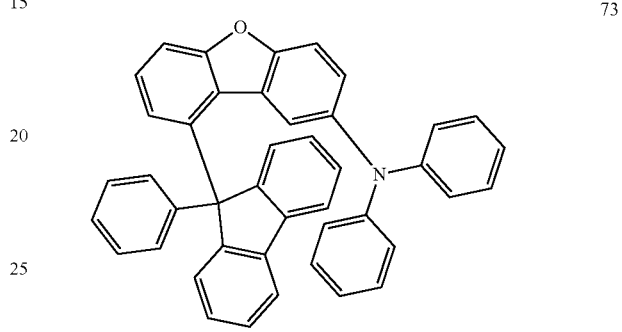
74
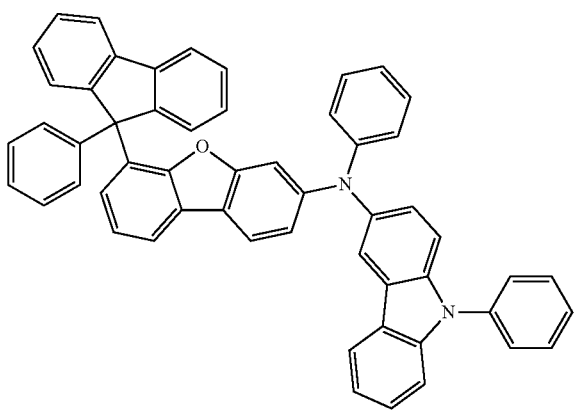
70
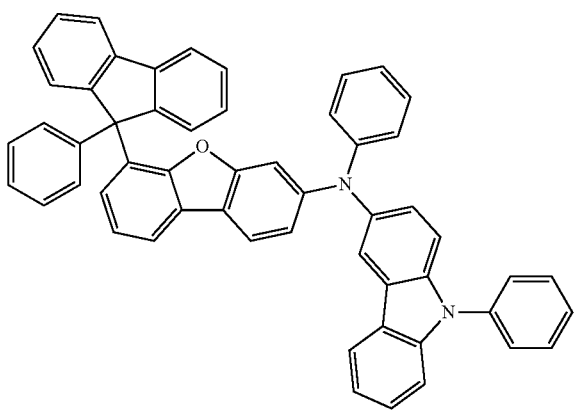
75
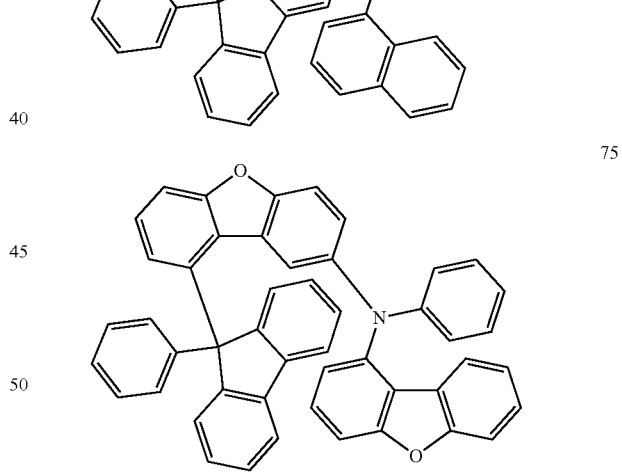
71
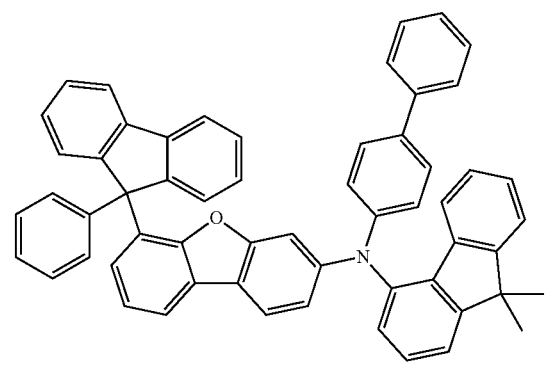
76
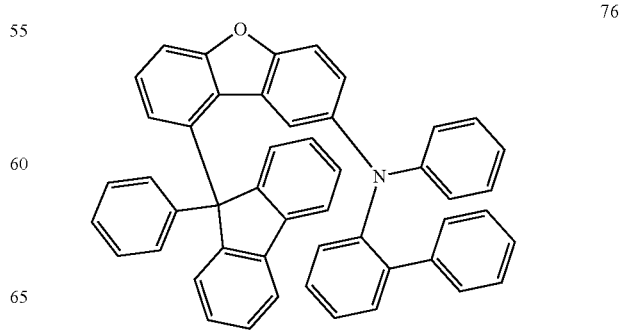

77
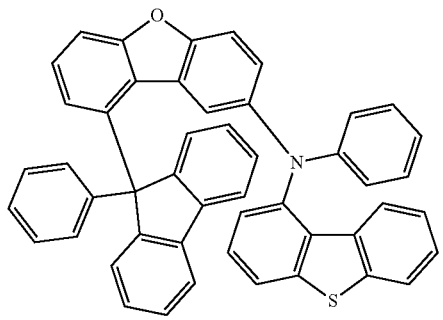
78
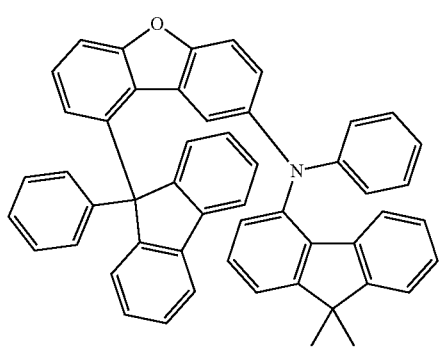
79
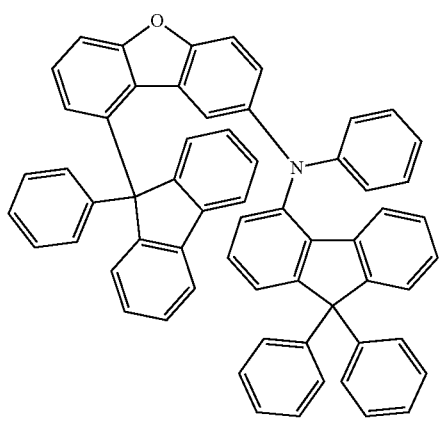
80
81
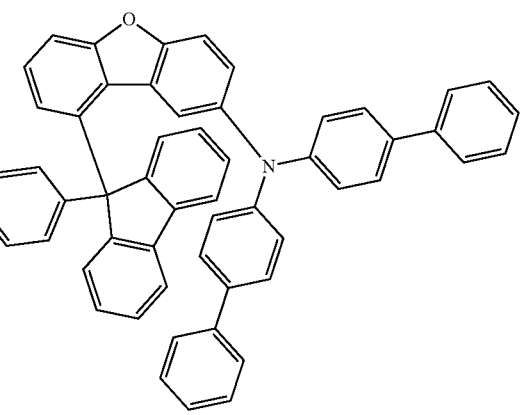
82
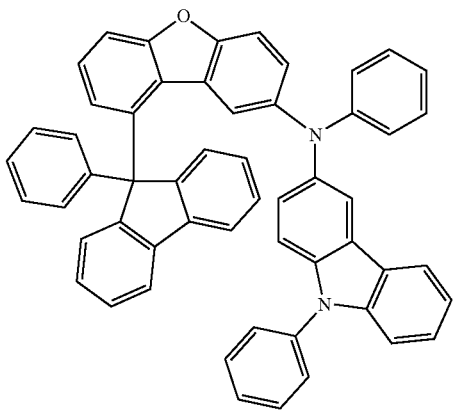
83
84
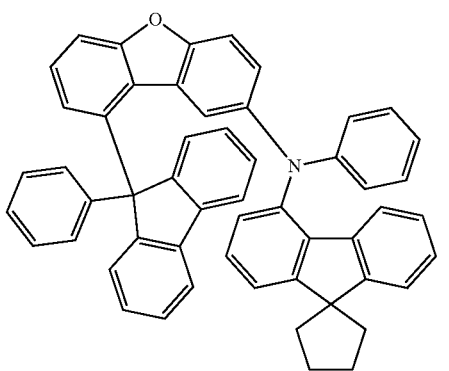

277
-continued
85
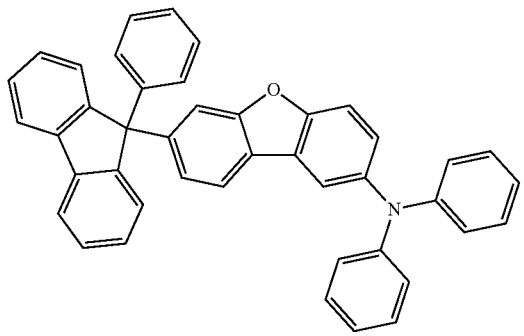
86
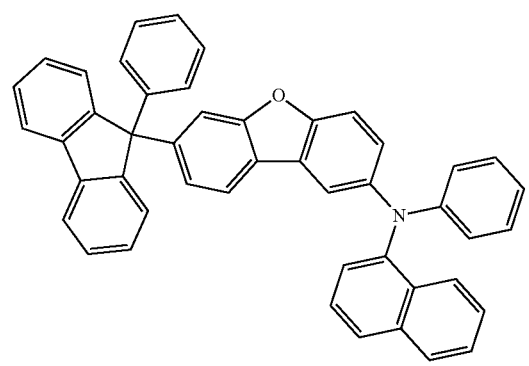
87
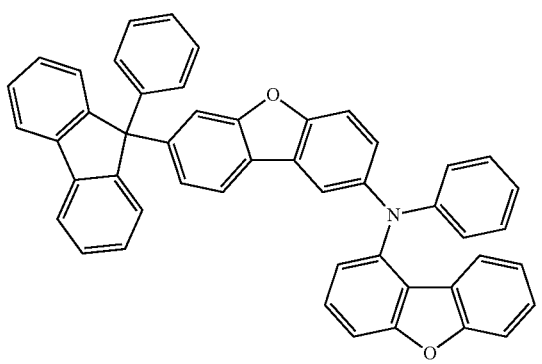
88
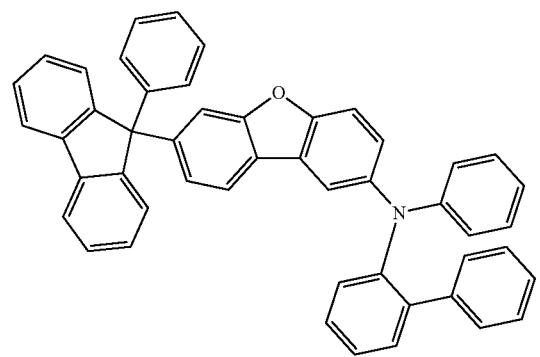
278
-continued
89
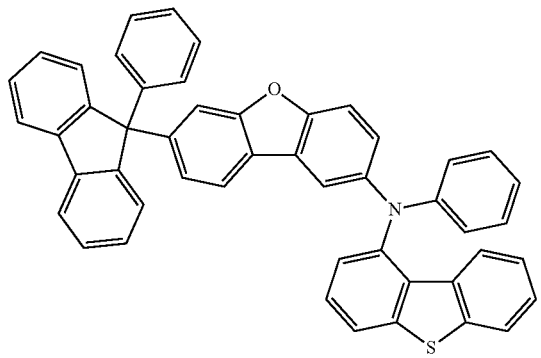
90
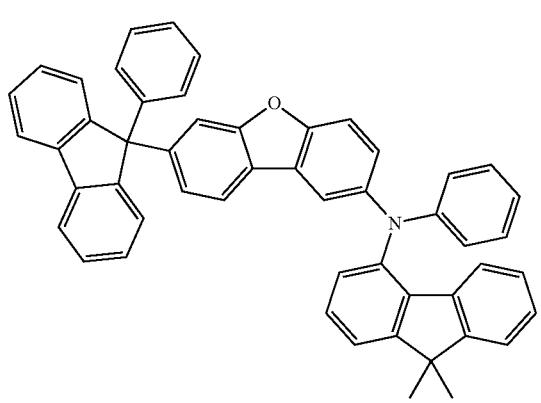
91
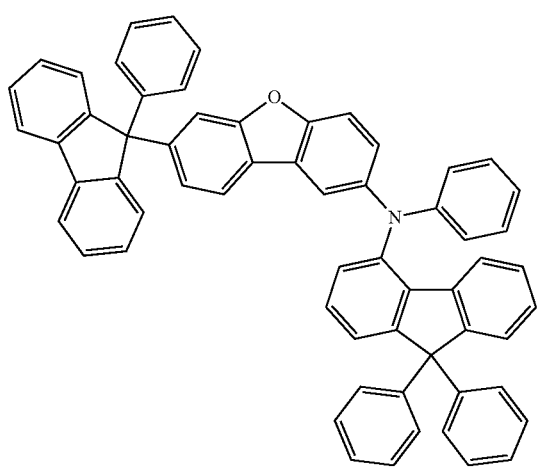

279
-continued
92
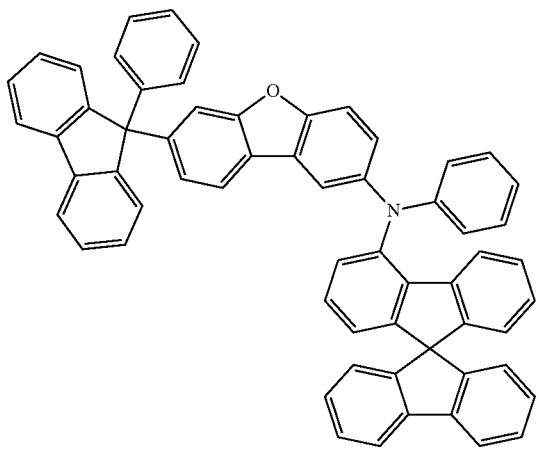
93
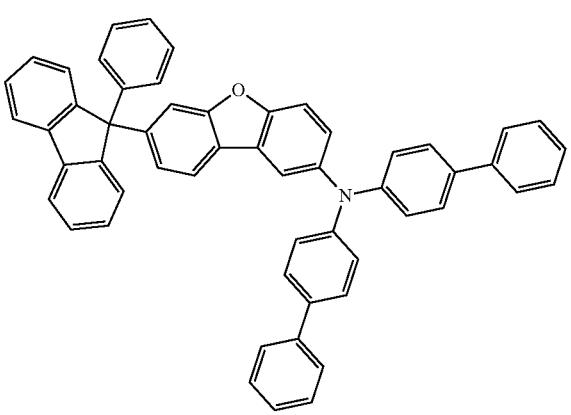
94
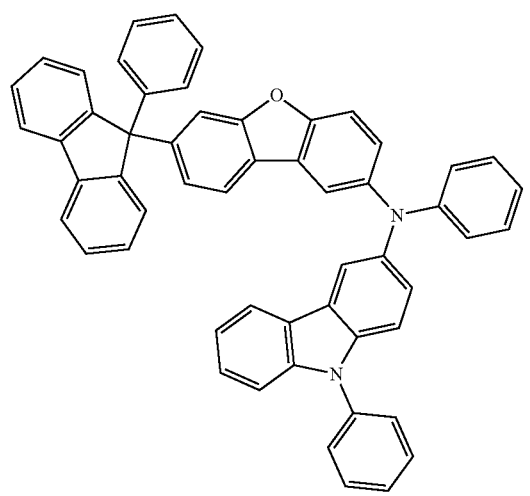
280
-continued
95
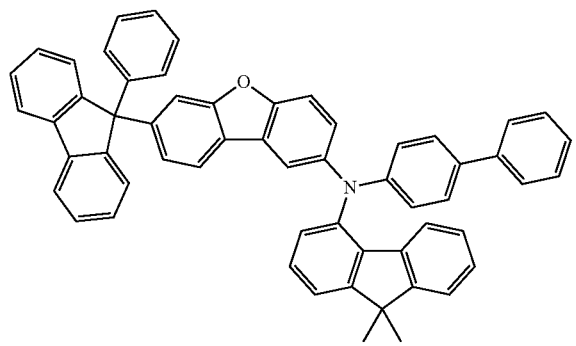
96
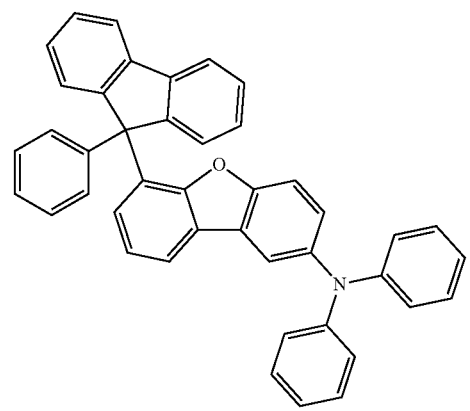
97
98
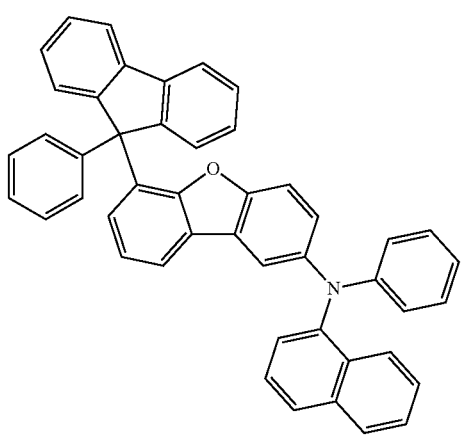

281
-continued
99
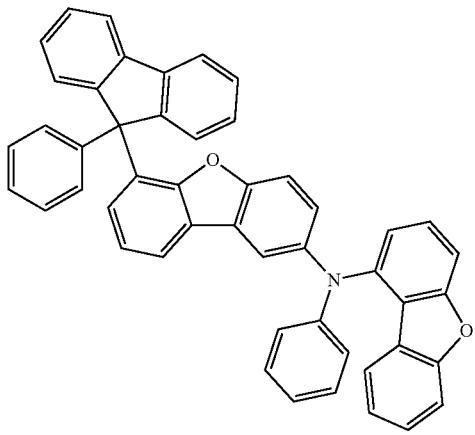
100
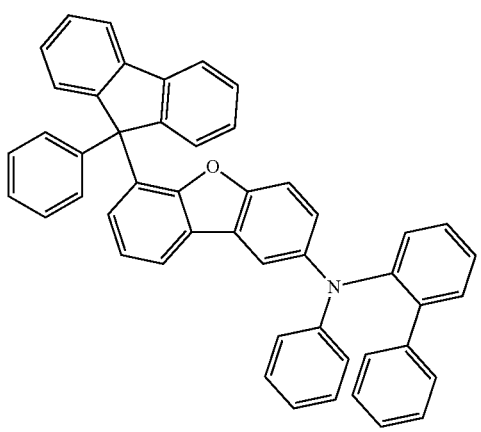
101
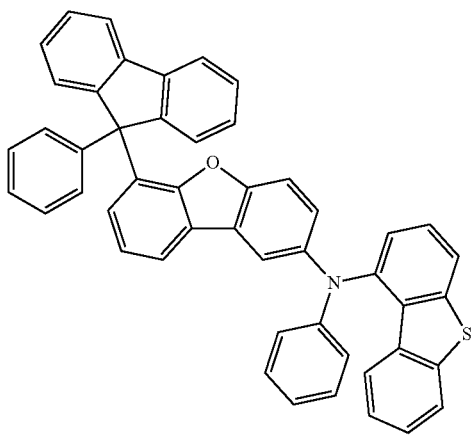
282
-continued
102
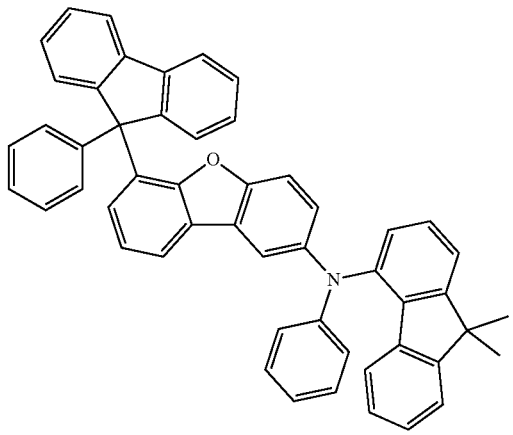
103
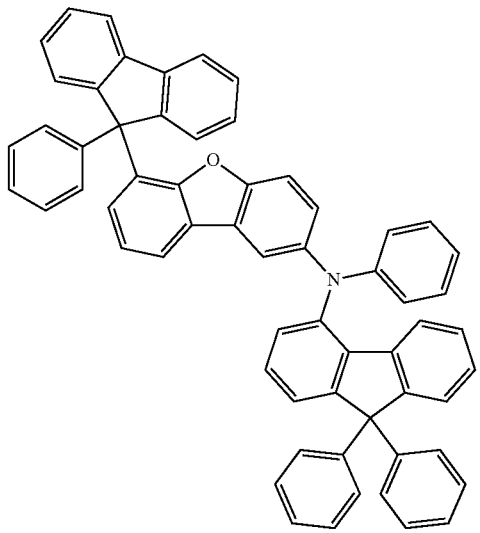
104
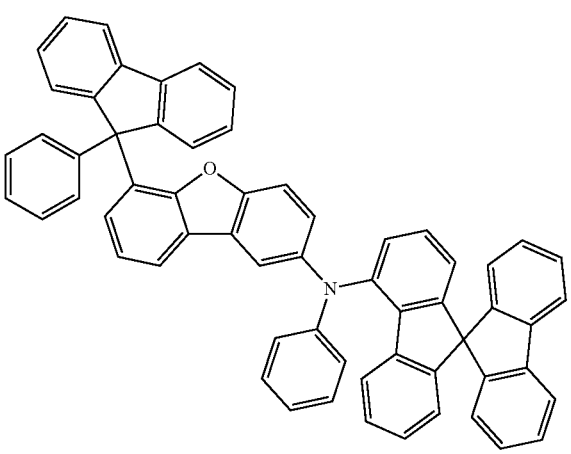

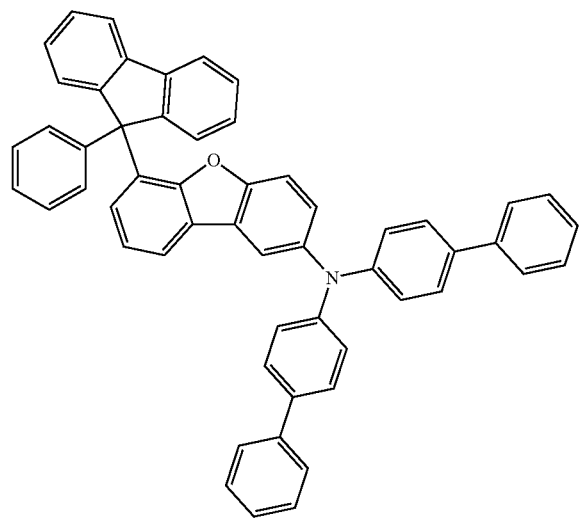
105
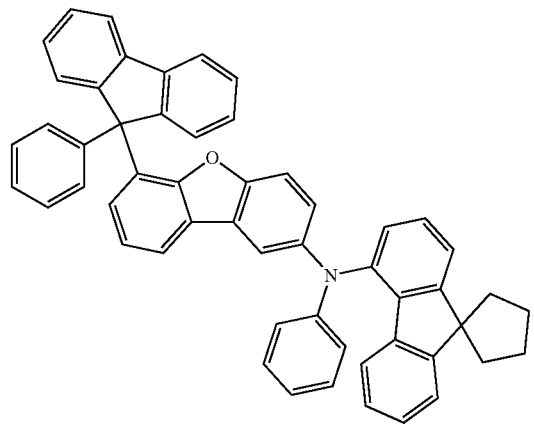
108
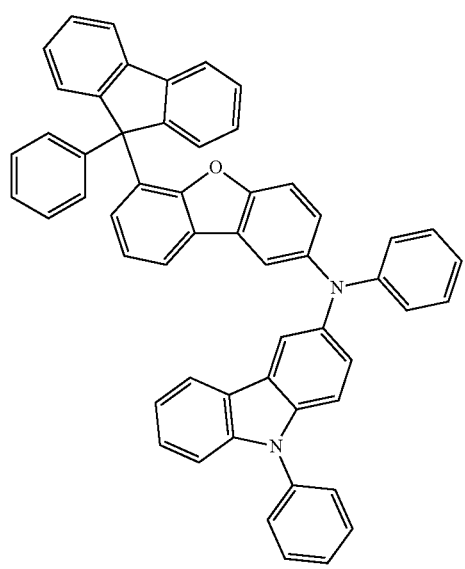
106
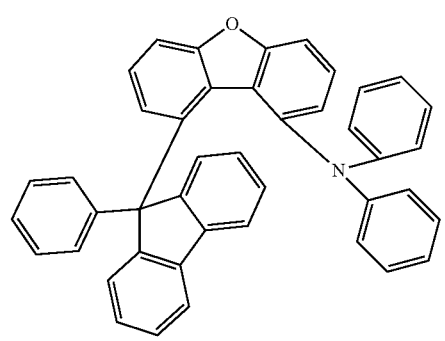
109
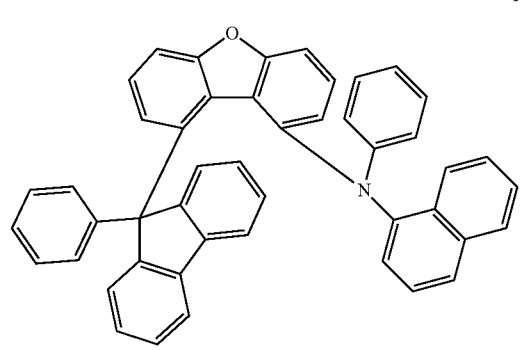
110
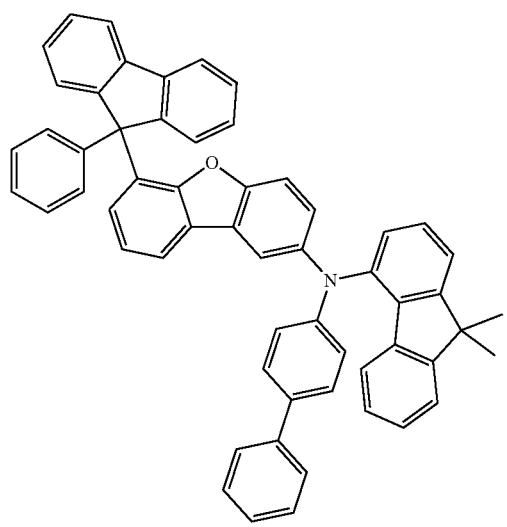
107
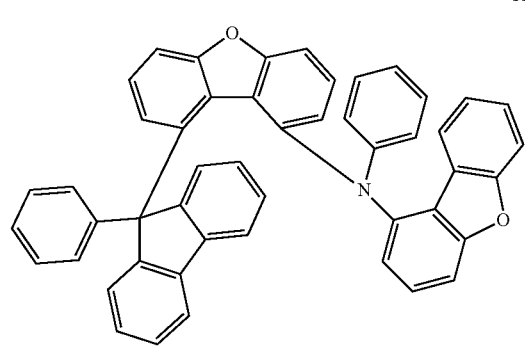
111

112
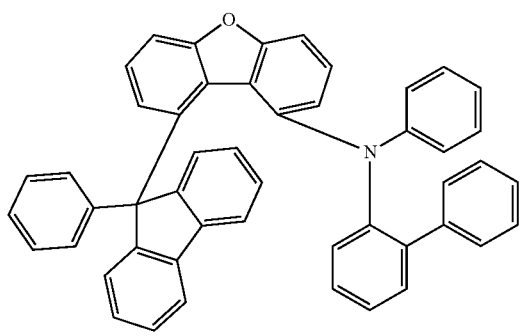
113
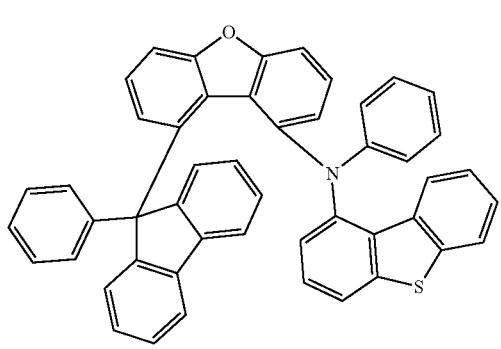
114
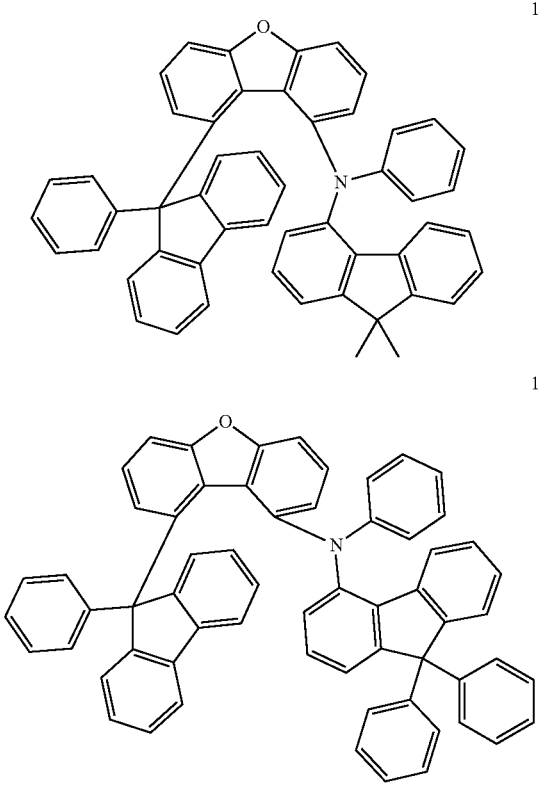
115
116
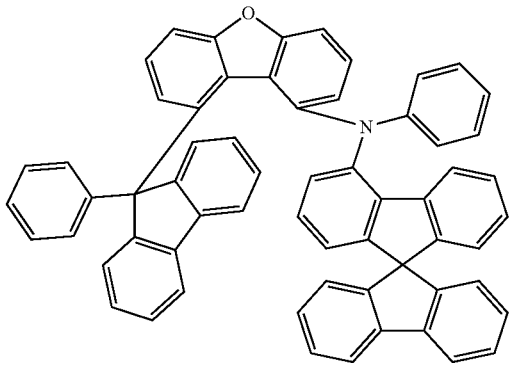
117
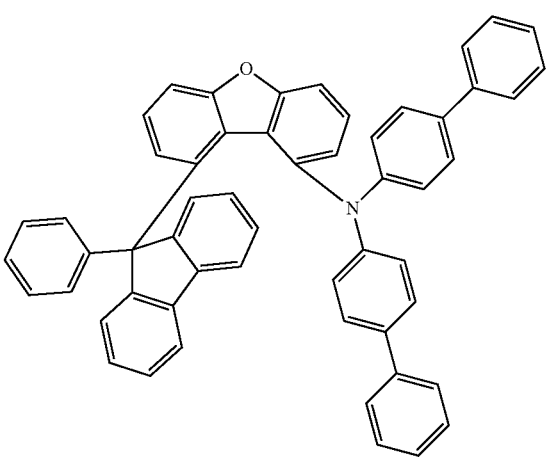
118
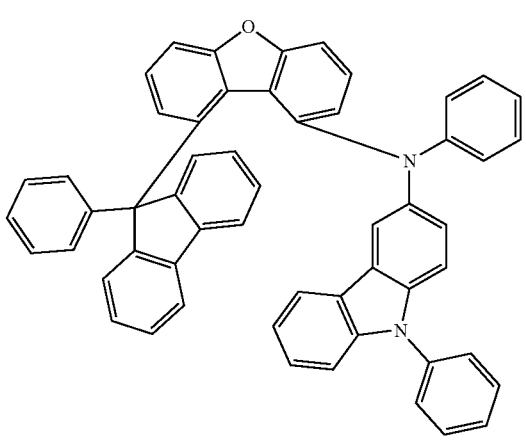

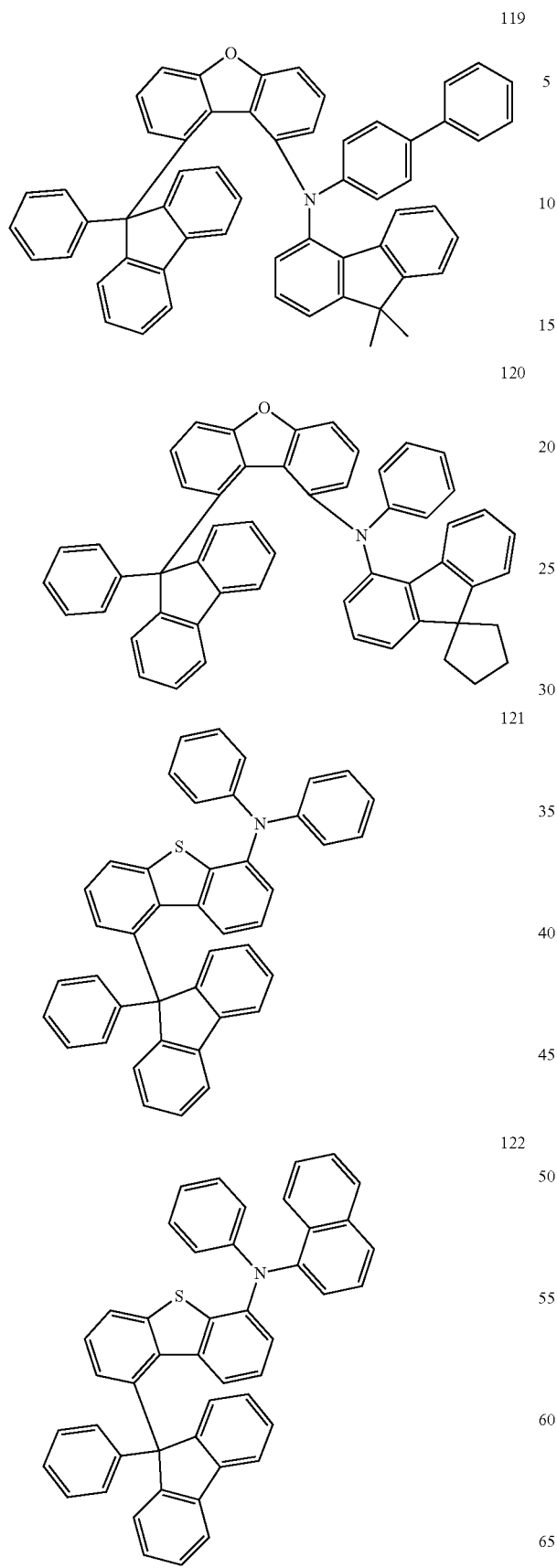
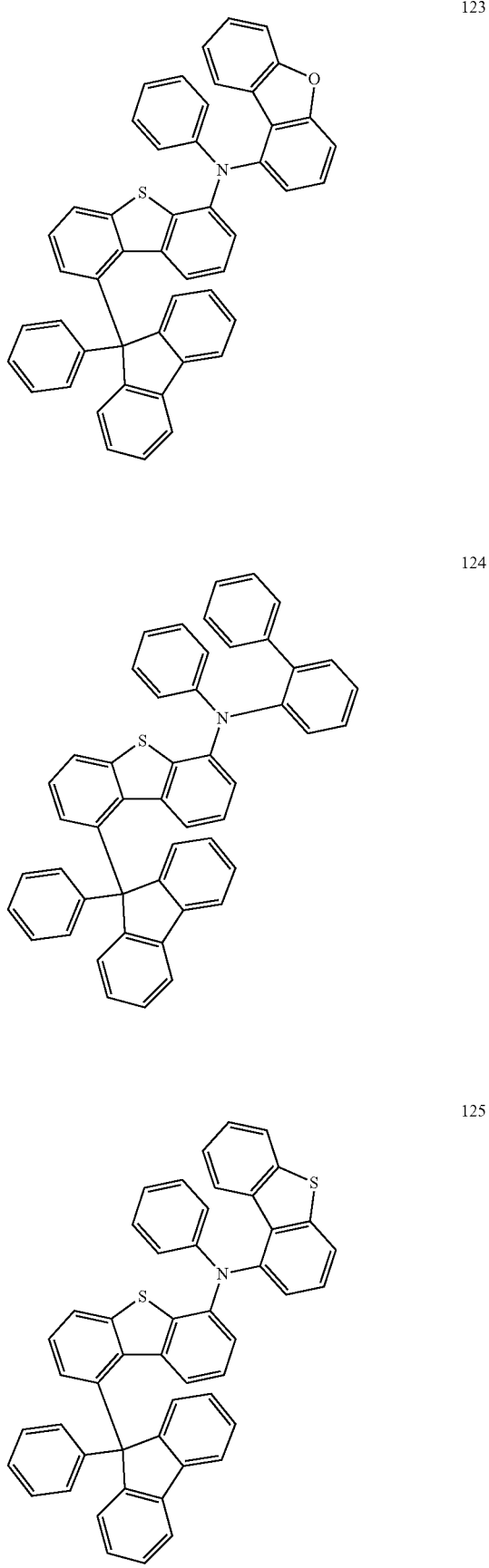

126 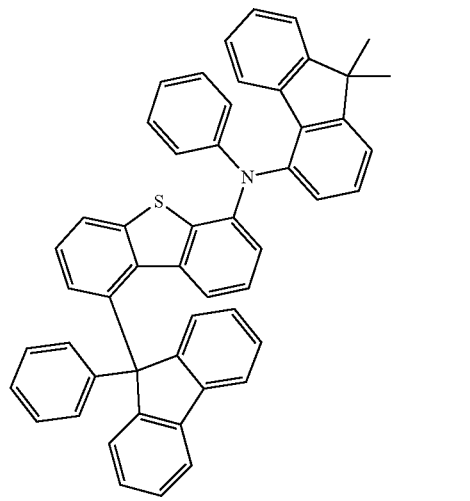
127 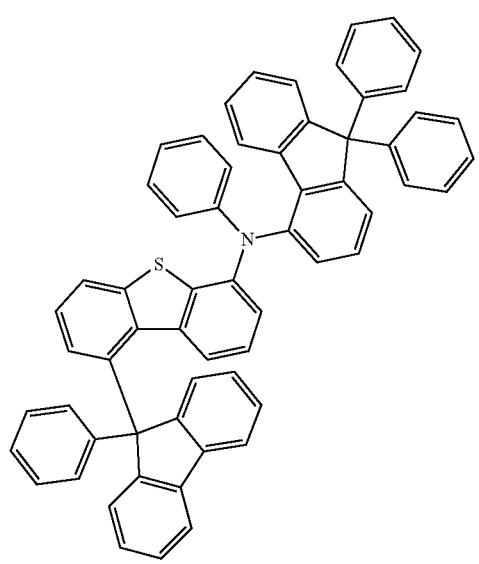
128 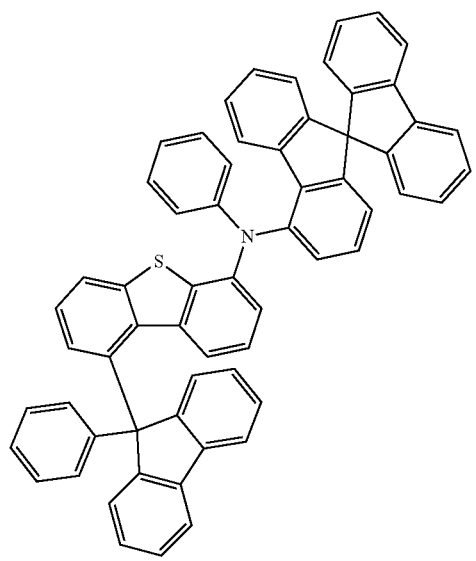
129 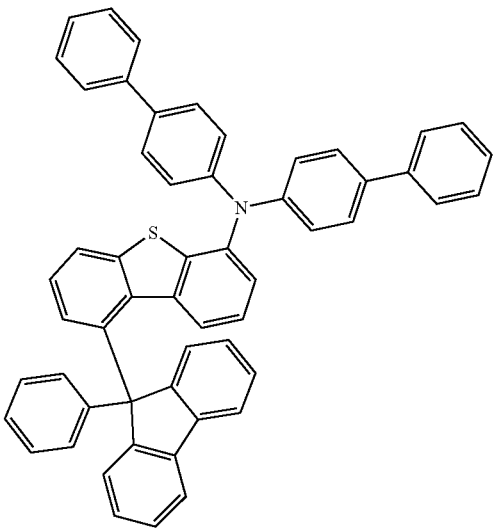
130 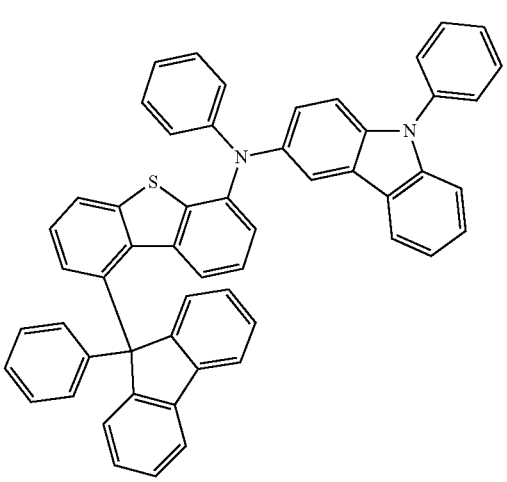
131 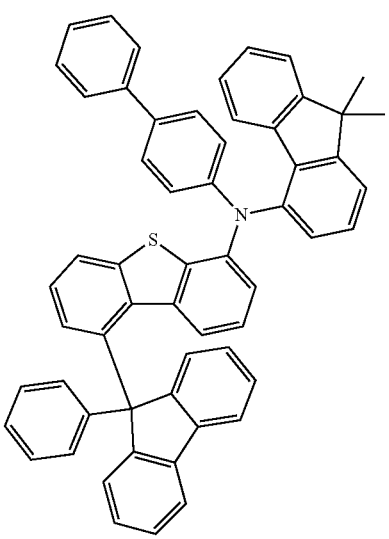

291
-continued
132
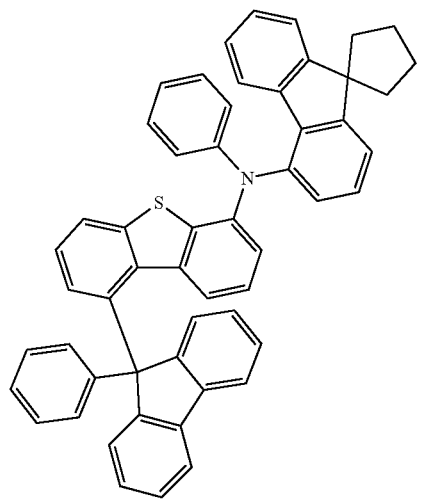
133
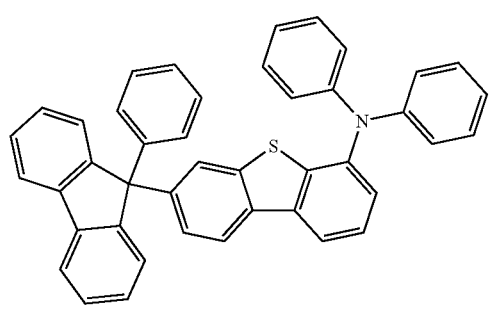
134
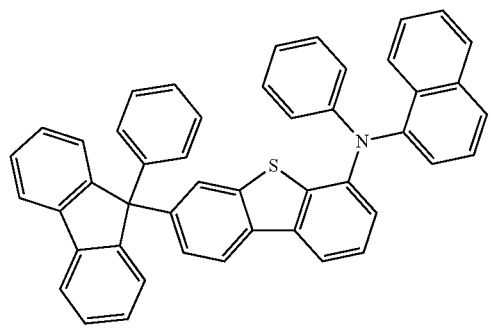
135
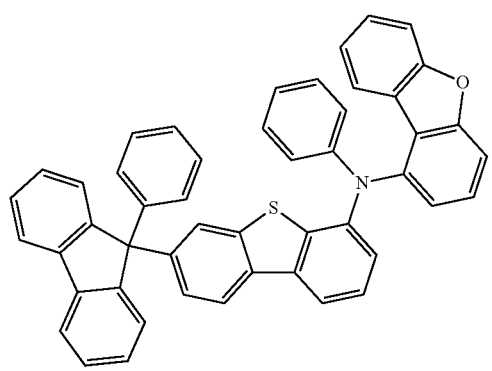
292
-continued
136
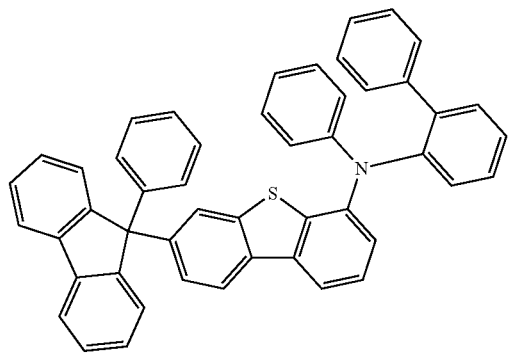
137
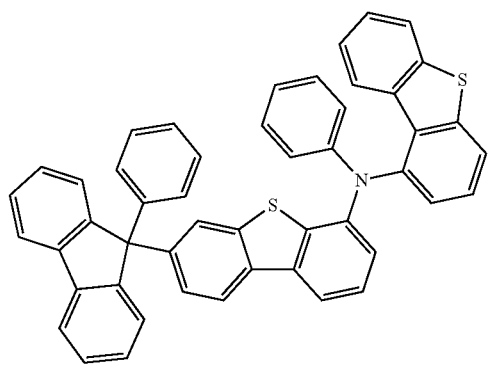
138
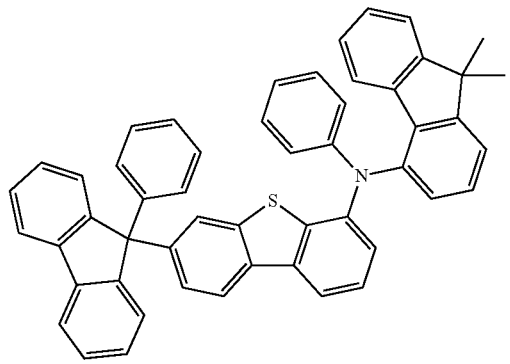
139
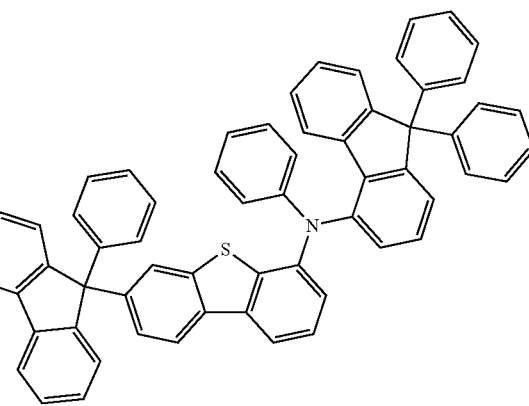

140
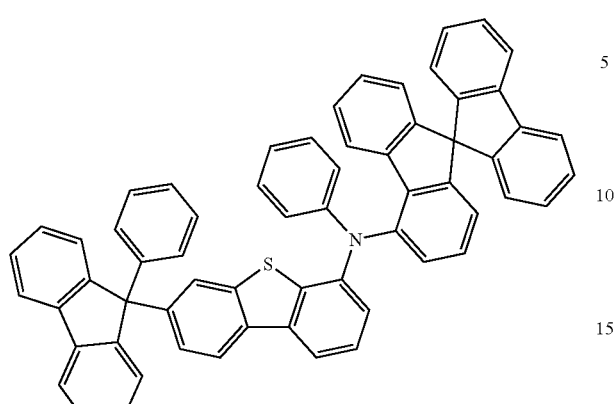
141
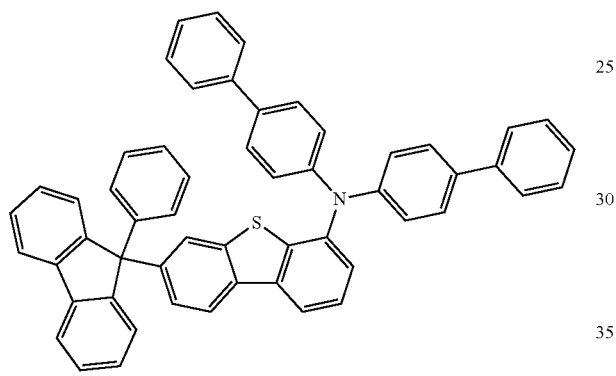
142
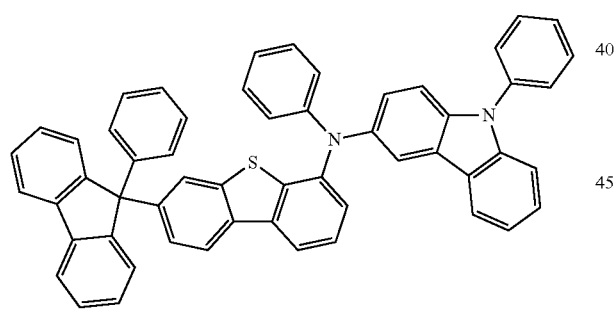
143
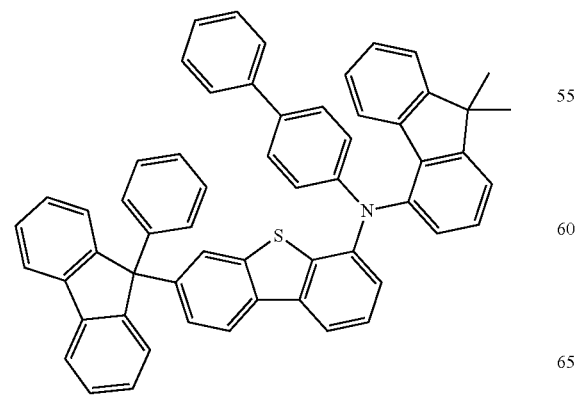
144
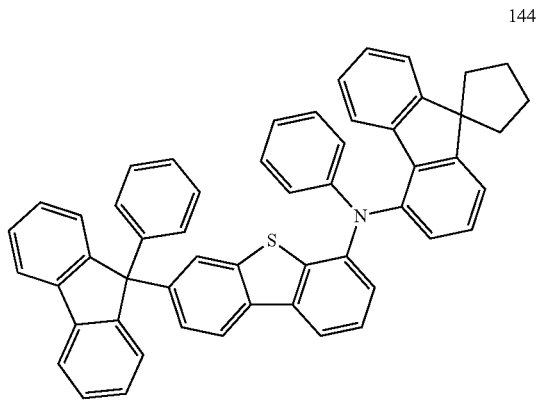
145
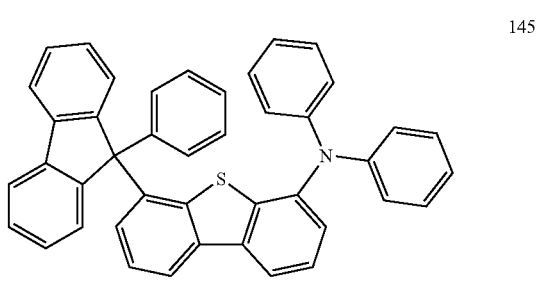
146
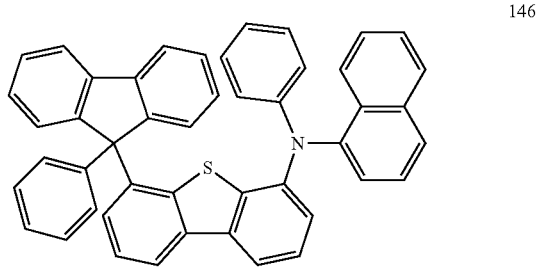
147
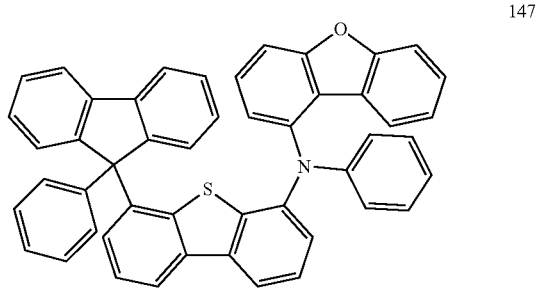
148
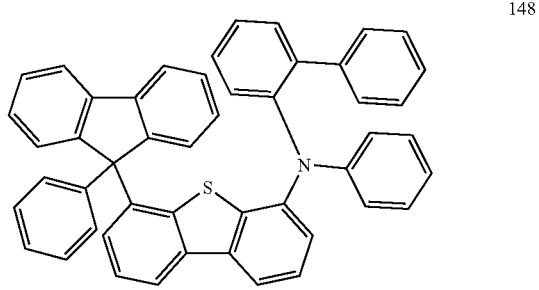

149
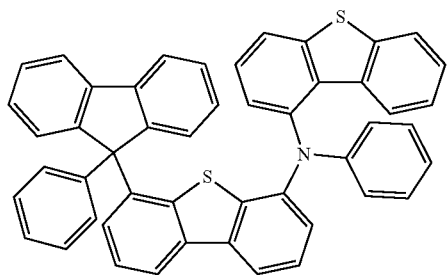
150
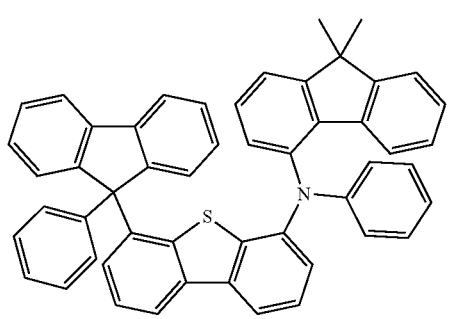
151
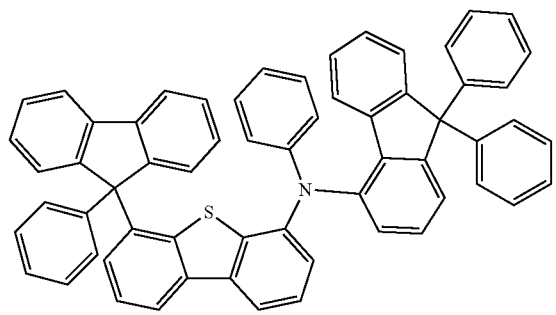
152
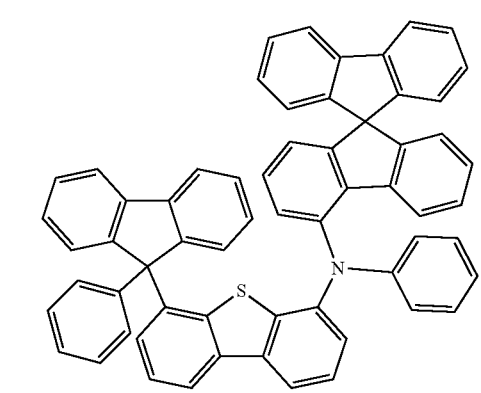
153
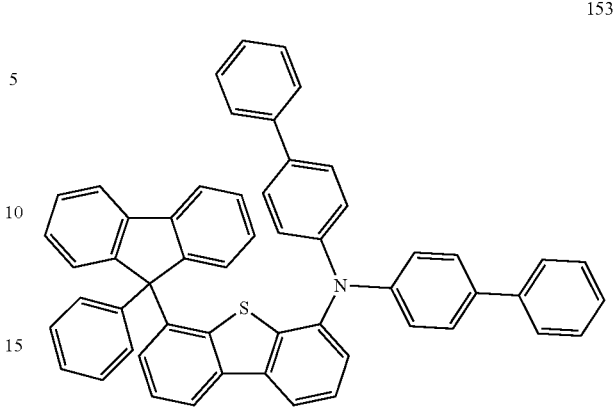
154
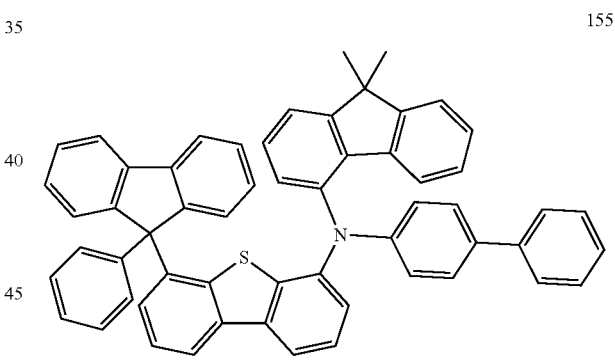
155
156
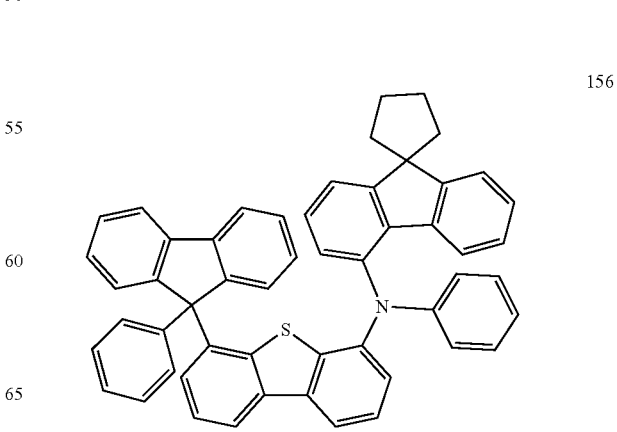

157
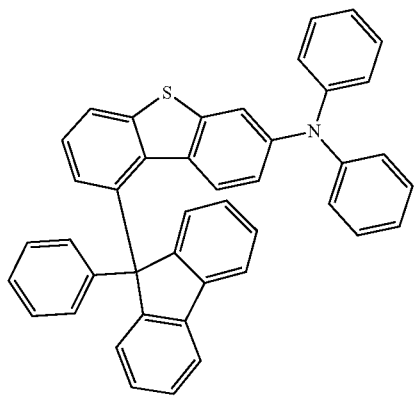
158
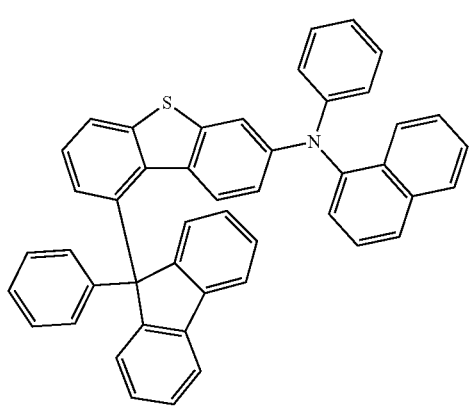
159
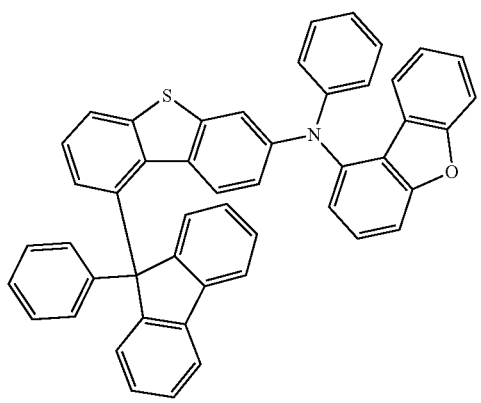
160
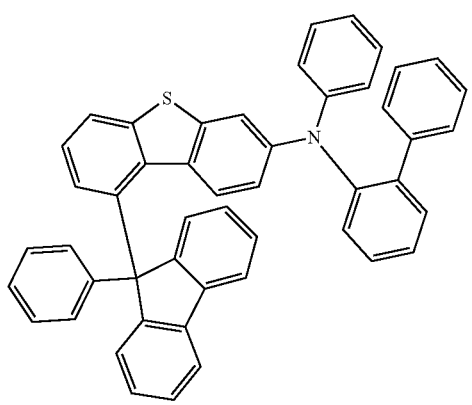
161
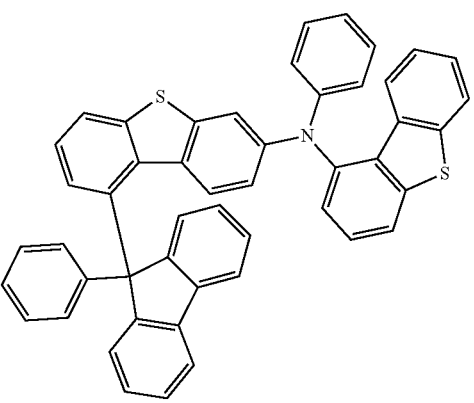
162
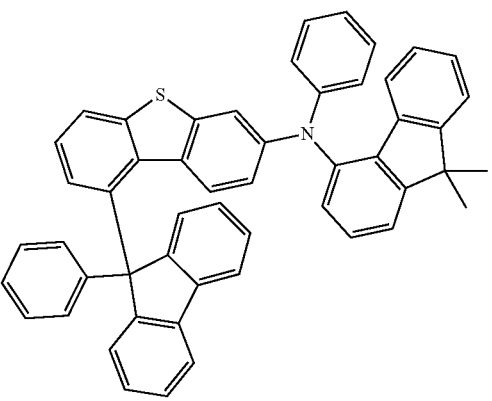
163
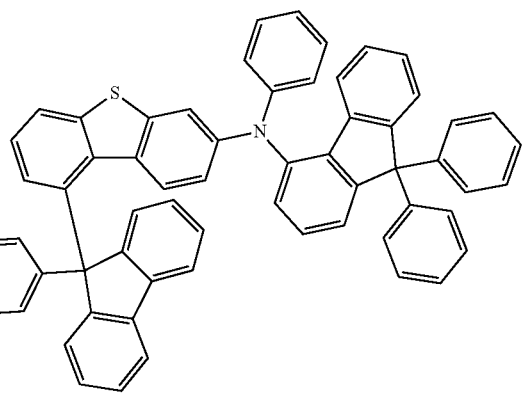
164
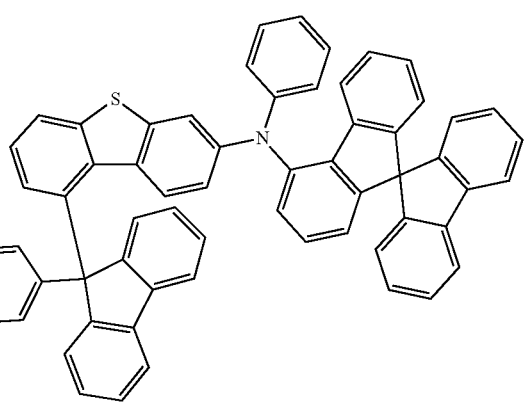

165
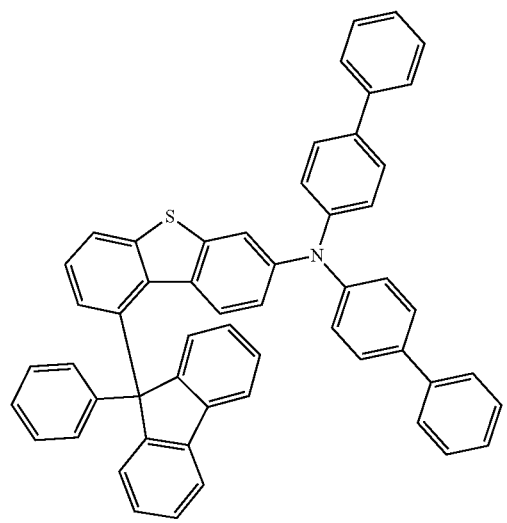
166
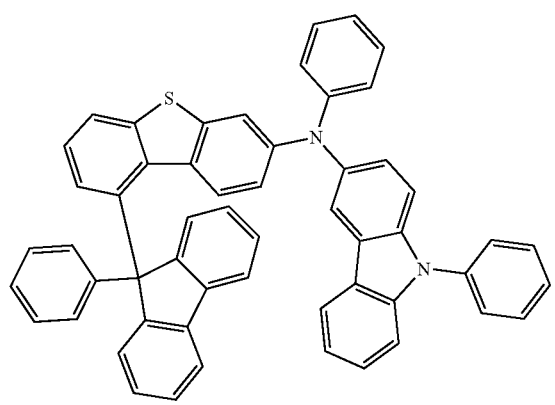
167
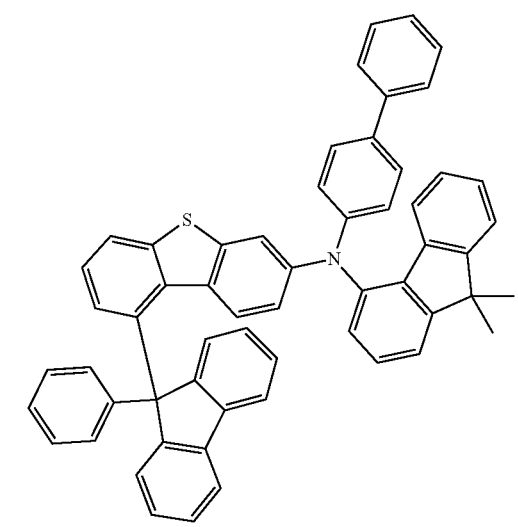
168
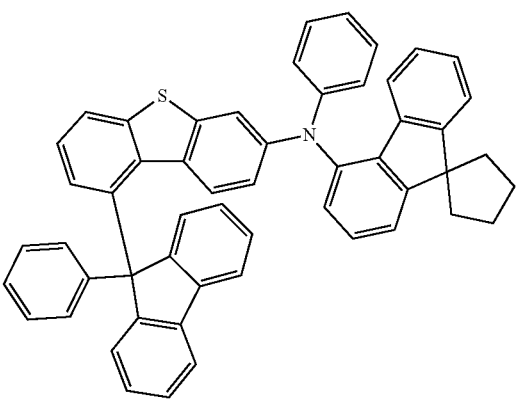
169
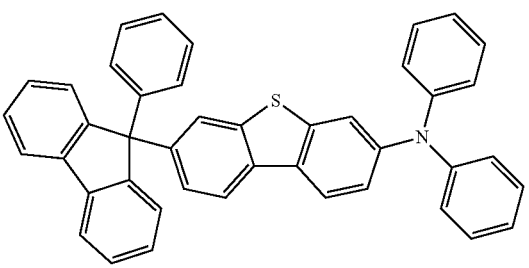
170
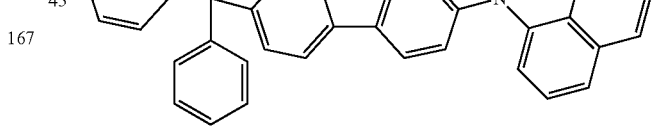
171
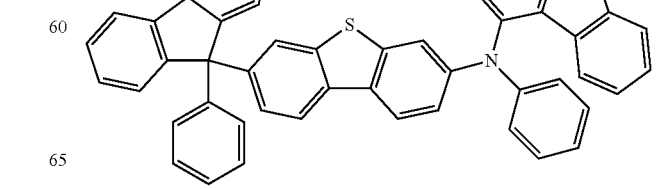

301
-continued
172
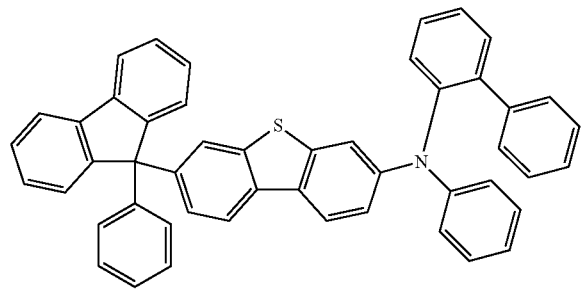
173
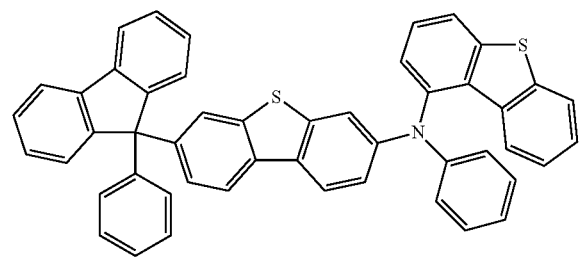
174
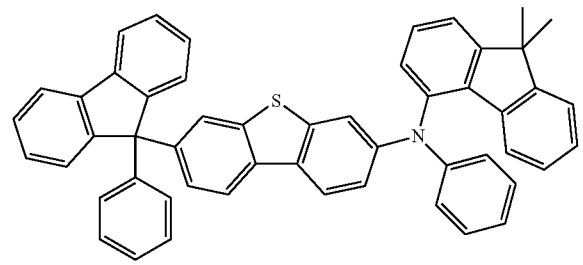
175
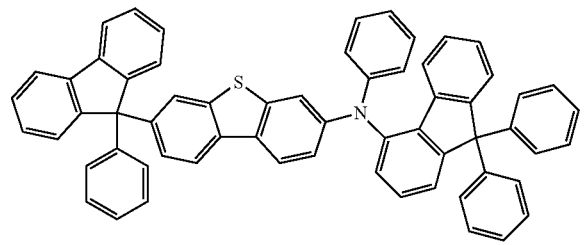
176
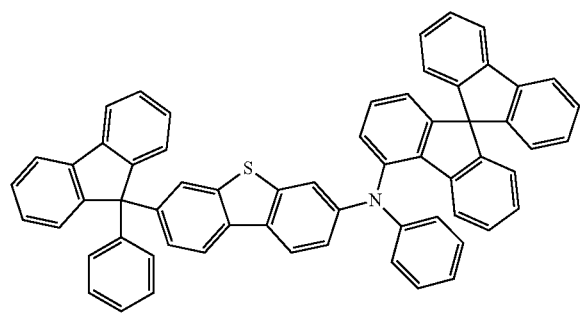
302
-continued
177
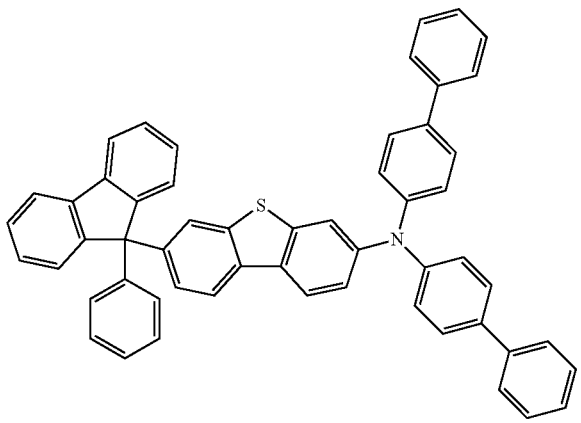
178
179
180
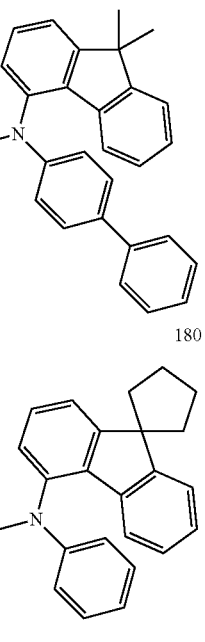

303
-continued
181
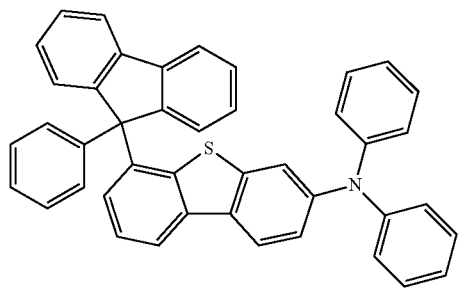
182
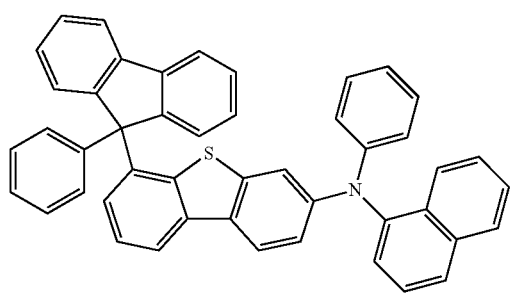
183
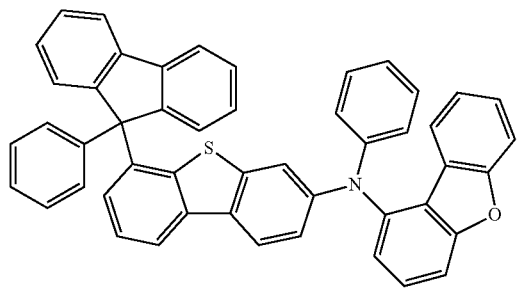
184
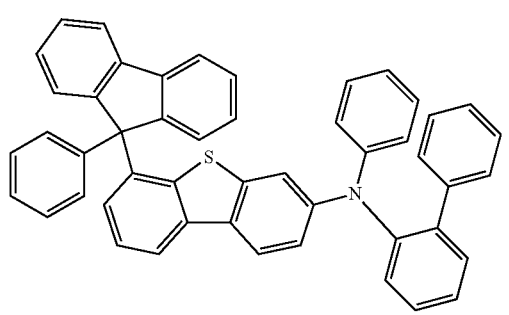
185
304
-continued
186
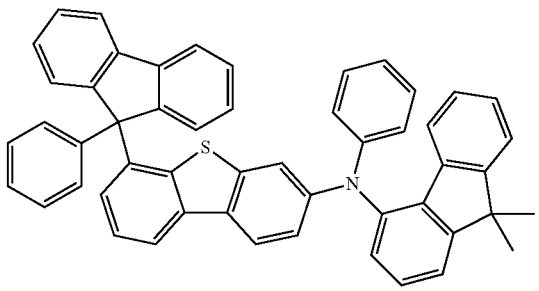
187
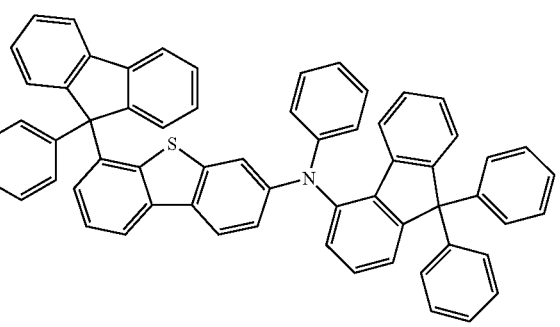
188
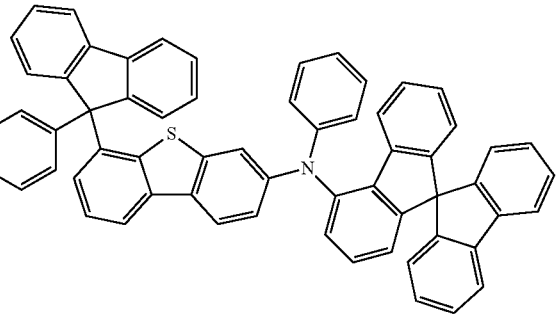
189
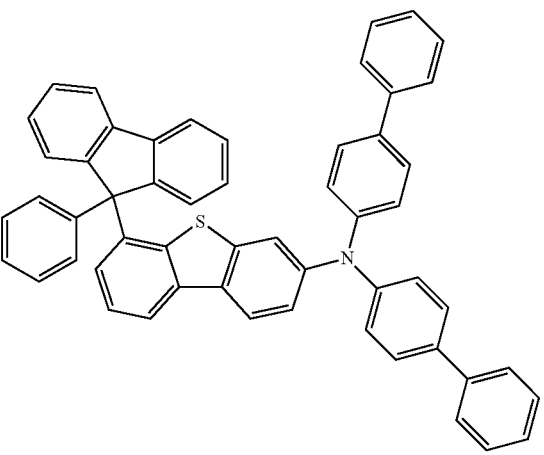

190
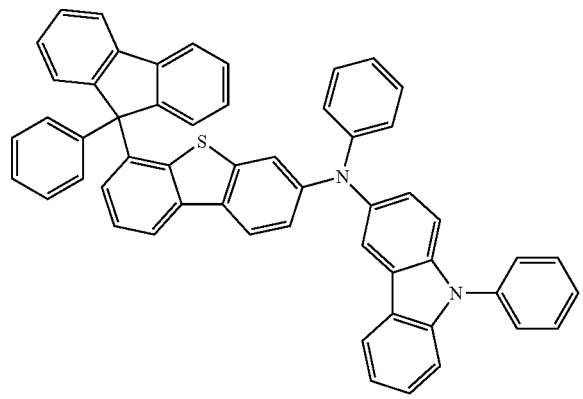
191
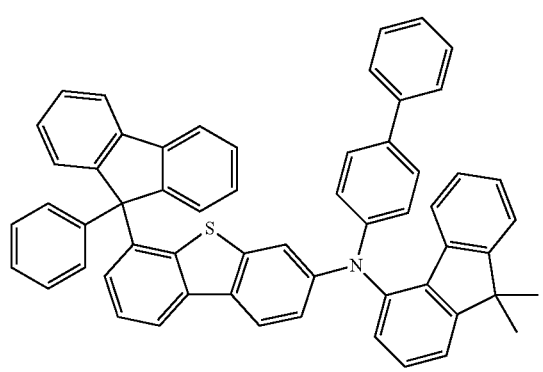
192
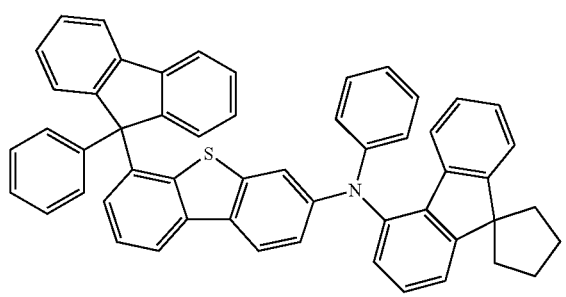
193
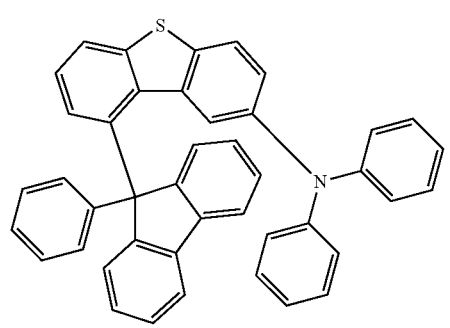
194
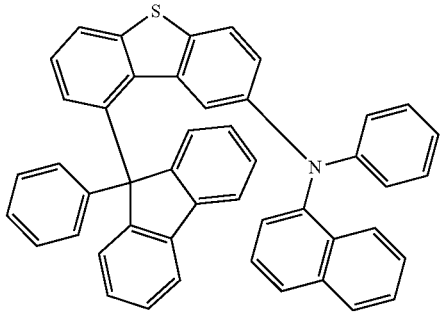
195
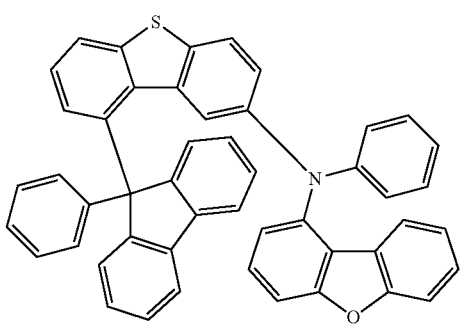
196
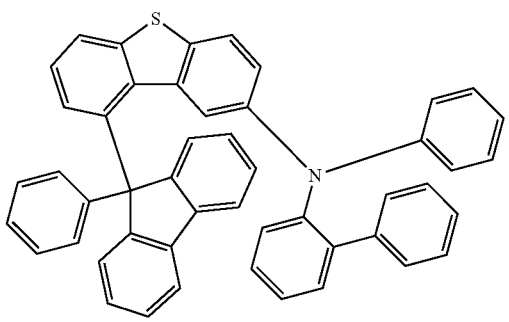
197
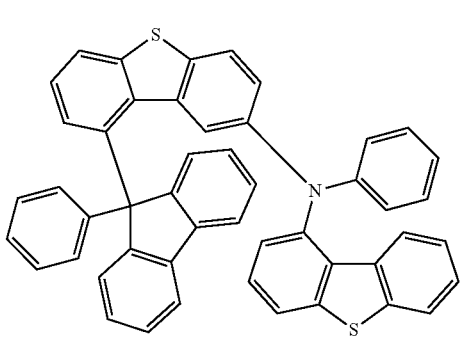

198
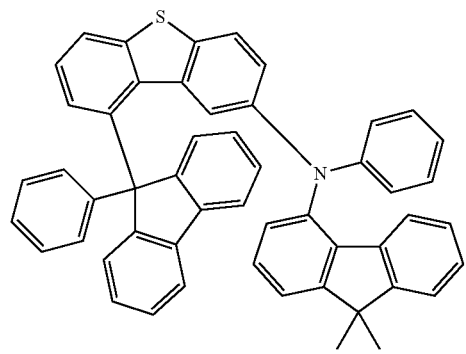
199
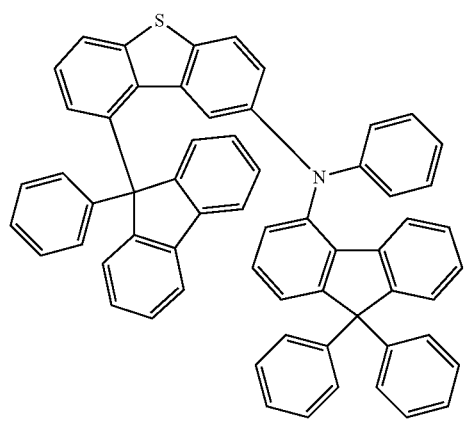
200
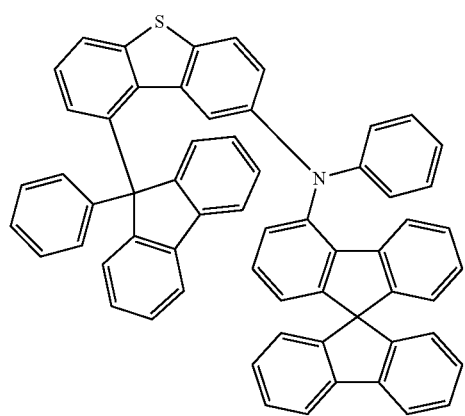
201
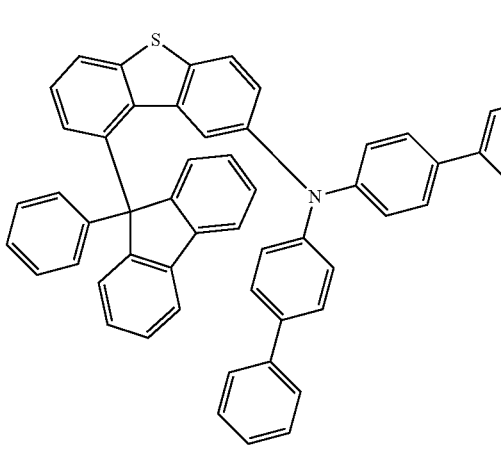
202
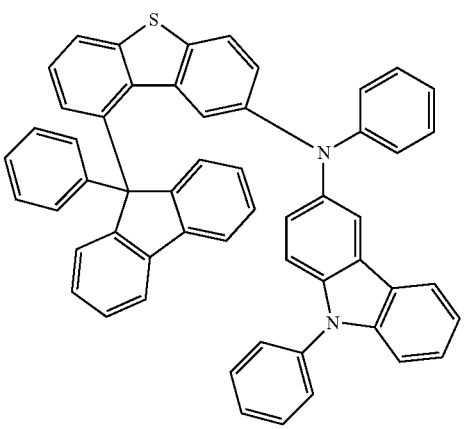
203
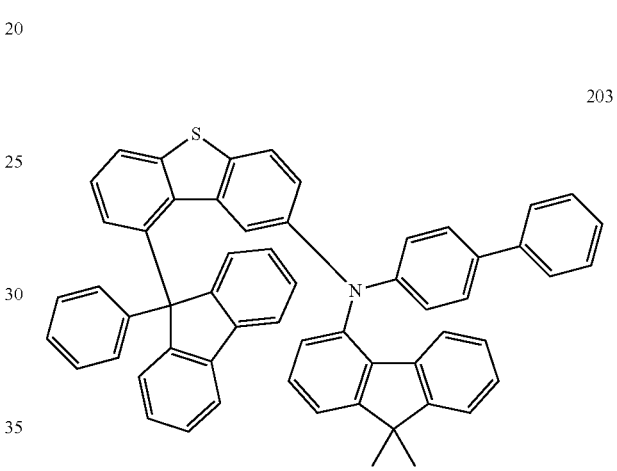
204
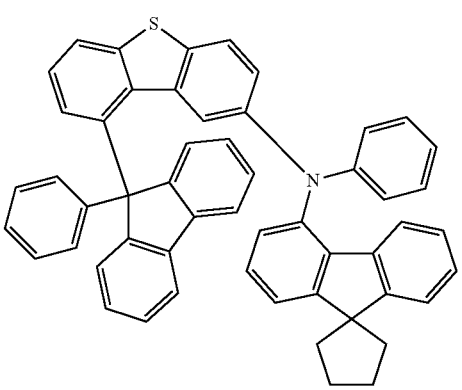
205
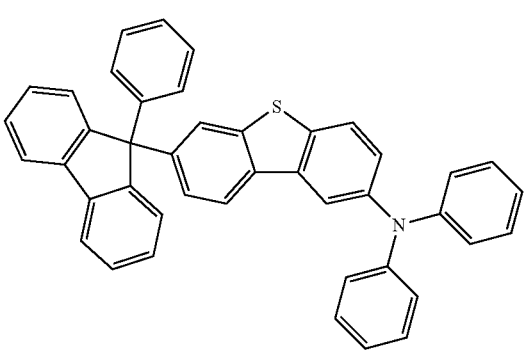

206
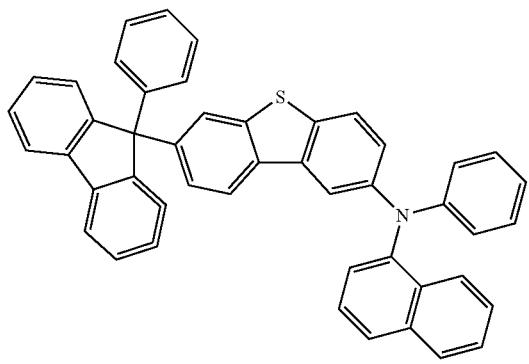
207
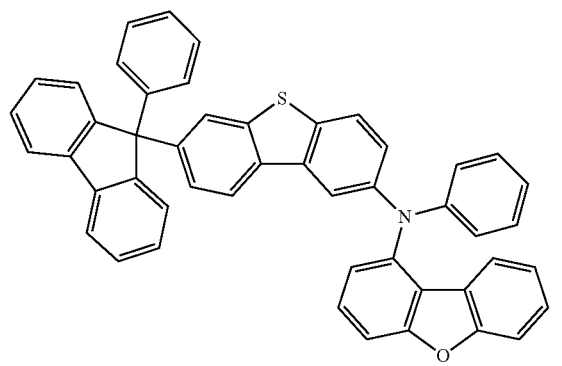
208
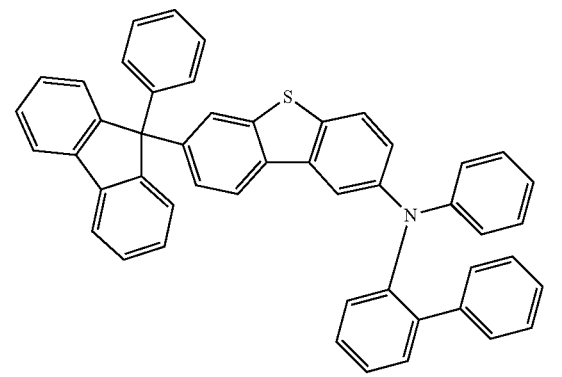
209
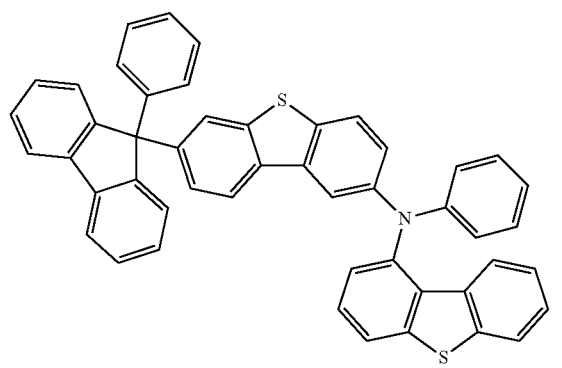
210
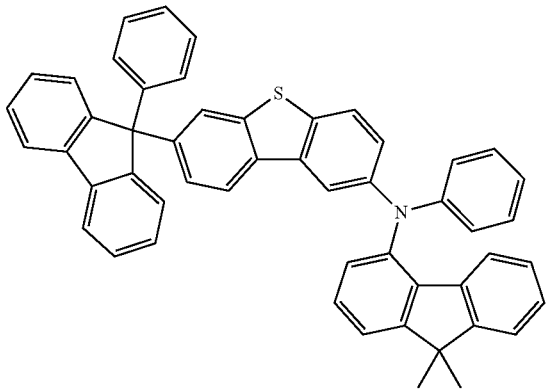
211
212
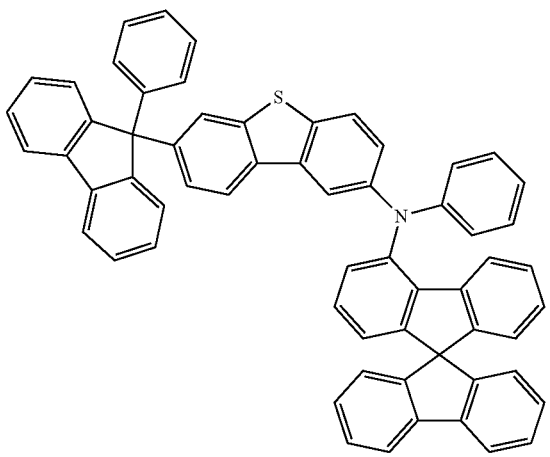

213
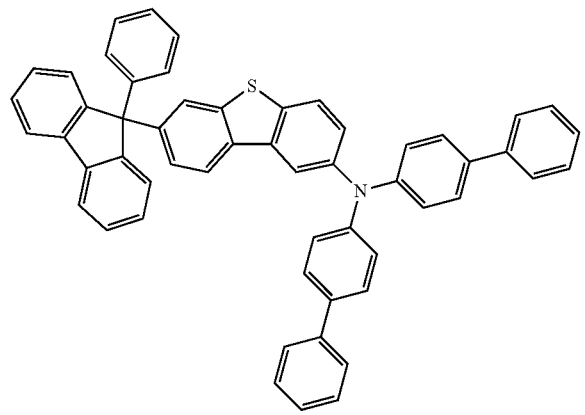
214
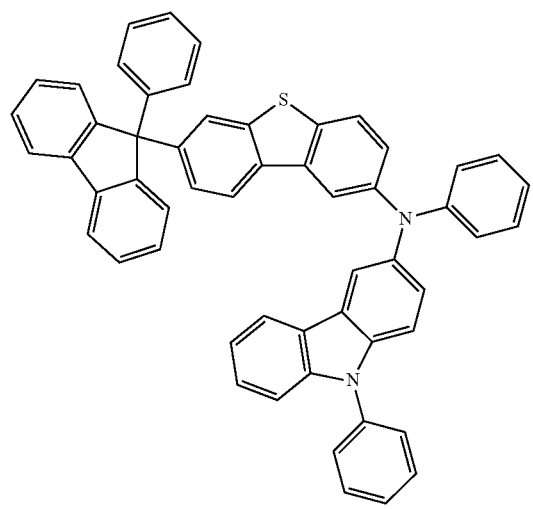
215
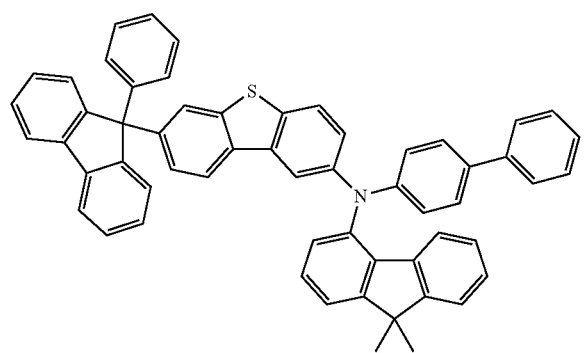
216
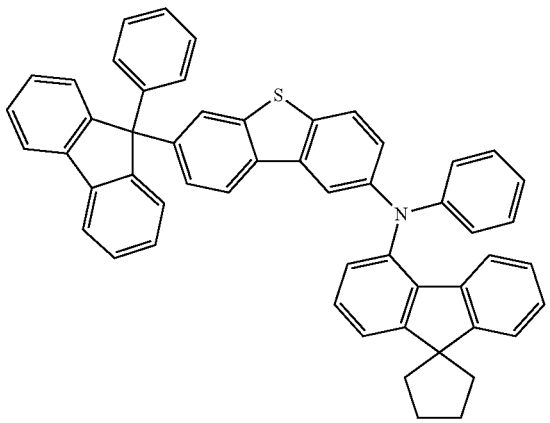
217
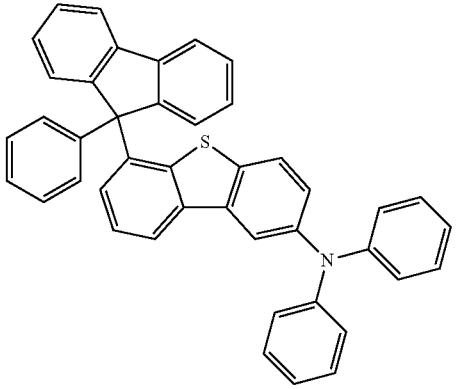
218
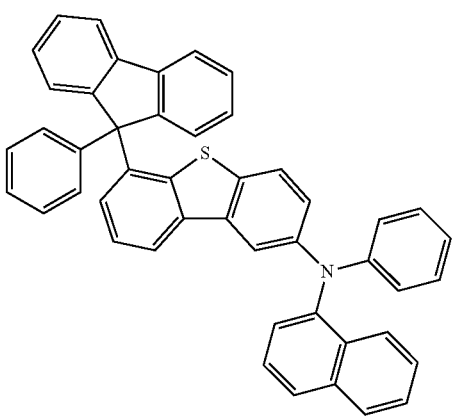

313
-continued
219
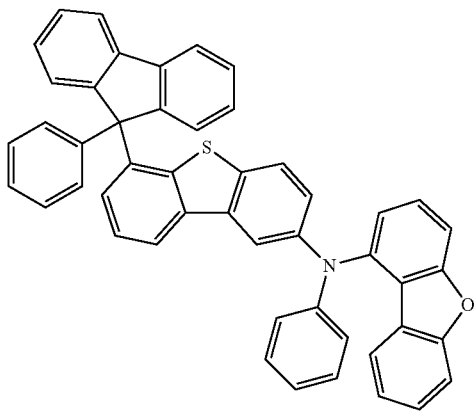
220
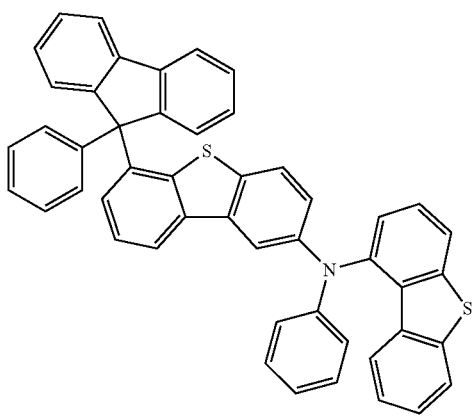
221
314
-continued
222
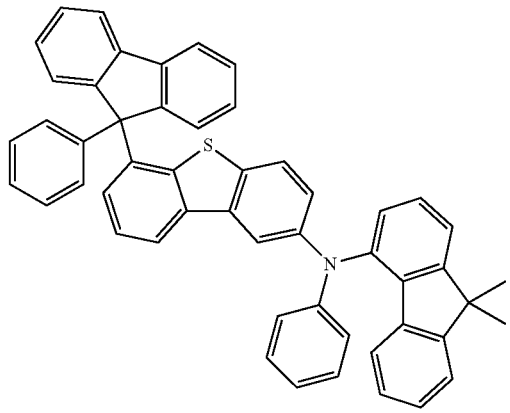
223
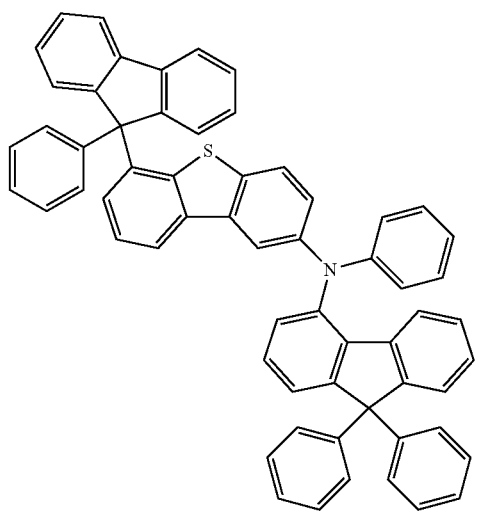
224
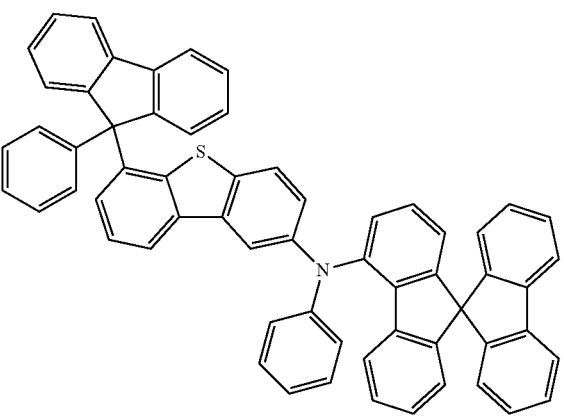

225
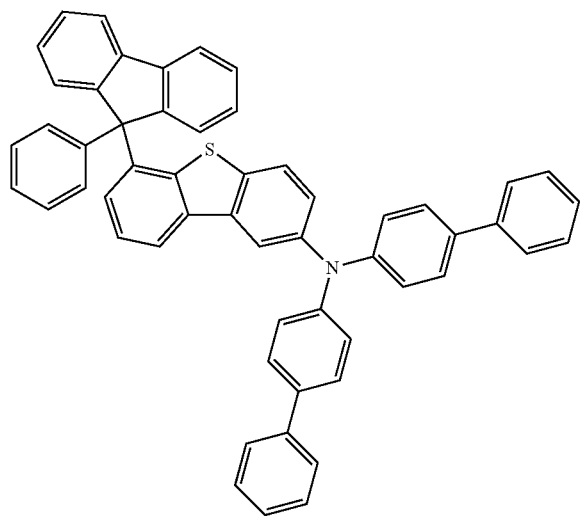
228
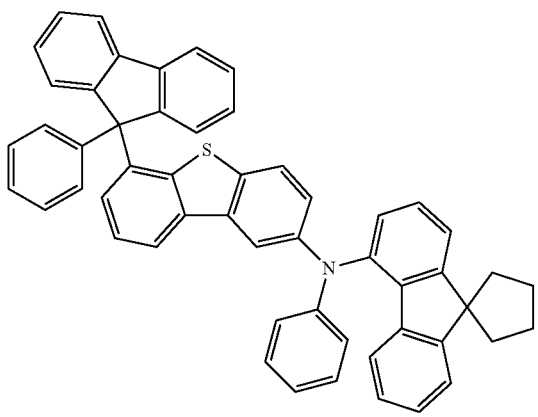
226
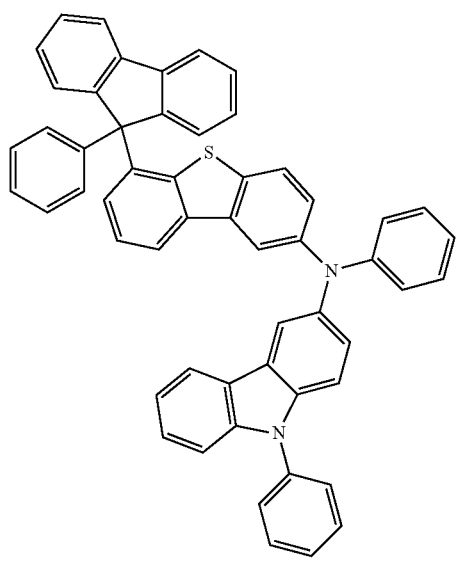
229
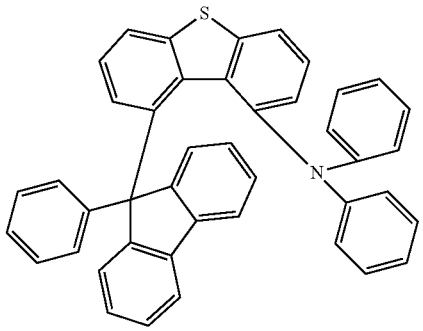
230
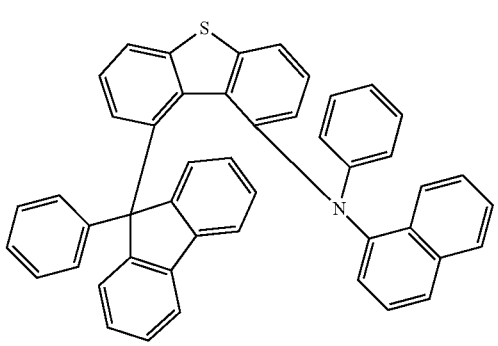
227
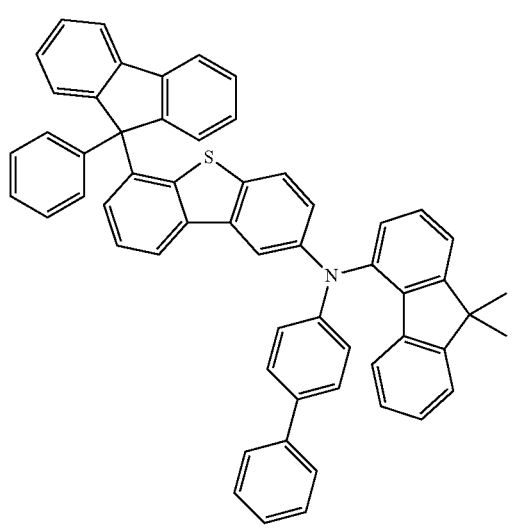
231
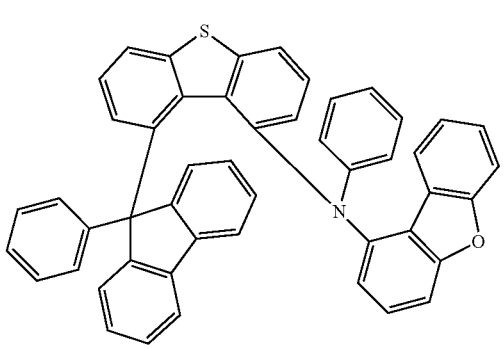

317
-continued
232
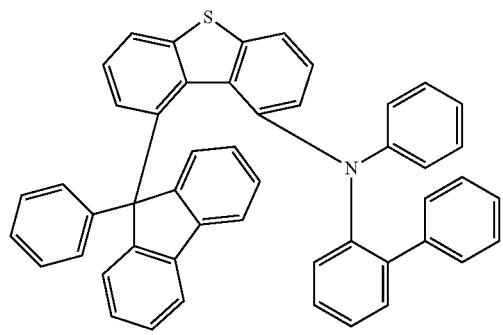
233
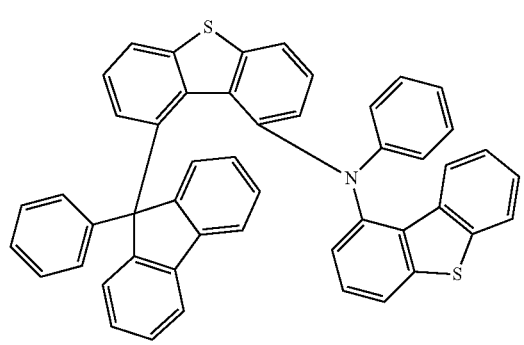
234
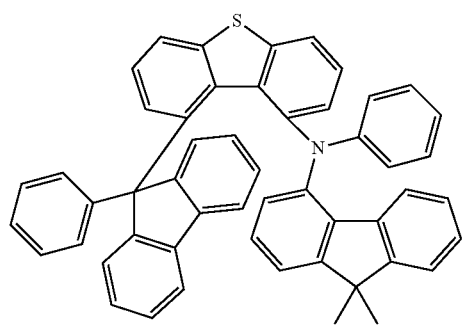
235
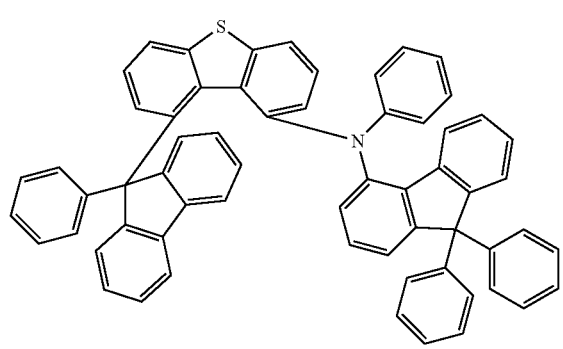
318
-continued
236
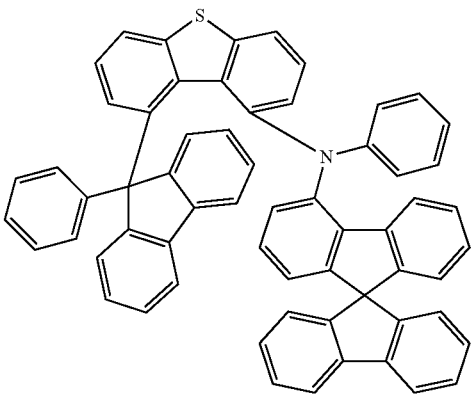
237
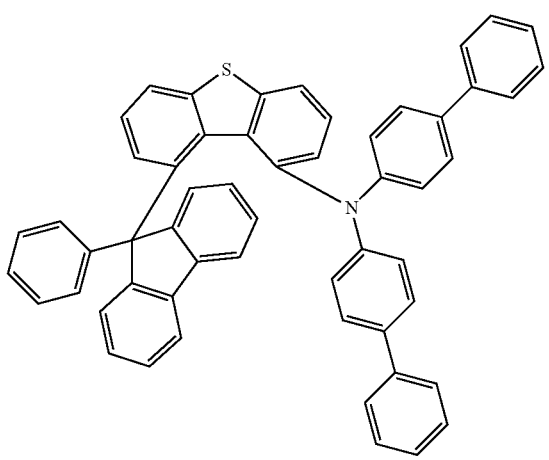
238
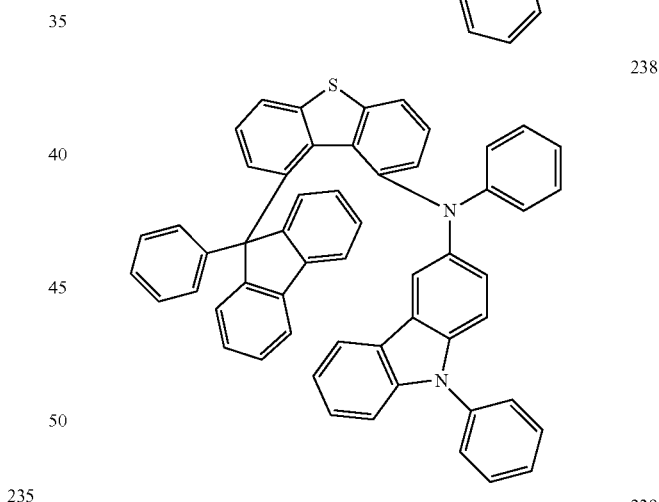
239
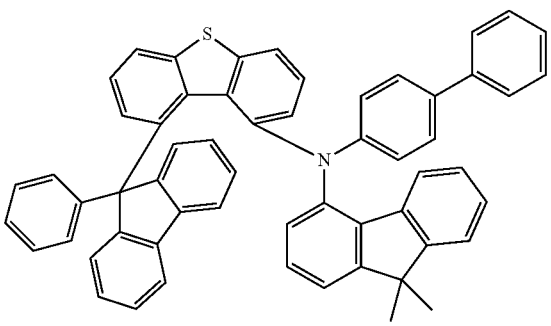

240
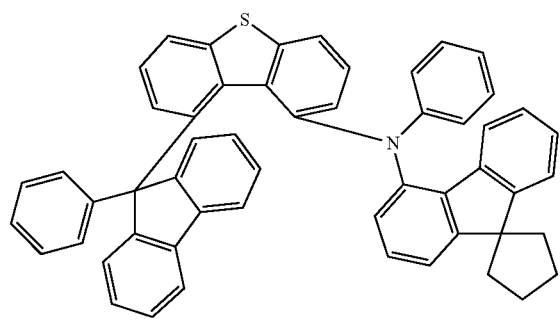
241
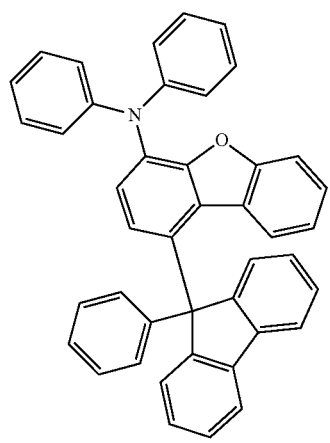
242
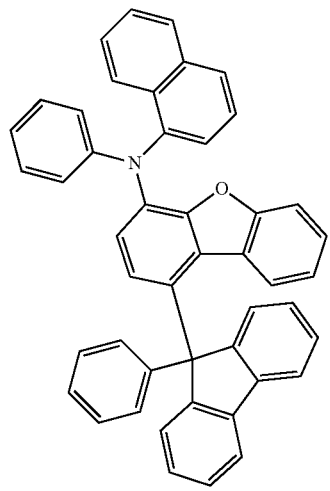
243
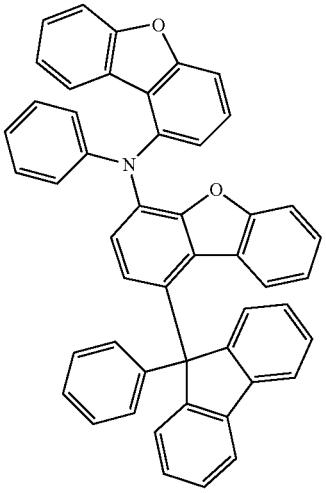
244
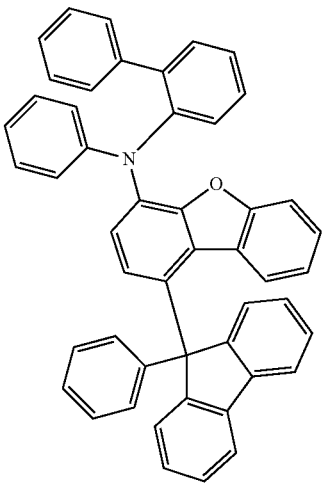
245
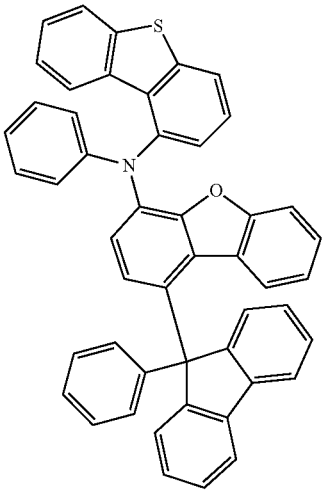

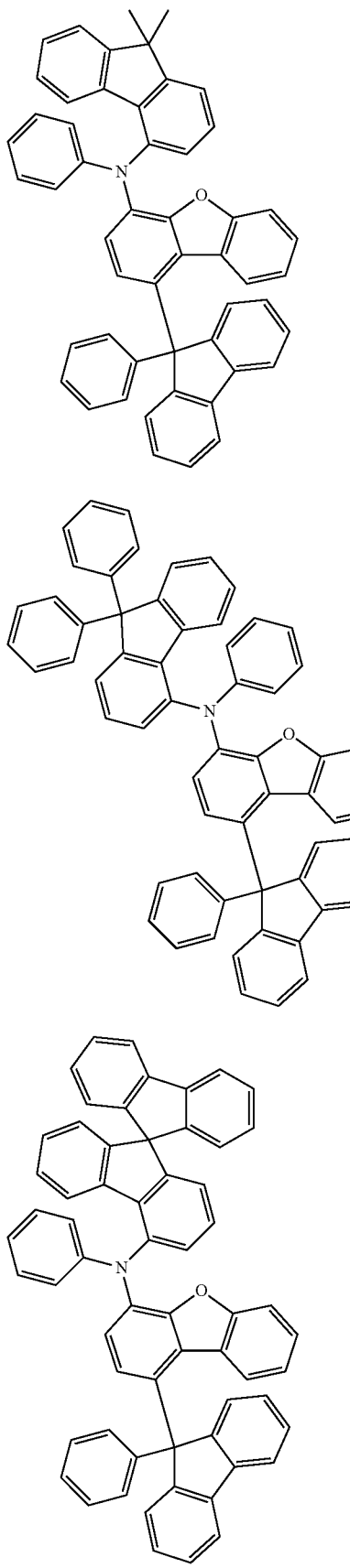
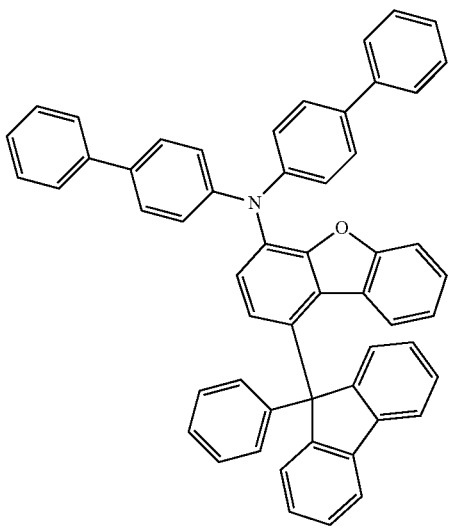
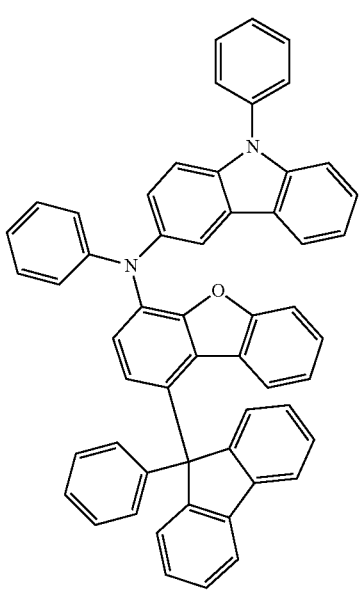
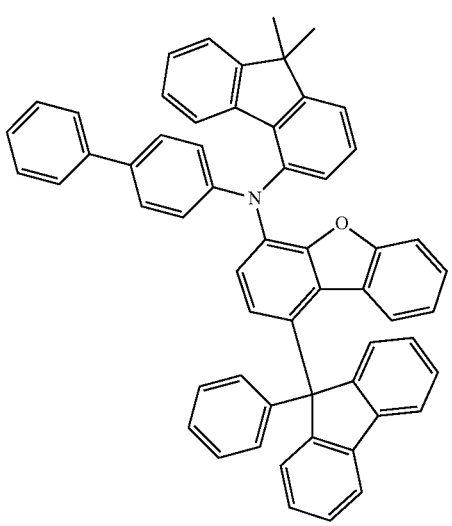

323
-continued
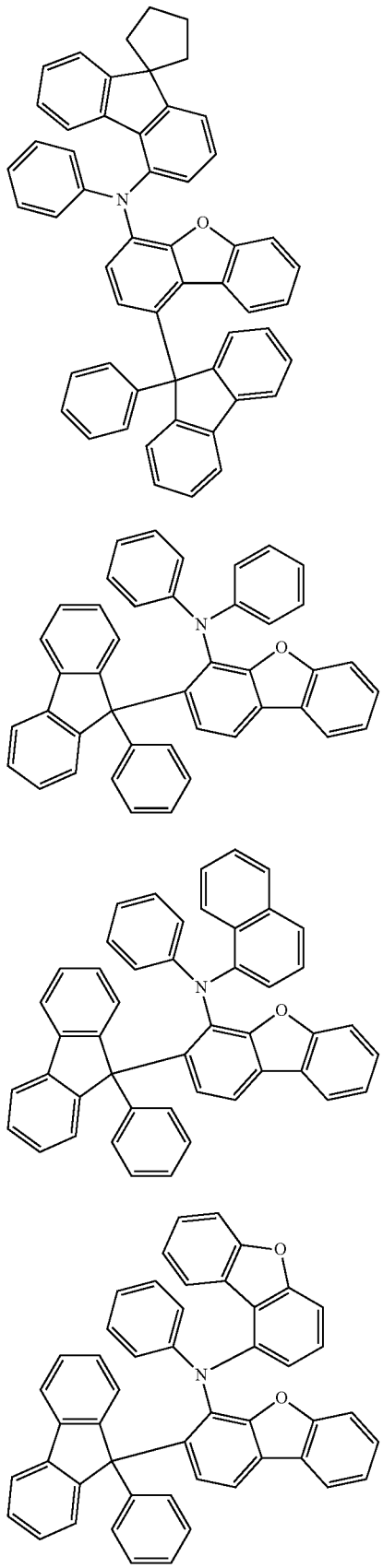
324
-continued
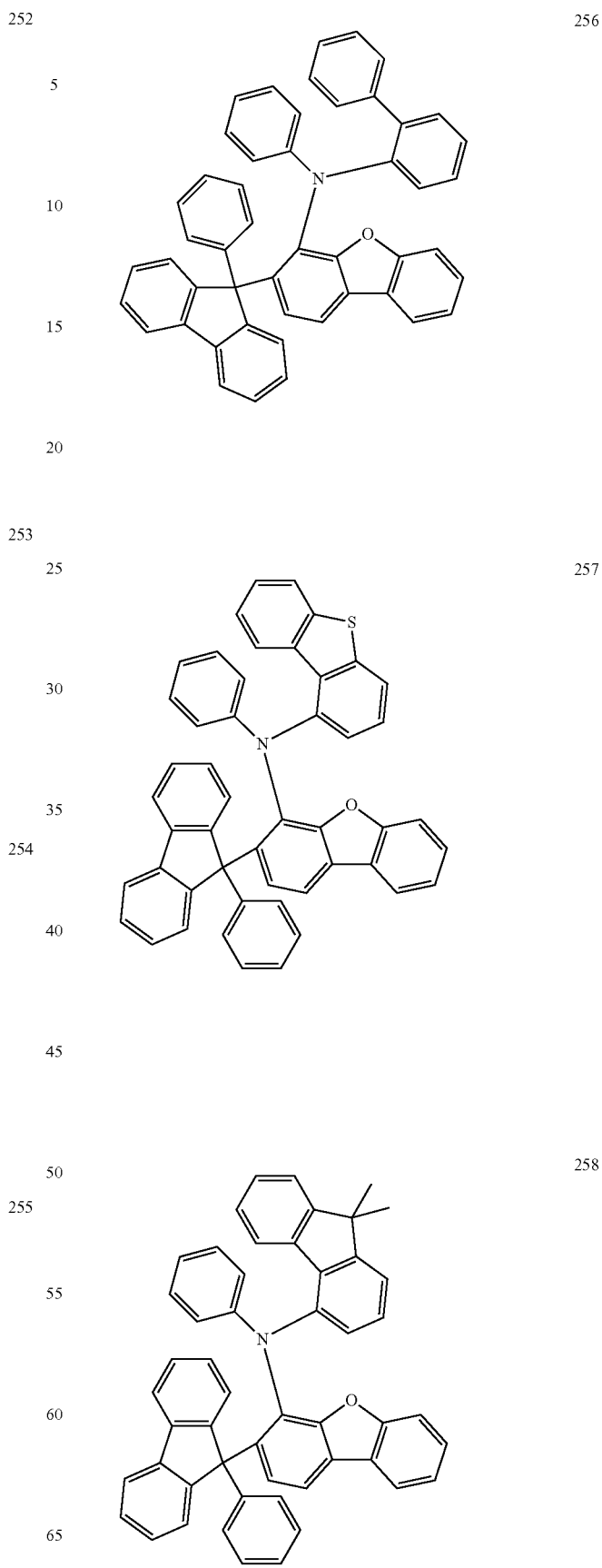

259
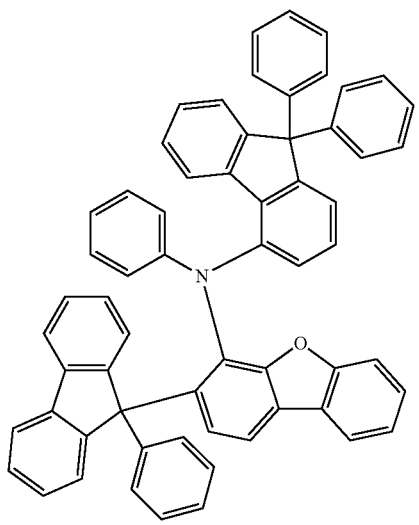
260
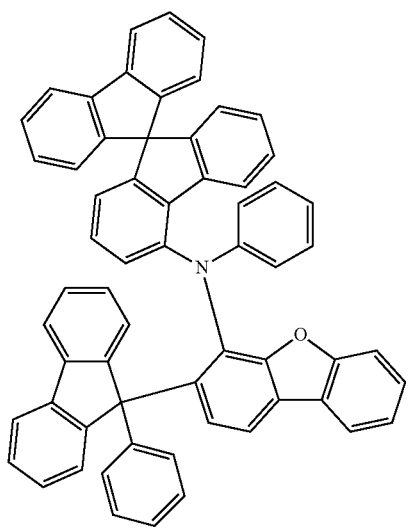
261
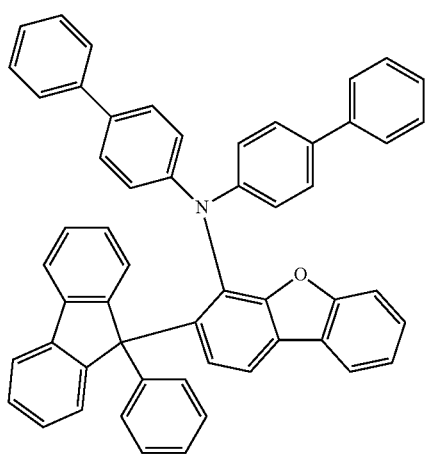
262
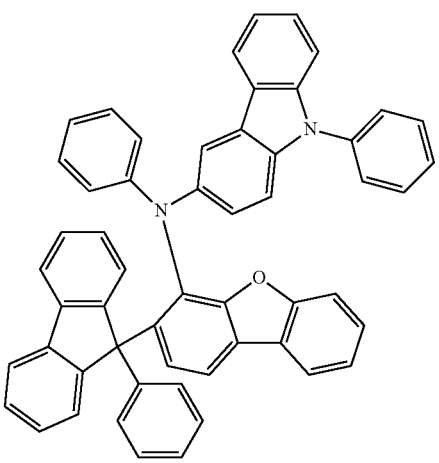
263
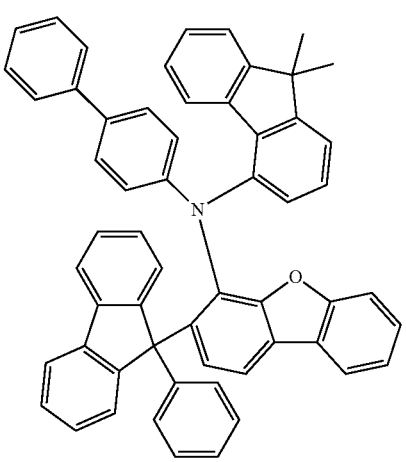
264
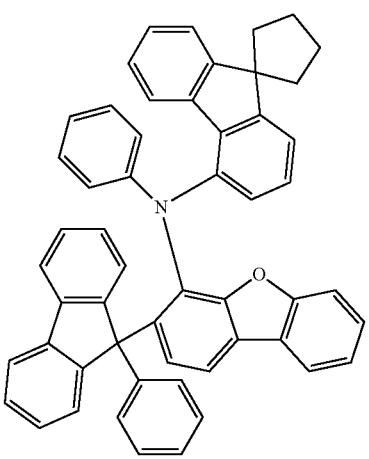

327
-continued
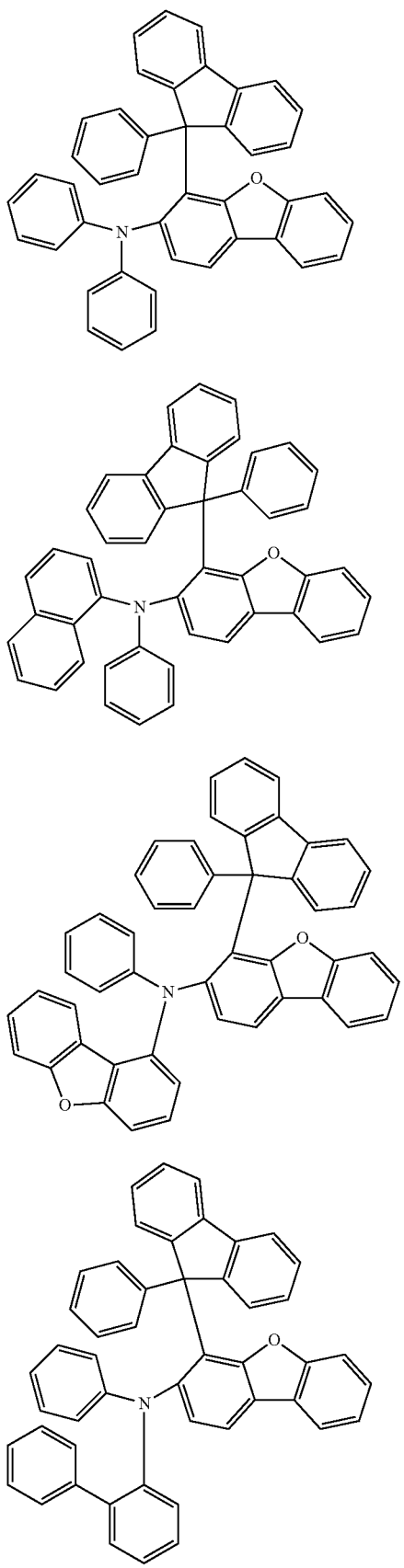
328
-continued
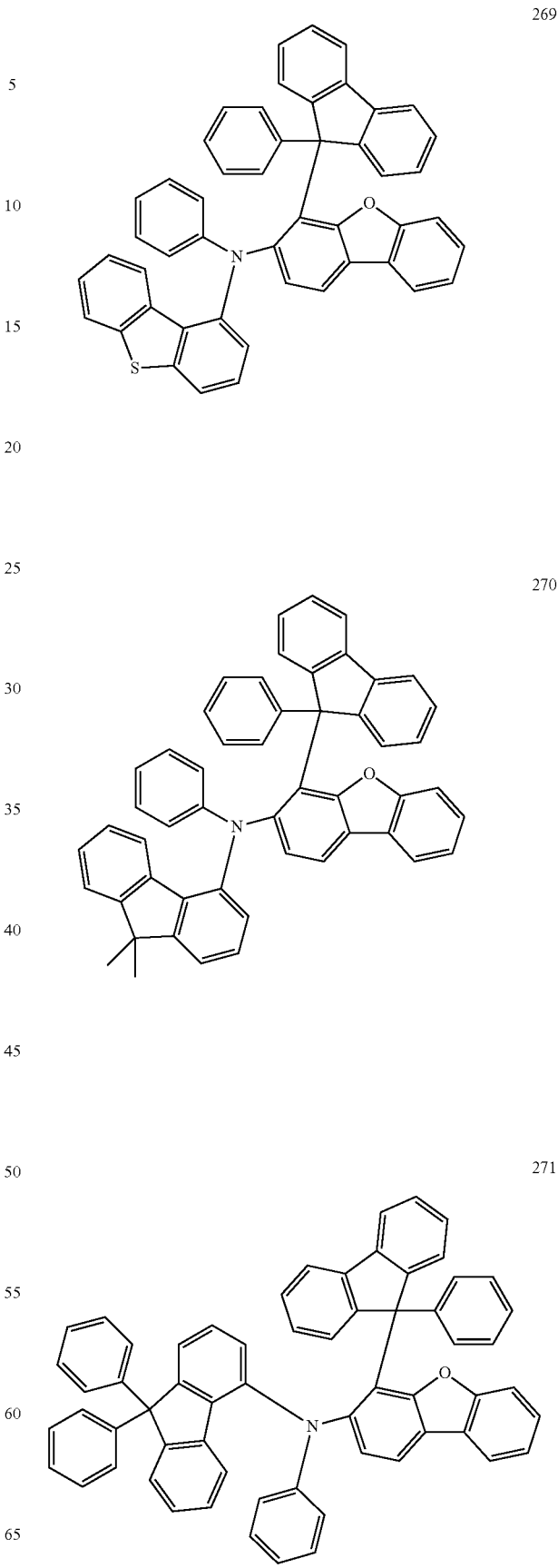

272
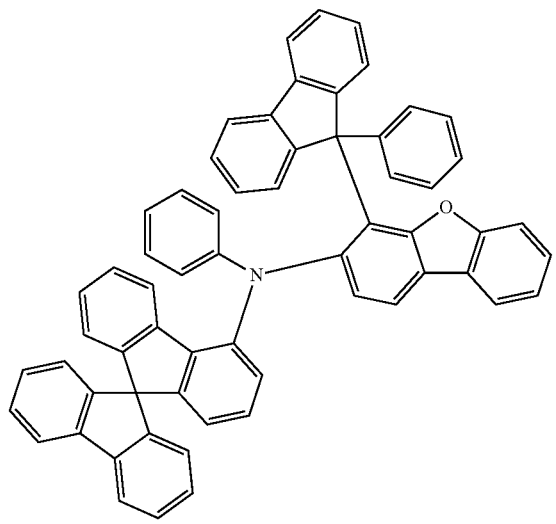
273
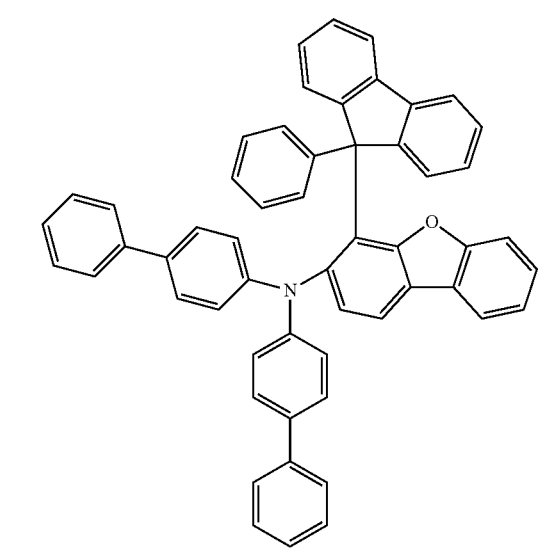
274
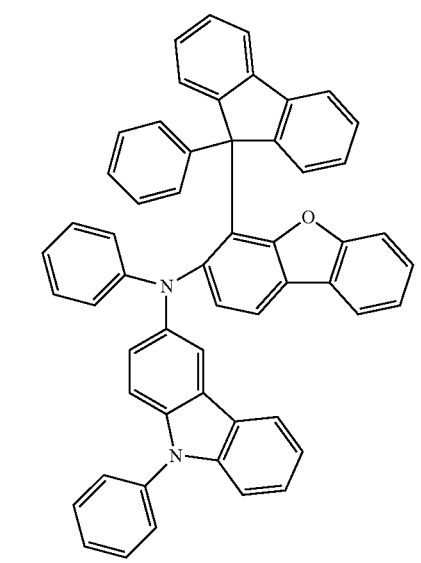
275
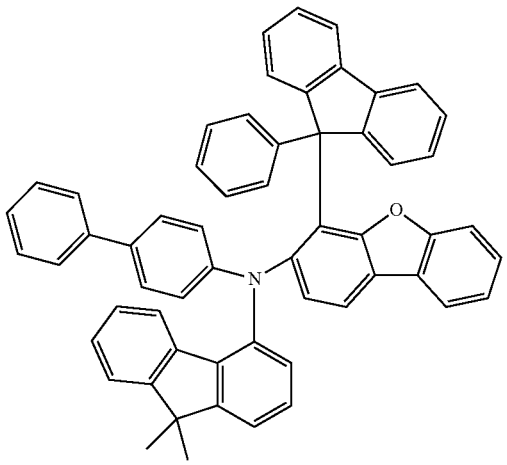
276
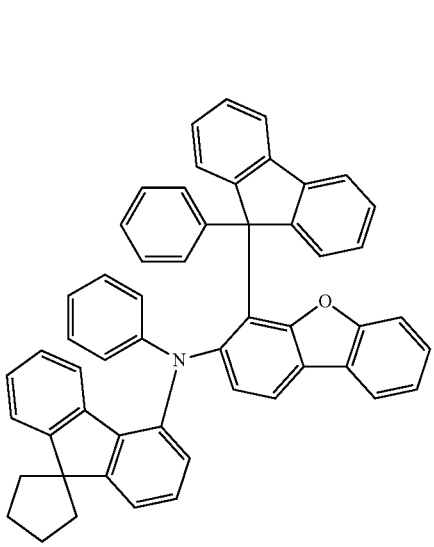
277
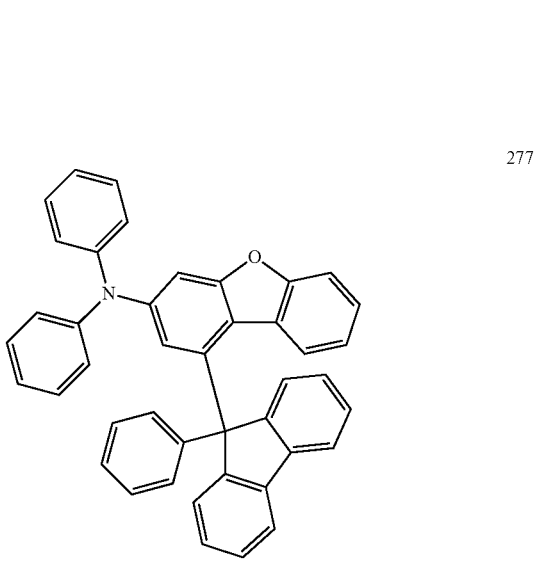

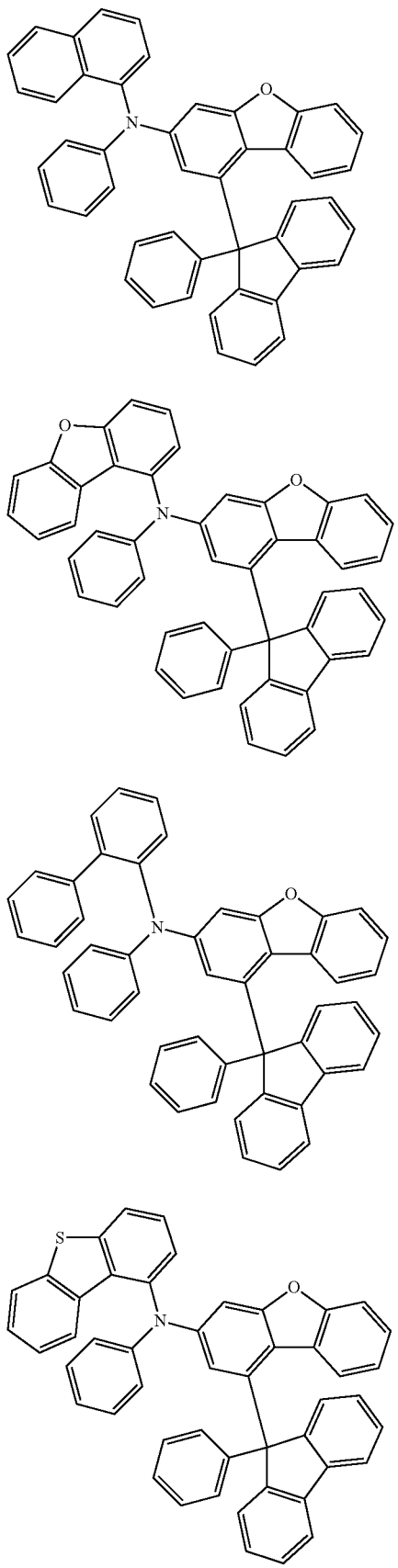
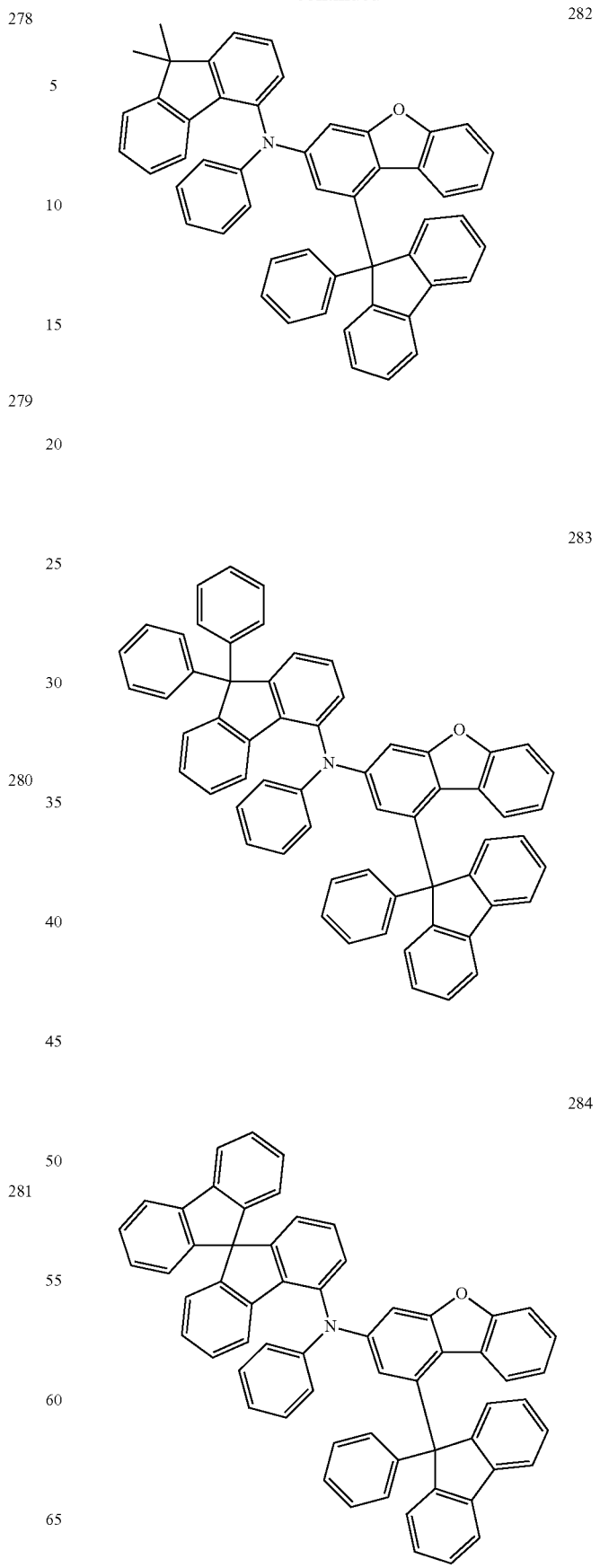

285
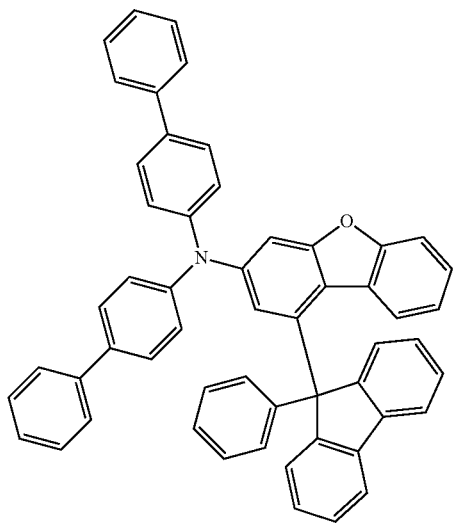
286
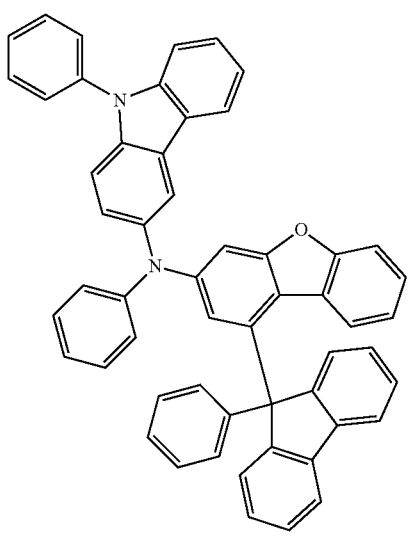
287
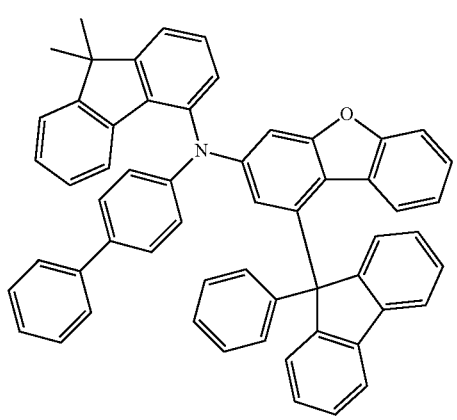
288
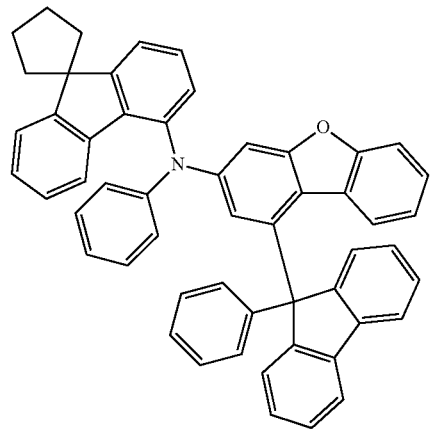
289
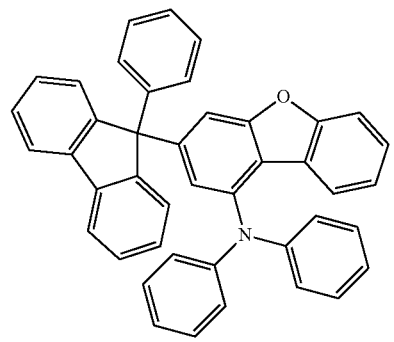
290
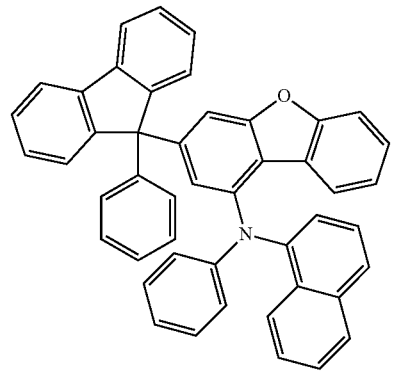
291
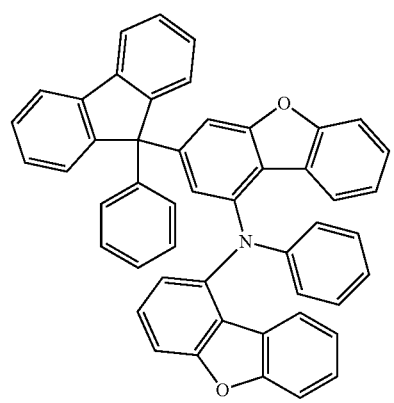

335
-continued
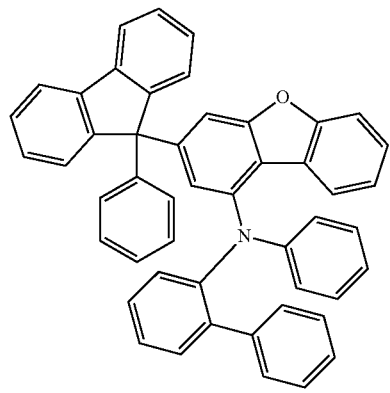
292
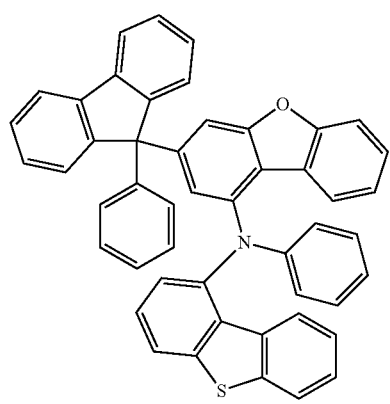
293
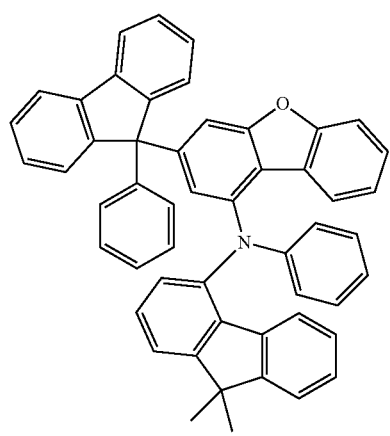
294
336
-continued
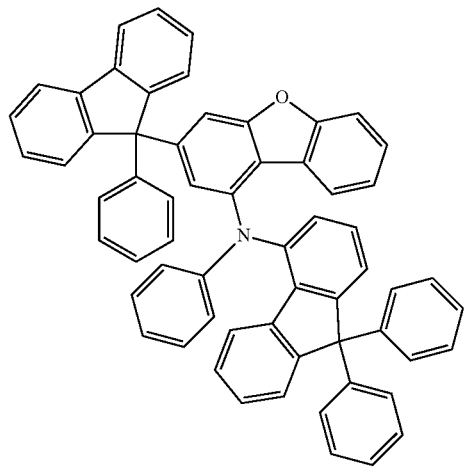
295
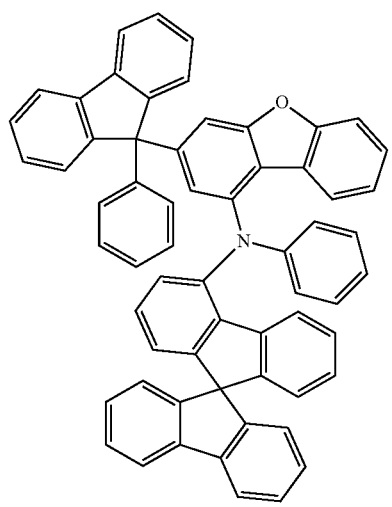
296
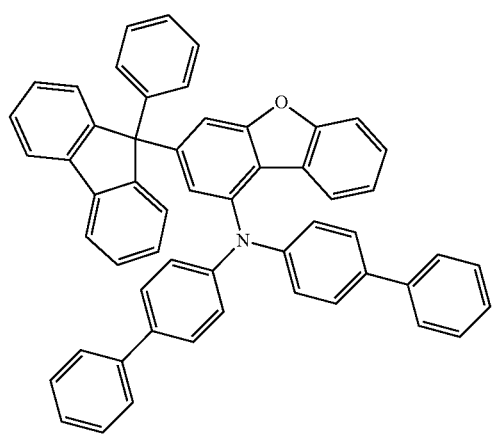
297

-continued
298
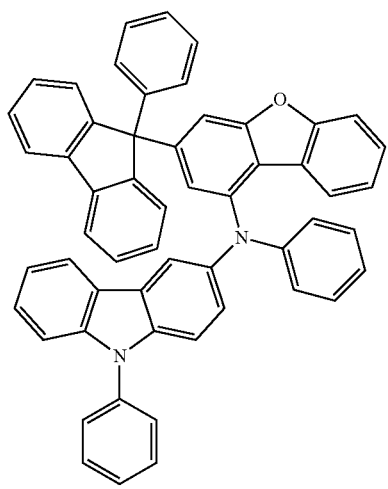
299
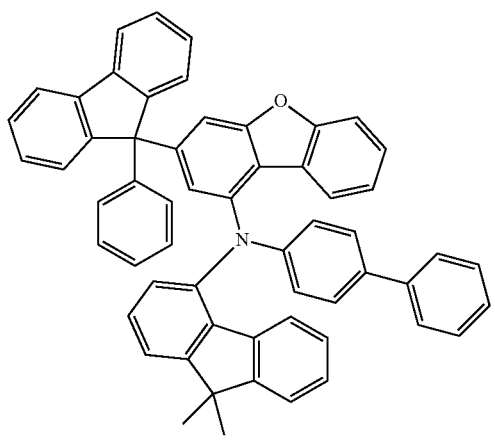
300
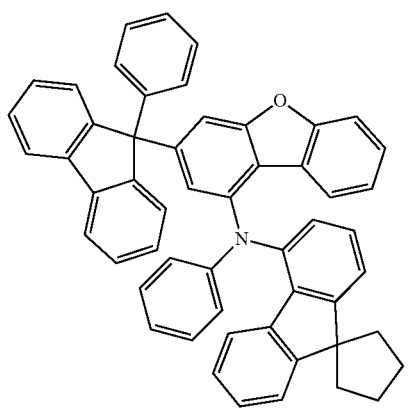
-continued
301
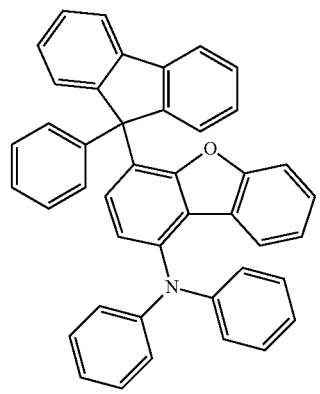
302
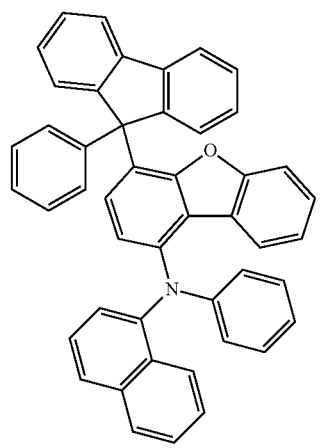
303
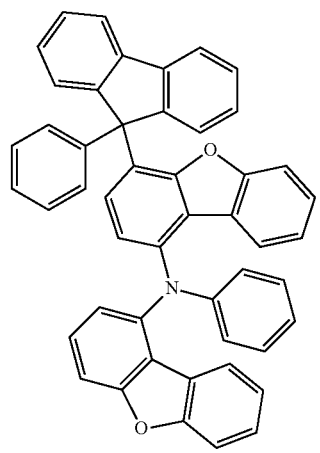

339
-continued
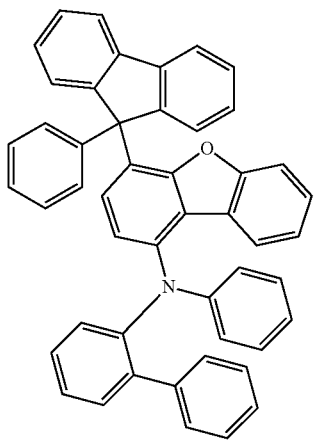
304
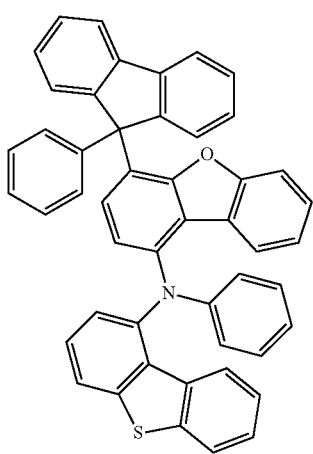
305
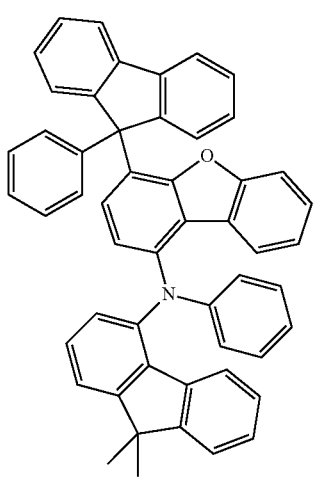
306
340
-continued
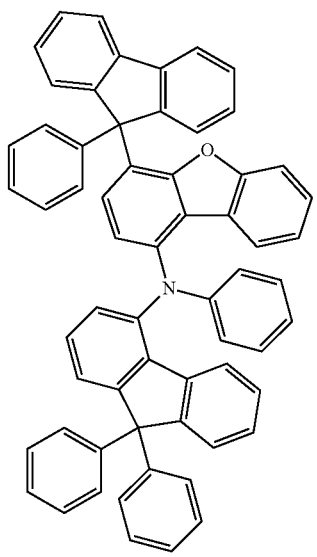
307
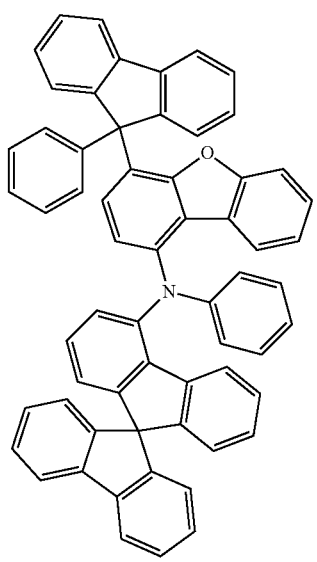
308
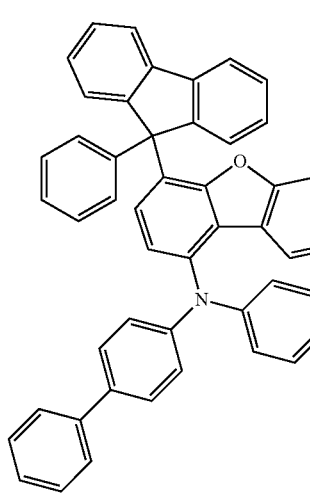
309

341
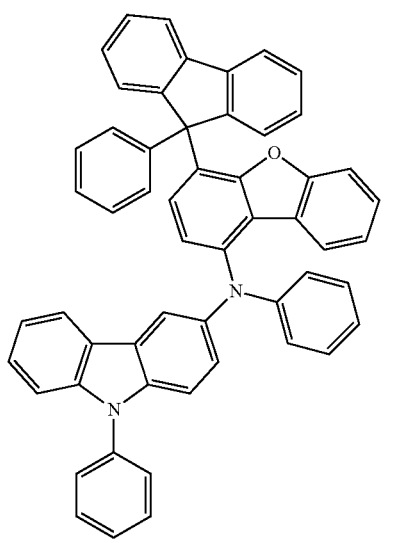
310
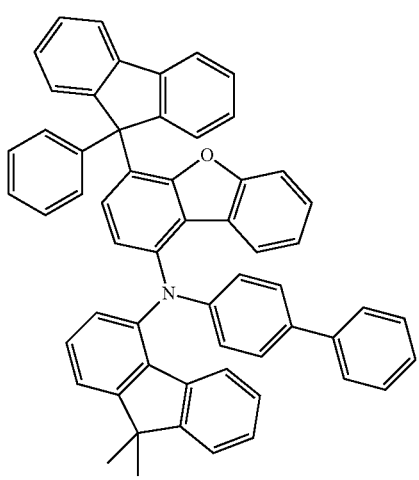
311
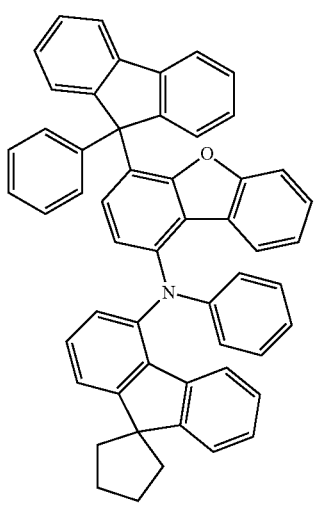
312
342
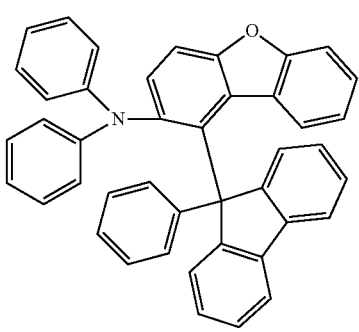
313
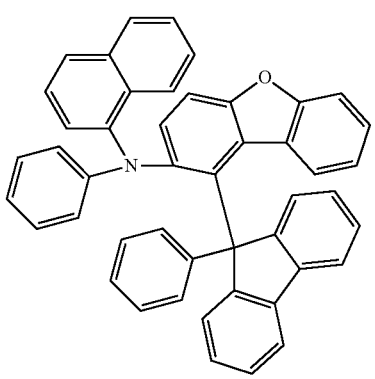
314
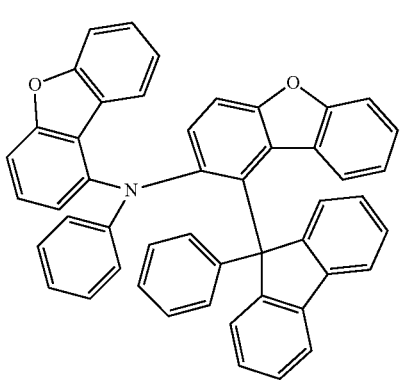
315
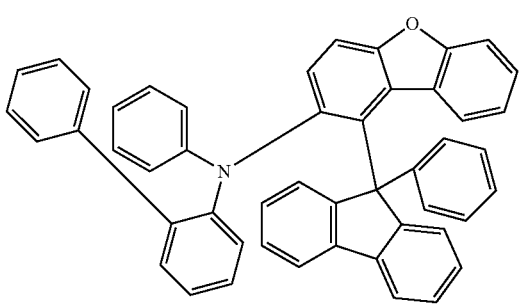
316

317
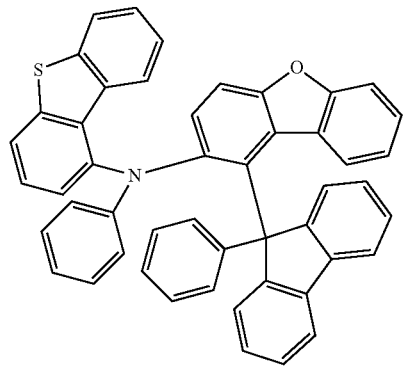
318
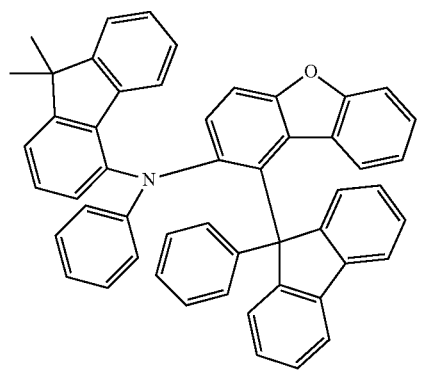
319
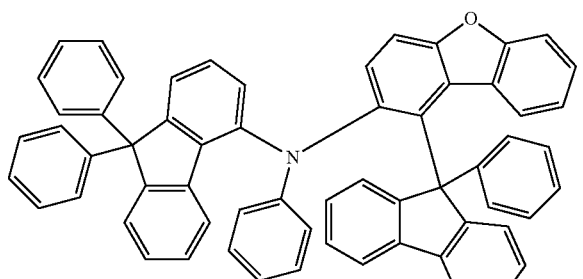
320
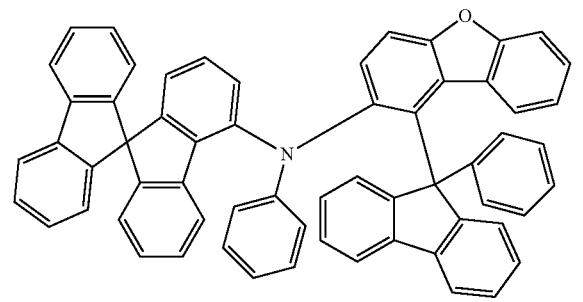
321
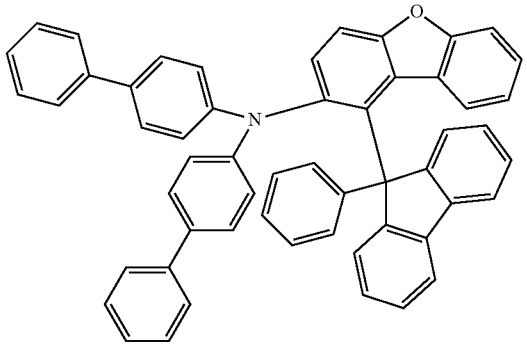
322
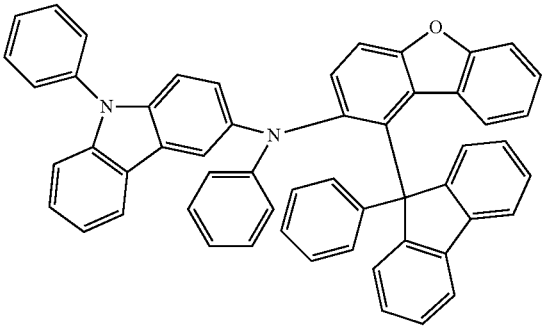
323
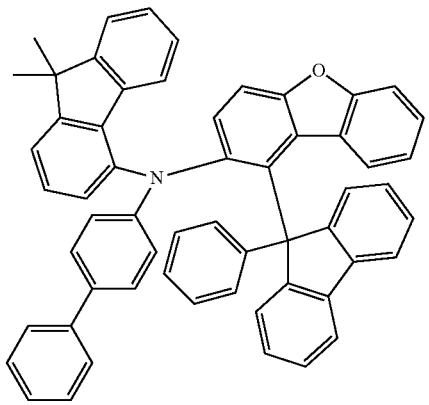
324
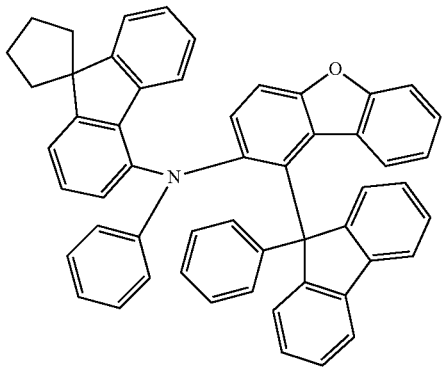

325 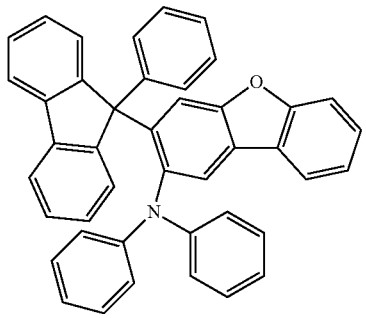
326 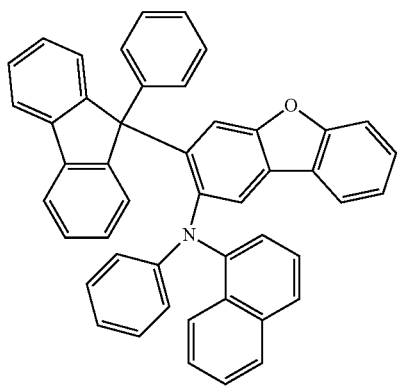
327 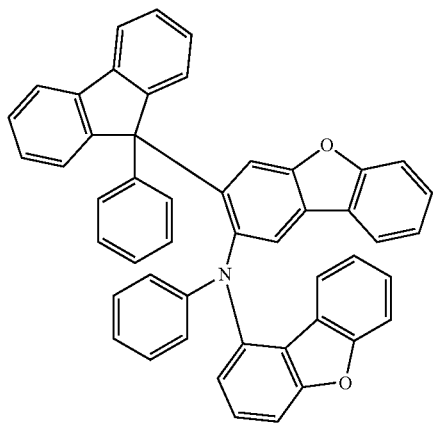
328 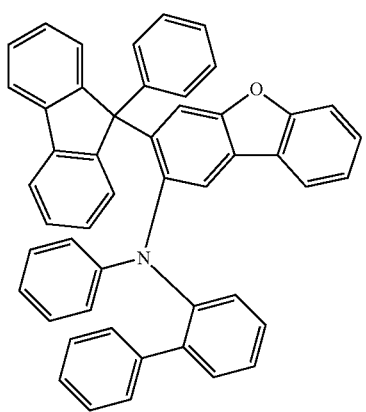
329 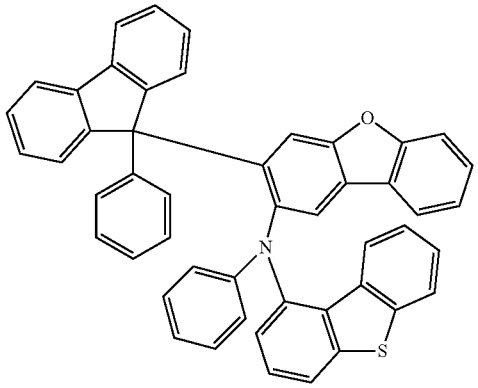
330 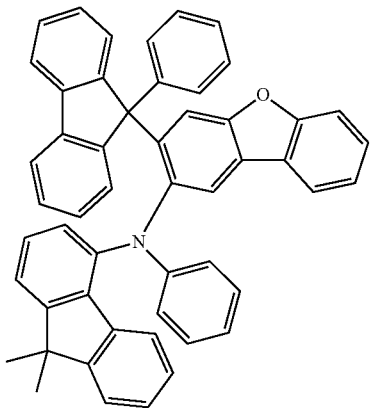
331 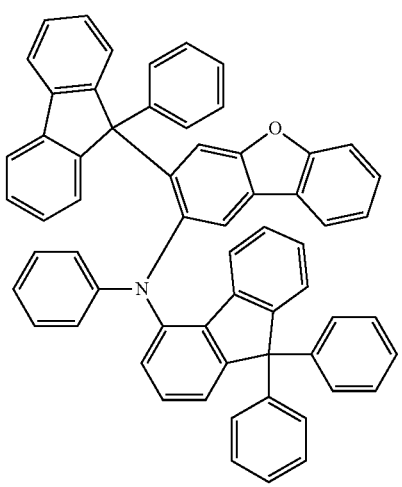

332
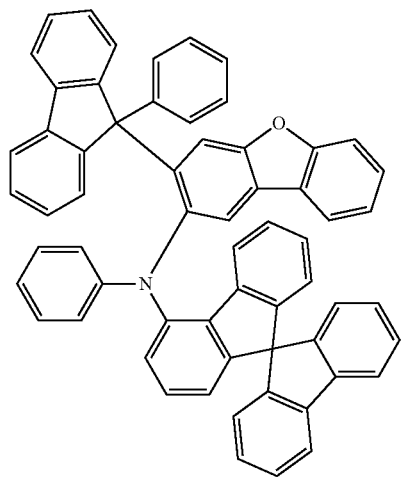
335
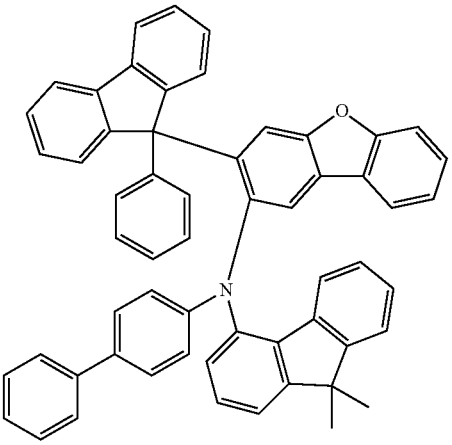
333
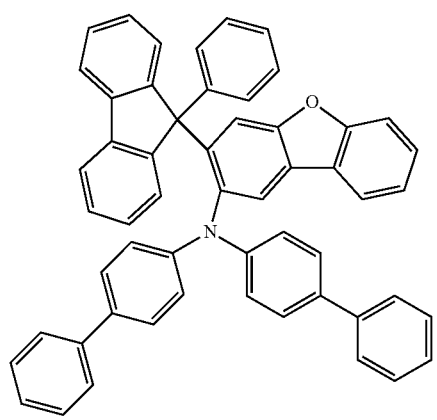
336
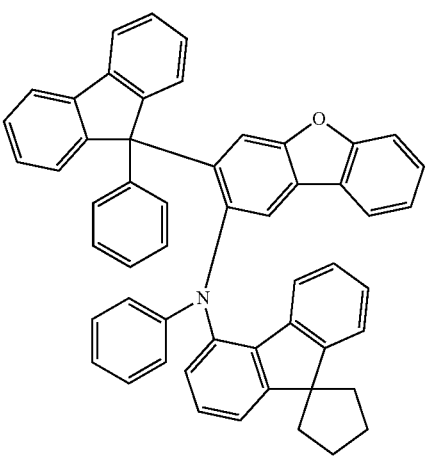
334
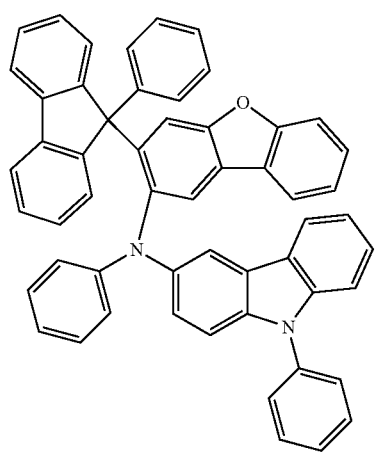
337
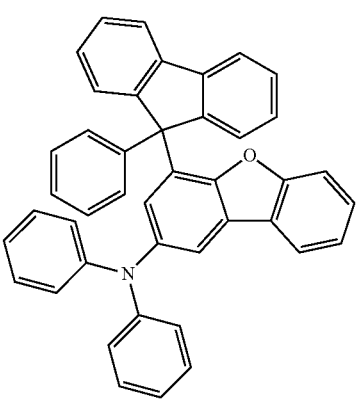

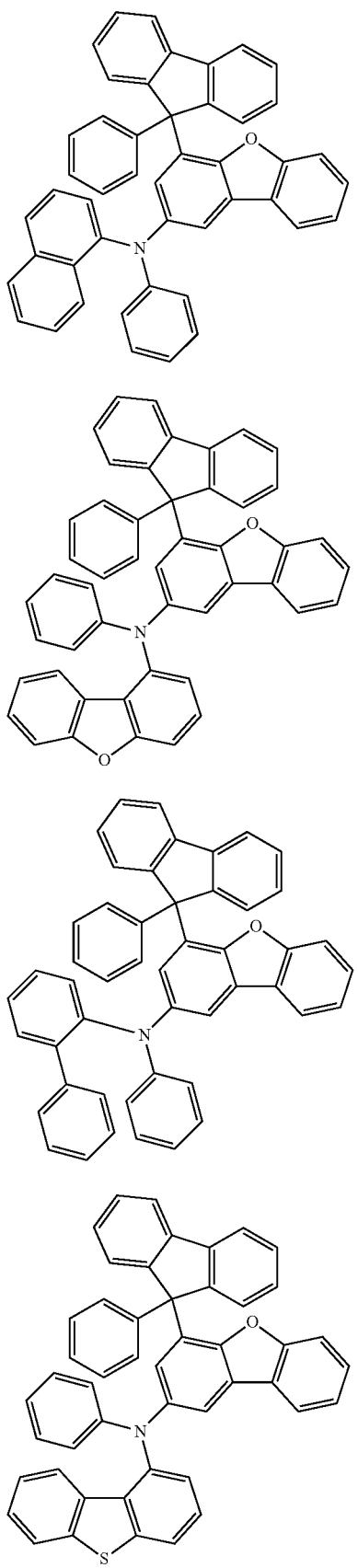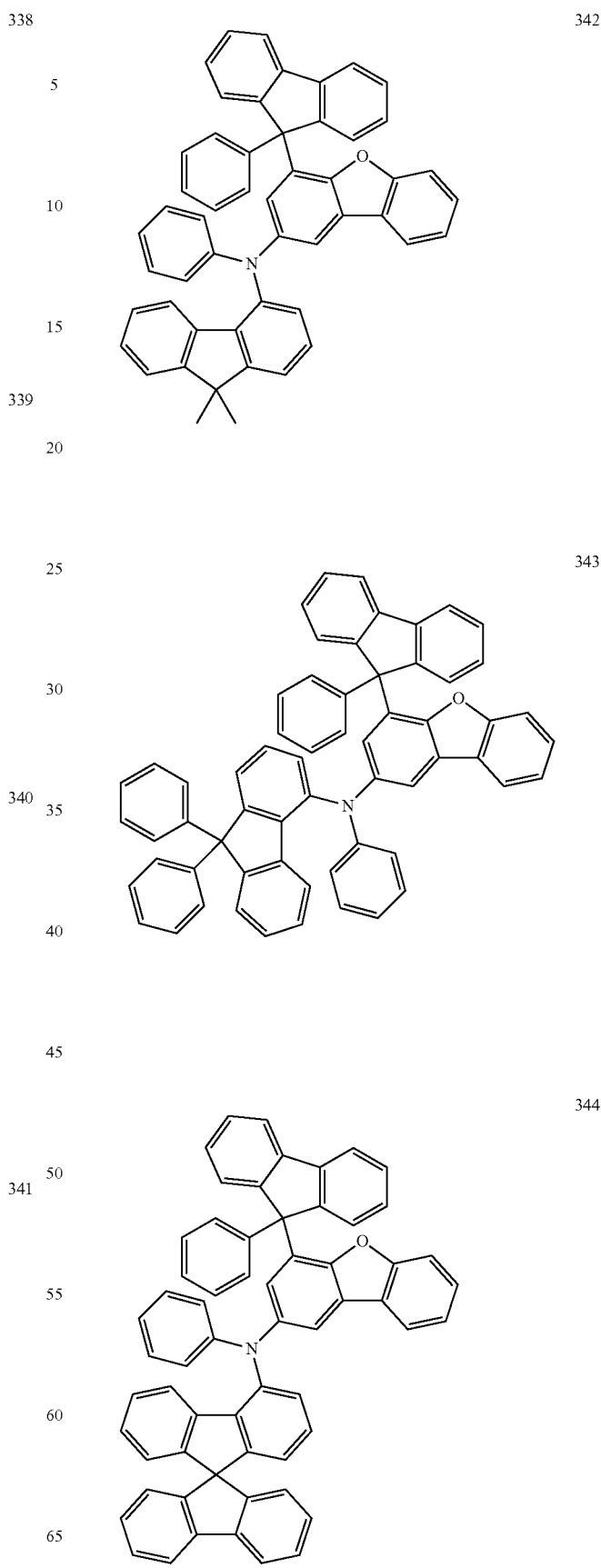

351
-continued
352
-continued
345
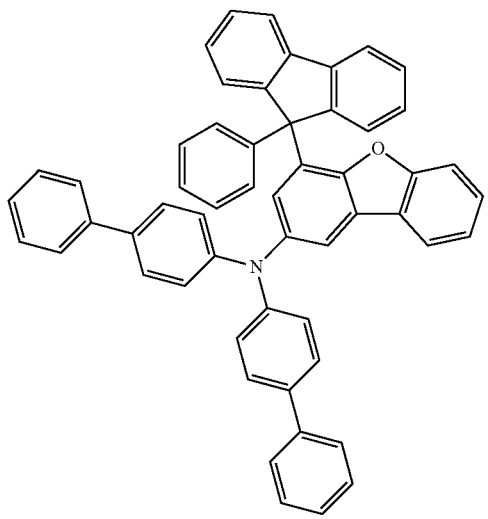
347
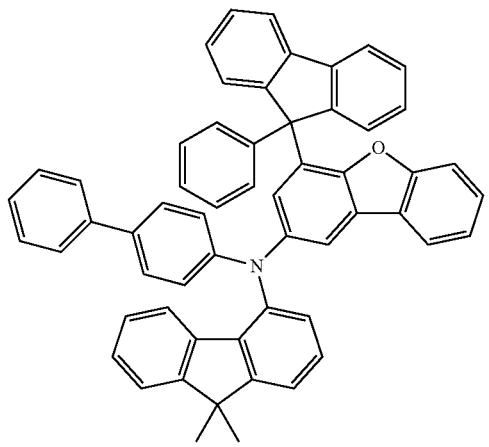
346
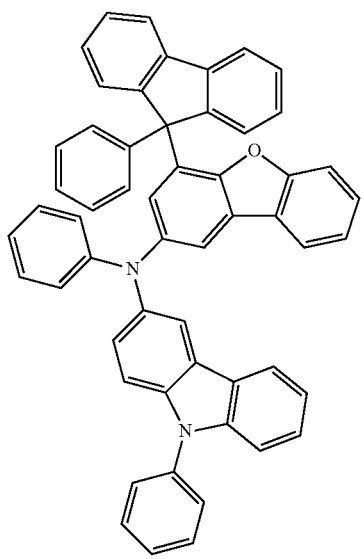
348
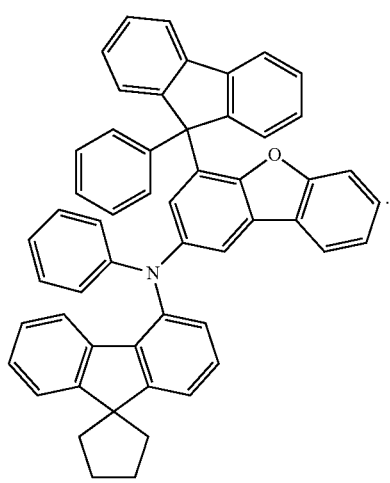
* * * * *